United States Patent
Manjunath et al.

(10) Patent No.: US 8,138,393 B2
(45) Date of Patent: Mar. 20, 2012

(54) PRODUCTION OF HIGH TRYPTOPHAN MAIZE BY CHLOROPLAST TARGETED EXPRESSION OF ANTHRANILATE SYNTHASE

(75) Inventors: Siva Manjunath, Chesterfield, MO (US); Santiago Xavier Navarro, St. Louis, MO (US); William D. Rapp, Wildwood, MO (US); Xiaohong Shi, Ballwin, MO (US); Marguerite J. Varagona, Ballwin, MO (US); Jennifer L. Winson, Godfrey, IL (US); Guangning Ye, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1258 days.

(21) Appl. No.: 11/836,690

(22) Filed: Aug. 9, 2007

(65) Prior Publication Data

US 2008/0050506 A1 Feb. 28, 2008

Related U.S. Application Data

(60) Provisional application No. 60/837,200, filed on Aug. 11, 2006.

(51) Int. Cl.
*C12N 15/00* (2006.01)
*A01H 1/00* (2006.01)
*C07H 21/04* (2006.01)
*C07K 14/415* (2006.01)

(52) U.S. Cl. ........ 800/295; 435/6.1; 435/69.1; 435/468; 435/183; 435/419; 435/320.1; 530/370; 536/23.2; 536/23.6; 800/278

(58) Field of Classification Search .................. 435/6.1, 435/69.1, 468, 419, 320.1, 183; 536/23.2; 800/278, 295; 530/370
See application file for complete search history.

(56) References Cited

U.S. PATENT DOCUMENTS

| | | | |
|---|---|---|---|
| 5,188,642 | A | 2/1993 | Shah et al. ................. 47/58 |
| 5,545,545 | A | 8/1996 | Gengenbach et al. ..... 435/172.3 |
| 5,728,925 | A | 3/1998 | Herrera-Estrella et al. .. 800/205 |
| 6,118,047 | A | 9/2000 | Anderson et al. ............. 800/278 |
| 6,248,876 | B1 | 6/2001 | Barry et al. ................ 536/24.3 |
| 6,271,016 | B1 | 8/2001 | Anderson et al. ............. 435/418 |
| 6,515,201 | B2 | 2/2003 | Anderson et al. ............. 800/278 |
| 7,217,865 | B2 | 5/2007 | Weaver et al. ................ 800/300 |
| 7,288,403 | B2 | 10/2007 | Anderson et al. ............ 536/23.2 |
| 2003/0167514 | A1 | 9/2003 | Anderson et al. ............ 800/300 |
| 2003/0213010 | A1 | 11/2003 | Weaver et al. ................ 800/278 |
| 2007/0028321 | A1 | 2/2007 | Manjunath et al. ........... 800/278 |

FOREIGN PATENT DOCUMENTS

| | | | |
|---|---|---|---|
| WO | WO9726366 | * | 7/1997 |
| WO | WO 02/090497 | | 11/2002 |
| WO | WO 03/092363 | | 11/2003 |

OTHER PUBLICATIONS

U.S. Appl. No. 08/113,561, Adams, filed Aug. 25, 1993.
Archer et al., "Current views of chloroplast import and hypotheses on the origin of the transport mechanism," *J. Bioenerg Biomembr*, 22:789-810, 1990.
Bae et al., "*Rhizobium meliloti* anthranilate synthase gene: cloning, sequence, and expression in *Escherichia coli*," *J. of Bacteriology*, 171(6):3471-3478, 1989.
Schnell et al., "Signal peptide analogs derived from two chloroplast precursors interact with the signal recognition system of the chloroplast envelope," *J. Bio. Chem.*, 266(5):3335-3342, 1991.
Silva-Filho et al., "Mitochondrial and chloroplast targeting sequences in tandem modify protein import specificity in plant organelles," *Plant Mol. Biol.*, 30:769-780, 1996.

* cited by examiner

*Primary Examiner* — Phuong Bui
(74) *Attorney, Agent, or Firm* — SNR Denton US LLP; Chuping Li, Esq.

(57) ABSTRACT

Novel expression vectors and constructs encoding a chloroplast transit peptide (CTP) operably linked to a monomeric anthranilate synthase are provided. Additionally, novel polynucleotide sequences encoding monomeric anthranilate synthases are provided. Also provided are methods for increasing the levels of free tryptophan in transgenic plants containing the expression vectors and constructs.

19 Claims, 19 Drawing Sheets

Anti-maize ASα (plastidic marker)   Anti-pea GS1 (cytosolic marker)   Anti-Agro AS

H  S  P1  P2       H  S  P1  P2       H  S  P1  P2

SEQUENCE LISTING

```
<160> NUMBER OF SEQ ID NOS: 231

<210> SEQ ID NO 1
<211> LENGTH: 228
<212> TYPE: DNA
<213> ORGANISM: Arabidopsis thaliana

<400> SEQUENCE: 1
atggcgcaag ttagcagaat ctgcaatggt gtgcagaacc catctcttat ctccaatctc      60
tcgaaatcca gtcaacgcaa atctcccta tcggtttctc tgaagacgca gcagcatcca     120
cgagcttatc cgatttcgtc gtcgtgggga ttgaagaaga gtgggatgac gttaattggc     180
```

```
tctgagcttc gtcctcttaa ggtcatgtct tctgtttcca cggcgtgc         228
```

```
<210> SEQ ID NO 2
<211> LENGTH: 231
<212> TYPE: DNA
<213> ORGANISM: Arabidopsis thaliana

<400> SEQUENCE: 2
atggcgcaag ttagcagaat ctgcaatggt gtgcagaacc catctcttat ctccaatctc    60
tcgaaatcca gtcaacgcaa atctcccttc tcggtttctc tgaagacgca gcagcatcca   120
cgagcttatc cgatttcgtc gtcgtgggga ttgaagaaga gtgggatgac gttaattggc   180
tctgagcttc gtcctcttaa ggtcatgtct tctgtttcca cggcggagaa a           231
```

```
<210> SEQ ID NO 3
<211> LENGTH: 258
<212> TYPE: DNA
<213> ORGANISM: Arabidopsis thaliana

<400> SEQUENCE: 3
atggcgcaag ttagcagaat ctgcaatggt gtgcagaacc catctcttat ctccaatctc    60
tcgaaatcca gtcaacgcaa atctcccttc tcggtttctc tgaagacgca gcagcatcca   120
cgagcttatc cgatttcgtc gtcgtgggga ttgaagaaga gtgggatgac gttaattggc   180
tctgagcttc gtcctcttaa ggtcatgtct tctgtttcca cggcggagaa agcgtcggag   240
attgtacttc aacccatt                                                258
```

```
<210> SEQ ID NO 4
<211> LENGTH: 243
<212> TYPE: DNA
<213> ORGANISM: Arabidopsis thaliana

<400> SEQUENCE: 4
atggcgcaag ttagcagaat ctgcaatggt gtgcagaacc catctcttat ctccaatctc    60
tcgaaatcca gtcaacgcaa atctcccttc tcggtttctc tgaagacgca gcagcatcca   120
cgagcttatc cgatttcgtc gtcgtgggga ttgaagaaga gtgggatgac gttaattggc   180
tctgagcttc gtcctcttaa ggtcatgtct tctgtttcca cggcggagaa agcgtcggag   240
att                                                                243
```

```
<210> SEQ ID NO 5
<211> LENGTH: 96
<212> TYPE: DNA
<213> ORGANISM: Zea mays

<400> SEQUENCE: 5
atggccaccg ccagcctcgc gctctcgctg cgcctcgcgc cgtactcgca cccgctgagc    60
ctccgccgcc gcggcgccgc cggcgtcacc tgccgc                             96
```

```
<210> SEQ ID NO 6
<211> LENGTH: 156
<212> TYPE: DNA
<213> ORGANISM: Zea mays

<400> SEQUENCE: 6
atggccaccg ccagcctcgc gctctcgctg cgcctcgcgc cgtactcgca cccgctgagc    60
ctccgccgcc gcggcgccgc cggcgtcacc tgccgcgcca ccaccgccac gttccaccag   120
cttgacgccg tcgcggtgag ggaggaggag tccagg                            156
```

```
<210> SEQ ID NO 7
<211> LENGTH: 142
<212> TYPE: DNA
<213> ORGANISM: Zea mays

<400> SEQUENCE: 7
atggaatccc tagccgccac ctccgtgttc gcgccctccc gcgtcgccgt cccggcggcg      60
cgggccctgg ttagggcggg gacggtggta ccaaccaggc ggacgagcag ccggagcgga     120
accagcgggg tgaaatgctc ta                                              142

<210> SEQ ID NO 8
<211> LENGTH: 191
<212> TYPE: DNA
<213> ORGANISM: Zea mays

<400> SEQUENCE: 8
atggaatccc tagccgccac ctccgtgttc gcgccctccc gcgtcgccgt cccggcggcg      60
cgggccctgg ttagggcggg gacggtggta ccaaccaggc ggacgagcag ccggagcgga     120
accagcgggg tgaaatgctc tgctgccgtg acgccgatgg taacgatcat tcaggatgac    180
ggagcggaga c                                                         191

<210> SEQ ID NO 9
<211> LENGTH: 195
<212> TYPE: DNA
<213> ORGANISM: Zea mays

<400> SEQUENCE: 9
atggaatccc tagccgccac ctccgtgttc gcgccctccc gcgtcgccgt cccggcggcg      60
cgggccctgg ttagggcggg gacggtggta ccaaccaggc ggacgagcag ccggagcgga     120
accagcgggg tgaaatgctc tgctgccgtg acgccgcagg cgagcccagt gattagcagg    180
agcgctgcgg cggcc                                                     195

<210> SEQ ID NO 10
<211> LENGTH: 227
<212> TYPE: DNA
<213> ORGANISM: Oryza sativa

<400> SEQUENCE: 10
gcggctctca ccacgtccca gctcgccacc tcggccaccg gcttcggcat cgccgacagg      60
tcggcgccgt cgtcgctgct ccgccacggg ttccagggcc tcaagcccg cagccccgcc     120 ggcggcgacg cgacgtcgct cagcgtgacg accagcgcgc gcgcgacgcc caagcagcag    180
cggtcggtgc agcgtggcag ccggaggttc ccctccgtcg tcgtgtg                  227

<210> SEQ ID NO 11
<211> LENGTH: 242
<212> TYPE: DNA
<213> ORGANISM: Oryza sativa

<400> SEQUENCE: 11
gcggctctca ccacgtccca gctcgccacc tcggccaccg gcttcggcat cgccgacagg      60
tcggcgccgt cgtcgctgct ccgccacggg ttccagggcc tcaagccacg cagcccagcc    120
ggcggcgacg cgacgtcgct cagcgtgacg accagcgcgc gcgcgacgcc caagcagcag    180
cggtcggtgc agcgtggcag ccggaggttc ccatccgtcg tcgtgtacgc caccggcgcc    240
gg                                                                   242
```

<210> SEQ ID NO 12
<211> LENGTH: 291
<212> TYPE: DNA
<213> ORGANISM: Oryza sativa

<400> SEQUENCE: 12

```
atggcggctc tcaccacgtc ccagctcgcc acctcggcca ccggcttcgg catcgccgac      60
aggtcggcgc cgtcgtcgct gctccgccac gggttccagg gcctcaagcc acgcagccca     120
gccggcggcg acgcgacgtc gctcagcgtg acgaccagcg cgcgcgcgac gcccaagcag     180
cagcggtcgg tgcagcgtgg cagccggagg ttcccatccg tcgtcgtgta cgccaccggc     240
gccggcatga acgtcgtgtt cgtcggcgcc gagatggccc cctggagcaa g              291
```

<210> SEQ ID NO 13
<211> LENGTH: 215
<212> TYPE: DNA
<213> ORGANISM: Ruta graveolens

<400> SEQUENCE: 13

```
atgagtgcag cggcaacgtc gatgcaatcc cttaaattct ccaaccgtct ggtcccaccc      60
agtcgccgtc tgtctccggt tccgaacaat gtcacctgca ataacctccc caagtctgca     120
gctcccgtcc ggacagtcaa atgctgcgct tcttcctgga acagtaccat caacggcgcg     180
gccgccacga ccaacggtgc gtccgccgcc agttc                                215
```

<210> SEQ ID NO 14
<211> LENGTH: 275
<212> TYPE: DNA
<213> ORGANISM: Ruta graveolens

<400> SEQUENCE: 14

```
atgagtgcag cggcaacgtc gatgcaatcc cttaaattct ccaaccgtct ggtcccaccc      60
agtcgccgtc tgtctccggt tccgaacaat gtcacctgca ataacctccc caagtctgca     120
gctcccgtcc ggacagtcaa atgctgcgct tcttcctgga acagtaccat caacggcgcc     180
gccgccacga ccaacggtgc gtccgccgcc agtaacggcg catccacgac caccactaca     240
tatgttagtg atgcaaccag atttatcgac tcttc                                275
```

<210> SEQ ID NO 15
<211> LENGTH: 162
<212> TYPE: DNA
<213> ORGANISM: Zea mays

<400> SEQUENCE: 15

```
atgatttcgc cgacgaatct cctcccggcg cggaagatca cccctgtctc aaatggcggc      60
gcagcgacgg cgagcccctc ttctccctcg gtggccgcac ggccacggcg actcccttca     120
ggcctccaat ctgtgactgg tagagggaag gtttccttgg ca                        162
```

<210> SEQ ID NO 16
<211> LENGTH: 190
<212> TYPE: DNA
<213> ORGANISM: Zea mays

<400> SEQUENCE: 16

```
atgatttcgc cgacgaatct cctcccggcg cggaagatca cccctgtctc aaatggcggc      60
gcagcgacgg cgagcccctc ttctccctcg gtggccgcac ggccacggcg actcccttca     120
ggcctccaat ctgtgactgg tagagggaag gtttccttgg cagccatcac tctggatgat     180
```
taccttccaa                                                              190

<210> SEQ ID NO 17
<211> LENGTH: 222
<212> TYPE: DNA
<213> ORGANISM: Zea mays

<400> SEQUENCE: 17
atgatttcgc cgacgaatct cctcccggcg cggaagatca cccctgtctc aaatggcggc     60
gcagcgacgg cgagcccctc ttctccctcg gtggccgcac ggccacggcg actcccttca    120
ggcctccaat ctgtgactgg tagagggaag gtttccttgg cagccatcac tctggatgat    180
taccttccaa tgcgaagcac tgaagtgaag aaccggacat ca                       222

<210> SEQ ID NO 18
<211> LENGTH: 171
<212> TYPE: DNA
<213> ORGANISM: Zea mays

<400> SEQUENCE: 18
atgatttcgc cgacgaatct cctcccggcg cggaagatca cccctgtctc aaatggcggc     60
gcagcgacgg cgagcccctc ttctccctcg gtggccgcac ggccacggcg actcccttca    120
ggcctccaat ctgtgactgg tagagggaag gtttccttgg cagccatcac c             171

<210> SEQ ID NO 19
<211> LENGTH: 261
<212> TYPE: DNA
<213> ORGANISM: Arabidopsis thaliana

<400> SEQUENCE: 19
gcttcctcta tgctctcttc cgctactatg gttgcctctc cggctcaggc cactatggtc     60
gctcctttca acggacttaa gtcctccgct gccttcccag ccaccccgcaa ggctaacaac   120 gacattactt ccatcacaag caacggcgga agagttaact gcatgcaggt gtggcctccg    180
attggaaaga agaagtttga gactctctct taccttcctg accttaccga ttccggtggt    240
cgcgtcaact gcatgcaggc c                                              261

<210> SEQ ID NO 20
<211> LENGTH: 76
<212> TYPE: PRT
<213> ORGANISM: Arabidopsis thaliana

<400> SEQUENCE: 20

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 21
<211> LENGTH: 77
<212> TYPE: PRT
<213> ORGANISM: Arabidopsis thaliana

<400> SEQUENCE: 21

```
Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
        50                  55                  60

Pro Leu Lys Val Met Ser Ser Val Ser Thr Ala Glu Lys
65                  70                  75
```

<210> SEQ ID NO 22
<211> LENGTH: 86
<212> TYPE: PRT
<213> ORGANISM: Arabidopsis thaliana

<400> SEQUENCE: 22

```
Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
        50                  55                  60

Pro Leu Lys Val Met Ser Ser Val Ser Thr Ala Glu Lys Ala Ser Glu
65                  70                  75                  80

Ile Val Leu Gln Pro Ile
                85
```

<210> SEQ ID NO 23
<211> LENGTH: 81
<212> TYPE: PRT
<213> ORGANISM: Arabidopsis thaliana

<400> SEQUENCE: 23

```
Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
        50                  55                  60

Pro Leu Lys Val Met Ser Ser Val Ser Thr Ala Glu Lys Ala Ser Glu
65                  70                  75                  80

Ile
```

<210> SEQ ID NO 24
<211> LENGTH: 32
<212> TYPE: PRT
<213> ORGANISM: Zea mays

<400> SEQUENCE: 24

```
Met Ala Thr Ala Ser Leu Ala Leu Ser Leu Arg Leu Ala Pro Tyr Ser
1               5                   10                  15

His Pro Leu Ser Leu Arg Arg Arg Gly Ala Ala Gly Val Thr Cys Arg
                20                  25                  30
```

<210> SEQ ID NO 25
<211> LENGTH: 52
<212> TYPE: PRT
<213> ORGANISM: Zea mays

<400> SEQUENCE: 25

```
Met Ala Thr Ala Ser Leu Ala Leu Ser Leu Arg Leu Ala Pro Tyr Ser
1               5                   10                  15
His Pro Leu Ser Leu Arg Arg Arg Gly Ala Ala Gly Val Thr Cys Arg
            20                  25                  30
Ala Thr Thr Ala Thr Phe His Gln Leu Asp Ala Val Ala Val Arg Glu
        35                  40                  45
Glu Glu Ser Arg
    50
```

<210> SEQ ID NO 26
<211> LENGTH: 47
<212> TYPE: PRT
<213> ORGANISM: Zea mays

<400> SEQUENCE: 26

```
Met Glu Ser Leu Ala Ala Thr Ser Val Phe Ala Pro Ser Arg Val Ala
1               5                   10                  15
Val Pro Ala Ala Arg Ala Leu Val Arg Ala Gly Thr Val Val Pro Thr
            20                  25                  30
Arg Arg Thr Ser Ser Arg Ser Gly Thr Ser Gly Val Lys Cys Ser
        35                  40                  45
```

<210> SEQ ID NO 27
<211> LENGTH: 63
<212> TYPE: PRT
<213> ORGANISM: Zea mays

<400> SEQUENCE: 27

```
Met Glu Ser Leu Ala Ala Thr Ser Val Phe Ala Pro Ser Arg Val Ala
1               5                   10                  15
Val Pro Ala Ala Arg Ala Leu Val Arg Ala Gly Thr Val Val Pro Thr
            20                  25                  30
Arg Arg Thr Ser Ser Arg Ser Gly Thr Ser Gly Val Lys Cys Ser Ala
        35                  40                  45
Ala Val Thr Pro Met Val Thr Ile Ile Gln Asp Asp Gly Ala Glu
    50                  55                  60
```

<210> SEQ ID NO 28
<211> LENGTH: 65
<212> TYPE: PRT
<213> ORGANISM: Zea mays

<400> SEQUENCE: 28

```
Met Glu Ser Leu Ala Ala Thr Ser Val Phe Ala Pro Ser Arg Val Ala
1               5                   10                  15
Val Pro Ala Ala Arg Ala Leu Val Arg Ala Gly Thr Val Val Pro Thr
            20                  25                  30
Arg Arg Thr Ser Ser Arg Ser Gly Thr Ser Gly Val Lys Cys Ser Ala
        35                  40                  45
Ala Val Thr Pro Gln Ala Ser Pro Val Ile Ser Arg Ser Ala Ala Ala
    50                  55                  60
Ala
65
```

```
<210> SEQ ID NO 29
<211> LENGTH: 75
<212> TYPE: PRT
<213> ORGANISM: Oryza sativa

<400> SEQUENCE: 29

Ala Ala Leu Thr Thr Ser Gln Leu Ala Thr Ser Ala Thr Gly Phe Gly
1               5                   10                  15

Ile Ala Asp Arg Ser Ala Pro Ser Ser Leu Leu Arg His Gly Phe Gln
                20                  25                  30

Gly Leu Lys Pro Arg Ser Pro Ala Gly Gly Asp Ala Thr Ser Leu Ser
            35                  40                  45

Val Thr Thr Ser Ala Arg Ala Thr Pro Lys Gln Gln Arg Ser Val Gln
        50                  55                  60

Arg Gly Ser Arg Arg Phe Pro Ser Val Val Val
65                  70                  75

<210> SEQ ID NO 30
<211> LENGTH: 80
<212> TYPE: PRT
<213> ORGANISM: Oryza sativa

<400> SEQUENCE: 30

Ala Ala Leu Thr Thr Ser Gln Leu Ala Thr Ser Ala Thr Gly Phe Gly
1               5                   10                  15

Ile Ala Asp Arg Ser Ala Pro Ser Ser Leu Leu Arg His Gly Phe Gln
                20                  25                  30

Gly Leu Lys Pro Arg Ser Pro Ala Gly Gly Asp Ala Thr Ser Leu Ser
            35                  40                  45

Val Thr Thr Ser Ala Arg Ala Thr Pro Lys Gln Gln Arg Ser Val Gln
        50                  55                  60

Arg Gly Ser Arg Arg Phe Pro Ser Val Val Val Tyr Ala Thr Gly Ala
65                  70                  75                  80

<210> SEQ ID NO 31
<211> LENGTH: 96
<212> TYPE: PRT
<213> ORGANISM: Oryza sativa

<400> SEQUENCE: 31

Ala Ala Leu Thr Thr Ser Gln Leu Ala Thr Ser Ala Thr Gly Phe Gly
1               5                   10                  15

Ile Ala Asp Arg Ser Ala Pro Ser Ser Leu Leu Arg His Gly Phe Gln
                20                  25                  30

Gly Leu Lys Pro Arg Ser Pro Ala Gly Gly Asp Ala Thr Ser Leu Ser
            35                  40                  45

Val Thr Thr Ser Ala Arg Ala Thr Pro Lys Gln Gln Arg Ser Val Gln
        50                  55                  60

Arg Gly Ser Arg Arg Phe Pro Ser Val Val Val Tyr Ala Thr Gly Ala
65                  70                  75                  80

Gly Met Asn Val Val Phe Val Gly Ala Glu Met Ala Pro Trp Ser Lys
                85                  90                  95

<210> SEQ ID NO 32
<211> LENGTH: 71
<212> TYPE: PRT
<213> ORGANISM: Ruta graveolens

<400> SEQUENCE: 32
```

Met Ser Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
            35                  40                  45

Cys Ala Ser Ser Trp Asn Ser Thr Ile Asn Gly Ala Ala Ala Thr Thr
50                  55                  60

Asn Gly Ala Ser Ala Ala Ser
65                  70

<210> SEQ ID NO 33
<211> LENGTH: 91
<212> TYPE: PRT
<213> ORGANISM: Ruta graveolens

<400> SEQUENCE: 33

Met Ser Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
            35                  40                  45

Cys Ala Ser Ser Trp Asn Ser Thr Ile Asn Gly Ala Ala Ala Thr Thr
50                  55                  60

Asn Gly Ala Ser Ala Ala Ser Asn Gly Ala Ser Thr Thr Thr Thr Thr
65                  70                  75                  80

Tyr Val Ser Asp Ala Thr Arg Phe Ile Asp Ser
                85                  90

<210> SEQ ID NO 34
<211> LENGTH: 54
<212> TYPE: PRT
<213> ORGANISM: Zea mays

<400> SEQUENCE: 34

Met Ile Ser Pro Thr Asn Leu Leu Pro Ala Arg Lys Ile Thr Pro Val
1               5                   10                  15

Ser Asn Gly Gly Ala Ala Thr Ala Ser Pro Ser Ser Pro Ser Val Ala
            20                  25                  30

Ala Arg Pro Arg Arg Leu Pro Ser Gly Leu Gln Ser Val Thr Gly Arg
            35                  40                  45

Gly Lys Val Ser Leu Ala
            50

<210> SEQ ID NO 35
<211> LENGTH: 63
<212> TYPE: PRT
<213> ORGANISM: Zea mays

<400> SEQUENCE: 35

Met Ile Ser Pro Thr Asn Leu Leu Pro Ala Arg Lys Ile Thr Pro Val
1               5                   10                  15

Ser Asn Gly Gly Ala Ala Thr Ala Ser Pro Ser Ser Pro Ser Val Ala
            20                  25                  30

Ala Arg Pro Arg Arg Leu Pro Ser Gly Leu Gln Ser Val Thr Gly Arg
            35                  40                  45

Gly Lys Val Ser Leu Ala Ala Ile Thr Leu Asp Asp Tyr Leu Pro
            50                  55                  60

<210> SEQ ID NO 36
<211> LENGTH: 74
<212> TYPE: PRT
<213> ORGANISM: Zea mays

<400> SEQUENCE: 36

Met Ile Ser Pro Thr Asn Leu Leu Pro Ala Arg Lys Ile Thr Pro Val
1               5                   10                  15

Ser Asn Gly Gly Ala Ala Thr Ala Ser Pro Ser Ser Pro Ser Val Ala
            20                  25                  30

Ala Arg Pro Arg Arg Leu Pro Ser Gly Leu Gln Ser Val Thr Gly Arg
        35                  40                  45

Gly Lys Val Ser Leu Ala Ala Ile Thr Leu Asp Asp Tyr Leu Pro Met
    50                  55                  60

Arg Ser Thr Glu Val Lys Asn Arg Thr Ser
65                  70

<210> SEQ ID NO 37
<211> LENGTH: 57
<212> TYPE: PRT
<213> ORGANISM: Zea mays

<400> SEQUENCE: 37

Met Ile Ser Pro Thr Asn Leu Leu Pro Ala Arg Lys Ile Thr Pro Val
1               5                   10                  15

Ser Asn Gly Gly Ala Ala Thr Ala Ser Pro Ser Ser Pro Ser Val Ala
            20                  25                  30

Ala Arg Pro Arg Arg Leu Pro Ser Gly Leu Gln Ser Val Thr Gly Arg
        35                  40                  45

Gly Lys Val Ser Leu Ala Ala Ile Thr
    50                  55

<210> SEQ ID NO 38
<211> LENGTH: 87
<212> TYPE: PRT
<213> ORGANISM: Arabidopsis thaliana

<400> SEQUENCE: 38

Ala Ser Ser Met Leu Ser Ser Ala Thr Met Val Ala Ser Pro Ala Gln
1               5                   10                  15

Ala Thr Met Val Ala Pro Phe Asn Gly Leu Lys Ser Ser Ala Ala Phe
            20                  25                  30

Pro Ala Thr Arg Lys Ala Asn Asn Asp Ile Thr Ser Ile Thr Ser Asn
        35                  40                  45

Gly Gly Arg Val Asn Cys Met Gln Val Trp Pro Pro Ile Gly Lys Lys
    50                  55                  60

Lys Phe Glu Thr Leu Ser Tyr Leu Pro Asp Leu Thr Asp Ser Gly Gly
65                  70                  75                  80

Arg Val Asn Cys Met Gln Ala
                85

<210> SEQ ID NO 39
<211> LENGTH: 1134
<212> TYPE: DNA
<213> ORGANISM: Arabidopsis thaliana

<400> SEQUENCE: 39
atggcgcaag ttagcagaat ctgcaatggt gtgcagaacc catctcttat ctccaatctc    60

```
tcgaaatcca gtcaacgcaa atctccctta tcggtttctc tgaagacgca gcagcatcca      120
cgagcttatc cgatttcgtc gtcgtgggga ttgaagaaga gtgggatgac gttaattggc      180
tctgagcttc gtcctcttaa ggtcatgtct tctgtttcca cggcgtgcat gggcaagggc      240
gaggaactgt tcactggcgt ggtcccaatc ctggtggaac tggatggtga tgtgaacggg      300
cacaagttct ccgtcagcgg agagggtgaa ggtgatgcca cctacggaaa gctcaccctg      360
aagttcatct gcactaccgg aaagctccct gttccgtggc caaccctcgt caccactttc      420
acctacggtg ttcagtgctt ctcccggtac ccagatcaca tgaagcagca tgacttcttc      480
aagagcgcca tgcccgaagg ctacgtgcaa gaaaggacta tctctttcaa ggatgacggg      540
aactacaaga cacgtgccga gtcaagttc gaaggtgata ccctggtgaa ccgcatcgag       600
ctgaaaggta agtttctgct tctacctttg atatatatat aataattatc attaattagt      660
agtaatataa tatttcaaat attttttttca aaataaaaga atgtagtata tagcaattgc     720
ttttctgtag tttataagtg tgtatatttt aatttataac ttttctaata tatgaccaaa     780
atttgttgat gtgcaggtat cgatttcaag gaagatggaa acatcctcgg acacaagctg     840
gagtacaact acaactccca caacgtatac atcacggccg acaagcagaa gaacggcatc    900
aaggctaact tcaagatcag gcacaacatc gaagatggaa gcgtgcaact ggcggaccac    960
taccagcaga cacgcccat cggcgatggc cctgtcctgc tgccggacaa ccattacctg    1020
tccacgcaat ctgccctctc caaggacccc aacgagaaga gggaccacat ggtcctgctg    1080
gagttcgtga cggctgctgg gatcacgcat ggcatggatg aactctacaa gtga           1134

<210> SEQ ID NO 40
<211> LENGTH: 1060
<212> TYPE: DNA
<213> ORGANISM: Zea mays

<400> SEQUENCE: 40
atggaatccc tagccgccac ctccgtgttc gcgccctccc gcgtcgccgt cccggcggcg      60
cgggccctgg ttagggcggg gacggtggta ccaaccaggc ggacgagcag ccggagcgga    120
accagcgggg tgaaatgctc ggatccagga gcaaccatgg caagggcgag gaactgttca    180
ctggcgtggt cccaatcctg gtggaactgg atggtgatgt gaacgggcac aagttctccg    240
tcagcggaga gggtgaaggt gatgccacct acggaaagct caccctgaag ttcatctgca    300
ctaccggaaa gctcccctgtt ccgtggccaa ccctcgtcac cactttcacc tacggtgttc    360
agtgcttctc ccggtaccca gatcacatga agcagcatga cttcttcaag agcgcatgcc    420
cgaaggctac gtgcaagaaa ggactatctc tttcaaggat gacgggaact acaagacacg    480
tgccgaagtc aagttcgaag gtgataccct ggtgaaccgc atcgagctga aggtaagtt    540 tctgcttcta ccttttgatat atatataata attatcatta ttagtagta atataatatt    600 tcaaatattt ttttcaaaat aaaagaatgt agtatatagc aattgctttt ctgtagttta    660
taagtgtgta tattttaatt tataactttt ctaatatatg accaaaattt gttgatgtgc    720
aggtatcgat ttcaaggaag atggaaacat cctcggacac aagctggagt acaactacaa    780
ctcccacaac gtatacatca cggccgacaa gcagaagaac ggcatcaagg ctaacttcaa    840
gatcaggcac aacatcgaag atggaagcgt gcaactggcg gaccactacc agcagaacac    900
gcccatcggc gatggccctg tcctgctgcc ggacaaccat tacctgtcca cgcaatctgc    960
cctctccaag gaccccaacg agaagaggga ccacatggtc ctgctggagt tcgtgacggc    1020
tgctgggatc acgcatggca tggatgaact ctacaagtga                          1060
```

<210> SEQ ID NO 41
<211> LENGTH: 606
<212> TYPE: DNA
<213> ORGANISM: Oryza sativa

<400> SEQUENCE: 41

```
gcggctctca ccacgtccca gctcgccacc tcggccaccg gcttcggcat cgccgacagg      60
tcggcgccgt cgtcgctgct ccgccacggg ttccagggcc tcaagcccg cagcccgcc      120
ggcggcgacg cgacgtcgct cagcgtgacg accagcgcgc gcgcgacgcc caagcagcag     180
cggtcggtgc agcgtggcag ccggaggttc ccctccgtcg tcgtgtgatg ggcaagggcg     240
aggaactgtt cactggcgtg gtcccaatcc tggtggaact ggatggtgat gtgaacgggc     300
acaagttctc cgtcagcgga gagggtgaag gtgatgccac ctacggaaag ctcaccctga     360
agttcatctg cactaccgga aagctccctg ttccgtggcc aaccctcgtc accactttca     420
cctacggtgt tcagtgcttc tcccggtacc cagatcacat gaagcagcat gacttcttca     480
agagcgccat gcccgaaggc tacgtgcaag aaaggactat ctctttcaag gatgacggga     540
actacaagac acgtgccgaa gtcaagttcg aaggtgatac cctggtgaac cgcatcgagc     600
tgaaag                                                                606
```

<210> SEQ ID NO 42
<211> LENGTH: 1140
<212> TYPE: DNA
<213> ORGANISM: Ruta graveolens

<400> SEQUENCE: 42

```
atgagtgcag cggcaacgtc gatgcaatcc cttaaattct ccaaccgtct ggtcccaccc      60
agtcgccgtc tgtctccggt tccgaacaat gtcacctgca ataacctccc caagtctgca     120
gctcccgtcc ggacagtcaa atgctgcgct tcttcctgga acagtaccat caacggcgcg     180
gccgccacga ccaacggtgc gtccgccgcc agttcgcgcg gatccaggagc aaccatgggc    240
aagggcgagg aactgttcac tggcgtggtc ccaatcctgg tggaactgga tggtgatgtg     300
aacgggcaca agttctccgt cagcggagag ggtgaaggtg atgccaccta cggaaagctc     360
accctgaagt catctgcac taccggaaag ctccctgttc cgtggccaac cctcgtcacc     420
actttcacct acggtgttca gtgcttctcc cggtacccag atcacatgaa gcagcatgac     480
ttcttcaaga gcgccatgcc cgaaggctac gtgcaagaaa ggactatctc tttcaaggat     540
gacgggaact acaagacacg tgccgaagtc aagttcgaag gtgatacct ggtgaaccgc      600
atcgagctga aggtaagtt tctgcttcta cctttgatat atataata attatcatta       660
attagtagta atataatatt tcaaatattt ttttcaaat aaaagaatgt agtatatagc      720
aattgctttt ctgtagttta taagtgtgta tattttaatt tataacttt ctaatatatg      780
accaaaattt gttgatgtgc aggtatcgat ttcaaggaag atggaaacat cctcggacac     840
aagctggagt acaactacaa ctcccacaac gtatacatca cggccgacaa gcagaagaac     900
ggcatcaagg ctaacttcaa gatcaggcac aacatcgaag atggaagcgt gcaactggcg     960
gaccactacc agcagaacac gcccatcggc gatggccctg tcctgctgcc ggacaaccat    1020
tacctgtcca cgcaatctgc cctctccaag gaccccaacg agaagaggga ccacatggtc    1080
ctgctggagt tcgtgacggc tgctgggatc acgcatggca tggatgaact ctacaagtga   1140
```

<210> SEQ ID NO 43
<211> LENGTH: 1083

```
<212> TYPE: DNA
<213> ORGANISM: Zea mays

<400> SEQUENCE: 43
atgatttcgc cgacgaatct cctcccggcg cggaagatca cccctgtctc aaatggcggc      60
gcagcgacgg cgagcccctc ttctccctcg gtggccgcac ggccacggcg actcccttca     120
ggcctccaat ctgtgactgg tagagggaag gtttccttgg cggatccagg agcaaccatg     180
ggcaagggcg aggaactgtt cactggcgtg gtcccaatcc tggtggaact ggatggtgat     240
gtgaacgggc acaagttctc cgtcagcgga gagggtgaag gtgatgccac ctacggaaag     300
ctcaccctga agttcatctg cactaccgga aagctccctg ttccgtggcc aaccctcgtc     360
accactttca cctacggtgt tcagtgcttc tcccggtacc cagatcacat gaagcagcat     420
gacttcttca gagcgccat gcccgaaggc tacgtgcaag aaaggactat ctctttcaag     480
gatgacggga actacaagac acgtgccgaa gtcaagttcg aaggtgatac cctggtgaac     540
cgcatcgagc tgaaaggtaa gtttctgctt ctacctttga tatatatata ataattatca     600
ttaattagta gtaatataat atttcaaata tttttttcaa ataaaagaa tgtagtatat     660
agcaattgct tttctgtagt ttataagtgt gtatatttta atttataact tttctaatat     720
atgaccaaaa tttgttgatg tgcaggtatc gatttcaagg aagatggaaa catcctcgga     780
cacaagctgg agtacaacta caactcccac aacgtataca tcacggccga caagcagaag     840
aacggcatca aggctaactt caagatcagg cacaacatcg aagatggaag cgtgcaactg     900
gcggaccact accagcagaa cacgcccatc ggcgatggcc ctgtcctgct gccggacaac     960
cattacctgt ccacgcaatc tgccctctcc aaggacccca acgagaagag ggaccacatg    1020
gtcctgctgg agttcgtgac ggctgctggg atcacgcatg gcatggatga actctacaag    1080
tga                                                                 1083

<210> SEQ ID NO 44
<211> LENGTH: 1098
<212> TYPE: DNA
<213> ORGANISM: Zea mays

<400> SEQUENCE: 44
atgatttcgc cgacgaatct cctcccggcg cggaagatca cccctgtctc aaatggcggc      60
gcagcgacgg cgagcccctc ttctccctcg gtggccgcac ggccacggcg actcccttca     120
ggcctccaat ctgtgactgg tagagggaag gtttccttgg cagccatcac tctggaggat     180
ccaggagcaa ccatgggcaa gggcgaggaa ctgttcactg gcgtggtccc aatcctggtg     240
gaactggatg gtgatgtgaa cgggcacaag ttctccgtca gcggagaggg tgaaggtgat     300
gccacctacg gaaagctcac cctgaagttc atctgcacta ccggaaagct ccctgttccg     360
tggccaaccc tcgtcaccac tttcacctac ggtgttcagt gcttctcccg gtacccagat     420
cacatgaagc agcatgactt cttcaagagc gccatgcccg aaggctacgt gcaagaaagg     480
actatctctt tcaaggatga cgggaactac aagacacgtg ccgaagtcaa gttcgaaggt     540
gataccctgg tgaaccgcat cgagctgaaa ggtaagtttc tgcttctacc tttgatatat     600
atataataat tatcattaat tagtagtaat ataatatttc aaatattttt ttcaaaataa     660
aagaatgtag tatatagcaa ttgctttttct gtagtttata gtgtgtata ttttaattta     720
taacttttct aatatatgac caaaatttgt tgatgtgcag gtatcgattt caaggaagat     780
ggaaacatcc tcggacacaa gctggagtac aactacaact cccacaacgt atacatcacg     840
gccgacaagc agaagaacgg catcaaggct aacttcaaga tcaggcacaa catcgaagat     900
```

| | |
|---|---|
| ggaagcgtgc aactggcgga ccactaccag cagaacacgc ccatcggcga tggccctgtc | 960 |
| ctgctgccgg acaaccatta cctgtccacg caatctgccc tctccaagga ccccaacgag | 1020 |
| aagagggacc acatggtcct gctggagttc gtgacggctg ctgggatcac gcatggcatg | 1080 |
| gatgaactct acaagtga | 1098 |

<210> SEQ ID NO 45
<211> LENGTH: 2420
<212> TYPE: DNA
<213> ORGANISM: Arabidopsis thaliana
<400> SEQUENCE: 45

| | |
|---|---|
| atggcgcaag ttagcagaat ctgcaatggt gtgcagaacc catctcttat ctccaatctc | 60 |
| tcgaaatcca gtcaacgcaa atctcccttα tcggtttctc tgaagacgca gcagcatcca | 120 |
| cgagcttatc cgatttcgtc gtcgtgggga ttgaagaaga gtgggatgac gttaattggc | 180 |
| tctgagcttc gtcctcttaa ggtcatgtct tctgtttcca cggcggagaa aatggcagcg | 240 |
| gtaattctag aagacggcgc ggagagttat accacgaagg gtggcatcgt cgtcacccgc | 300 |
| aggcggcgtg aggcatccta cagcgacgcg atcgccggtt atgtcgaccg gctggacgaa | 360 |
| cgccgcggcg cggtcttttc ctcgaactac gaatatcccg ccgctatac ccgctgggac | 420 |
| actgcggtgg tcgacccgcc gcttgccatc tcctccttcg gtcgtcgct ctggatcgaa | 480 |
| gcctataacg aacgcggcga agtgctgctg gcgctgatcg ccgaggatct gaagtccgtt | 540 |
| gccgacatca cgctcggctc acttgccgcc cgccgcctcg acctcaccat caacgagccc | 600 |
| gatcgtgtct tcaccgagga agagcggtcg aagatgccga cggtctttac ggttcttcgc | 660 |
| gcggtgacga acctcttcca ctcggaggag gactcgaacc tcggcctcta tggcgccttc | 720 |
| ggctacgacc tcgccttcca gttcgatgcg atcgaactga agctttcgcg tccggacgac | 780 |
| cagcgcgaca tggttctctt tctgccggac gagatccttg tggtcgatca ctatgcggcc | 840 |
| aaggcctgga tcgaccgcta cgatttcgcc agggagaacc tttcgaccga gggcaaggca | 900 |
| gcggacattg ctcccgagcc gttccgcagc gtcgacagca tcccgccgca cggggatcac | 960 |
| cgcccgggcg aatatgccga gctcgtcgtc aaggcgaagg aaagcttccg tcgcggcgat | 1020 |
| cttttcgaag tggtgccggg gcagaaattc tacgagcgct cgaaagccg cccgtccgag | 1080 |
| atttccaacc ggctgaaggc gatcaatccg tcgccctatt ccttcttcat caatctcggc | 1140 |
| aaccaggaat atctcgtcgg tgcttcgccg gagatgttcg tgcgcgtttc cggccggcgc | 1200 |
| atcgagacct gcccgatctc cggtacgatc aagcgcggcg acgatccgat cgccgacagc | 1260 |
| gagcagatcc tgaagctctt gaactcgaag aaggacgagt ccgagctcac catgtgctcg | 1320 |
| gacgtcgacc gcaacgacaa gagccgggtc tgcgtgccgg gctcggtcaa ggtgatcggc | 1380 |
| cggcgtcaga tcgagatgta ttcgcggctg atccacacgg tcgatcacat cgaggggcgc | 1440 |
| ctgcgcgacg atatgacgc cttcgacggg ttcctcagcc acgcctgggc ggtgaccgtt | 1500 |
| accggcgcgc caaagctctg gccatgcgc ttcatcgaga gccacgagaa gagcccgcgt | 1560 |
| gcctggtatg gcggcgcgat cggcatggtc ggcttcaacg gcgacatgaa taccgggctg | 1620 |
| accttgcgta ccatccgcat caaggacggg atcgccgagg tgagggcggg tgcgacgctc | 1680 |
| ctctatgatt ccaatccgga agaagaagaa gccgaaaccg aactgaaggc ctctgccatg | 1740 |
| attgcagcca tccgcgacgc gaaatccgca aacagcgcca aatccgcgcg cgatgtcgcc | 1800 |
| gccgtcggcg ccggagtcag catcctgctc gtcgatcacg aggacagctt cgtccatacc | 1860 |
| ctcgcgaact acttccgcca gaccggcgcg tccgtcacca ccgtgcgcac gccggtggcc | 1920 |

| | |
|---|---|
| gaggaaatct tcgaccgggt caagccggac ctcgtcgtgc tttcgcccgg tcccggcacc | 1980 |
| ccgaaggact tcgactgcaa ggcgacgatc aagaaggcgc gggcgcggga cctgccgatc | 2040 |
| ttcggcgtct gcctggggct gcaggcgctc gcggaggcct atggcggcga ccttcgtcaa | 2100 |
| ctggcgatcc cgatgcatgg gaagccctcg cgcatccgcg tgctcgaacc cggcatcgtc | 2160 |
| ttctccggcc tcggcaagga ggtgacggtc gggcgctatc attcgatttt cgccgatccg | 2220 |
| tccaacctgc cgcgcgaatt cgtgatcacg gccgaaagcg aagatggtac gatcatgggc | 2280 |
| atcgaacaca gcaaggagcc ggtggcggcc gtgcagttcc atccggaatc gatcatgacg | 2340 |
| ctgggcggcg acgccggcat gcggatgatc gagaacgtgg ttgcccatct cgccaagcgg | 2400 |
| gcgaagacca aggcagcctg | 2420 |

<210> SEQ ID NO 46
<211> LENGTH: 2447
<212> TYPE: DNA
<213> ORGANISM: Arabidopsis thaliana

<400> SEQUENCE: 46

| | |
|---|---|
| atggcgcaag ttagcagaat ctgcaatggt gtgcagaacc catctcttat ctccaatctc | 60 |
| tcgaaatcca gtcaacgcaa atctccctta tcggtttctc tgaagacgca gcagcatcca | 120 |
| cgagcttatc cgatttcgtc gtcgtgggga ttgaagaaga gtgggatgac gttaattggc | 180 |
| tctgagcttc gtcctcttaa ggtcatgtct tctgttttcca cggcggagaa agcgtcggag | 240 |
| attgtacttc aacccattat ggcagcggta attctagaag acggcgcgga gagttatacc | 300 |
| acgaagggtg gcatcgtcgt cacccgcagg cggcgtgagg catcctacag cgacgcgatc | 360 |
| gccggttatg tcgaccggct ggacgaacgc gcggcgcgg tcttttcctc gaactacgaa | 420 |
| tatcccggcc gctataccccg ctgggacact gcggtggtcg acccgccgct tgccatctcc | 480 |
| tccttcggtc gctcgctctg gatcgaagcc tataacgaac gcggcgaagt gctgctggcg | 540 |
| ctgatcgccg aggatctgaa gtccgttgcc gacatcacgc tcggctcact tgccgcccgc | 600 |
| cgcctcgacc tcaccatcaa cgagcccgat cgtgtcttca ccgaggaaga gcggtcgaag | 660 |
| atgccgacgg tctttacggt tcttcgcgcg gtgacgaacc tcttccactc ggaggaggac | 720 |
| tcgaaccctcg gcctctatgg cgccttcggc tacgacctcg ccttccagtt cgatgcgatc | 780 |
| gaactgaagc tttcgcgtcc ggacgaccag cgcgacatgg ttctcttctt gccggacgag | 840 |
| atccttgtgg tcgatcacta tgcggccaag gcctggatcg accgctacga tttcgccagg | 900 |
| gagaaccttt cgaccgaggg caaggcagcg gacattgctc ccgagccgtt ccgcagcgtc | 960 |
| gacagcatcc cgccgcacgg ggatcaccgc ccgggcgaat atgccgagct cgtcgtcaag | 1020 |
| gcgaaggaaa gcttccgtcg cggcgatctt ttcgaagtgg tgccggggca gaaattctac | 1080 |
| gagcgctgcg aaagccgccc gtccgagatt tccaaccggc tgaaggcgat caatccgtcg | 1140 |
| ccctattcct tcttcatcaa tctcggcaac caggaatatc tcgtcggtgc ttcgccggag | 1200 |
| atgttcgtgc gcgtttccgg ccggcgcatc gagacctgcc cgatctccgg tacgatcaag | 1260 |
| cgcggcgacg atccgatcgc cgacagcgag cagatcctga gctcttgaa ctcgaagaag | 1320 |
| gacgagtccg agctcaccat gtgctcggac gtcgaccgca cgacaagag ccgggtctgc | 1380 |
| gtgccggggct cggtcaaggt gatcggccgg cgtcagatcg agatgtattc gcggctgatc | 1440 |
| cacacggtcg atcacatcga ggggcgcctg cgcgacgata tggacgcctt cgacgggttc | 1500 |
| ctcagccacg cctgggcggt gaccgttacc ggcgcgccaa agctctgggc catgcgcttc | 1560 |
| atcgagagcc acgagaagag cccgcgtgcc tggtatggcg gcgcgatcgg catggtcggc | 1620 |

```
ttcaacggcg acatgaatac cgggctgacc ttgcgtacca tccgcatcaa ggacgggatc      1680
gccgaggtga gggcgggtgc gacgctcctc tatgattcca atccggaaga agaagaagcc      1740
gaaaccgaac tgaaggcctc tgccatgatt gcagccatcc gcgacgcgaa atccgcaaac      1800
agcgccaaat ccgcgcgcga tgtcgccgcc gtcggcgccg gagtcagcat cctgctcgtc      1860
gatcacgagg acagcttcgt ccatacccct gcgaactact tccgccagac cggcgcgtcc      1920
gtcaccaccg tgcgcacgcc ggtggccgag gaaatcttcg accgggtcaa gccggacctc      1980
gtcgtgcttt cgcccggtcc cggcaccccg aaggacttcg actgcaaggc gacgatcaag      2040
aaggcgcggg cgcgggacct gccgatcttc ggcgtctgcc tggggctgca ggcgctcgcg      2100
gaggcctatg gcggcgacct tcgtcaactg gcgatcccga tgcatgggaa gccctcgcgc      2160
atccgcgtgc tcgaacccgg catcgtcttc tccggcctcg gcaaggaggt gacggtcggg      2220
cgctatcatt cgattttcgc cgatccgtcc aacctgccgc gcgaattcgt gatcacggcc      2280
gaaagcgaag atggtacgat catgggcatc gaacacagca aggagccggt ggcggccgtg      2340
cagttccatc cggaatcgat catgacgctg ggcggcgacg ccggcatgcg gatgatcgag      2400
aacgtggttg cccatctcgc caagcgggcg aagaccaagg cagcctg                   2447

<210> SEQ ID NO 47
<211> LENGTH: 2330
<212> TYPE: DNA
<213> ORGANISM: Zea mays

<400> SEQUENCE: 47
atggaatccc tagccgccac ctccgtgttc gcgccctccc gcgtcgccgt cccggcggcg        60
cgggccctgg ttagggcggg gacggtggta ccaaccaggc ggacgagcag ccggagcgga       120
accagcgggg tgaaatgctc tatggcagcg gtaattctag aagacggcgc ggagagttat       180
accacgaagg gtggcatcgt cgtcacccgc aggcggcgtg aggcatccta cagcgacgcg       240
atcgccggtt atgtcgaccg gctggacgaa cgccgcggcg cggtcttttc ctcgaactac       300
gaatatcccg ccgctatac ccgctgggac actgcgtgg tcgacccgcc gcttgccatc       360
tcctccttcg gtcgctcgct ctggatcgaa gcctataacg aacgcggcga agtgctgctg       420
gcgctgatcg ccgaggatct gaagtccgtt gccgacatca cgctcggctc acttgccgcc       480
cgccgcctcg acctcaccat caacgagccc gatcgtgtct tcaccgagga agagcggtcg       540
aagatgccga cggtctttac ggttcttcgc gcggtgacga acctcttcca ctcggaggag       600
gactcgaacc tcggcctcta tggcgccttc ggctacgacc tcgccttcca gttcgatgcg       660
atcgaactga agcttcgcg tccggacgac cagcgcgaca tggttctctt tctgccggac       720
gagatccttg tggtcgatca ctatgcggcc aaggcctgga tcgaccgcta cgatttcgcc       780
agggagaacc tttcgaccga gggcaaggca gcggacattg ctcccgagcc gttccgcagc       840
gtcgacagca tcccgccgca cggggatcac cgcccgggcg aatatgccga gctcgtcgtc       900
aaggcgaagg aaagcttccg tcgcggcgat ctttttcgaag tggtgccggg gcagaaattc       960
tacgagcgct gcgaaagccg cccgtccgag atttccaacc ggctgaaggc gatcaatccg      1020
tcgccctatt ccttcttcat caatctcggc aaccaggaat atctcgtcgg tgcttcgccg      1080
gagatgttcg tgcgcgtttc cggccggcgc atcgagacct gccgatctc cggtacgatc      1140 aagcgcggcg acgatccgat cgccgacagc gagcagatcc tgaagctctt gaactcgaag      1200
aaggacgagt ccgagctcac catgtgctcg gactcgacc gcaacgacaa gagccgggtc      1260
tgcgtgccgg gctcggtcaa ggtgatcggc cggcgtcaga tcgagatgta ttcgcggctg      1320
```

```
atccacacgg tcgatcacat cgagggggcgc ctgcgcgacg atatggacgc cttcgacggg   1380
ttcctcagcc acgcctgggc ggtgaccgtt accggcgcgc caaagctctg ggccatgcgc   1440
ttcatcgaga gccacgagaa gagcccgcgt gcctggtatg cggcgcgat cggcatggtc    1500 ggcttcaacg gcgacatgaa taccgggctg accttgcgta ccatccgcat caaggacggg   1560
atcgccgagg tgagggcggg tgcgacgctc ctctatgatt ccaatccgga agaagaagaa   1620
gccgaaaccg aactgaaggc ctctgccatg attgcagcca tccgcgacgc gaaatccgca   1680
aacagcgcca atccgcgcg cgatgtcgcc gccgtcggcg ccggagtcag catcctgctc    1740
gtcgatcacg aggacagctt cgtccatacc ctcgcgaact acttccgcca gaccggcgcg   1800
tccgtcacca ccgtgcgcac gccggtggcc gaggaaatct tcgaccgggt caagccggac   1860
ctcgtcgtgc tttcgcccgg tcccggcacc ccgaaggact tcgactgcaa ggcgacgatc   1920
aagaaggcgc gggcgcggga cctgccgatc ttcggcgtct gcctggggct gcaggcgctc   1980
gcggaggcct atggcggcga ccttcgtcaa ctggcgatcc cgatgcatgg gaagccctcg   2040
cgcatccgcg tgctcgaacc cggcatcgtc ttctccggcc tcggcaagga ggtgacggtc   2100
gggcgctatc attcgatttt cgccgatccg tccaacctgc cgcgcgaatt cgtgatcacg   2160
gccgaaagcg aagatggtac gatcatgggc atcgaacaca gcaaggagcc ggtggcggcc   2220
gtgcagttcc atccggaatc gatcatgacg ctgggcggcg acgccggcat gcggatgatc   2280
gagaacgtgg ttgcccatct cgccaagcgg gcgaagacca aggcagcctg             2330

<210> SEQ ID NO 48
<211> LENGTH: 2384
<212> TYPE: DNA
<213> ORGANISM: Zea mays

<400> SEQUENCE: 48
atggaatccc tagccgccac ctccgtgttc gcgccctccc gcgtcgccgt cccggcggcg     60
cgggccctgg ttagggcggg gacggtggta ccaaccaggc ggacgagcag ccggagcgga    120
accagcgggg tgaaatgctc tgctgccgtg acgccgcagg cgagcccagt gattagcagg    180
agcgctgcgg cggcgatggc agcggtaatt ctagaagacg gcgcggagag ttataccacg    240
aagggtggca tcgtcgtcac ccgcaggcgg cgtgaggcat cctacagcga gcgatcgcc    300 ggttatgtcg accggctgga cgaacgccgc ggcgcggtct tttcctcgaa ctacgaatat    360
cccggccgct ataccgcgctg ggacactgcg gtggtcgacc cgccgcttgc catctcctcc    420
ttcggtcgct cgctctggat cgaagcctat aacgaacgcg gcgaagtgct gctggcgctg    480
atcgccgagg atctgaagtc cgttgccgac atcacgctcg gctcacttgc cgcccgccgc    540
ctcgacctca ccatcaacga gcccgatcgt gtcttcaccg aggaagagcg gtcgaagatg    600
ccgacggtct ttacggttct tcgcgcggtg acgaacctct tccactcgga ggaggactcg    660
aacctcggcc tctatggcgc cttcggctac gacctcgcct tccagttcga tgcgatcgaa    720
ctgaagcttt cgcgtccgga cgaccagcgc gacatggttc tctttctgcc ggacgagatc    780
cttgtggtcg atcactatgc ggccaaggcc tggatcgacc gctacgattt cgccaggag    840 aaccttttcga ccgagggcaa ggcagcggac attgctcccg agccgttccg cagcgtcgac    900
agcatcccgc cgcacgggga tcaccgcccg ggcgaatatg ccgagctcgt cgtcaaggcg    960
aaggaaagct tccgtcgcgg cgatctttc gaagtggtgc cggggcagaa attctacgag   1020
cgctgcgaaa gccgccgtc cgagatttcc aaccggctga aggcgatcaa tccgtcgccc   1080
tattccttct tcatcaatct cggcaaccag gaatatctcg tcggtgcttc gccggagatg   1140
```

| | |
|---|---:|
| ttcgtgcgcg tttccggccg gcgcatcgag acctgcccga tctccggtac gatcaagcgc | 1200 |
| ggcgacgatc cgatcgccga cagcgagcag atcctgaagc tcttgaactc gaagaaggac | 1260 |
| gagtccgagc tcaccatgtg ctcggacgtc gaccgcaacg acaagagccg gtctgcgtg | 1320 |
| ccgggctcgg tcaaggtgat cggccggcgt cagatcgaga tgtattcgcg gctgatccac | 1380 |
| acggtcgatc acatcgaggg cgcctgcgc gacgatatgg acgccttcga cgggttcctc | 1440 |
| agccacgcct gggcggtgac cgttaccggc gcgccaaagc tctgggccat gcgcttcatc | 1500 |
| gagagccacg agaagagccc gcgtgcctgg tatggcggcg cgatcggcat ggtcggcttc | 1560 |
| aacgcgaca tgaataccgg gctgaccttg cgtaccatcc gcatcaagga cgggatcgcc | 1620 |
| gaggtgaggg cgggtgcgac gctcctctat gattccaatc cggaagaaga agaagccgaa | 1680 |
| accgaactga aggcctctgc catgattgca gccatccgcg acgcgaaatc cgcaaacagc | 1740 |
| gccaaatccg cgcgcgatgt cgccgccgtc ggcgccggag tcagcatcct gctcgtcgat | 1800 |
| cacgaggaca gcttcgtcca taccctcgcg aactacttcc gccagaccgg cgcgtccgtc | 1860 |
| accaccgtgc gcacgccggt ggccgaggaa atcttcgacc gggtcaagcc ggacctcgtc | 1920 |
| gtgctttcgc ccgtgcccgg caccccgaag gacttcgact gcaaggcgac gatcaagaag | 1980 |
| gcgcgggcgc gggacctgcc gatcttcggc gtctgcctgg ggctgcaggc gctcgcggag | 2040 |
| gcctatggcg gcgaccttcg tcaactggcg atcccgatgc atgggaagcc ctcgcgcatc | 2100 |
| cgcgtgctcg aacccggcat cgtcttctcc ggcctcggca aggaggtgac ggtcgggcgc | 2160 |
| tatcattcga ttttcgccga tccgtccaac ctgccgcgcg aattcgtgat cacggccgaa | 2220 |
| agcgaagatg gtacgatcat gggcatcgaa cacagcaagg agccggtggc ggccgtgcag | 2280 |
| ttccatccgg aatcgatcat gacgctgggc ggcgacgccg gcatgcggat gatcgagaac | 2340 |
| gtggttgccc atctcgccaa gcgggcgaag accaaggcag cctg | 2384 |

<210> SEQ ID NO 49
<211> LENGTH: 2379
<212> TYPE: DNA
<213> ORGANISM: Zea mays

<400> SEQUENCE: 49

| | |
|---|---:|
| atggaatccc tagccgccac ctccgtgttc gcgccctccc gcgtcgccgt cccggcggcg | 60 |
| cgggccctgg ttagggcggg gacggtggta ccaaccaggc ggacgagcag ccggagcgga | 120 |
| accagcgggg tgaaatgctc tgctgccgtg acgccgcagg cgagcccagt gattagcagg | 180 |
| agcgctgcgg cggccgtaac gatcattcag gatgacggag cggagaccta cgagacgaaa | 240 |
| ggcggcatcc aggtcagccg aaagcgccgg cccaccgatt atgccaacgc catcgataat | 300 |
| tacatcgaaa agcttgattc ccatcgcggc gcggtttttt cgtccaacta tgaatatccg | 360 |
| ggccgttaca cccgctggga tacggccatc gtcgatccgc cgctcggcat ttcctgtttt | 420 |
| ggccgcaaga tgtggatcga agcctataat ggccgcggcg aagtgctgct cgatttcatt | 480 |
| acggaaaagc tgaaggcgac acccgatctc accctcggcg cttcctcgac ccgccggctc | 540 |
| gatcttaccg tcaacgaacc ggaccgtgtc ttcaccgaag aagaacgctc gaaaatcccg | 600 |
| acggtcttca ccgctctcag agccatcgtc gacctcttct attcgagcgc ggattcggcc | 660 |
| atcggcctgt tcggtgcctt cggttacgat ctcgccttcc agttcgacgc gatcaagctt | 720 |
| tcgctggcgc gtccggaaga ccagcgtgac atggtgctgt ttctgcccga tgaaatcctc | 780 |
| gtcgttgatc actattccgc caaggcctgg atcgaccgtt acgatttcga gaaggacggc | 840 |
| atgacgacgg acggcaaatc ctccgacatt accccgatc ccttcaagac caccgatacc | 900 |

```
atcccgccca agggcgatca ccgtcccggc gaatattccg agcttgtggt gaaggccaag    960
gaaagcttcc gccgcggcga cctgttcgag gtcgttcccg ccagaaatt catggagcgt   1020
tgcgaaagca atccgtcggc gatttcccgc cgcctgaagg cgatcaaccc gtcgccctat   1080
tccttcttca tcaatctcgg cgatcaggaa tatctggtcg gcgcctcgcc ggaaatgttc   1140
gtgcgcgtct ccggccgtcg catcgagacc tgcccgatat caggcaccat caagcgcggc   1200
gacgatccga ttgccgacag cgagcagatt ttgaaactgc tcaactcgaa aaaggacgaa   1260
tccgaactga ccatgtgctc ggacgtggac cgcaacgaca agagccgcgt ctgcgagccg   1320
ggttcggtga aggtcattgg ccgccgccag atcgagatgt attcacgcct catccacacc   1380
gtcgatcaca tcgaaggccg cctgcgcgac gatatgacg cctttgacgg tttcctcagc   1440
cacgcctggg ccgtcaccgt caccggtgca ccaaagctgt gggccatgcg cttcatcgaa   1500
ggtcatgaaa agagcccgcg cgcctggtat ggcggtgcga tcggcatggt cggcttcaac   1560
ggcgacatga ataccggcct gacgctgcgc accatccgga tcaaggacgg tattgccgaa   1620
gtgcgcgccg gcgcgaccct gctcaatgat ccaacccgc aggaagaaga agccgaaacc   1680
gaactgaagg cctccgccat gatatcagcc attcgtgacg caaaaggcac caactctgcc   1740
gccaccaagc gtgatgccgc caaagtcggc accggcgtca agatcctgct cgtcgaccac   1800
gaagacagct tcgtgcacac gctggcgaat tatttccgcc agacgggcgc gacggtctcg   1860
accgtcagat caccggtcgc agccgacgtg ttcgatcgct ccagccgga cctcgttgtc   1920
ctgtcgcccg gacccggcag cccgacggat ttcgactgca aggcaacgat caaggccgcc   1980
cgcgcccgcg atctgccgat cttcggcgtt tgcctcggtc tgcaggcatt ggcagaagcc   2040
tatggcggcg agctgcgcca gcttgctgtg cccatgcacg gcaagccttc gcgcatccgc   2100
gtgctggaac ccggcctcgt cttctccggt ctcggcaagg aagtcacggt cggtcgttac   2160
cattcgatct tcgccgatcc cgccaccctg ccgcgtgatt tcatcatcac cgcagaaagc   2220
gaggacggca cgatcatggg catcgaacac gccaaggaac cggtggccgc cgttcagttc   2280
cacccggaat cgatcatgac gctcggacag gacgcgggca tgcggatgat cgagaatgtc   2340
gtggtgcatc tgacccgcaa ggcgaagacc aaggccgcg                         2379
```

<210> SEQ ID NO 50  
<211> LENGTH: 314  
<212> TYPE: PRT  
<213> ORGANISM: Arabidopsis thaliana

<400> SEQUENCE: 50

```
Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys Met Gly Lys Gly
65                  70                  75                  80

Glu Glu Leu Phe Thr Gly Val Val Pro Ile Leu Val Glu Leu Asp Gly
                85                  90                  95

Asp Val Asn Gly His Lys Phe Ser Val Ser Gly Glu Gly Glu Gly Asp
            100                 105                 110
```

```
Ala Thr Tyr Gly Lys Leu Thr Leu Lys Phe Ile Cys Thr Gly Lys
            115                 120                 125

Leu Pro Val Pro Trp Pro Thr Leu Val Thr Thr Phe Thr Tyr Gly Val
130                 135                 140

Gln Cys Phe Ser Arg Tyr Pro Asp His Met Lys Gln His Asp Phe Phe
145                 150                 155                 160

Lys Ser Ala Met Pro Glu Gly Tyr Val Gln Glu Arg Thr Ile Ser Phe
                165                 170                 175

Lys Asp Asp Gly Asn Tyr Lys Thr Arg Ala Glu Val Lys Phe Glu Gly
                180                 185                 190

Asp Thr Leu Val Asn Arg Ile Glu Leu Lys Gly Ile Asp Phe Lys Glu
                195                 200                 205

Asp Gly Asn Ile Leu Gly His Lys Leu Glu Tyr Asn Tyr Asn Ser His
            210                 215                 220

Asn Val Tyr Ile Thr Ala Asp Lys Gln Lys Asn Gly Ile Lys Ala Asn
225                 230                 235                 240

Phe Lys Ile Arg His Asn Ile Glu Asp Gly Ser Val Gln Leu Ala Asp
                245                 250                 255

His Tyr Gln Gln Asn Thr Pro Ile Gly Asp Gly Pro Val Leu Leu Pro
                260                 265                 270

Asp Asn His Tyr Leu Ser Thr Gln Ser Ala Leu Ser Lys Asp Pro Asn
            275                 280                 285

Glu Lys Arg Asp His Met Val Leu Leu Glu Phe Val Thr Ala Ala Gly
            290                 295                 300

Ile Thr His Gly Met Asp Glu Leu Tyr Lys
305                 310

<210> SEQ ID NO 51
<211> LENGTH: 290
<212> TYPE: PRT
<213> ORGANISM: Zea mays

<400> SEQUENCE: 51

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
                20                  25                  30

Arg Arg Thr Ser Ser Arg Ser Gly Thr Ser Gly Val Lys Cys Ser Asp
                35                  40                  45

Pro Gly Ala Thr Met Gly Lys Gly Glu Glu Leu Phe Thr Gly Val Val
            50                  55                  60

Pro Ile Leu Val Glu Leu Asp Gly Asp Val Asn Gly His Lys Phe Ser
65                  70                  75                  80

Val Ser Gly Glu Gly Glu Gly Asp Ala Thr Tyr Gly Lys Leu Thr Leu
                85                  90                  95

Lys Phe Ile Cys Thr Thr Gly Lys Leu Pro Val Pro Trp Pro Thr Leu
                100                 105                 110

Val Thr Thr Phe Thr Tyr Gly Val Gln Cys Phe Ser Arg Tyr Pro Asp
            115                 120                 125

His Met Lys Gln His Asp Phe Phe Lys Ser Ala Met Pro Glu Gly Tyr
        130                 135                 140

Val Gln Glu Arg Thr Ile Ser Phe Lys Asp Asp Gly Asn Tyr Lys Thr
145                 150                 155                 160

Arg Ala Glu Val Lys Phe Glu Gly Asp Thr Leu Val Asn Arg Ile Glu
                165                 170                 175
```

```
Leu Lys Gly Ile Asp Phe Lys Glu Asp Gly Asn Ile Leu Gly His Lys
            180                 185                 190

Leu Glu Tyr Asn Tyr Asn Ser His Asn Val Tyr Ile Thr Ala Asp Lys
        195                 200                 205

Gln Lys Asn Gly Ile Lys Ala Asn Phe Lys Ile Arg His Asn Ile Glu
210                 215                 220

Asp Gly Ser Val Gln Leu Ala Asp His Tyr Gln Gln Asn Thr Pro Ile
225                 230                 235                 240

Gly Asp Gly Pro Val Leu Leu Pro Asp Asn His Tyr Leu Ser Thr Gln
                245                 250                 255

Ser Ala Leu Ser Lys Asp Pro Asn Glu Lys Arg Asp His Met Val Leu
            260                 265                 270

Leu Glu Phe Val Thr Ala Ala Gly Ile Thr His Gly Met Asp Glu Leu
        275                 280                 285

Tyr Lys
    290

<210> SEQ ID NO 52
<211> LENGTH: 201
<212> TYPE: PRT
<213> ORGANISM: Oryza sativa

<400> SEQUENCE: 52

Ala Ala Leu Thr Thr Ser Gln Leu Ala Thr Ser Ala Thr Gly Phe Gly
1               5                   10                  15

Ile Ala Asp Arg Ser Ala Pro Ser Ser Leu Leu Arg His Gly Phe Gln
            20                  25                  30

Gly Leu Lys Pro Arg Ser Pro Ala Gly Gly Asp Ala Thr Ser Leu Ser
        35                  40                  45

Val Thr Thr Ser Ala Arg Ala Thr Pro Lys Gln Gln Arg Ser Val Gln
    50                  55                  60

Arg Gly Ser Arg Arg Phe Pro Ser Val Val Met Gly Lys Gly Glu
65                  70                  75                  80

Glu Leu Phe Thr Gly Val Val Pro Ile Leu Val Glu Leu Asp Gly Asp
                85                  90                  95

Val Asn Gly His Lys Phe Ser Val Ser Gly Glu Gly Glu Gly Asp Ala
            100                 105                 110

Thr Tyr Gly Lys Leu Thr Leu Lys Phe Ile Cys Thr Thr Gly Lys Leu
        115                 120                 125

Pro Val Pro Trp Pro Thr Leu Val Thr Thr Phe Thr Tyr Gly Val Gln
    130                 135                 140

Cys Phe Ser Arg Tyr Pro Asp His Met Lys Gln His Asp Phe Phe Lys
145                 150                 155                 160

Ser Ala Met Pro Glu Gly Tyr Val Gln Glu Arg Thr Ile Ser Phe Lys
                165                 170                 175

Asp Asp Gly Asn Tyr Lys Thr Arg Ala Glu Val Lys Phe Glu Gly Asp
            180                 185                 190

Thr Leu Val Asn Arg Ile Glu Leu Lys
        195                 200

<210> SEQ ID NO 53
<211> LENGTH: 316
<212> TYPE: PRT
<213> ORGANISM: Ruta graveolens

<400> SEQUENCE: 53

Met Ser Ala Ala Ala Thr Ser Met Gln Ser Leu Lys Phe Ser Asn Arg
```

```
              1               5                  10                 15
Leu Val Pro Pro Ser Arg Arg Leu Ser Pro Val Pro Asn Asn Val Thr
                        20                  25                 30

Cys Asn Asn Leu Pro Lys Ser Ala Ala Pro Val Arg Thr Val Lys Cys
                35                  40                  45

Cys Ala Ser Ser Trp Asn Ser Thr Ile Asn Gly Ala Ala Thr Thr
 50                      55                  60

Asn Gly Ala Ser Ala Ala Ser Ser Ala Asp Pro Gly Ala Thr Met Gly
 65                  70                  75                  80

Lys Gly Glu Glu Leu Phe Thr Gly Val Val Pro Ile Leu Val Glu Leu
                        85                  90                  95

Asp Gly Asp Val Asn Gly His Lys Phe Ser Val Ser Gly Glu Gly Glu
                100                 105                 110

Gly Asp Ala Thr Tyr Gly Lys Leu Thr Leu Lys Phe Ile Cys Thr Thr
                115                 120                 125

Gly Lys Leu Pro Val Pro Trp Pro Thr Leu Val Thr Thr Phe Thr Tyr
                130                 135                 140

Gly Val Gln Cys Phe Ser Arg Tyr Pro Asp His Met Lys Gln His Asp
145                 150                 155                 160

Phe Phe Lys Ser Ala Met Pro Glu Gly Tyr Val Gln Glu Arg Thr Ile
                165                 170                 175

Ser Phe Lys Asp Asp Gly Asn Tyr Lys Thr Arg Ala Glu Val Lys Phe
                180                 185                 190

Glu Gly Asp Thr Leu Val Asn Arg Ile Glu Leu Lys Gly Ile Asp Phe
                195                 200                 205

Lys Glu Asp Gly Asn Ile Leu Gly His Lys Leu Glu Tyr Asn Tyr Asn
210                 215                 220

Ser His Asn Val Tyr Ile Thr Ala Asp Lys Gln Lys Asn Gly Ile Lys
225                 230                 235                 240

Ala Asn Phe Lys Ile Arg His Asn Ile Glu Asp Gly Ser Val Gln Leu
                245                 250                 255

Ala Asp His Tyr Gln Gln Asn Thr Pro Ile Gly Asp Gly Pro Val Leu
                260                 265                 270

Leu Pro Asp Asn His Tyr Leu Ser Thr Gln Ser Ala Leu Ser Lys Asp
                275                 280                 285

Pro Asn Glu Lys Arg Asp His Met Val Leu Leu Glu Phe Val Thr Ala
                290                 295                 300

Ala Gly Ile Thr His Gly Met Asp Glu Leu Tyr Lys
305                 310                 315

<210> SEQ ID NO 54
<211> LENGTH: 297
<212> TYPE: PRT
<213> ORGANISM: Zea mays

<400> SEQUENCE: 54

Met Ile Ser Pro Thr Asn Leu Leu Pro Ala Arg Lys Ile Thr Pro Val
1               5                   10                  15

Ser Asn Gly Gly Ala Ala Thr Ala Ser Pro Ser Ser Pro Ser Val Ala
                20                  25                  30

Ala Arg Pro Arg Arg Leu Pro Ser Gly Leu Gln Ser Val Thr Gly Arg
                35                  40                  45

Gly Lys Val Ser Leu Ala Asp Pro Gly Ala Thr Met Gly Lys Gly Glu
                50                  55                  60

Glu Leu Phe Thr Gly Val Val Pro Ile Leu Val Glu Leu Asp Gly Asp
```

```
            65                  70                  75                  80
Val Asn Gly His Lys Phe Ser Val Ser Gly Glu Gly Glu Gly Asp Ala
                    85                  90                  95

Thr Tyr Gly Lys Leu Thr Leu Lys Phe Ile Cys Thr Thr Gly Lys Leu
                100                 105                 110

Pro Val Pro Trp Pro Thr Leu Val Thr Thr Phe Thr Tyr Gly Val Gln
                115                 120                 125

Cys Phe Ser Arg Tyr Pro Asp His Met Lys Gln His Asp Phe Phe Lys
            130                 135                 140

Ser Ala Met Pro Glu Gly Tyr Val Gln Glu Arg Thr Ile Ser Phe Lys
145                 150                 155                 160

Asp Asp Gly Asn Tyr Lys Thr Arg Ala Glu Val Lys Phe Glu Gly Asp
                165                 170                 175

Thr Leu Val Asn Arg Ile Glu Leu Lys Gly Ile Asp Phe Lys Glu Asp
                180                 185                 190

Gly Asn Ile Leu Gly His Lys Leu Glu Tyr Asn Tyr Asn Ser His Asn
                195                 200                 205

Val Tyr Ile Thr Ala Asp Lys Gln Lys Asn Gly Ile Lys Ala Asn Phe
210                 215                 220

Lys Ile Arg His Asn Ile Glu Asp Gly Ser Val Gln Leu Ala Asp His
225                 230                 235                 240

Tyr Gln Gln Asn Thr Pro Ile Gly Asp Gly Pro Val Leu Leu Pro Asp
                245                 250                 255

Asn His Tyr Leu Ser Thr Gln Ser Ala Leu Ser Lys Asp Pro Asn Glu
                260                 265                 270

Lys Arg Asp His Met Val Leu Leu Glu Phe Val Thr Ala Ala Gly Ile
                275                 280                 285

Thr His Gly Met Asp Glu Leu Tyr Lys
                290                 295

<210> SEQ ID NO 55
<211> LENGTH: 302
<212> TYPE: PRT
<213> ORGANISM: Zea mays

<400> SEQUENCE: 55

Met Ile Ser Pro Thr Asn Leu Leu Pro Ala Arg Lys Ile Thr Pro Val
1               5                   10                  15

Ser Asn Gly Gly Ala Ala Thr Ala Ser Pro Ser Ser Pro Ser Val Ala
                20                  25                  30

Ala Arg Pro Arg Arg Leu Pro Ser Gly Leu Gln Ser Val Thr Gly Arg
            35                  40                  45

Gly Lys Val Ser Leu Ala Ala Ile Thr Leu Glu Asp Pro Gly Ala Thr
    50                  55                  60

Met Gly Lys Gly Glu Glu Leu Phe Thr Gly Val Val Pro Ile Leu Val
65                  70                  75                  80

Glu Leu Asp Gly Asp Val Asn Gly His Lys Phe Ser Val Ser Gly Glu
                85                  90                  95

Gly Glu Gly Asp Ala Thr Tyr Gly Lys Leu Thr Leu Lys Phe Ile Cys
                100                 105                 110

Thr Thr Gly Lys Leu Pro Val Pro Trp Pro Thr Leu Val Thr Thr Phe
            115                 120                 125

Thr Tyr Gly Val Gln Cys Phe Ser Arg Tyr Pro Asp His Met Lys Gln
        130                 135                 140

His Asp Phe Phe Lys Ser Ala Met Pro Glu Gly Tyr Val Gln Glu Arg
```

```
                145                 150                 155                 160
Thr Ile Ser Phe Lys Asp Asp Gly Asn Tyr Lys Thr Arg Ala Glu Val
                165                 170                 175

Lys Phe Glu Gly Asp Thr Leu Val Asn Arg Ile Glu Leu Lys Gly Ile
            180                 185                 190

Asp Phe Lys Glu Asp Gly Asn Ile Leu Gly His Lys Leu Glu Tyr Asn
            195                 200                 205

Tyr Asn Ser His Asn Val Tyr Ile Thr Ala Asp Lys Gln Lys Asn Gly
            210                 215                 220

Ile Lys Ala Asn Phe Lys Ile Arg His Asn Ile Glu Asp Gly Ser Val
225                 230                 235                 240

Gln Leu Ala Asp His Tyr Gln Gln Asn Thr Pro Ile Gly Asp Gly Pro
                245                 250                 255

Val Leu Leu Pro Asp Asn His Tyr Leu Ser Thr Gln Ser Ala Leu Ser
                260                 265                 270

Lys Asp Pro Asn Glu Lys Arg Asp His Met Val Leu Leu Glu Phe Val
                275                 280                 285

Thr Ala Ala Gly Ile Thr His Gly Met Asp Glu Leu Tyr Lys
                290                 295                 300

<210> SEQ ID NO 56
<211> LENGTH: 806
<212> TYPE: PRT
<213> ORGANISM: Arabidopsis thaliana

<400> SEQUENCE: 56

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
        50                  55                  60

Pro Leu Lys Val Met Ser Ser Val Ser Thr Ala Glu Lys Met Ala Ala
65                  70                  75                  80

Val Ile Leu Glu Asp Gly Ala Glu Ser Tyr Thr Thr Lys Gly Gly Ile
                85                  90                  95

Val Val Thr Arg Arg Arg Arg Glu Ala Ser Tyr Ser Asp Ala Ile Ala
                100                 105                 110

Gly Tyr Val Asp Arg Leu Asp Glu Arg Arg Gly Ala Val Phe Ser Ser
            115                 120                 125

Asn Tyr Glu Tyr Pro Gly Arg Tyr Thr Arg Trp Asp Thr Ala Val Val
        130                 135                 140

Asp Pro Pro Leu Ala Ile Ser Ser Phe Gly Arg Ser Leu Trp Ile Glu
145                 150                 155                 160

Ala Tyr Asn Glu Arg Gly Glu Val Leu Leu Ala Leu Ile Ala Glu Asp
                165                 170                 175

Leu Lys Ser Val Ala Asp Ile Thr Leu Gly Ser Leu Ala Ala Arg Arg
            180                 185                 190

Leu Asp Leu Thr Ile Asn Glu Pro Asp Arg Val Phe Thr Glu Glu
            195                 200                 205

Arg Ser Lys Met Pro Thr Val Phe Thr Val Leu Arg Ala Val Thr Asn
        210                 215                 220

Leu Phe His Ser Glu Glu Asp Ser Asn Leu Gly Leu Tyr Gly Ala Phe
```

```
            225                 230                 235                 240
Gly Tyr Asp Leu Ala Phe Gln Phe Asp Ala Ile Glu Leu Lys Leu Ser
                245                 250                 255

Arg Pro Asp Asp Gln Arg Asp Met Val Leu Phe Leu Pro Asp Glu Ile
            260                 265                 270

Leu Val Val Asp His Tyr Ala Ala Lys Ala Trp Ile Asp Arg Tyr Asp
                275                 280                 285

Phe Ala Arg Glu Asn Leu Ser Thr Glu Gly Lys Ala Ala Asp Ile Ala
            290                 295                 300

Pro Glu Pro Phe Arg Ser Val Asp Ser Ile Pro Pro His Gly Asp His
305                 310                 315                 320

Arg Pro Gly Glu Tyr Ala Glu Leu Val Val Lys Ala Lys Glu Ser Phe
                325                 330                 335

Arg Arg Gly Asp Leu Phe Glu Val Val Pro Gly Gln Lys Phe Tyr Glu
                340                 345                 350

Arg Cys Glu Ser Arg Pro Ser Glu Ile Ser Asn Arg Leu Lys Ala Ile
                355                 360                 365

Asn Pro Ser Pro Tyr Ser Phe Phe Ile Asn Leu Gly Asn Gln Glu Tyr
            370                 375                 380

Leu Val Gly Ala Ser Pro Glu Met Phe Val Arg Val Ser Gly Arg Arg
385                 390                 395                 400

Ile Glu Thr Cys Pro Ile Ser Gly Thr Ile Lys Arg Gly Asp Asp Pro
                405                 410                 415

Ile Ala Asp Ser Glu Gln Ile Leu Lys Leu Leu Asn Ser Lys Lys Asp
            420                 425                 430

Glu Ser Glu Leu Thr Met Cys Ser Asp Val Asp Arg Asn Asp Lys Ser
            435                 440                 445

Arg Val Cys Val Pro Gly Ser Val Lys Val Ile Gly Arg Arg Gln Ile
            450                 455                 460

Glu Met Tyr Ser Arg Leu Ile His Thr Val Asp His Ile Glu Gly Arg
465                 470                 475                 480

Leu Arg Asp Asp Met Asp Ala Phe Asp Gly Phe Leu Ser His Ala Trp
                485                 490                 495

Ala Val Thr Val Thr Gly Ala Pro Lys Leu Trp Ala Met Arg Phe Ile
                500                 505                 510

Glu Ser His Glu Lys Ser Pro Arg Ala Trp Tyr Gly Gly Ala Ile Gly
            515                 520                 525

Met Val Gly Phe Asn Gly Asp Met Asn Thr Gly Leu Thr Leu Arg Thr
            530                 535                 540

Ile Arg Ile Lys Asp Gly Ile Ala Glu Val Arg Ala Gly Ala Thr Leu
545                 550                 555                 560

Leu Tyr Asp Ser Asn Pro Glu Glu Glu Ala Glu Thr Glu Leu Lys
                565                 570                 575

Ala Ser Ala Met Ile Ala Ala Ile Arg Asp Ala Lys Ser Ala Asn Ser
                580                 585                 590

Ala Lys Ser Ala Arg Asp Val Ala Ala Val Gly Ala Gly Val Ser Ile
            595                 600                 605

Leu Leu Val Asp His Glu Asp Ser Phe Val His Thr Leu Ala Asn Tyr
            610                 615                 620

Phe Arg Gln Thr Gly Ala Ser Val Thr Thr Val Arg Thr Pro Val Ala
625                 630                 635                 640

Glu Glu Ile Phe Asp Arg Val Lys Pro Asp Leu Val Val Leu Ser Pro
                645                 650                 655
```

```
Gly Pro Gly Thr Pro Lys Asp Phe Asp Cys Lys Ala Thr Ile Lys Lys
            660                 665                 670

Ala Arg Ala Arg Asp Leu Pro Ile Phe Gly Val Cys Leu Gly Leu Gln
            675                 680                 685

Ala Leu Ala Glu Ala Tyr Gly Gly Asp Leu Arg Gln Leu Ala Ile Pro
            690                 695                 700

Met His Gly Lys Pro Ser Arg Ile Arg Val Leu Glu Pro Gly Ile Val
705                 710                 715                 720

Phe Ser Gly Leu Gly Lys Glu Val Thr Val Gly Arg Tyr His Ser Ile
                725                 730                 735

Phe Ala Asp Pro Ser Asn Leu Pro Arg Glu Phe Val Ile Thr Ala Glu
            740                 745                 750

Ser Glu Asp Gly Thr Ile Met Gly Ile Glu His Ser Lys Glu Pro Val
            755                 760                 765

Ala Ala Val Gln Phe His Pro Glu Ser Ile Met Thr Leu Gly Gly Asp
            770                 775                 780

Ala Gly Met Arg Met Ile Glu Asn Val Val Ala His Leu Ala Lys Arg
785                 790                 795                 800

Ala Lys Thr Lys Ala Ala
            805

<210> SEQ ID NO 57
<211> LENGTH: 815
<212> TYPE: PRT
<213> ORGANISM: Arabidopsis thaliana

<400> SEQUENCE: 57

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Glu Lys Ala Ser Glu
65                  70                  75                  80

Ile Val Leu Gln Pro Ile Met Ala Ala Val Ile Leu Glu Asp Gly Ala
                85                  90                  95

Glu Ser Tyr Thr Thr Lys Gly Gly Ile Val Val Thr Arg Arg Arg
            100                 105                 110

Glu Ala Ser Tyr Ser Asp Ala Ile Ala Gly Tyr Val Asp Arg Leu Asp
            115                 120                 125

Glu Arg Arg Gly Ala Val Phe Ser Ser Asn Tyr Glu Tyr Pro Gly Arg
            130                 135                 140

Tyr Thr Arg Trp Asp Thr Ala Val Val Asp Pro Leu Ala Ile Ser
145                 150                 155                 160

Ser Phe Gly Arg Ser Leu Trp Ile Glu Ala Tyr Asn Glu Arg Gly Glu
                165                 170                 175

Val Leu Leu Ala Leu Ile Ala Glu Asp Leu Lys Ser Val Ala Asp Ile
            180                 185                 190

Thr Leu Gly Ser Leu Ala Ala Arg Leu Asp Leu Thr Ile Asn Glu
            195                 200                 205

Pro Asp Arg Val Phe Thr Glu Glu Arg Ser Lys Met Pro Thr Val
210                 215                 220
```

-continued

Phe Thr Val Leu Arg Ala Val Thr Asn Leu Phe His Ser Glu Glu Asp
225                 230                 235                 240

Ser Asn Leu Gly Leu Tyr Gly Ala Phe Gly Tyr Asp Leu Ala Phe Gln
            245                 250                 255

Phe Asp Ala Ile Glu Leu Lys Leu Ser Arg Pro Asp Asp Gln Arg Asp
        260                 265                 270

Met Val Leu Phe Leu Pro Asp Glu Ile Leu Val Val Asp His Tyr Ala
    275                 280                 285

Ala Lys Ala Trp Ile Asp Arg Tyr Asp Phe Ala Arg Glu Asn Leu Ser
290                 295                 300

Thr Glu Gly Lys Ala Ala Asp Ile Ala Pro Pro Phe Arg Ser Val
305                 310                 315                 320

Asp Ser Ile Pro Pro His Gly Asp His Arg Pro Gly Glu Tyr Ala Glu
            325                 330                 335

Leu Val Val Lys Ala Lys Glu Ser Phe Arg Arg Gly Asp Leu Phe Glu
        340                 345                 350

Val Val Pro Gly Gln Lys Phe Tyr Glu Arg Cys Glu Ser Arg Pro Ser
    355                 360                 365

Glu Ile Ser Asn Arg Leu Lys Ala Ile Asn Pro Ser Pro Tyr Ser Phe
370                 375                 380

Phe Ile Asn Leu Gly Asn Gln Glu Tyr Leu Val Gly Ala Ser Pro Glu
385                 390                 395                 400

Met Phe Val Arg Val Ser Gly Arg Arg Ile Glu Thr Cys Pro Ile Ser
            405                 410                 415

Gly Thr Ile Lys Arg Gly Asp Asp Pro Ile Ala Asp Ser Glu Gln Ile
        420                 425                 430

Leu Lys Leu Leu Asn Ser Lys Lys Asp Glu Ser Glu Leu Thr Met Cys
    435                 440                 445

Ser Asp Val Asp Arg Asn Asp Lys Ser Arg Val Cys Val Pro Gly Ser
450                 455                 460

Val Lys Val Ile Gly Arg Arg Gln Ile Glu Met Tyr Ser Arg Leu Ile
465                 470                 475                 480

His Thr Val Asp His Ile Glu Gly Arg Leu Arg Asp Asp Met Asp Ala
            485                 490                 495

Phe Asp Gly Phe Leu Ser His Ala Trp Ala Val Thr Val Thr Gly Ala
        500                 505                 510

Pro Lys Leu Trp Ala Met Arg Phe Ile Glu Ser His Glu Lys Ser Pro
    515                 520                 525

Arg Ala Trp Tyr Gly Gly Ala Ile Gly Met Val Gly Phe Asn Gly Asp
530                 535                 540

Met Asn Thr Gly Leu Thr Leu Arg Thr Ile Arg Ile Lys Asp Gly Ile
545                 550                 555                 560

Ala Glu Val Arg Ala Gly Ala Thr Leu Leu Tyr Asp Ser Asn Pro Glu
            565                 570                 575

Glu Glu Glu Ala Glu Thr Glu Leu Lys Ala Ser Ala Met Ile Ala Ala
        580                 585                 590

Ile Arg Asp Ala Lys Ser Ala Asn Ser Ala Lys Ser Ala Arg Asp Val
    595                 600                 605

Ala Ala Val Gly Ala Gly Val Ser Ile Leu Leu Val Asp His Glu Asp
610                 615                 620

Ser Phe Val His Thr Leu Ala Asn Tyr Phe Arg Gln Thr Gly Ala Ser
625                 630                 635                 640

Val Thr Thr Val Arg Thr Pro Val Ala Glu Glu Ile Phe Asp Arg Val
            645                 650                 655

```
Lys Pro Asp Leu Val Val Leu Ser Pro Gly Pro Gly Thr Pro Lys Asp
            660                 665                 670

Phe Asp Cys Lys Ala Thr Ile Lys Lys Ala Arg Ala Arg Asp Leu Pro
            675                 680                 685

Ile Phe Gly Val Cys Leu Gly Leu Gln Ala Leu Ala Glu Ala Tyr Gly
            690                 695                 700

Gly Asp Leu Arg Gln Leu Ala Ile Pro Met His Gly Lys Pro Ser Arg
705                 710                 715                 720

Ile Arg Val Leu Glu Pro Gly Ile Val Phe Ser Gly Leu Gly Lys Glu
                    725                 730                 735

Val Thr Val Gly Arg Tyr His Ser Ile Phe Ala Asp Pro Ser Asn Leu
                740                 745                 750

Pro Arg Glu Phe Val Ile Thr Ala Glu Ser Asp Gly Thr Ile Met
            755                 760                 765

Gly Ile Glu His Ser Lys Glu Pro Val Ala Val Gln Phe His Pro
            770                 775                 780

Glu Ser Ile Met Thr Leu Gly Asp Ala Gly Met Arg Met Ile Glu
785                 790                 795                 800

Asn Val Val Ala His Leu Ala Lys Arg Ala Lys Thr Lys Ala Ala
                805                 810                 815

<210> SEQ ID NO 58
<211> LENGTH: 776
<212> TYPE: PRT
<213> ORGANISM: Zea mays

<400> SEQUENCE: 58

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser Met
        35                  40                  45

Ala Ala Val Ile Leu Glu Asp Gly Ala Glu Ser Tyr Thr Thr Lys Gly
    50                  55                  60

Gly Ile Val Val Thr Arg Arg Arg Glu Ala Ser Tyr Ser Asp Ala
65                  70                  75                  80

Ile Ala Gly Tyr Val Asp Arg Leu Asp Glu Arg Arg Gly Ala Val Phe
                85                  90                  95

Ser Ser Asn Tyr Glu Tyr Pro Gly Arg Tyr Thr Arg Trp Asp Thr Ala
            100                 105                 110

Val Val Asp Pro Pro Leu Ala Ile Ser Ser Phe Gly Arg Ser Leu Trp
        115                 120                 125

Ile Glu Ala Tyr Asn Glu Arg Gly Glu Val Leu Leu Ala Leu Ile Ala
    130                 135                 140

Glu Asp Leu Lys Ser Val Ala Asp Ile Thr Leu Gly Ser Leu Ala Ala
145                 150                 155                 160

Arg Arg Leu Asp Leu Thr Ile Asn Glu Pro Asp Arg Val Phe Thr Glu
                165                 170                 175

Glu Glu Arg Ser Lys Met Pro Thr Val Phe Thr Val Leu Arg Ala Val
            180                 185                 190

Thr Asn Leu Phe His Ser Glu Glu Asp Ser Asn Leu Gly Leu Tyr Gly
        195                 200                 205

Ala Phe Gly Tyr Asp Leu Ala Phe Gln Phe Asp Ala Ile Glu Leu Lys
    210                 215                 220
```

Leu Ser Arg Pro Asp Asp Gln Arg Asp Met Val Leu Phe Leu Pro Asp
225                 230                 235                 240

Glu Ile Leu Val Val Asp His Tyr Ala Ala Lys Ala Trp Ile Asp Arg
                245                 250                 255

Tyr Asp Phe Ala Arg Glu Asn Leu Ser Thr Glu Gly Lys Ala Ala Asp
            260                 265                 270

Ile Ala Pro Glu Pro Phe Arg Ser Val Asp Ser Ile Pro Pro His Gly
        275                 280                 285

Asp His Arg Pro Gly Glu Tyr Ala Glu Leu Val Val Lys Ala Lys Glu
    290                 295                 300

Ser Phe Arg Arg Gly Asp Leu Phe Glu Val Val Pro Gly Gln Lys Phe
305                 310                 315                 320

Tyr Glu Arg Cys Glu Ser Arg Pro Ser Glu Ile Ser Asn Arg Leu Lys
                325                 330                 335

Ala Ile Asn Pro Ser Pro Tyr Ser Phe Phe Ile Asn Leu Gly Asn Gln
            340                 345                 350

Glu Tyr Leu Val Gly Ala Ser Pro Glu Met Phe Val Arg Val Ser Gly
        355                 360                 365

Arg Arg Ile Glu Thr Cys Pro Ile Ser Gly Thr Ile Lys Arg Gly Asp
370                 375                 380

Asp Pro Ile Ala Asp Ser Glu Gln Ile Leu Lys Leu Leu Asn Ser Lys
385                 390                 395                 400

Lys Asp Glu Ser Glu Leu Thr Met Cys Ser Asp Val Asp Arg Asn Asp
                405                 410                 415

Lys Ser Arg Val Cys Val Pro Gly Ser Val Lys Val Ile Gly Arg Arg
            420                 425                 430

Gln Ile Glu Met Tyr Ser Arg Leu Ile His Thr Val Asp His Ile Glu
        435                 440                 445

Gly Arg Leu Arg Asp Asp Met Asp Ala Phe Asp Gly Phe Leu Ser His
    450                 455                 460

Ala Trp Ala Val Thr Val Thr Gly Ala Pro Lys Leu Trp Ala Met Arg
465                 470                 475                 480

Phe Ile Glu Ser His Glu Lys Ser Pro Arg Ala Trp Tyr Gly Gly Ala
                485                 490                 495

Ile Gly Met Val Gly Phe Asn Gly Asp Met Asn Thr Gly Leu Thr Leu
            500                 505                 510

Arg Thr Ile Arg Ile Lys Asp Gly Ile Ala Glu Val Arg Ala Gly Ala
        515                 520                 525

Thr Leu Leu Tyr Asp Ser Asn Pro Glu Glu Glu Ala Glu Thr Glu
    530                 535                 540

Leu Lys Ala Ser Ala Met Ile Ala Ala Ile Arg Asp Ala Lys Ser Ala
545                 550                 555                 560

Asn Ser Ala Lys Ser Ala Arg Asp Val Ala Val Gly Ala Gly Val
                565                 570                 575

Ser Ile Leu Leu Val Asp His Glu Asp Ser Phe Val His Thr Leu Ala
            580                 585                 590

Asn Tyr Phe Arg Gln Thr Gly Ala Ser Val Thr Thr Val Arg Thr Pro
        595                 600                 605

Val Ala Glu Glu Ile Phe Asp Arg Val Lys Pro Asp Leu Val Val Leu
    610                 615                 620

Ser Pro Gly Pro Gly Thr Pro Lys Asp Phe Asp Cys Lys Ala Thr Ile
625                 630                 635                 640

Lys Lys Ala Arg Ala Arg Asp Leu Pro Ile Phe Gly Val Cys Leu Gly

```
                        645                 650                 655
Leu Gln Ala Leu Ala Glu Ala Tyr Gly Gly Asp Leu Arg Gln Leu Ala
                660                 665                 670

Ile Pro Met His Gly Lys Pro Ser Arg Ile Arg Val Leu Glu Pro Gly
            675                 680                 685

Ile Val Phe Ser Gly Leu Gly Lys Glu Val Thr Val Gly Arg Tyr His
        690                 695                 700

Ser Ile Phe Ala Asp Pro Ser Asn Leu Pro Arg Glu Phe Val Ile Thr
705                 710                 715                 720

Ala Glu Ser Glu Asp Gly Thr Ile Met Gly Ile Glu His Ser Lys Glu
                725                 730                 735

Pro Val Ala Ala Val Gln Phe His Pro Glu Ser Ile Met Thr Leu Gly
            740                 745                 750

Gly Asp Ala Gly Met Arg Met Ile Glu Asn Val Val Ala His Leu Ala
        755                 760                 765

Lys Arg Ala Lys Thr Lys Ala Ala
770                 775
```

```
<210> SEQ ID NO 59
<211> LENGTH: 794
<212> TYPE: PRT
<213> ORGANISM: Zea mays

<400> SEQUENCE: 59

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala Met Ala Ala Val Ile Leu Glu Asp Gly Ala Glu Ser Tyr Thr Thr
65                  70                  75                  80

Lys Gly Gly Ile Val Val Thr Arg Arg Arg Arg Glu Ala Ser Tyr Ser
                85                  90                  95

Asp Ala Ile Ala Gly Tyr Val Arg Leu Asp Glu Arg Gly Ala
            100                 105                 110

Val Phe Ser Ser Asn Tyr Glu Tyr Pro Gly Arg Tyr Thr Arg Trp Asp
        115                 120                 125

Thr Ala Val Val Asp Pro Pro Leu Ala Ile Ser Ser Phe Gly Arg Ser
    130                 135                 140

Leu Trp Ile Glu Ala Tyr Asn Glu Arg Gly Val Leu Leu Ala Leu
145                 150                 155                 160

Ile Ala Glu Asp Leu Lys Ser Val Ala Asp Ile Thr Leu Gly Ser Leu
                165                 170                 175

Ala Ala Arg Arg Leu Asp Leu Thr Ile Asn Glu Pro Asp Arg Val Phe
            180                 185                 190

Thr Glu Glu Glu Arg Ser Lys Met Pro Thr Val Phe Thr Val Leu Arg
        195                 200                 205

Ala Val Thr Asn Leu Phe His Ser Glu Glu Asp Ser Asn Leu Gly Leu
    210                 215                 220

Tyr Gly Ala Phe Gly Tyr Asp Leu Ala Phe Gln Phe Asp Ala Ile Glu
225                 230                 235                 240

Leu Lys Leu Ser Arg Pro Asp Asp Gln Arg Asp Met Val Leu Phe Leu
```

-continued

```
                245                 250                 255
Pro Asp Glu Ile Leu Val Val Asp His Tyr Ala Ala Lys Ala Trp Ile
            260                 265                 270
Asp Arg Tyr Asp Phe Ala Arg Glu Asn Leu Ser Thr Glu Gly Lys Ala
        275                 280                 285
Ala Asp Ile Ala Pro Glu Pro Phe Arg Ser Val Asp Ser Ile Pro Pro
    290                 295                 300
His Gly Asp His Arg Pro Gly Glu Tyr Ala Leu Val Val Lys Ala
305                 310                 315                 320
Lys Glu Ser Phe Arg Arg Gly Asp Leu Phe Glu Val Val Pro Gly Gln
                325                 330                 335
Lys Phe Tyr Glu Arg Cys Glu Ser Arg Pro Ser Glu Ile Ser Asn Arg
            340                 345                 350
Leu Lys Ala Ile Asn Pro Ser Pro Tyr Ser Phe Phe Ile Asn Leu Gly
        355                 360                 365
Asn Gln Glu Tyr Leu Val Gly Ala Ser Pro Glu Met Phe Val Arg Val
    370                 375                 380
Ser Gly Arg Arg Ile Glu Thr Cys Pro Ile Ser Gly Thr Ile Lys Arg
385                 390                 395                 400
Gly Asp Asp Pro Ile Ala Asp Ser Glu Gln Ile Leu Lys Leu Leu Asn
                405                 410                 415
Ser Lys Lys Asp Glu Ser Glu Leu Thr Met Cys Ser Val Asp Arg
            420                 425                 430
Asn Asp Lys Ser Arg Val Cys Val Pro Gly Ser Val Lys Val Ile Gly
        435                 440                 445
Arg Arg Gln Ile Glu Met Tyr Ser Arg Leu Ile His Thr Val Asp His
    450                 455                 460
Ile Glu Gly Arg Leu Arg Asp Asp Met Asp Ala Phe Asp Gly Phe Leu
465                 470                 475                 480
Ser His Ala Trp Ala Val Thr Val Thr Gly Ala Pro Lys Leu Trp Ala
                485                 490                 495
Met Arg Phe Ile Glu Ser His Glu Lys Ser Pro Arg Ala Trp Tyr Gly
            500                 505                 510
Gly Ala Ile Gly Met Val Gly Phe Asn Gly Asp Met Asn Thr Gly Leu
        515                 520                 525
Thr Leu Arg Thr Ile Arg Ile Lys Asp Gly Ile Ala Glu Val Arg Ala
    530                 535                 540
Gly Ala Thr Leu Leu Tyr Asp Ser Asn Pro Glu Glu Glu Glu Ala Glu
545                 550                 555                 560
Thr Glu Leu Lys Ala Ser Ala Met Ile Ala Ala Ile Arg Asp Ala Lys
                565                 570                 575
Ser Ala Asn Ser Ala Lys Ser Ala Arg Asp Val Ala Ala Val Gly Ala
            580                 585                 590
Gly Val Ser Ile Leu Leu Val Asp His Glu Asp Ser Phe Val His Thr
        595                 600                 605
Leu Ala Asn Tyr Phe Arg Gln Thr Gly Ala Ser Val Thr Thr Val Arg
    610                 615                 620
Thr Pro Val Ala Glu Glu Ile Phe Asp Arg Val Lys Pro Asp Leu Val
625                 630                 635                 640
Val Leu Ser Pro Gly Pro Gly Thr Pro Lys Asp Phe Asp Cys Lys Ala
                645                 650                 655
Thr Ile Lys Lys Ala Arg Ala Arg Asp Leu Pro Ile Phe Gly Val Cys
            660                 665                 670
```

```
Leu Gly Leu Gln Ala Leu Ala Glu Ala Tyr Gly Gly Asp Leu Arg Gln
        675                 680                 685

Leu Ala Ile Pro Met His Gly Lys Pro Ser Arg Ile Arg Val Leu Glu
    690                 695                 700

Pro Gly Ile Val Phe Ser Gly Leu Gly Lys Glu Val Thr Val Gly Arg
705                 710                 715                 720

Tyr His Ser Ile Phe Ala Asp Pro Ser Asn Leu Pro Arg Glu Phe Val
                725                 730                 735

Ile Thr Ala Glu Ser Glu Asp Gly Thr Ile Met Gly Ile Glu His Ser
            740                 745                 750

Lys Glu Pro Val Ala Ala Val Gln Phe His Pro Glu Ser Ile Met Thr
        755                 760                 765

Leu Gly Gly Asp Ala Gly Met Arg Met Ile Glu Asn Val Val Ala His
    770                 775                 780

Leu Ala Lys Arg Ala Lys Thr Lys Ala Ala
785                 790
```

<210> SEQ ID NO 60
<211> LENGTH: 793
<212> TYPE: PRT
<213> ORGANISM: Zea mays

<400> SEQUENCE: 60

```
Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Pro Thr
            20                  25                  30

Arg Arg Thr Ser Ser Arg Ser Gly Thr Ser Gly Val Lys Cys Ser Ala
            35                  40                  45

Ala Val Thr Pro Gln Ala Ser Pro Val Ile Ser Arg Ser Ala Ala Ala
        50                  55                  60

Ala Val Thr Ile Ile Gln Asp Asp Gly Ala Glu Thr Tyr Glu Thr Lys
65                  70                  75                  80

Gly Gly Ile Gln Val Ser Arg Lys Arg Pro Thr Asp Tyr Ala Asn
                85                  90                  95

Ala Ile Asp Asn Tyr Ile Glu Lys Leu Asp Ser His Arg Gly Ala Val
                100                 105                 110

Phe Ser Ser Asn Tyr Glu Tyr Pro Gly Arg Tyr Thr Arg Trp Asp Thr
            115                 120                 125

Ala Ile Val Asp Pro Pro Leu Gly Ile Ser Cys Phe Gly Arg Lys Met
        130                 135                 140

Trp Ile Glu Ala Tyr Asn Gly Arg Gly Glu Val Leu Leu Asp Phe Ile
145                 150                 155                 160

Thr Glu Lys Leu Lys Ala Thr Pro Asp Leu Thr Leu Gly Ala Ser Ser
                165                 170                 175

Thr Arg Arg Leu Asp Leu Thr Val Asn Glu Pro Asp Arg Val Phe Thr
            180                 185                 190

Glu Glu Glu Arg Ser Lys Ile Pro Thr Val Phe Thr Ala Leu Arg Ala
        195                 200                 205

Ile Val Asp Leu Phe Tyr Ser Ser Ala Asp Ser Ala Ile Gly Leu Phe
    210                 215                 220

Gly Ala Phe Gly Tyr Asp Leu Ala Phe Gln Phe Asp Ala Ile Lys Leu
225                 230                 235                 240

Ser Leu Ala Arg Pro Glu Asp Gln Arg Asp Met Val Leu Phe Leu Pro
                245                 250                 255
```

-continued

```
Asp Glu Ile Leu Val Asp His Tyr Ser Ala Lys Ala Trp Ile Asp
        260                 265                 270

Arg Tyr Asp Phe Glu Lys Asp Gly Met Thr Thr Asp Gly Lys Ser Ser
            275                 280                 285

Asp Ile Thr Pro Asp Pro Phe Lys Thr Thr Asp Thr Ile Pro Pro Lys
        290                 295                 300

Gly Asp His Arg Pro Gly Glu Tyr Ser Glu Leu Val Val Lys Ala Lys
305                 310                 315                 320

Glu Ser Phe Arg Arg Gly Asp Leu Phe Glu Val Val Pro Gly Gln Lys
            325                 330                 335

Phe Met Glu Arg Cys Glu Ser Asn Pro Ser Ala Ile Ser Arg Arg Leu
        340                 345                 350

Lys Ala Ile Asn Pro Ser Pro Tyr Ser Phe Phe Ile Asn Leu Gly Asp
        355                 360                 365

Gln Glu Tyr Leu Val Gly Ala Ser Pro Glu Met Phe Val Arg Val Ser
        370                 375                 380

Gly Arg Arg Ile Glu Thr Cys Pro Ile Ser Gly Thr Ile Lys Arg Gly
385                 390                 395                 400

Asp Asp Pro Ile Ala Asp Ser Glu Gln Ile Leu Lys Leu Leu Asn Ser
            405                 410                 415

Lys Lys Asp Glu Ser Glu Leu Thr Met Cys Ser Asp Val Asp Arg Asn
        420                 425                 430

Asp Lys Ser Arg Val Cys Glu Pro Gly Ser Val Lys Val Ile Gly Arg
        435                 440                 445

Arg Gln Ile Glu Met Tyr Ser Arg Leu Ile His Thr Val Asp His Ile
        450                 455                 460

Glu Gly Arg Leu Arg Asp Asp Met Asp Ala Phe Asp Gly Phe Leu Ser
465                 470                 475                 480

His Ala Trp Ala Val Thr Val Thr Gly Ala Pro Lys Leu Trp Ala Met
            485                 490                 495

Arg Phe Ile Glu Gly His Glu Lys Ser Pro Arg Ala Trp Tyr Gly Gly
        500                 505                 510

Ala Ile Gly Met Val Gly Phe Asn Gly Asp Met Asn Thr Gly Leu Thr
        515                 520                 525

Leu Arg Thr Ile Arg Ile Lys Asp Gly Ile Ala Glu Val Arg Ala Gly
530                 535                 540

Ala Thr Leu Leu Asn Asp Ser Asn Pro Gln Glu Glu Ala Glu Thr
545                 550                 555                 560

Glu Leu Lys Ala Ser Ala Met Ile Ser Ala Ile Arg Asp Ala Lys Gly
            565                 570                 575

Thr Asn Ser Ala Ala Thr Lys Arg Asp Ala Ala Lys Val Gly Thr Gly
        580                 585                 590

Val Lys Ile Leu Leu Val Asp His Glu Asp Ser Phe Val His Thr Leu
        595                 600                 605

Ala Asn Tyr Phe Arg Gln Thr Gly Ala Thr Val Ser Thr Val Arg Ser
        610                 615                 620

Pro Val Ala Ala Asp Val Phe Asp Arg Phe Gln Pro Asp Leu Val Val
625                 630                 635                 640

Leu Ser Pro Gly Pro Gly Ser Pro Thr Asp Phe Asp Cys Lys Ala Thr
            645                 650                 655

Ile Lys Ala Ala Arg Ala Arg Asp Leu Pro Ile Phe Gly Val Cys Leu
        660                 665                 670

Gly Leu Gln Ala Leu Ala Glu Ala Tyr Gly Gly Glu Leu Arg Gln Leu
        675                 680                 685
```

```
Ala Val Pro Met His Gly Lys Pro Ser Arg Ile Arg Val Leu Glu Pro
        690                 695                 700

Gly Leu Val Phe Ser Gly Leu Gly Lys Glu Val Thr Val Gly Arg Tyr
705                 710                 715                 720

His Ser Ile Phe Ala Asp Pro Ala Thr Leu Pro Arg Asp Phe Ile Ile
                725                 730                 735

Thr Ala Glu Ser Glu Asp Gly Thr Ile Met Gly Ile Glu His Ala Lys
            740                 745                 750

Glu Pro Val Ala Ala Val Gln Phe His Pro Glu Ser Ile Met Thr Leu
        755                 760                 765

Gly Gln Asp Ala Gly Met Arg Met Ile Glu Asn Val Val His Leu
770                 775                 780

Thr Arg Lys Ala Lys Thr Lys Ala Ala
785                 790

<210> SEQ ID NO 61
<211> LENGTH: 31
<212> TYPE: DNA
<213> ORGANISM: Artificial Sequence
<220> FEATURE:
<223> OTHER INFORMATION: primer

<400> SEQUENCE: 61
tattggatcc agaacaatgg cttcctctat g                               31

<210> SEQ ID NO 62
<211> LENGTH: 27
<212> TYPE: DNA
<213> ORGANISM: Artificial Sequence
<220> FEATURE:
<223> OTHER INFORMATION: primer

<400> SEQUENCE: 62
tattggatcc atggcctgca tgcagtt                                    27

<210> SEQ ID NO 63
<211> LENGTH: 27
<212> TYPE: DNA
<213> ORGANISM: Artificial Sequence
<220> FEATURE:
<223> OTHER INFORMATION: primer

<400> SEQUENCE: 63
tattggatcc gcggccttgg tcttcgc                                    27

<210> SEQ ID NO 64
<211> LENGTH: 38
<212> TYPE: DNA
<213> ORGANISM: Artificial Sequence
<220> FEATURE:
<223> OTHER INFORMATION: primer

<400> SEQUENCE: 64
tattggatcc agaacaatgg taacgatcat tcaggatg                        38

<210> SEQ ID NO 65
<211> LENGTH: 36
<212> TYPE: DNA
<213> ORGANISM: Artificial Sequence
<220> FEATURE:
<223> OTHER INFORMATION: primer

<400> SEQUENCE: 65
```
tattggatcc agaacaatgg aatccctagc cgccac          36

<210> SEQ ID NO 66
<211> LENGTH: 33
<212> TYPE: DNA
<213> ORGANISM: Artificial Sequence
<220> FEATURE:
<223> OTHER INFORMATION: primer

<400> SEQUENCE: 66
tattggatcc tctttgtcta caaaagctga ctc          33

<210> SEQ ID NO 67
<211> LENGTH: 37
<212> TYPE: DNA
<213> ORGANISM: Artificial Sequence
<220> FEATURE:
<223> OTHER INFORMATION: primer

<400> SEQUENCE: 67
tattggatcc agaacaatgg ctgccgtgac gccgcag          37

<210> SEQ ID NO 68
<211> LENGTH: 30
<212> TYPE: DNA
<213> ORGANISM: Artificial Sequence
<220> FEATURE:
<223> OTHER INFORMATION: primer

<400> SEQUENCE: 68
tattggatcc agaaccatgg cggctctcac          30

<210> SEQ ID NO 69
<211> LENGTH: 28
<212> TYPE: DNA
<213> ORGANISM: Artificial Sequence
<220> FEATURE:
<223> OTHER INFORMATION: primer

<400> SEQUENCE: 69
tattggatcc gcaccgtgaa gcatgcac          28

<210> SEQ ID NO 70
<211> LENGTH: 34
<212> TYPE: DNA
<213> ORGANISM: Artificial Sequence
<220> FEATURE:
<223> OTHER INFORMATION: primer

<400> SEQUENCE: 70
tattggatcc agaaccatga gtgcagcggc aacg          34

<210> SEQ ID NO 71
<211> LENGTH: 29
<212> TYPE: DNA
<213> ORGANISM: Artificial Sequence
<220> FEATURE:
<223> OTHER INFORMATION: primer

<400> SEQUENCE: 71
tattggattc cgcggaactg gcggcggac          29

<210> SEQ ID NO 72
<211> LENGTH: 38
<212> TYPE: DNA
<213> ORGANISM: Artificial Sequence
<220> FEATURE:

<223> OTHER INFORMATION: primer

<400> SEQUENCE: 72
tttctagagg atccagaacc atgagtgcag cggcaacg                                38

<210> SEQ ID NO 73
<211> LENGTH: 27
<212> TYPE: DNA
<213> ORGANISM: Artificial Sequence
<220> FEATURE:
<223> OTHER INFORMATION: primer

<400> SEQUENCE: 73
ttaacgtacg tctccgctcc gtcatcc                                            27

<210> SEQ ID NO 74
<211> LENGTH: 22
<212> TYPE: DNA
<213> ORGANISM: Artificial Sequence
<220> FEATURE:
<223> OTHER INFORMATION: primer

<400> SEQUENCE: 74
ctagtctaga atgatttcgc cg                                                 22

<210> SEQ ID NO 75
<211> LENGTH: 24
<212> TYPE: DNA
<213> ORGANISM: Artificial Sequence
<220> FEATURE:
<223> OTHER INFORMATION: primer

<400> SEQUENCE: 75
cgtctcgtac gtctccgctc cgtc                                               24

<210> SEQ ID NO 76
<211> LENGTH: 27
<212> TYPE: DNA
<213> ORGANISM: Artificial Sequence
<220> FEATURE:
<223> OTHER INFORMATION: primer

<400> SEQUENCE: 76
tgctctagaa tggcgcaagt tagcaga                                            27

<210> SEQ ID NO 77
<211> LENGTH: 32
<212> TYPE: DNA
<213> ORGANISM: Artificial Sequence
<220> FEATURE:
<223> OTHER INFORMATION: primer

<400> SEQUENCE: 77
tcttctagaa ttaccgctgc catgcacgcc gt                                      32

<210> SEQ ID NO 78
<211> LENGTH: 35
<212> TYPE: DNA
<213> ORGANISM: Artificial Sequence
<220> FEATURE:
<223> OTHER INFORMATION: primer

<400> SEQUENCE: 78
tcttctagaa ttaccgctgc cattttctcc gccgt                                   35

<210> SEQ ID NO 79

```
<211> LENGTH: 38
<212> TYPE: DNA
<213> ORGANISM: Artificial Sequence
<220> FEATURE:
<223> OTHER INFORMATION: primer

<400> SEQUENCE: 79
tcttctagaa ttaccgctgc cataatgggt tgaagtac                            38

<210> SEQ ID NO 80
<211> LENGTH: 27
<212> TYPE: DNA
<213> ORGANISM: Artificial Sequence
<220> FEATURE:
<223> OTHER INFORMATION: primer

<400> SEQUENCE: 80
tgctctagaa tggaatccct agccgcc                                        27

<210> SEQ ID NO 81
<211> LENGTH: 35
<212> TYPE: DNA
<213> ORGANISM: Artificial Sequence
<220> FEATURE:
<223> OTHER INFORMATION: primer

<400> SEQUENCE: 81
tcttctagaa ttaccgctgc catagagcat ttcac                               35

<210> SEQ ID NO 82
<211> LENGTH: 21
<212> TYPE: DNA
<213> ORGANISM: Artificial Sequence
<220> FEATURE:
<223> OTHER INFORMATION: primer

<400> SEQUENCE: 82
tgctctagaa tggccaccgc c                                              21

<210> SEQ ID NO 83
<211> LENGTH: 38
<212> TYPE: DNA
<213> ORGANISM: Artificial Sequence
<220> FEATURE:
<223> OTHER INFORMATION: primer

<400> SEQUENCE: 83
tcttctagaa ttaccgctgc catcgccgcc gcagcgct                            38

<210> SEQ ID NO 84
<211> LENGTH: 66
<212> TYPE: DNA
<213> ORGANISM: Artificial Sequence
<220> FEATURE:
<223> OTHER INFORMATION: primer

<400> SEQUENCE: 84
tattggatcc agaaccatgg taacgatcat tcaggatgac ggagcggaga cgtacgagac    60
gaaagg                                                               66

<210> SEQ ID NO 85
<211> LENGTH: 41
<212> TYPE: DNA
<213> ORGANISM: Artificial Sequence
<220> FEATURE:
<223> OTHER INFORMATION: primer
```

<400> SEQUENCE: 85
tttccatggc gcaagttagc agaatctgca atggtgtgca g                41

<210> SEQ ID NO 86
<211> LENGTH: 40
<212> TYPE: DNA
<213> ORGANISM: Artificial Sequence
<220> FEATURE:
<223> OTHER INFORMATION: primer

<400> SEQUENCE: 86
aacccatctc ttatctccaa tctctcgaaa tccagtcaac                  40

<210> SEQ ID NO 87
<211> LENGTH: 39
<212> TYPE: DNA
<213> ORGANISM: Artificial Sequence
<220> FEATURE:
<223> OTHER INFORMATION: primer

<400> SEQUENCE: 87
gcaaatctcc cttatcggtt tctctgaaga cgcagcagc                   39

<210> SEQ ID NO 88
<211> LENGTH: 41
<212> TYPE: DNA
<213> ORGANISM: Artificial Sequence
<220> FEATURE:
<223> OTHER INFORMATION: primer

<400> SEQUENCE: 88
atccacgagc ttatccgatt tcgtcgtcgt ggggattgaa g                41

<210> SEQ ID NO 89
<211> LENGTH: 40
<212> TYPE: DNA
<213> ORGANISM: Artificial Sequence
<220> FEATURE:
<223> OTHER INFORMATION: primer

<400> SEQUENCE: 89
aagagtggga tgacgttaat tggctctgag cttcgtcctc                  40

<210> SEQ ID NO 90
<211> LENGTH: 40
<212> TYPE: DNA
<213> ORGANISM: Artificial Sequence
<220> FEATURE:
<223> OTHER INFORMATION: primer

<400> SEQUENCE: 90
ttaaggtcat gtcttctgtt tccacggcgt gcatggtaac                  40

<210> SEQ ID NO 91
<211> LENGTH: 36
<212> TYPE: DNA
<213> ORGANISM: Artificial Sequence
<220> FEATURE:
<223> OTHER INFORMATION: primer

<400> SEQUENCE: 91
gatcattcag gatgacggag cggagacgta cgagac                      36

<210> SEQ ID NO 92
<211> LENGTH: 19
<212> TYPE: DNA

```
<213> ORGANISM: Artificial Sequence
<220> FEATURE:
<223> OTHER INFORMATION: primer

<400> SEQUENCE: 92
gtctcgtacg tctccgctc                                                          19

<210> SEQ ID NO 93
<211> LENGTH: 40
<212> TYPE: DNA
<213> ORGANISM: Artificial Sequence
<220> FEATURE:
<223> OTHER INFORMATION: primer

<400> SEQUENCE: 93
cgtcatcctg aatgatcgtt accatgcacg ccgtggaaac                                   40

<210> SEQ ID NO 94
<211> LENGTH: 43
<212> TYPE: DNA
<213> ORGANISM: Artificial Sequence
<220> FEATURE:
<223> OTHER INFORMATION: primer

<400> SEQUENCE: 94
agaagacatg accttaagag gacgaagctc agagccaatt aac                               43

<210> SEQ ID NO 95
<211> LENGTH: 39
<212> TYPE: DNA
<213> ORGANISM: Artificial Sequence
<220> FEATURE:
<223> OTHER INFORMATION: primer

<400> SEQUENCE: 95
gtcatcccac tcttcttcaa tccccacgac gacgaaatc                                    39

<210> SEQ ID NO 96
<211> LENGTH: 38
<212> TYPE: DNA
<213> ORGANISM: Artificial Sequence
<220> FEATURE:
<223> OTHER INFORMATION: primer

<400> SEQUENCE: 96
ggataagctc gtggatgctg ctgcgtcttc agagaaac                                     38

<210> SEQ ID NO 97
<211> LENGTH: 40
<212> TYPE: DNA
<213> ORGANISM: Artificial Sequence
<220> FEATURE:
<223> OTHER INFORMATION: primer

<400> SEQUENCE: 97
cgataaggga gatttgcgtt gactggattt cgagagattg                                   40

<210> SEQ ID NO 98
<211> LENGTH: 39
<212> TYPE: DNA
<213> ORGANISM: Artificial Sequence
<220> FEATURE:
<223> OTHER INFORMATION: primer

<400> SEQUENCE: 98
gagataagag atgggttctg cacaccattg cagattctg                                    39
```

<210> SEQ ID NO 99
<211> LENGTH: 43
<212> TYPE: DNA
<213> ORGANISM: Artificial Sequence
<220> FEATURE:
<223> OTHER INFORMATION: primer

<400> SEQUENCE: 99
ttaaggtcat gtcttctgtt tccacggcgg agaaaatggt aac          43

<210> SEQ ID NO 100
<211> LENGTH: 43
<212> TYPE: DNA
<213> ORGANISM: Artificial Sequence
<220> FEATURE:
<223> OTHER INFORMATION: primer

<400> SEQUENCE: 100
cgtcatcctg aatgatcgtt accattttct ccgccgtgga aac          43

<210> SEQ ID NO 101
<211> LENGTH: 36
<212> TYPE: DNA
<213> ORGANISM: Artificial Sequence
<220> FEATURE:
<223> OTHER INFORMATION: primer

<400> SEQUENCE: 101
ttaaggtcat gtcttctgtt tccacggcgg agaaag              36

<210> SEQ ID NO 102
<211> LENGTH: 34
<212> TYPE: DNA
<213> ORGANISM: Artificial Sequence
<220> FEATURE:
<223> OTHER INFORMATION: primer

<400> SEQUENCE: 102
cgtcggagat tgtacttcaa cccattatgg taac               34

<210> SEQ ID NO 103
<211> LENGTH: 37
<212> TYPE: DNA
<213> ORGANISM: Artificial Sequence
<220> FEATURE:
<223> OTHER INFORMATION: primer

<400> SEQUENCE: 103
cgtcatcctg aatgatcgta accataatgg gttgaag             37

<210> SEQ ID NO 104
<211> LENGTH: 33
<212> TYPE: DNA
<213> ORGANISM: Artificial Sequence
<220> FEATURE:
<223> OTHER INFORMATION: primer

<400> SEQUENCE: 104
tacaatctcc gacgctttct ccgccgtgga aac                33

<210> SEQ ID NO 105
<211> LENGTH: 55
<212> TYPE: DNA
<213> ORGANISM: Artificial Sequence
<220> FEATURE:
<223> OTHER INFORMATION: primer

```
<400> SEQUENCE: 105
ttaaggtcat gtcttctgtt tccacggcgg agaaagcgtc ggagattatg gtaac      55

<210> SEQ ID NO 106
<211> LENGTH: 55
<212> TYPE: DNA
<213> ORGANISM: Artificial Sequence
<220> FEATURE:
<223> OTHER INFORMATION: primer

<400> SEQUENCE: 106
cgtcatcctg aatgatcgtt accataatct ccgacgcttt ctccgccgtg gaaac      55

<210> SEQ ID NO 107
<211> LENGTH: 33
<212> TYPE: DNA
<213> ORGANISM: Artificial Sequence
<220> FEATURE:
<223> OTHER INFORMATION: primer

<400> SEQUENCE: 107
tctagaggat ccagaaccat ggccaccgcc agc                              33

<210> SEQ ID NO 108
<211> LENGTH: 33
<212> TYPE: DNA
<213> ORGANISM: Artificial Sequence
<220> FEATURE:
<223> OTHER INFORMATION: primer

<400> SEQUENCE: 108
ctgcgcctcg cgccgtactc gcacccgctg agc                              33

<210> SEQ ID NO 109
<211> LENGTH: 32
<212> TYPE: DNA
<213> ORGANISM: Artificial Sequence
<220> FEATURE:
<223> OTHER INFORMATION: primer

<400> SEQUENCE: 109
gccgcggcgc cgccggcgtc acctgccgcg cc                               32

<210> SEQ ID NO 110
<211> LENGTH: 25
<212> TYPE: DNA
<213> ORGANISM: Artificial Sequence
<220> FEATURE:
<223> OTHER INFORMATION: primer

<400> SEQUENCE: 110
tggccatggt tctggatcct ctaga                                       25

<210> SEQ ID NO 111
<211> LENGTH: 32
<212> TYPE: DNA
<213> ORGANISM: Artificial Sequence
<220> FEATURE:
<223> OTHER INFORMATION: primer

<400> SEQUENCE: 111
agtacggcgc gaggcgcagc gagagcgcga gg                               32

<210> SEQ ID NO 112
<211> LENGTH: 32
<212> TYPE: DNA
```

```
<213> ORGANISM: Artificial Sequence
<220> FEATURE:
<223> OTHER INFORMATION: primer

<400> SEQUENCE: 112
acgccggcgg cgccgcggcg gcggaggctc ag                              32

<210> SEQ ID NO 113
<211> LENGTH: 33
<212> TYPE: DNA
<213> ORGANISM: Artificial Sequence
<220> FEATURE:
<223> OTHER INFORMATION: primer

<400> SEQUENCE: 113
cgtcatcctg aatgatcgtt accatggcgc ggc                             33

<210> SEQ ID NO 114
<211> LENGTH: 32
<212> TYPE: DNA
<213> ORGANISM: Artificial Sequence
<220> FEATURE:
<223> OTHER INFORMATION: primer

<400> SEQUENCE: 114
gccgcggcgc cgccggcgtc acctgccgcg cc                              32

<210> SEQ ID NO 115
<211> LENGTH: 33
<212> TYPE: DNA
<213> ORGANISM: Artificial Sequence
<220> FEATURE:
<223> OTHER INFORMATION: primer

<400> SEQUENCE: 115
accagcttga cgccgtcgcg gtgagggagg agc                             33

<210> SEQ ID NO 116
<211> LENGTH: 33
<212> TYPE: DNA
<213> ORGANISM: Artificial Sequence
<220> FEATURE:
<223> OTHER INFORMATION: primer

<400> SEQUENCE: 116
gcgacggcgt caagctggtg gaacgtggcg gtc                             33

<210> SEQ ID NO 117
<211> LENGTH: 34
<212> TYPE: DNA
<213> ORGANISM: Artificial Sequence
<220> FEATURE:
<223> OTHER INFORMATION: primer

<400> SEQUENCE: 117
cgtcatcctg aatgatcgtt accatcctgg actc                            34

<210> SEQ ID NO 118
<211> LENGTH: 40
<212> TYPE: DNA
<213> ORGANISM: Artificial Sequence
<220> FEATURE:
<223> OTHER INFORMATION: primer

<400> SEQUENCE: 118
ctagtctaga ggatccagaa ccatggaatc cctagccgcc                      40
```

```
<210> SEQ ID NO 119
<211> LENGTH: 40
<212> TYPE: DNA
<213> ORGANISM: Artificial Sequence
<220> FEATURE:
<223> OTHER INFORMATION: primer

<400> SEQUENCE: 119
acctccgtgt tcgcgccctc ccgcgtcgcc gtcccggcgg                              40

<210> SEQ ID NO 120
<211> LENGTH: 40
<212> TYPE: DNA
<213> ORGANISM: Artificial Sequence
<220> FEATURE:
<223> OTHER INFORMATION: primer

<400> SEQUENCE: 120
cgcgggccct ggttagggcg gggacggtgg taccaaccag                              40

<210> SEQ ID NO 121
<211> LENGTH: 40
<212> TYPE: DNA
<213> ORGANISM: Artificial Sequence
<220> FEATURE:
<223> OTHER INFORMATION: primer

<400> SEQUENCE: 121
gcggacgagc agccggagcg gaaccagcgg ggtgaaatgc                              40

<210> SEQ ID NO 122
<211> LENGTH: 40
<212> TYPE: DNA
<213> ORGANISM: Artificial Sequence
<220> FEATURE:
<223> OTHER INFORMATION: primer

<400> SEQUENCE: 122
tctatggtaa cgatcattca ggatgacgga gcggagacgt                              40

<210> SEQ ID NO 123
<211> LENGTH: 40
<212> TYPE: DNA
<213> ORGANISM: Artificial Sequence
<220> FEATURE:
<223> OTHER INFORMATION: primer

<400> SEQUENCE: 123
cgtctcgtac gtctccgctc cgtcatcctg aatgatcgtt                              40

<210> SEQ ID NO 124
<211> LENGTH: 40
<212> TYPE: DNA
<213> ORGANISM: Artificial Sequence
<220> FEATURE:
<223> OTHER INFORMATION: primer

<400> SEQUENCE: 124
accatagagc atttcacccc gctggttccg ctccggctgc                              40

<210> SEQ ID NO 125
<211> LENGTH: 40
<212> TYPE: DNA
<213> ORGANISM: Artificial Sequence
<220> FEATURE:
<223> OTHER INFORMATION: primer
```

<400> SEQUENCE: 125
tcgtccgcct ggttggtacc accgtccccg ccctaaccag            40

<210> SEQ ID NO 126
<211> LENGTH: 40
<212> TYPE: DNA
<213> ORGANISM: Artificial Sequence
<220> FEATURE:
<223> OTHER INFORMATION: primer

<400> SEQUENCE: 126
ggcccgcgcc gccgggacgg cgacgcggga gggcgcgaac            40

<210> SEQ ID NO 127
<211> LENGTH: 40
<212> TYPE: DNA
<213> ORGANISM: Artificial Sequence
<220> FEATURE:
<223> OTHER INFORMATION: primer

<400> SEQUENCE: 127
acggaggtgg cggctaggga ttccatggtt ctggatcctc            40

<210> SEQ ID NO 128
<211> LENGTH: 40
<212> TYPE: DNA
<213> ORGANISM: Artificial Sequence
<220> FEATURE:
<223> OTHER INFORMATION: primer

<400> SEQUENCE: 128
tctgctgccg tgacgccgat ggtaacgatc attcaggatg            40

<210> SEQ ID NO 129
<211> LENGTH: 30
<212> TYPE: DNA
<213> ORGANISM: Artificial Sequence
<220> FEATURE:
<223> OTHER INFORMATION: primer

<400> SEQUENCE: 129
accatcggcg tcacggcagc agagcatttc            30

<210> SEQ ID NO 130
<211> LENGTH: 24
<212> TYPE: DNA
<213> ORGANISM: Artificial Sequence
<220> FEATURE:
<223> OTHER INFORMATION: primer

<400> SEQUENCE: 130
ccccgctggt tccgctccgg ctgc            24

<210> SEQ ID NO 131
<211> LENGTH: 35
<212> TYPE: DNA
<213> ORGANISM: Artificial Sequence
<220> FEATURE:
<223> OTHER INFORMATION: primer

<400> SEQUENCE: 131
tctgctgccg tgacgccgca ggcgagccca gtgat            35

<210> SEQ ID NO 132
<211> LENGTH: 35
<212> TYPE: DNA

```
<213> ORGANISM: Artificial Sequence
<220> FEATURE:
<223> OTHER INFORMATION: primer

<400> SEQUENCE: 132
ggtaacgatc attcaggatg acggagcgga gacgt                              35

<210> SEQ ID NO 133
<211> LENGTH: 35
<212> TYPE: DNA
<213> ORGANISM: Artificial Sequence
<220> FEATURE:
<223> OTHER INFORMATION: primer

<400> SEQUENCE: 133
accatcactg ggctcgcctg cggcgtcacg gcagc                              35

<210> SEQ ID NO 134
<211> LENGTH: 35
<212> TYPE: DNA
<213> ORGANISM: Artificial Sequence
<220> FEATURE:
<223> OTHER INFORMATION: primer

<400> SEQUENCE: 134
agagcatttc accccgctgg ttccgctccg gctgc                              35

<210> SEQ ID NO 135
<211> LENGTH: 22
<212> TYPE: DNA
<213> ORGANISM: Artificial Sequence
<220> FEATURE:
<223> OTHER INFORMATION: primer

<400> SEQUENCE: 135
ctagtctaga atggaatccc ta                                            22

<210> SEQ ID NO 136
<211> LENGTH: 22
<212> TYPE: DNA
<213> ORGANISM: Artificial Sequence
<220> FEATURE:
<223> OTHER INFORMATION: primer

<400> SEQUENCE: 136
tcctggatcc ggcgtcacgg ca                                            22

<210> SEQ ID NO 137
<211> LENGTH: 33
<212> TYPE: DNA
<213> ORGANISM: Artificial Sequence
<220> FEATURE:
<223> OTHER INFORMATION: primer

<400> SEQUENCE: 137
tctagaggat ccagaaccat ggcggctctc acc                                33

<210> SEQ ID NO 138
<211> LENGTH: 33
<212> TYPE: DNA
<213> ORGANISM: Artificial Sequence
<220> FEATURE:
<223> OTHER INFORMATION: primer

<400> SEQUENCE: 138
agctcgccac ctccgccacc ggcttcggca tcg                                33
```

<210> SEQ ID NO 139
<211> LENGTH: 33
<212> TYPE: DNA
<213> ORGANISM: Artificial Sequence
<220> FEATURE:
<223> OTHER INFORMATION: primer

<400> SEQUENCE: 139
gtcggcgccg tcgtcgctgc tccgccacgg gtt         33

<210> SEQ ID NO 140
<211> LENGTH: 33
<212> TYPE: DNA
<213> ORGANISM: Artificial Sequence
<220> FEATURE:
<223> OTHER INFORMATION: primer

<400> SEQUENCE: 140
ctcaagccac gcagcccagc cggcggcgac gcc         33

<210> SEQ ID NO 141
<211> LENGTH: 33
<212> TYPE: DNA
<213> ORGANISM: Artificial Sequence
<220> FEATURE:
<223> OTHER INFORMATION: primer

<400> SEQUENCE: 141
tcagcgtgac gaccagcgcg cgcgcgacgc cca         33

<210> SEQ ID NO 142
<211> LENGTH: 33
<212> TYPE: DNA
<213> ORGANISM: Artificial Sequence
<220> FEATURE:
<223> OTHER INFORMATION: primer

<400> SEQUENCE: 142
cggtcggtgc agcgtcgcag ccggagcttc cca         33

<210> SEQ ID NO 143
<211> LENGTH: 34
<212> TYPE: DNA
<213> ORGANISM: Artificial Sequence
<220> FEATURE:
<223> OTHER INFORMATION: primer

<400> SEQUENCE: 143
gtcgtgtgca tggtaacgat cattcaggat gacc        34

<210> SEQ ID NO 144
<211> LENGTH: 20
<212> TYPE: DNA
<213> ORGANISM: Artificial Sequence
<220> FEATURE:
<223> OTHER INFORMATION: primer

<400> SEQUENCE: 144
atggttctgg atcctctaga            20

<210> SEQ ID NO 145
<211> LENGTH: 33
<212> TYPE: DNA
<213> ORGANISM: Artificial Sequence
<220> FEATURE:
<223> OTHER INFORMATION: primer

<400> SEQUENCE: 145
gtggccgagg tggcgagctg ggacgtggtg aga                                33

<210> SEQ ID NO 146
<211> LENGTH: 33
<212> TYPE: DNA
<213> ORGANISM: Artificial Sequence
<220> FEATURE:
<223> OTHER INFORMATION: primer

<400> SEQUENCE: 146
cagcgacgac ggcgccgacc tgtcggcgat gcc                                33

<210> SEQ ID NO 147
<211> LENGTH: 33
<212> TYPE: DNA
<213> ORGANISM: Artificial Sequence
<220> FEATURE:
<223> OTHER INFORMATION: primer

<400> SEQUENCE: 147
ctgggctgcg tggcttgagg ccctggaacc cgt                                33

<210> SEQ ID NO 148
<211> LENGTH: 33
<212> TYPE: DNA
<213> ORGANISM: Artificial Sequence
<220> FEATURE:
<223> OTHER INFORMATION: primer

<400> SEQUENCE: 148
gcgctggtcg tcacgctgag cgacgtcgcg tcg                                33

<210> SEQ ID NO 149
<211> LENGTH: 33
<212> TYPE: DNA
<213> ORGANISM: Artificial Sequence
<220> FEATURE:
<223> OTHER INFORMATION: primer

<400> SEQUENCE: 149
tgccacgctg caccgaccgc tgctgcttcg gcg                                33

<210> SEQ ID NO 150
<211> LENGTH: 33
<212> TYPE: DNA
<213> ORGANISM: Artificial Sequence
<220> FEATURE:
<223> OTHER INFORMATION: primer

<400> SEQUENCE: 150
atcgttacca tgcacacgac gacggatggg aac                                33

<210> SEQ ID NO 151
<211> LENGTH: 33
<212> TYPE: DNA
<213> ORGANISM: Artificial Sequence
<220> FEATURE:
<223> OTHER INFORMATION: primer

<400> SEQUENCE: 151
gtctcgtacg tctccgctcc gtcatcctga atg                                33

<210> SEQ ID NO 152
<211> LENGTH: 33
<212> TYPE: DNA

```
<213> ORGANISM: Artificial Sequence
<220> FEATURE:
<223> OTHER INFORMATION: primer

<400> SEQUENCE: 152
gtcgtgtacg ccaccggcgc cggcatggta acg                              33

<210> SEQ ID NO 153
<211> LENGTH: 33
<212> TYPE: DNA
<213> ORGANISM: Artificial Sequence
<220> FEATURE:
<223> OTHER INFORMATION: primer

<400> SEQUENCE: 153
atcattcagg atgacggagc ggagacgtac gag                              33

<210> SEQ ID NO 154
<211> LENGTH: 33
<212> TYPE: DNA
<213> ORGANISM: Artificial Sequence
<220> FEATURE:
<223> OTHER INFORMATION: primer

<400> SEQUENCE: 154
cgccggtggc gtacacgacg acggatggga acc                              33

<210> SEQ ID NO 155
<211> LENGTH: 34
<212> TYPE: DNA
<213> ORGANISM: Artificial Sequence
<220> FEATURE:
<223> OTHER INFORMATION: primer

<400> SEQUENCE: 155
gtctcgtacg tctccgctcc gtcatcctga atga                             34

<210> SEQ ID NO 156
<211> LENGTH: 33
<212> TYPE: DNA
<213> ORGANISM: Artificial Sequence
<220> FEATURE:
<223> OTHER INFORMATION: primer

<400> SEQUENCE: 156
gtcgtgtacg ccaccggcgc cggcatgaac gtc                              33

<210> SEQ ID NO 157
<211> LENGTH: 33
<212> TYPE: DNA
<213> ORGANISM: Artificial Sequence
<220> FEATURE:
<223> OTHER INFORMATION: primer

<400> SEQUENCE: 157
tcggcgccga gatggccccc tggagcaaga tgg                              33

<210> SEQ ID NO 158
<211> LENGTH: 33
<212> TYPE: DNA
<213> ORGANISM: Artificial Sequence
<220> FEATURE:
<223> OTHER INFORMATION: primer

<400> SEQUENCE: 158
atcattcagg atgacggagc ggagacgtac gag                              33
```

<210> SEQ ID NO 159
<211> LENGTH: 33
<212> TYPE: DNA
<213> ORGANISM: Artificial Sequence
<220> FEATURE:
<223> OTHER INFORMATION: primer

<400> SEQUENCE: 159
gggccatctc ggcgccgacg aacacgacgt tca                                    33

<210> SEQ ID NO 160
<211> LENGTH: 34
<212> TYPE: DNA
<213> ORGANISM: Artificial Sequence
<220> FEATURE:
<223> OTHER INFORMATION: primer

<400> SEQUENCE: 160
gtctcgtacg tctccgctcc gtcatcctga atga                                   34

<210> SEQ ID NO 161
<211> LENGTH: 40
<212> TYPE: DNA
<213> ORGANISM: Artificial Sequence
<220> FEATURE:
<223> OTHER INFORMATION: primer

<400> SEQUENCE: 161
ctagtctaga ggatccagaa ccatgatttc gccgacgaat                             40

<210> SEQ ID NO 162
<211> LENGTH: 40
<212> TYPE: DNA
<213> ORGANISM: Artificial Sequence
<220> FEATURE:
<223> OTHER INFORMATION: primer

<400> SEQUENCE: 162
ctcctcccgg cgcggaagat cacccctgtc tcaaatggcg                             40

<210> SEQ ID NO 163
<211> LENGTH: 40
<212> TYPE: DNA
<213> ORGANISM: Artificial Sequence
<220> FEATURE:
<223> OTHER INFORMATION: primer

<400> SEQUENCE: 163
gcgcagcgac ggcgagcccc tcttctccct cggtggccgc                             40

<210> SEQ ID NO 164
<211> LENGTH: 40
<212> TYPE: DNA
<213> ORGANISM: Artificial Sequence
<220> FEATURE:
<223> OTHER INFORMATION: primer

<400> SEQUENCE: 164
acggccacgg cgactccctt caggcctcca atctgtgact                             40

<210> SEQ ID NO 165
<211> LENGTH: 45
<212> TYPE: DNA
<213> ORGANISM: Artificial Sequence
<220> FEATURE:
<223> OTHER INFORMATION: primer

```
<400> SEQUENCE: 165
ggtagaggga aggtttcctt ggcaatggta acgatcattc aggat        45

<210> SEQ ID NO 166
<211> LENGTH: 45
<212> TYPE: DNA
<213> ORGANISM: Artificial Sequence
<220> FEATURE:
<223> OTHER INFORMATION: primer

<400> SEQUENCE: 166
cgtctcgtac gtctccgctc cgtcatcctg aatgatcgtt accat        45

<210> SEQ ID NO 167
<211> LENGTH: 44
<212> TYPE: DNA
<213> ORGANISM: Artificial Sequence
<220> FEATURE:
<223> OTHER INFORMATION: primer

<400> SEQUENCE: 167
tgccaaggaa accttccctc taccagtcac agattggagg cctg         44

<210> SEQ ID NO 168
<211> LENGTH: 41
<212> TYPE: DNA
<213> ORGANISM: Artificial Sequence
<220> FEATURE:
<223> OTHER INFORMATION: primer

<400> SEQUENCE: 168
aagggagtcg ccgtggccgt gcggccaccg agggagaaga g            41

<210> SEQ ID NO 169
<211> LENGTH: 40
<212> TYPE: DNA
<213> ORGANISM: Artificial Sequence
<220> FEATURE:
<223> OTHER INFORMATION: primer

<400> SEQUENCE: 169
gggctcgccg tcgctgcgcc gccatttgag acagggtga               40

<210> SEQ ID NO 170
<211> LENGTH: 40
<212> TYPE: DNA
<213> ORGANISM: Artificial Sequence
<220> FEATURE:
<223> OTHER INFORMATION: primer

<400> SEQUENCE: 170
tcttccgcgc cgggaggaga ttcgtcggcg aaatcatggt              40

<210> SEQ ID NO 171
<211> LENGTH: 40
<212> TYPE: DNA
<213> ORGANISM: Artificial Sequence
<220> FEATURE:
<223> OTHER INFORMATION: primer

<400> SEQUENCE: 171
ggtagaggga aggtttcctt ggcagccatc actctggatg              40

<210> SEQ ID NO 172
<211> LENGTH: 40
<212> TYPE: DNA
```

```
<213> ORGANISM: Artificial Sequence
<220> FEATURE:
<223> OTHER INFORMATION: primer

<400> SEQUENCE: 172
attaccttcc aatggtaacg atcattcagg atgacggagc                           40

<210> SEQ ID NO 173
<211> LENGTH: 40
<212> TYPE: DNA
<213> ORGANISM: Artificial Sequence
<220> FEATURE:
<223> OTHER INFORMATION: primer

<400> SEQUENCE: 173
accattggaa ggtaatcatc cagagtgatg gctgccaagg                           40

<210> SEQ ID NO 174
<211> LENGTH: 36
<212> TYPE: DNA
<213> ORGANISM: Artificial Sequence
<220> FEATURE:
<223> OTHER INFORMATION: primer

<400> SEQUENCE: 174
aaaccttccc tctaccagtc acagattgga ggcctg                              36

<210> SEQ ID NO 175
<211> LENGTH: 40
<212> TYPE: DNA
<213> ORGANISM: Artificial Sequence
<220> FEATURE:
<223> OTHER INFORMATION: primer

<400> SEQUENCE: 175
attaccttcc aatgcgaagc actgaagtga agaaccggac                           40

<210> SEQ ID NO 176
<211> LENGTH: 40
<212> TYPE: DNA
<213> ORGANISM: Artificial Sequence
<220> FEATURE:
<223> OTHER INFORMATION: primer

<400> SEQUENCE: 176
atcaatggta acgatcattc aggatgacgg agcggagacg                           40

<210> SEQ ID NO 177
<211> LENGTH: 40
<212> TYPE: DNA
<213> ORGANISM: Artificial Sequence
<220> FEATURE:
<223> OTHER INFORMATION: primer

<400> SEQUENCE: 177
accattgatg tccggttctt cacttcagtg cttcgcattg                           40

<210> SEQ ID NO 178
<211> LENGTH: 40
<212> TYPE: DNA
<213> ORGANISM: Artificial Sequence
<220> FEATURE:
<223> OTHER INFORMATION: primer

<400> SEQUENCE: 178
gaaggtaatc atccagagtg atggctgcca aggaaacctt                           40
```

```
<210> SEQ ID NO 179
<211> LENGTH: 29
<212> TYPE: DNA
<213> ORGANISM: Artificial Sequence
<220> FEATURE:
<223> OTHER INFORMATION: primer

<400> SEQUENCE: 179
ccctctacca gtcacagatt ggaggcctg                                            29

<210> SEQ ID NO 180
<211> LENGTH: 40
<212> TYPE: DNA
<213> ORGANISM: Artificial Sequence
<220> FEATURE:
<223> OTHER INFORMATION: primer

<400> SEQUENCE: 180
ggtagaggga aggtttcctt ggcagccatc actctggata                                40

<210> SEQ ID NO 181
<211> LENGTH: 40
<212> TYPE: DNA
<213> ORGANISM: Artificial Sequence
<220> FEATURE:
<223> OTHER INFORMATION: primer

<400> SEQUENCE: 181
tggtaacgat cattcaggat gacggagcgg agacgtacga                                40

<210> SEQ ID NO 182
<211> LENGTH: 40
<212> TYPE: DNA
<213> ORGANISM: Artificial Sequence
<220> FEATURE:
<223> OTHER INFORMATION: primer

<400> SEQUENCE: 182
cgtctcgtac gtctccgctc cgtcatcctg aatgatcgtt                                40

<210> SEQ ID NO 183
<211> LENGTH: 40
<212> TYPE: DNA
<213> ORGANISM: Artificial Sequence
<220> FEATURE:
<223> OTHER INFORMATION: primer

<400> SEQUENCE: 183
accatatcca gagtgatggc tgccaaggaa accttccctc                                40

<210> SEQ ID NO 184
<211> LENGTH: 24
<212> TYPE: DNA
<213> ORGANISM: Artificial Sequence
<220> FEATURE:
<223> OTHER INFORMATION: primer

<400> SEQUENCE: 184
taccagtcac agattggagg cctg                                                 24

<210> SEQ ID NO 185
<211> LENGTH: 22
<212> TYPE: DNA
<213> ORGANISM: Artificial Sequence
<220> FEATURE:
<223> OTHER INFORMATION: primer
```

```
<400> SEQUENCE: 185
ctagtctaga atgatttcgc cg                                              22

<210> SEQ ID NO 186
<211> LENGTH: 22
<212> TYPE: DNA
<213> ORGANISM: Artificial Sequence
<220> FEATURE:
<223> OTHER INFORMATION: primer

<400> SEQUENCE: 186
tcctggatcc tccagagtga tg                                              22

<210> SEQ ID NO 187
<211> LENGTH: 40
<212> TYPE: DNA
<213> ORGANISM: Artificial Sequence
<220> FEATURE:
<223> OTHER INFORMATION: primer

<400> SEQUENCE: 187
ctagtctaga ggatccagaa ccatgatttc gccgacgaat                           40

<210> SEQ ID NO 188
<211> LENGTH: 40
<212> TYPE: DNA
<213> ORGANISM: Artificial Sequence
<220> FEATURE:
<223> OTHER INFORMATION: primer

<400> SEQUENCE: 188
ctcctcccgg cgcggaagat cacccctgtc tcaaatggcg                           40

<210> SEQ ID NO 189
<211> LENGTH: 40
<212> TYPE: DNA
<213> ORGANISM: Artificial Sequence
<220> FEATURE:
<223> OTHER INFORMATION: primer

<400> SEQUENCE: 189
gcgcagcgac ggcgagcccc tcttctccct cggtggccgc                           40

<210> SEQ ID NO 190
<211> LENGTH: 40
<212> TYPE: DNA
<213> ORGANISM: Artificial Sequence
<220> FEATURE:
<223> OTHER INFORMATION: primer

<400> SEQUENCE: 190
acggccacgg cgactccctt caggcctcca atctgtgact                           40

<210> SEQ ID NO 191
<211> LENGTH: 40
<212> TYPE: DNA
<213> ORGANISM: Artificial Sequence
<220> FEATURE:
<223> OTHER INFORMATION: primer

<400> SEQUENCE: 191
gggctcgccg tcgctgcgcc gccatttgag acagggtga                            40

<210> SEQ ID NO 192
<211> LENGTH: 40
<212> TYPE: DNA
```

<213> ORGANISM: Artificial Sequence
<220> FEATURE:
<223> OTHER INFORMATION: primer

<400> SEQUENCE: 192
tcttccgcgc cgggaggaga ttcgtcggcg aaatcatggt     40

<210> SEQ ID NO 193
<211> LENGTH: 40
<212> TYPE: DNA
<213> ORGANISM: Artificial Sequence
<220> FEATURE:
<223> OTHER INFORMATION: primer

<400> SEQUENCE: 193
ggtagaggga aggtttcctt ggcagccatc actctggata     40

<210> SEQ ID NO 194
<211> LENGTH: 40
<212> TYPE: DNA
<213> ORGANISM: Artificial Sequence
<220> FEATURE:
<223> OTHER INFORMATION: primer

<400> SEQUENCE: 194
tggtaacgat cattcaggat gacggagcgg agacgtacga     40

<210> SEQ ID NO 195
<211> LENGTH: 40
<212> TYPE: DNA
<213> ORGANISM: Artificial Sequence
<220> FEATURE:
<223> OTHER INFORMATION: primer

<400> SEQUENCE: 195
cgtctcgtac gtctccgctc cgtcatcctg aatgatcgtt     40

<210> SEQ ID NO 196
<211> LENGTH: 40
<212> TYPE: DNA
<213> ORGANISM: Artificial Sequence
<220> FEATURE:
<223> OTHER INFORMATION: primer

<400> SEQUENCE: 196
accatatcca gagtgatggc tgccaaggaa accttccctc     40

<210> SEQ ID NO 197
<211> LENGTH: 24
<212> TYPE: DNA
<213> ORGANISM: Artificial Sequence
<220> FEATURE:
<223> OTHER INFORMATION: primer

<400> SEQUENCE: 197
taccagtcac agattggagg cctg     24

<210> SEQ ID NO 198
<211> LENGTH: 40
<212> TYPE: DNA
<213> ORGANISM: Artificial Sequence
<220> FEATURE:
<223> OTHER INFORMATION: primer

<400> SEQUENCE: 198
accattggaa ggtaatcatc cagagtgatg gctgccaagg     40

<210> SEQ ID NO 199
<211> LENGTH: 2190
<212> TYPE: DNA
<213> ORGANISM: Agrobacterium tumefaciens

<400> SEQUENCE: 199

| | | | | | |
|---|---|---|---|---|---|
| atggtaacga | tcattcagga | tgacggagcg | gagacctacg | agacgaaagg | cggcatccag | 60 |
| gtcagccgaa | agcgccggcc | caccgattat | gccaacgcca | tcgataatta | catcgaaaag | 120 |
| cttgattccc | atcgcggcgc | ggttttttcg | tccaactatg | aatatccggg | ccgttacacc | 180 |
| cgctgggata | cggccatcgt | cgatccgccg | ctcggcattt | cctgttttgg | ccgcaagatg | 240 |
| tggatcgaag | cctataatgg | ccgcggcgaa | gtgctgctcg | atttcattac | ggaaaagctg | 300 |
| aaggcgacac | ccgatctcac | cctcggcgct | tcctcgaccc | gccggctcga | tcttaccgtc | 360 |
| aacgaaccgg | accgtgtctt | caccgaagaa | gaacgctcga | aaatcccgac | ggtcttcacc | 420 |
| gctctcagag | ccatcgtcga | cctcttctat | tcgagcgcgg | attcggccat | cggcctgttc | 480 |
| ggtgccttcg | gttacgatct | cgccttccag | ttcgacgcga | tcaagctttc | gctggcgcgt | 540 |
| ccggaagacc | agcgtgacat | ggtgctgttt | ctgcccgatg | aaatcctcgt | cgttgatcac | 600 |
| tattccgcca | aggcctggat | cgaccgttac | gatttcgaga | aggacggcat | gacgacggac | 660 |
| ggcaaatcct | ccgacattac | ccccgatccc | ttcaagacca | ccgataccat | cccgcccaag | 720 |
| ggcgatcacc | gtcccggcga | atattccgag | cttgtggtga | aggccaagga | aagcttccgc | 780 |
| cgcggcgacc | tgttcgaggt | cgttcccggc | cagaaattca | tggagcgttg | cgaaagcaat | 840 |
| ccgtcggcga | tttccgcccg | cctgaaggcg | atcaacccgt | cgccctattc | cttcttcatc | 900 |
| aatctcggcg | atcaggaata | tctggtcggc | gcctcgccgg | aaatgttcgt | gcgcgtctcc | 960 |
| ggccgtcgca | tcgagacctg | cccgatatca | ggcaccatca | agcgcggcga | cgatccgatt | 1020 |
| gccgacagcg | agcagatttt | gaaactgctc | aactcgaaaa | aggacgaatc | cgaactgacc | 1080 |
| atgtgctcgg | acgtggaccg | caacgacaag | agccgcgtct | gcgagccggg | ttcggtgaag | 1140 |
| gtcattggcc | gccgccagat | cgagatgtat | tcacgcctca | tccacaccgt | cgatcacatc | 1200 |
| gaaggccgcc | tgcgcgacga | tatggacgcc | tttgacggtt | tcctcagcca | cgcctgggcc | 1260 |
| gtcaccgtca | ccggtgcacc | aaagctgtgg | gccatgcgct | tcatcgaagg | tcatgaaaag | 1320 |
| agcccgcgcg | cctggtatgg | cggtgcgatc | ggcatggtcg | gcttcaacgg | cgacatgaat | 1380 |
| accggcctga | cgctgcgcac | catccggatc | aaggacggta | ttgccgaagt | gcgcgccggc | 1440 |
| gcgaccctgc | tcaatgattc | caacccgcag | gaagaagaag | ccgaaaccga | actgaaggcc | 1500 |
| tccgccatga | tatcagccat | tcgtgacgca | aaaggcacca | actctgccgc | caccaagcgt | 1560 |
| gatgccgcca | aagtcggcac | cggcgtcaag | atcctgctcg | tcgaccacga | agacagcttc | 1620 |
| gtgcacacgc | tggcgaatta | tttccgccag | acgggcgcga | cggtctcgac | cgtcagatca | 1680 |
| ccggtcgcag | ccgacgtgtt | cgatcgcttc | cagccggacc | tcgttgtcct | gtcgcccgga | 1740 |
| cccggcagcc | cgacggattt | cgactgcaag | gcaacgatca | aggccgcccg | cgcccgcgat | 1800 |
| ctgccgatct | tcggcgtttg | cctcggtctg | caggcattgg | cagaagccta | tggcggcgag | 1860 |
| ctgcgccagc | ttgctgtgcc | catgcacggc | aagccttcgc | gcatccgcgt | gctggaaccc | 1920 |
| ggcctcgtct | tctccggtct | cggcaaggaa | gtcacggtcg | tcgttaccat | tcgatcttc | 1980 |
| gccgatcccg | ccaccctgcc | gcgtgatttc | atcatcaccg | cagaaagcga | ggacggcacg | 2040 |
| atcatgggca | tcgaacacgc | caaggaaccg | gtggccgccg | ttcagttcca | cccggaatcg | 2100 |
| atcatgacgc | tcggacagga | cgcgggcatg | cggatgatcg | agaatgtcgt | ggtgcatctg | 2160 | acccgcaagg cgaagaccaa ggccgcgtga                                              2190

<210> SEQ ID NO 200
<211> LENGTH: 729
<212> TYPE: PRT
<213> ORGANISM: Agrobacterium tumefaciens

<400> SEQUENCE: 200

Met Val Thr Ile Ile Gln Asp Asp Gly Ala Glu Thr Tyr Glu Thr Lys
1               5                   10                  15

Gly Gly Ile Gln Val Ser Arg Lys Arg Arg Pro Thr Asp Tyr Ala Asn
            20                  25                  30

Ala Ile Asp Asn Tyr Ile Glu Lys Leu Asp Ser His Arg Gly Ala Val
        35                  40                  45

Phe Ser Ser Asn Tyr Glu Tyr Pro Gly Arg Tyr Thr Arg Trp Asp Thr
    50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
    130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
    210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285

Lys Ala Ile Asn Pro Ser Pro Tyr Ser Phe Phe Ile Asn Leu Gly Asp
    290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg

```
                370            375            380
Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
                420                 425                 430

Arg Phe Ile Glu Gly His Glu Lys Ser Pro Arg Ala Trp Tyr Gly Gly
                435                 440                 445

Ala Ile Gly Met Val Gly Phe Asn Gly Asp Met Asn Thr Gly Leu Thr
                450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
                485                 490                 495

Glu Leu Lys Ala Ser Ala Met Ile Ser Ala Ile Arg Asp Ala Lys Gly
                500                 505                 510

Thr Asn Ser Ala Ala Thr Lys Arg Asp Ala Ala Lys Val Gly Thr Gly
                515                 520                 525

Val Lys Ile Leu Leu Val Asp His Glu Asp Ser Phe Val His Thr Leu
530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
                580                 585                 590

Ile Lys Ala Ala Arg Ala Arg Asp Leu Pro Ile Phe Gly Val Cys Leu
                595                 600                 605

Gly Leu Gln Ala Leu Ala Glu Ala Tyr Gly Gly Glu Leu Arg Gln Leu
                610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
                660                 665                 670

Thr Ala Glu Ser Glu Asp Gly Thr Ile Met Gly Ile Glu His Ala Lys
                675                 680                 685

Glu Pro Val Ala Ala Val Gln Phe His Pro Glu Ser Ile Met Thr Leu
                690                 695                 700

Gly Gln Asp Ala Gly Met Arg Met Ile Glu Asn Val Val Val His Leu
705                 710                 715                 720

Thr Arg Lys Ala Lys Thr Lys Ala Ala
                725

<210> SEQ ID NO 201
<211> LENGTH: 2190
<212> TYPE: DNA
<213> ORGANISM: Agrobacterium tumefaciens

<400> SEQUENCE: 201
atggtaacga tcattcagga tgacggagcg gagacctacg agacgaaagg cggcatccag      60
gtcagccgaa agcgccggcc caccgattat gccaacgcca tcgataatta catcgaaaag     120
```

```
cttgattccc atcgcggcgc ggttttttcg tccaactatg aatatccggg ccgttacacc    180
cgctgggata cggccatcgt cgatccgccg ctcggcattt cctgttttgg ccgcaagatg    240
tggatcgaag cctataatgg ccgcggcgaa gtgctgctcg atttcattac ggaaaagctg    300
aaggcgacac ccgatctcac cctcggcgct tcctcgaccc gccggctcga tcttaccgtc    360
aacgaaccgg accgtgtctt caccgaagaa gaacgctcga aaatcccgac ggtcttcacc    420
gctctcagag ccatcgtcga cctcttctat tcgagcgcgg attcggccat cggcctgttc    480
ggtgccttcg gttacgatct cgccttccag ttcgacgcga tcaagctttc gctggcgcgt    540
ccggaagacc agcgtgacat ggtgctgttt ctgcccgatg aaatcctcgt cgttgatcac    600
tattccgcca aggcctggat cgaccgttac gatttcgaga aggacggcat gacgacggac    660
ggcaaatcct ccgacattac ccccgatccc ttcaagacca ccgataccat cccgcccaag    720
ggcgatcacc gtcccggcga atattccgag cttgtggtga aggccaagga aagcttccgc    780
cgcggcgacc tgttcgaggt cgttcccggc cagaaattca tggagcgttg cgaaagcaat    840
ccgtcggcga tttccgccg  cctgaaggcg atcaacccgt cgccctattc ctggttcatc    900
aatctcggcg atcaggaata tctggtcggc gcctcgccgg aaatgttcgt gcgcgtctcc    960
ggccgtcgca tcgagacctg cccgatatca ggcaccatca agcgcggcga cgatccgatt   1020
gccgacagcg agcagatttt gaaactgctc aactcgaaaa aggacgaatc cgaactgacc   1080
atgtgctcgg acgtggaccg caacgacaag agccgcgtct gcgagccggg ttcggtgaag   1140
gtcattggcc gccgccagat cgagatgtat tcacgcctca tccacaccgt cgatcacatc   1200
gaaggccgcc tgcgcgacga tatggacgcc tttgacggtt cctcagccac gcctgggcc    1260
gtcaccgtca ccggtgcacc aaagctgtgg gccatgcgct tcatcgaagg tcatgaaaag   1320
agcccgcgcg cctggtatgg cggtgcgatc ggcatggtcg gcttcaacgg cgacatgaat   1380
accggcctga cgctgcgcac catccggatc aaggacggta ttgccgaagt gcgcgccggc   1440
gcgaccctgc tcaatgattc caacccgcag gaagaagaag ccgaaaccga actgaaggcc   1500
tccgccatga tatcagccat tcgtgacgca aaaggcacca actctgccgc caccaagcgt   1560
gatgccgcca aagtcggcac cggcgtcaag atcctgctcg tcgaccacga agacagcttc   1620
gtgcacacgc tggcgaatta tttccgccag acgggcgcga cggtctcgac cgtcagatca   1680
ccggtcgcag ccgacgtgtt cgatcgcttc cagccggacc tcgttgtcct gtcgcccgga   1740
cccggcagcc cgacggattt cgactgcaag gcaacgatca aggccgcccg cgcccgcgat   1800
ctgccgatct tcggcgtttg cctcggtctg caggcattgg cagaagccta tggcggcgag   1860
ctgcgccagc ttgctgtgcc catgcacggc aagccttcgc gcatccgcgt gctggaaccc   1920
ggcctcgtct tctccggtct cggcaaggaa gtcacggtcg gtcgttacca ttcgatcttc   1980
gccgatcccg ccaccctgcc gcgtgatttc atcatcaccg cagaaagcga ggacggcacg   2040
atcatgggca tcgaacacgc caaggaaccg gtggccgccg ttcagttcca cccggaatcg   2100
atcatgacgc tcggacagga cgcgggcatg cggatgatcg agaatgtcgt ggtgcatctg   2160
acccgcaagg cgaagaccaa ggccgcgtga                                    2190
```

<210> SEQ ID NO 202
<211> LENGTH: 729
<212> TYPE: PRT
<213> ORGANISM: Agrobacterium tumefaciens

<400> SEQUENCE: 202

Met Val Thr Ile Ile Gln Asp Asp Gly Ala Glu Thr Tyr Glu Thr Lys
1               5                   10                  15

-continued

```
Gly Gly Ile Gln Val Ser Arg Lys Arg Arg Pro Thr Asp Tyr Ala Asn
            20              25              30

Ala Ile Asp Asn Tyr Ile Glu Lys Leu Asp Ser His Arg Gly Ala Val
        35              40              45

Phe Ser Ser Asn Tyr Glu Tyr Pro Gly Arg Tyr Thr Arg Trp Asp Thr
50              55              60

Ala Ile Val Asp Pro Pro Leu Gly Ile Ser Cys Phe Gly Arg Lys Met
65              70              75              80

Trp Ile Glu Ala Tyr Asn Gly Arg Gly Glu Val Leu Leu Asp Phe Ile
            85              90              95

Thr Glu Lys Leu Lys Ala Thr Pro Asp Leu Thr Leu Gly Ala Ser Ser
            100             105             110

Thr Arg Arg Leu Asp Leu Thr Val Asn Glu Pro Asp Arg Val Phe Thr
            115             120             125

Glu Glu Glu Arg Ser Lys Ile Pro Thr Val Phe Thr Ala Leu Arg Ala
    130             135             140

Ile Val Asp Leu Phe Tyr Ser Ser Ala Asp Ser Ala Ile Gly Leu Phe
145             150             155             160

Gly Ala Phe Gly Tyr Asp Leu Ala Phe Gln Phe Asp Ala Ile Lys Leu
            165             170             175

Ser Leu Ala Arg Pro Glu Asp Gln Arg Asp Met Val Leu Phe Leu Pro
            180             185             190

Asp Glu Ile Leu Val Val Asp His Tyr Ser Ala Lys Ala Trp Ile Asp
            195             200             205

Arg Tyr Asp Phe Glu Lys Asp Gly Met Thr Thr Asp Gly Lys Ser Ser
    210             215             220

Asp Ile Thr Pro Asp Pro Phe Lys Thr Thr Asp Thr Ile Pro Pro Lys
225             230             235             240

Gly Asp His Arg Pro Gly Glu Tyr Ser Glu Leu Val Val Lys Ala Lys
            245             250             255

Glu Ser Phe Arg Arg Gly Asp Leu Phe Glu Val Val Pro Gly Gln Lys
            260             265             270

Phe Met Glu Arg Cys Glu Ser Asn Pro Ser Ala Ile Ser Arg Arg Leu
            275             280             285

Lys Ala Ile Asn Pro Ser Pro Tyr Ser Trp Phe Ile Asn Leu Gly Asp
    290             295             300

Gln Glu Tyr Leu Val Gly Ala Ser Pro Glu Met Phe Val Arg Val Ser
305             310             315             320

Gly Arg Arg Ile Glu Thr Cys Pro Ile Ser Gly Thr Ile Lys Arg Gly
            325             330             335

Asp Asp Pro Ile Ala Asp Ser Glu Gln Ile Leu Lys Leu Leu Asn Ser
            340             345             350

Lys Lys Asp Glu Ser Glu Leu Thr Met Cys Ser Asp Val Asp Arg Asn
            355             360             365

Asp Lys Ser Arg Val Cys Glu Pro Gly Ser Val Lys Val Ile Gly Arg
            370             375             380

Arg Gln Ile Glu Met Tyr Ser Arg Leu Ile His Thr Val Asp His Ile
385             390             395             400

Glu Gly Arg Leu Arg Asp Asp Met Asp Ala Phe Asp Gly Phe Leu Ser
            405             410             415

His Ala Trp Ala Val Thr Val Thr Gly Ala Pro Lys Leu Trp Ala Met
            420             425             430

Arg Phe Ile Glu Gly His Glu Lys Ser Pro Arg Ala Trp Tyr Gly Gly
```

```
                435           440           445
Ala Ile Gly Met Val Gly Phe Asn Gly Asp Met Asn Thr Gly Leu Thr
450                 455                 460
Leu Arg Thr Ile Arg Ile Lys Asp Gly Ile Ala Glu Val Arg Ala Gly
465                 470                 475                 480
Ala Thr Leu Leu Asn Asp Ser Asn Pro Gln Glu Glu Ala Glu Thr
            485                 490                 495
Glu Leu Lys Ala Ser Ala Met Ile Ser Ala Ile Arg Asp Ala Lys Gly
                500                 505                 510
Thr Asn Ser Ala Ala Thr Lys Arg Asp Ala Ala Lys Val Gly Thr Gly
            515                 520                 525
Val Lys Ile Leu Leu Val Asp His Glu Asp Ser Phe Val His Thr Leu
530                 535                 540
Ala Asn Tyr Phe Arg Gln Thr Gly Ala Thr Val Ser Thr Val Arg Ser
545                 550                 555                 560
Pro Val Ala Ala Asp Val Phe Asp Arg Phe Gln Pro Asp Leu Val Val
            565                 570                 575
Leu Ser Pro Gly Pro Gly Ser Pro Thr Asp Phe Asp Cys Lys Ala Thr
            580                 585                 590
Ile Lys Ala Ala Arg Ala Arg Asp Leu Pro Ile Phe Gly Val Cys Leu
            595                 600                 605
Gly Leu Gln Ala Leu Ala Glu Ala Tyr Gly Gly Glu Leu Arg Gln Leu
            610                 615                 620
Ala Val Pro Met His Gly Lys Pro Ser Arg Ile Arg Val Leu Glu Pro
625                 630                 635                 640
Gly Leu Val Phe Ser Gly Leu Gly Lys Glu Val Thr Val Gly Arg Tyr
                645                 650                 655
His Ser Ile Phe Ala Asp Pro Ala Thr Leu Pro Arg Asp Phe Ile Ile
                660                 665                 670
Thr Ala Glu Ser Glu Asp Gly Thr Ile Met Gly Ile His Ala Lys
            675                 680                 685
Glu Pro Val Ala Ala Val Gln Phe His Pro Glu Ser Ile Met Thr Leu
690                 695                 700
Gly Gln Asp Ala Gly Met Arg Met Ile Glu Asn Val Val His Leu
705                 710                 715                 720
Thr Arg Lys Ala Lys Thr Lys Ala Ala
                725

<210> SEQ ID NO 203
<211> LENGTH: 2190
<212> TYPE: DNA
<213> ORGANISM: Agrobacterium tumefaciens

<400> SEQUENCE: 203
gtaacgatca ttcaggatga cggagcggag acctacgaga cgaaaggcgg catccaggtc    60
agccgaaagc gccggcccac cgattatgcc aacgccatcg ataattacat cgaaaagctt   120
gattcccatc gcggcgcggt tttttcgttc aactatgaat atccgggccg ttacacccgc   180
tgggatacgg ccatcgtcga tccgccgctc ggcatttcct gttttggccg caagatgtgg   240
atcgaagcct ataatggccg cggcgaagtg ctgctcgatt tcattacgga aaagctgaag   300
gcgacacccg atctcaccct cggcgcttcc tcgacccgcc ggctcgatct taccgtcaac   360
gaaccggacc gtgtcttcac cgaagaagaa cgctcgaaaa tccgacggt cttcaccgct   420
ctcagagcca tcgtcgacct cttctattcg agcgcggatt cggccatcgg cctgttcggt   480
```

```
gccttcggtt acgatctcgc cttccagttc gacgcgatca agctttcgct ggcgcgtccg    540
gaagaccagc gtgacatggt gctgtttctg cccgatgaaa tcctcgtcgt tgatcactat    600
tccgccaagg cctggatcga ccgttacgat ttcgagaagg acggcatgac gacggacggc    660
aaatcctccg acattacccc cgatcccttc aagaccaccg ataccatccc gcccaagggc    720
gatcaccgtc ccggcgaata ttccgagctt gtggtgaagg ccaaggaaag cttccgccgc    780
ggcgacctgt tcgaggtcgt tcccggccag aaattcatgg agcgttgcga agcaatccg    840 tcggcgattt cccgccgcct gaaggcgatc aacccgtcgc cctattcctt cttcatcaat    900
ctcggcgatc aggaatatct ggtcggcgcc tcgccggaaa tgttcgtgcg cgtctccggc    960
cgtcgcatcg agacctgccc gatatcaggc accatcaagc gcggcgacga tccgattgcc   1020
gacagcgagc agattttgaa actgctcaac tcgaaaaagg acgaatccga actgaccatg   1080
tgctcggacg tggaccgcaa cgacaagagc cgcgtctgcg agccgggttc ggtgaaggtc   1140 attgccgcc gccagatcga gatgtattca cgcctcatcc acaccgtcga tcacatcgaa   1200
ggccgcctgc gcgacgatat ggacgccttt gacggtttcc tcagccacgc ctgggccgtc   1260
accgtcaccg gtgcaccaaa gctgtgggcc atgcgcttca tcgaaggtca tgaaaagagc   1320
ccgcgcgcct ggtatggcgg tgcgatcggc atggtcggct tcaacggcga catgaatacc   1380
ggcctgacgc tgcgcaccat ccggatcaag gacggtattg ccgaagtgcg cgccggcgcg   1440
accctgctca atgattccaa cccgcaggaa gaagaagccg aaaccgaact gaaggcctcc   1500
gccatgatat cagccattcg tgacgcaaaa ggcaccaact ctgccgccac caagcgtgat   1560
gccgccaaag tcggcaccgg cgtcaagatc ctgctcgtcg accacgaaga cagcttcgtg   1620
cacacgctgg cgaattattt ccgccagacg ggcgcgacgg tctcgaccgt cagatcaccg   1680
gtcgcagccg acgtgttcga tcgcttccag ccggacctcg ttgtcctgtc gcccggaccc   1740
ggcagcccga cggatttcga ctgcaaggca acgatcaagg ccgccgcgc ccgcgatctg   1800 ccgatcttcg gcgtttgcct cggtctgcag gcattggcag aagcctatgg cggcgagctg   1860
cgccagcttg ctgtgcccat gcacggcaag ccttcgcgca tccgcgtgct ggaacccggc   1920
ctcgtcttct ccggtctcgg caaggaagtc acggtcggtc gttaccattc gatcttcgcc   1980
gatcccgcca ccctgccgcg tgatttcatc atcaccgcag aaagcgagga cggcacgatc   2040
atgggcatca acacgccaa ggaaccggtg ccgccgttc agttccaccc ggaatcgatc    2100
atgacgctcg acaggacgc gggcatgcgg atgatcgaga atgtcgtggt gcatctgacc   2160
cgcaaggcga agaccaaggc cgcgtgatgg                                    2190
```

<210> SEQ ID NO 204
<211> LENGTH: 728
<212> TYPE: PRT
<213> ORGANISM: Agrobacterium tumefaciens

<400> SEQUENCE: 204

```
Val Thr Ile Ile Gln Asp Asp Gly Ala Glu Thr Tyr Glu Thr Lys Gly
1               5                   10                  15

Gly Ile Gln Val Ser Arg Lys Arg Arg Pro Thr Asp Tyr Ala Asn Ala
            20                  25                  30

Ile Asp Asn Tyr Ile Glu Lys Leu Asp Ser His Arg Gly Ala Val Phe
        35                  40                  45

Ser Phe Asn Tyr Glu Tyr Pro Gly Arg Tyr Arg Trp Asp Thr Ala
    50                  55                  60

Ile Val Asp Pro Pro Leu Gly Ile Ser Cys Phe Gly Arg Lys Met Trp
65                  70                  75                  80
```

```
Ile Glu Ala Tyr Asn Gly Arg Gly Val Leu Leu Asp Phe Ile Thr
                 85                  90                  95

Glu Lys Leu Lys Ala Thr Pro Asp Leu Thr Leu Gly Ala Ser Ser Thr
            100                 105                 110

Arg Arg Leu Asp Leu Thr Val Asn Glu Pro Asp Arg Val Phe Thr Glu
            115                 120                 125

Glu Glu Arg Ser Lys Ile Pro Thr Val Phe Thr Ala Leu Arg Ala Ile
        130                 135                 140

Val Asp Leu Phe Tyr Ser Ser Ala Asp Ser Ala Ile Gly Leu Phe Gly
145                 150                 155                 160

Ala Phe Gly Tyr Asp Leu Ala Phe Gln Phe Asp Ala Ile Lys Leu Ser
                165                 170                 175

Leu Ala Arg Pro Glu Asp Gln Arg Asp Met Val Leu Phe Leu Pro Asp
            180                 185                 190

Glu Ile Leu Val Val Asp His Tyr Ser Ala Lys Ala Trp Ile Asp Arg
        195                 200                 205

Tyr Asp Phe Glu Lys Asp Gly Met Thr Thr Asp Gly Lys Ser Ser Asp
210                 215                 220

Ile Thr Pro Asp Pro Phe Lys Thr Thr Asp Thr Ile Pro Pro Lys Gly
225                 230                 235                 240

Asp His Arg Pro Gly Glu Tyr Ser Glu Leu Val Val Lys Ala Lys Glu
                245                 250                 255

Ser Phe Arg Arg Gly Asp Leu Phe Glu Val Val Pro Gly Gln Lys Phe
            260                 265                 270

Met Glu Arg Cys Glu Ser Asn Pro Ser Ala Ile Ser Arg Arg Leu Lys
        275                 280                 285

Ala Ile Asn Pro Ser Pro Tyr Ser Phe Phe Ile Asn Leu Gly Asp Gln
        290                 295                 300

Glu Tyr Leu Val Gly Ala Ser Pro Glu Met Phe Val Arg Val Ser Gly
305                 310                 315                 320

Arg Arg Ile Glu Thr Cys Pro Ile Ser Gly Thr Ile Lys Arg Gly Asp
                325                 330                 335

Asp Pro Ile Ala Asp Ser Glu Gln Ile Leu Lys Leu Leu Asn Ser Lys
            340                 345                 350

Lys Asp Glu Ser Glu Leu Thr Met Cys Ser Asp Val Asp Arg Asn Asp
        355                 360                 365

Lys Ser Arg Val Cys Glu Pro Gly Ser Val Lys Val Ile Gly Arg Arg
        370                 375                 380

Gln Ile Glu Met Tyr Ser Arg Leu Ile His Thr Val Asp His Ile Glu
385                 390                 395                 400

Gly Arg Leu Arg Asp Asp Met Asp Ala Phe Asp Gly Phe Leu Ser His
                405                 410                 415

Ala Trp Ala Val Thr Val Thr Gly Ala Pro Lys Leu Trp Ala Met Arg
            420                 425                 430

Phe Ile Glu Gly His Glu Lys Ser Pro Arg Ala Trp Tyr Gly Gly Ala
        435                 440                 445

Ile Gly Met Val Gly Phe Asn Gly Asp Met Asn Thr Gly Leu Thr Leu
        450                 455                 460

Arg Thr Ile Arg Ile Lys Asp Gly Ile Ala Glu Val Arg Ala Gly Ala
465                 470                 475                 480

Thr Leu Leu Asn Asp Ser Asn Pro Gln Glu Glu Glu Ala Glu Thr Glu
                485                 490                 495

Leu Lys Ala Ser Ala Met Ile Ser Ala Ile Arg Asp Ala Lys Gly Thr
```

|     |     |     | 500 |     |     |     | 505 |     |     |     | 510 |     |
| --- | --- | --- | --- | --- | --- | --- | --- | --- | --- | --- | --- | --- |
| Asn | Ser | Ala | Ala | Thr | Lys | Arg | Asp | Ala | Ala | Lys | Val | Gly | Thr | Gly | Val |
|     |     |     |     | 515 |     |     |     | 520 |     |     |     | 525 |

Lys Ile Leu Leu Val Asp His Glu Asp Ser Phe Val His Thr Leu Ala
        530                 535                 540

Asn Tyr Phe Arg Gln Thr Gly Ala Thr Val Ser Thr Val Arg Ser Pro
545                 550                 555                 560

Val Ala Ala Asp Val Phe Asp Arg Phe Gln Pro Asp Leu Val Val Leu
                565                 570                 575

Ser Pro Gly Pro Gly Ser Pro Thr Asp Phe Asp Cys Lys Ala Thr Ile
            580                 585                 590

Lys Ala Ala Arg Ala Arg Asp Leu Pro Ile Phe Gly Val Cys Leu Gly
            595                 600                 605

Leu Gln Ala Leu Ala Glu Ala Tyr Gly Gly Glu Leu Arg Gln Leu Ala
        610                 615                 620

Val Pro Met His Gly Lys Pro Ser Arg Ile Arg Val Leu Glu Pro Gly
625                 630                 635                 640

Leu Val Phe Ser Gly Leu Gly Lys Glu Val Thr Val Gly Arg Tyr His
                645                 650                 655

Ser Ile Phe Ala Asp Pro Ala Thr Leu Pro Arg Asp Phe Ile Ile Thr
            660                 665                 670

Ala Glu Ser Glu Asp Gly Thr Ile Met Gly Ile Glu His Ala Lys Glu
        675                 680                 685

Pro Val Ala Ala Val Gln Phe His Pro Glu Ser Ile Met Thr Leu Gly
            690                 695                 700

Gln Asp Ala Gly Met Arg Met Ile Glu Asn Val Val His Leu Thr
705                 710                 715                 720

Arg Lys Ala Lys Thr Lys Ala Ala
            725

```
<210> SEQ ID NO 205
<211> LENGTH: 2190
<212> TYPE: DNA
<213> ORGANISM: Agrobacterium tumefaciens

<400> SEQUENCE: 205
```

| | | |
|---|---|---|
| atggtaacga tcattcagga tgacggagcg gagacctacg agacgaaagg cggcatccag | 60 |
| gtcagccgaa agcgccggcc caccgattat gccaacgcca tcgataatta catcgaaaag | 120 |
| cttgattccc atcgcggcgc ggttttttcg tgcaactatg aatatccggg ccgttacacc | 180 |
| cgctgggata cggccatcgt cgatccgccg ctcggcattt cctgttttgg ccgcaagatg | 240 |
| tggatcgaag cctataatgg ccgcggcgaa gtgctgctcg atttcattac ggaaaagctg | 300 |
| aaggcgacac ccgatctcac cctcggcgct tcctcgaccc gccggctcga tcttaccgtc | 360 |
| aacgaaccgg accgtgtctt caccgaagaa gaacgctcga aaatcccgac ggtcttcacc | 420 |
| gctctcagag ccatcgtcga cctcttctat tcgagcgcgg attcggccat cggcctgttc | 480 |
| ggtgccttcg gttacgatct cgccttccag ttcgacgcga tcaagctttc gctggcgcgt | 540 |
| ccggaagacc agcgtgacat ggtgctgttt ctgcccgatg aaatcctcgt cgttgatcac | 600 |
| tattccgcca aggcctggat cgaccgttac gatttcgaga aggacggcat gacgacggac | 660 |
| ggcaaatcct ccgacattac ccccgatccc ttcaagacca ccgataccat cccgcccaag | 720 |
| ggcgatcacc gtcccggcga atattccgag cttgtggtga aggccaagga aagcttccgc | 780 |
| cgcggcgacc tgttcgaggt cgttcccggc cagaaattca tggagcgttg cgaaagcaat | 840 |

```
ccgtcggcga tttccgccg cctgaaggcg atcaacccgt cgccctattc cttcttcatc    900
aatctcggcg atcaggaata tctggtcggc gcctcgccgg aaatgttcgt gcgcgtctcc    960
ggccgtcgca tcgagacctg cccgatatca ggcaccatca agcgcggcga cgatccgatt   1020
gccgacagcg agcagatttt gaaactgctc aactcgaaaa aggacgaatc cgaactgacc   1080
atgtgctcgg acgtggaccg caacgacaag agccgcgtct gcgagccggg ttcggtgaag   1140
gtcattggcc gccgcagat cgagatgtat tcacgcctca tccacaccgt cgatcacatc    1200
gaaggccgcc tgcgcgacga tatggacgcc tttgacggtt cctcagcca cgcctgggcc   1260
gtcaccgtca ccggtgcacc aaagctgtgg gccatgcgct tcatcgaagg tcatgaaaag   1320
agcccgcgcg cctggtatgg cggtgcgatc ggcatggtcg gcttcaacgg cgacatgaat   1380
accggcctga cgctgcgcac catccggatc aaggacggta ttgccgaagt gcgcgccggc   1440
gcgaccctgc tcaatgattc caacccgcag gaagaagaag ccgaaaccga actgaaggcc   1500
tccgccatga tatcagccat tcgtgacgca aaaggcacca actctgccgc caccaagcgt   1560
gatgccgcca agtcggcac cggcgtcaag atcctgctcg tcgaccacga agacagcttc   1620
gtgcacacgc tggcgaatta ttcccgccag acgggcgcga cggtctcgac cgtcagatca   1680
ccggtcgcag ccgacgtgtt cgatcgcttc cagccggacc tcgttgtcct gtcgcccgga   1740
cccggcagcc cgacggattt cgactgcaag gcaacgatca aggccgcccg cgcccgcgat   1800
ctgccgatct tcggcgtttg cctcggtctg caggcattgg cagaagccta tggcggcgag   1860
ctgcgccagc ttgctgtgcc catgcacggc aagccttcgc gcatccgcgt gctggaaccc   1920
ggcctcgtct ctccggtct cggcaaggaa gtcacggtcg gtcgttacca ttcgatcttc   1980
gccgatcccg ccaccctgcc gcgtgatttc atcatcaccg cagaaagcga ggacggcacg   2040
atcatgggca tcgaacacgc caaggaaccg gtggccgccg ttcagttcca cccggaatcg   2100
atcatgacgc tcggacagga cgcgggcatg cggatgatcg agaatgtcgt ggtgcatctg   2160
acccgcaagg cgaagaccaa ggccgcgtga                                    2190
```

<210> SEQ ID NO 206
<211> LENGTH: 729
<212> TYPE: PRT
<213> ORGANISM: Agrobacterium tumefaciens

<400> SEQUENCE: 206

```
Met Val Thr Ile Ile Gln Asp Asp Gly Ala Glu Thr Tyr Glu Thr Lys
1               5                   10                  15

Gly Gly Ile Gln Val Ser Arg Lys Arg Arg Pro Thr Asp Tyr Ala Asn
            20                  25                  30

Ala Ile Asp Asn Tyr Ile Glu Lys Leu Asp Ser His Arg Gly Ala Val
        35                  40                  45

Phe Ser Cys Asn Tyr Glu Tyr Pro Gly Arg Tyr Thr Arg Trp Asp Thr
    50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
    130                 135                 140
```

-continued

```
Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
    210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285

Lys Ala Ile Asn Pro Ser Pro Tyr Ser Phe Phe Ile Asn Leu Gly Asp
    290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
    370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
                485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Lys Val Gly Thr Gly
        515                 520                 525

Val Lys Ile Leu Leu Val Asp His Glu Asp Ser Phe Val His Thr Leu
    530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
```

```
                    565                 570                 575
Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
        595                 600                 605

Gly Leu Gln Ala Leu Ala Glu Ala Tyr Gly Gly Glu Leu Arg Gln Leu
    610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
        675                 680                 685

Glu Pro Val Ala Ala Val Gln Phe His Pro Glu Ser Ile Met Thr Leu
    690                 695                 700

Gly Gln Asp Ala Gly Met Arg Met Ile Glu Asn Val Val Val His Leu
705                 710                 715                 720

Thr Arg Lys Ala Lys Thr Lys Ala Ala
                725

<210> SEQ ID NO 207
<211> LENGTH: 2190
<212> TYPE: DNA
<213> ORGANISM: Artificial Sequence
<220> FEATURE:
<223> OTHER INFORMATION: codon-optimized S51C allele from Agrobacterium
      tumefaciens anthranilate synthase

<400> SEQUENCE: 207
atggtgacca tcattcagga cgacggcgct gagacctacg agactaaggg cggtatccaa    60
gtgagccgta agcgtaggcc cactgactac gctaacgcca tcgacaacta catcgagaag   120
ctagactccc atcgcggcgc tgtgttctcc tgcaactacg aataccctgg cgctacacg    180 aggtgggata ccgccatcgt cgatcctcca ttgggcatct cctgttttgg cgtaagatg    240 tggatcgagg cgtacaacgg ccgtggcgaa gtcttgctgg acttcatcac ggagaagctc   300
aaggccacac cggacctcac cctcggcgct tcctcgaccc gccgcctcga ccttacggtc   360
aacgagccgg accgcgtgtt caccgaggaa gagcgtagca agatcccgac tgtcttcacc   420
gcgctcagag ccatcgtgga cctattctac tcttctgcgg acagcgccat cgggttgttc   480
ggtgccttcg gttacgacct cgcgttccag ttcgacgcca tcaagctctc gctcgcgcgg   540
ccggaggacc agcgagacat ggtgctcttc ctccctgacg agatcctggt cgtcgatcac   600
tattccgcga aggcgtggat cgaccggtac gacttcgaga aggatggcat gaccacggat   660
ggcaagagca gcgacatcac tcccgaccca ttcaagacca ccgacaccat ccctccaaag   720
ggcgatcacc gccctggcga gtattccgaa ctcgtggtga aggccaagga atccttccgg   780
cgcggcgatc tgtttgaggt ggttcccggc caaaagttca tggagaggtg cgagtcgaat   840
ccgtctgcga tcagtcgccg actgaaagcg atcaacccga gcccgtattc cttcttcatc   900
aacctcggcg atcaggaata tctggtcgga gcctcacccg agatgttcgt cagggtctcc   960
ggccgccgga tcgagacgtg cccaattttcc ggaaccatca agcgcggaga tgacccgata  1020
gccgactctg agcagatcct gaaactcttg aacagcaaga aggacgagtc cgagctgact  1080
atgtgctcag atgtggaccg aaacgacaag tcacgtgtct gcgagcccgg tagcgtcaag  1140
```

```
gtcattggcc gccgtcagat cgagatgtac tccaggctga ttcacacggt cgatcatatc    1200
gaagggcggc tgcgcgacga tatggacgca ttcgacgggt tcctcagtca cgcctgggcc    1260
gttactgtca ccggagcgcc taagctctgg gctatgaggt tcatcgaggg ccacgagaag    1320
agccctaggg cttggtatgg tggtgccatc ggcatggttg ggttcaacgg cgacatgaac    1380
accgggctga cgctccggac catcaggatc aaagacggca ttgccgaggt gagggccggt    1440
gccacgcttc tcaacgatag caaccctcag gaggaagagg cggagaccga gctgaaagcc    1500
tctgcgatga tctccgcgat tagagatgca aagggtacga acagtgctgc caccaagcgg    1560
gacgcagcca aggtgggcac cggcgtcaag attttacttg tcgatcacga ggactccttc    1620
gtgcacactc tggcgaacta cttccgccag acaggcgcga cggtctccac cgttaggtca    1680
ccggtggccg ctgacgtgtt cgataggttc cagcccgacc ttgtggtgct ctctcccggt    1740
cccggctcgc ccacggactt cgactgcaag gccaccatta aggccgccag gccagggat    1800 ctgccaatct tcggcgtttg cctcgggctt caggcattgg ccgaggcata cggtggagag    1860
ctgaggcagc tcgccgtccc gatgcacggg aagccatccc gcatcagagt cctggagccc    1920
ggcctcgtct tctccggtct cgggaaggag gtcacggtcg tcggtatca ttcgatcttc     1980 gccgatccgg caaccctccc gcgcgacttc atcataaccg ccgagtcgga ggacggaacg    2040
atcatgggaa tcaacacgc caaggagccc gtagctgcgg ttcagttcca ccctgagtcc     2100
atcatgaccc tcggtcaaga tgcgggtatg cggatgatcg agaatgtggt ggttcacctc    2160 acccgc

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
            195                 200                 205

Arg Tyr Asp Phe Glu Lys Asp Gly Met Thr Thr Asp Gly Lys Ser Ser
210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
                260                 265                 270

Phe Met Glu Arg Cys Glu Ser Asn Pro Ser Ala Ile Ser Arg Arg Leu
            275                 280                 285

Lys Ala Ile Asn Pro Ser Pro Tyr Ser Phe Phe Ile Asn Leu Gly Asp
            290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
            355                 360                 365

Asp Lys Ser Arg Val Cys Glu Pro Gly Ser Val Lys Val Ile Gly Arg
370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
            435                 440                 445

Ala Ile Gly Met Val Gly Phe Asn Gly Asp Met Asn Thr Gly Leu Thr
            450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
                485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Ala Lys Val Gly Thr Gly
            515                 520                 525

Val Lys Ile Leu Leu Val Asp His Glu Asp Ser Phe Val His Thr Leu
530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu

```
            595                 600                 605
Gly Leu Gln Ala Leu Ala Glu Ala Tyr Gly Glu Leu Arg Gln Leu
        610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
                660                 665                 670

Thr Ala Glu Ser Glu Asp Gly Thr Ile Met Gly Ile Glu His Ala Lys
                675                 680                 685

Glu Pro Val Ala Ala Val Gln Phe His Pro Glu Ser Ile Met Thr Leu
690                 695                 700

Gly Gln Asp Ala Gly Met Arg Met Ile Glu Asn Val Val Val His Leu
705                 710                 715                 720

Thr Arg Lys Ala Lys Thr Lys Ala Ala
                725

<210> SEQ ID NO 209
<211> LENGTH: 2191
<212> TYPE: DNA
<213> ORGANISM: Sinorhizobium meliloti

<400> SEQUENCE: 209
atggcagcgg taattctgga agacggcgcg gagagttata ccacgaaggg tggcatcgtc      60
gtcacccgca ggcggcgtga ggcatcctac agcgacgcga tcgccggtta tgtcgaccgg     120
ctggacgaac gccgcggcgc ggtcttttcc tcgaactacg aatatcccgg ccgctatacc     180
cgctgggaca ctgcggtggt cgaccgcgcc cttgccatct cctccttcgg tcgctcgctc     240
tggatcgaag cctataacga acgcggcgaa gtgctgctgg cgctgatcgc cgaggatctg     300
aagtccgttg ccgacatcac gctcggctca cttgccgccc ccgcctcga cctcaccatc     360 aacgagcccg atcgtgtctt caccgaggaa gagcggtcga agatgccgac ggtctttacg     420
gttcttcgcg cggtgacgaa cctcttccac tcggaggagg actcgaacct cggcctctat     480
ggcgccttcg gctacgacct cgccttccag ttcgatgcga tcgaactgaa gctttcgcgt     540
ccggacgacc agcgcgacat ggttctcttt ctgccggacg agatccttgt ggtcgatcac     600
tatgcggcca aggcctggat cgaccgctac gatttcgcca gggagaacct ttcgaccgag     660
ggcaaggcag cggacattgc tcccgagccg ttccgcagcg tcgacagcat cccgccgcac     720
ggggatcacc gcccgggcga atatgccgag ctcgtcgtca aggcgaagga aagcttccgt     780
cgcggcgatc ttttcgaagt ggtgccgggg cagaaattct acgagcgctg cgaaagccgc     840
ccgtccgaga tttccaaccg gctgaaggcg atcaatccgt cgccctattc cttcttcatc     900
aatctcggca accaggaata tctcgtcggt gcttcgccgg agatgttcgt gcgcgtttcc     960
ggccggcgca tcgagacctg cccgatctcc ggtacgatca agcgcggcga cgatccgatc    1020
gccgacagcg agcagatcct gaagctcttg aactcgaaga aggacgagtc cgagctcacc    1080
atgtgctcgg acgtcgaccg caacgacaag agccgggtct gcgtgccggg ctcggtcaag    1140
gtgatcggcc ggcgtcagat cgagatgtat tcgcggctga tccacacggt cgatcacatc    1200
gagggggcgc tgcgcgacga tatggacgcc ttcgacgggt tcctcagcca cgcctgggcg    1260
gtgaccgtta ccggcgcgcc aaagctctgg ccatgcgct tcatcgagag ccacgagaag    1320
agcccgcgtg cctggtatgg cggcgcgatc ggcatggtcg gcttcaacgg cgacatgaat    1380
```

-continued

```
accgggctga ccttgcgtac catccgcatc aaggacggga tcgccgaggt gagggcgggt    1440
gcgacgctcc tctatgattc caatccggaa gaagaagaag ccgaaaccga actgaaggcc    1500
tctgccatga ttgcagccat ccgcgacgcg aaatccgcaa acagcgccaa atccgcgcgc    1560
gatgtcgccg ccgtcggcgc cggagtcagc atcctgctcg tcgatcacga ggacagcttc    1620
gtccataccc tcgcgaacta cttccgccag accggcgcgt ccgtcaccac cgtgcgcacg    1680
ccggtggccg aggaaatctt cgaccgggtc aagccggacc tcgtcgtgct ttcgcccggt    1740
cccggcaccc cgaaggactt cgactgcaag gcgacgatca agaaggcgcg ggcgcgggac    1800
ctgccgatct tcggcgtctg cctggggctg caggcgctcg cggaggccta tggcggcgac    1860
cttcgtcaac tggcgatccc gatgcatggg aagccctcgc gcatccgcgt gctcgaaccc    1920
ggcatcgtct tctccggcct cggcaaggag gtgacggtcg ggcgctatca ttcgattttc    1980
gccgatccgt ccaacctgcc gcgcgaattc gtgatcacgg ccgaaagcga agatggtacg    2040
atcatgggca tcgaacacag caaggagccg gtggcggccg tgcagttcca tccggaatcg    2100
atcatgacgc tgggcggcga cgccggcatg cggatgatcg agaacgtggt tgcccatctc    2160
gccaagcggg cgaagaccaa ggcagcctga a                                    2191
```

<210> SEQ ID NO 210
<211> LENGTH: 729
<212> TYPE: PRT
<213> ORGANISM: Sinorhizobium meliloti

<400> SEQUENCE: 210

```
Met Ala Ala Val Ile Leu Glu Asp Gly Ala Glu Ser Tyr Thr Thr Lys
1               5                   10                  15

Gly Gly Ile Val Val Thr Arg Arg Arg Glu Ala Ser Tyr Ser Asp
            20                  25                  30

Ala Ile Ala Gly Tyr Val Asp Arg Leu Asp Glu Arg Arg Gly Ala Val
        35                  40                  45

Phe Ser Ser Asn Tyr Glu Tyr Pro Gly Arg Tyr Thr Arg Trp Asp Thr
    50                  55                  60

Ala Val Val Asp Pro Pro Leu Ala Ile Ser Ser Phe Gly Arg Ser Leu
65                  70                  75                  80

Trp Ile Glu Ala Tyr Asn Glu Arg Gly Glu Val Leu Leu Ala Leu Ile
                85                  90                  95

Ala Glu Asp Leu Lys Ser Val Ala Asp Ile Thr Leu Gly Ser Leu Ala
            100                 105                 110

Ala Arg Arg Leu Asp Leu Thr Ile Asn Glu Pro Asp Arg Val Phe Thr
        115                 120                 125

Glu Glu Glu Arg Ser Lys Met Pro Thr Val Phe Thr Val Leu Arg Ala
    130                 135                 140

Val Thr Asn Leu Phe His Ser Glu Glu Asp Ser Asn Leu Gly Leu Tyr
145                 150                 155                 160

Gly Ala Phe Gly Tyr Asp Leu Ala Phe Gln Phe Asp Ala Ile Glu Leu
                165                 170                 175

Lys Leu Ser Arg Pro Asp Asp Gln Arg Asp Met Val Leu Phe Leu Pro
            180                 185                 190

Asp Glu Ile Leu Val Val Asp His Tyr Ala Ala Lys Ala Trp Ile Asp
        195                 200                 205

Arg Tyr Asp Phe Ala Arg Glu Asn Leu Ser Thr Glu Gly Lys Ala Ala
    210                 215                 220

Asp Ile Ala Pro Glu Pro Phe Arg Ser Val Asp Ser Ile Pro Pro His
225                 230                 235                 240
```

```
Gly Asp His Arg Pro Gly Glu Tyr Ala Glu Leu Val Val Lys Ala Lys
            245                 250                 255

Glu Ser Phe Arg Arg Gly Asp Leu Phe Glu Val Val Pro Gly Gln Lys
        260                 265                 270

Phe Tyr Glu Arg Cys Glu Ser Arg Pro Ser Glu Ile Ser Asn Arg Leu
            275                 280                 285

Lys Ala Ile Asn Pro Ser Pro Tyr Ser Phe Phe Ile Asn Leu Gly Asn
        290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Val Pro Gly Ser Val Lys Val Ile Gly Arg
    370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Ser His Glu Lys Ser Pro Arg Ala Trp Tyr Gly Gly
        435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Tyr Asp Ser Asn Pro Glu Glu Glu Ala Glu Thr
                485                 490                 495

Glu Leu Lys Ala Ser Ala Met Ile Ala Ala Ile Arg Asp Ala Lys Ser
            500                 505                 510

Ala Asn Ser Ala Lys Ser Ala Arg Asp Val Ala Val Gly Ala Gly
        515                 520                 525

Val Ser Ile Leu Leu Val Asp His Glu Asp Ser Phe Val His Thr Leu
    530                 535                 540

Ala Asn Tyr Phe Arg Gln Thr Gly Ala Ser Val Thr Thr Val Arg Thr
545                 550                 555                 560

Pro Val Ala Glu Glu Ile Phe Asp Arg Val Lys Pro Asp Leu Val Val
                565                 570                 575

Leu Ser Pro Gly Pro Gly Thr Pro Lys Asp Phe Asp Cys Lys Ala Thr
            580                 585                 590

Ile Lys Lys Ala Arg Ala Arg Asp Leu Pro Ile Phe Gly Val Cys Leu
        595                 600                 605

Gly Leu Gln Ala Leu Ala Glu Ala Tyr Gly Gly Asp Leu Arg Gln Leu
    610                 615                 620

Ala Ile Pro Met His Gly Lys Pro Ser Arg Ile Arg Val Leu Glu Pro
625                 630                 635                 640

Gly Ile Val Phe Ser Gly Leu Gly Lys Glu Val Thr Val Gly Arg Tyr
                645                 650                 655

His Ser Ile Phe Ala Asp Pro Ser Asn Leu Pro Arg Glu Phe Val Ile
```

```
            660                 665                 670
Thr Ala Glu Ser Glu Asp Gly Thr Ile Met Gly Ile Glu His Ser Lys
            675                 680                 685

Glu Pro Val Ala Ala Val Gln Phe His Pro Glu Ser Ile Met Thr Leu
        690                 695                 700

Gly Gly Asp Ala Gly Met Arg Met Ile Glu Asn Val Val Ala His Leu
705                 710                 715                 720

Ala Lys Arg Ala Lys Thr Lys Ala Ala
                725

<210> SEQ ID NO 211
<211> LENGTH: 2190
<212> TYPE: DNA
<213> ORGANISM: Sinorhizobium meliloti

<400> SEQUENCE: 211
atggcagcgg taattctgga agacggcgcg gagagttata ccacgaaggg tggcatcgtc        60
gtcacccgca ggcggcgtga ggcatcctac agcgacgcga tcgccggtta tgtcgaccgg       120
ctggacgaac gccgcggcgc ggtcttttcc tgcaactacg aatatcccgg ccgctatacc       180
cgctgggaca ctgcggtggt cgacccgccg cttgccatct cctccttcgg tcgctcgctc       240
tggatcgaag cctataacga acgcggcgaa gtgctgctgg cgctgatcgc cgaggatctg       300
aagtccgttg ccgacatcac gctcggctca cttgccgccc gccgctcga cctcaccatc       360 aacgagcccg atcgtgtctt caccgaggaa gagcggtcga agatgccgac ggtctttacg       420
gttcttcgcg cggtgacgaa cctcttccac tcggaggagg actcgaacct cggcctctat       480
ggcgccttcg gctacgacct cgccttccag ttcgatgcga tcgaactgaa gctttcgcgt       540
ccggacgacc agcgcgacat ggttctcttt ctgccggacg agatccttgt ggtcgatcac       600
tatgcggcca aggcctggat cgaccgctac gatttcgcca gggagaacct ttcgaccgag       660
ggcaaggcag cggacattgc tcccgagccg ttccgcagcg tcgacagcat cccgccgcac       720
ggggatcacc gcccgggcga atatgccgag ctcgtcgtca aggcgaagga aagcttccgt       780
cgcggcgatc ttttcgaagt ggtgccgggg cagaaattct acgagcgctg cgaaagccgc       840
ccgtccgaga tttccaaccg gctgaaggcg atcaatccgt cgccctattc cttcttcatc       900
aatctcggca accaggaata tctcgtcggt gcttcgccgg agatgttcgt gcgcgtttcc       960
ggccggcgca tcgagacctg cccgatctcc ggtacgatca agcgcggcga cgatccgatc      1020
gccgacagcg agcagatcct gaagctcttg aactcgaaga aggacgagtc cgagctcacc      1080
atgtgctcgg acgtcgaccg caacgacaag agccgggtct gcgtgccggg ctcggtcaag      1140
gtgatcggcc ggcgtcagat cgagatgtat tcgcggctga tccacacggt cgatcacatc      1200
gaggggcgcc tgcgcgacga tatggacgcc ttcgacgggt tcctcagcca cgcctgggcg      1260
gtgaccgtta ccgcgcgcgcc aaagctctgg ccatgcgct tcatcgagag ccacgagaag      1320
agcccgcgtg cctggtatgg cggcgcgatc ggcatggtcg gcttcaacgg cgacatgaat      1380
accgggctga ccttgcgtac catccgcatc aaggacggga tcgccgaggt gagggcgggt      1440
gcgacgctcc tctatgattc aatccggaa gaagaagaag ccgaaaccga actgaaggcc       1500
tctgccatga ttgcagccat ccgcgacgcg aaatccgcaa acagcgccaa atccgcgcgc      1560
gatgtcgccg ccgtcggcgc cggagtcagc atcctgctcg tcgatcacga ggacagcttc      1620
gtccataccc tcgcgaacta cttccgccag accggcgcgt ccgtcaccac cgtgcgcacg      1680
ccggtggccg aggaaatctt cgaccgggtc aagccggacc tcgtcgtgct ttcgcccggt      1740
```

-continued

```
cccggcaccc cgaaggactt cgactgcaag gcgacgatca agaaggcgcg ggcgcgggac    1800
ctgccgatct tcggcgtctg cctggggctg caggcgctcg cggaggccta tgcggcgac     1860 cttcgtcaac tggcgatccc gatgcatggg aagccctcgc gcatccgcgt gctcgaaccc    1920
ggcatcgtct tctccggcct cggcaaggag gtgacggtcg ggcgctatca ttcgattttc    1980
gccgatccgt ccaacctgcc gcgcgaattc gtgatcacgg ccgaaagcga agatggtacg    2040
atcatgggca tcgaacacag caaggagccg gtggcggccg tgcagttcca tccggaatcg    2100
atcatgacgc tgggcggcga cgccggcatg cggatgatcg agaacgtggt tgcccatctc    2160
gccaagcggg cgaagaccaa ggcagcctga                                     2190
```

<210> SEQ ID NO 212
<211> LENGTH: 729
<212> TYPE: PRT
<213> ORGANISM: Sinorhizobium meliloti

<400> SEQUENCE: 212

```
Met Ala Ala Val Ile Leu Glu Asp Gly Ala Glu Ser Tyr Thr Thr Lys
1               5                  10                  15

Gly Gly Ile Val Val Thr Arg Arg Arg Glu Ala Ser Tyr Ser Asp
            20                  25                  30

Ala Ile Ala Gly Tyr Val Asp Arg Leu Asp Glu Arg Arg Gly Ala Val
        35                  40                  45

Phe Ser Cys Asn Tyr Glu Tyr Pro Gly Arg Tyr Thr Arg Trp Asp Thr
    50                  55                  60

Ala Val Val Asp Pro Pro Leu Ala Ile Ser Ser Phe Gly Arg Ser Leu
65                  70                  75                  80

Trp Ile Glu Ala Tyr Asn Glu Arg Gly Glu Val Leu Leu Ala Leu Ile
                85                  90                  95

Ala Glu Asp Leu Lys Ser Val Ala Asp Ile Thr Leu Gly Ser Leu Ala
            100                 105                 110

Ala Arg Arg Leu Asp Leu Thr Ile Asn Glu Pro Asp Arg Val Phe Thr
        115                 120                 125

Glu Glu Glu Arg Ser Lys Met Pro Thr Val Phe Thr Val Leu Arg Ala
    130                 135                 140

Val Thr Asn Leu Phe His Ser Glu Glu Asp Ser Asn Leu Gly Leu Tyr
145                 150                 155                 160

Gly Ala Phe Gly Tyr Asp Leu Ala Phe Gln Phe Asp Ala Ile Glu Leu
                165                 170                 175

Lys Leu Ser Arg Pro Asp Asp Gln Arg Asp Met Val Leu Phe Leu Pro
            180                 185                 190

Asp Glu Ile Leu Val Val Asp His Tyr Ala Ala Lys Ala Trp Ile Asp
        195                 200                 205

Arg Tyr Asp Phe Ala Arg Glu Asn Leu Ser Thr Glu Gly Lys Ala Ala
    210                 215                 220

Asp Ile Ala Pro Glu Pro Phe Arg Ser Val Asp Ser Ile Pro Pro His
225                 230                 235                 240

Gly Asp His Arg Pro Gly Glu Tyr Ala Glu Leu Val Val Lys Ala Lys
                245                 250                 255

Glu Ser Phe Arg Arg Gly Asp Leu Phe Glu Val Val Pro Gly Gln Lys
            260                 265                 270

Phe Tyr Glu Arg Cys Glu Ser Arg Pro Ser Glu Ile Ser Asn Arg Leu
        275                 280                 285

Lys Ala Ile Asn Pro Ser Pro Tyr Ser Phe Phe Ile Asn Leu Gly Asn
    290                 295                 300
```

```
Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
                340                 345                 350

Lys Lys Asp Glu Ser Glu Leu Thr Met Cys Ser Asp Val Asp Arg Asn
                355                 360                 365

Asp Lys Ser Arg Val Cys Val Pro Gly Ser Val Lys Val Ile Gly Arg
        370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
                420                 425                 430

Arg Phe Ile Glu Ser His Glu Lys Ser Pro Arg Ala Trp Tyr Gly Gly
                435                 440                 445

Ala Ile Gly Met Val Gly Phe Asn Gly Asp Met Asn Thr Gly Leu Thr
450                 455                 460

Leu Arg Thr Ile Arg Ile Lys Asp Gly Ile Ala Glu Val Arg Ala Gly
465                 470                 475                 480

Ala Thr Leu Leu Tyr Asp Ser Asn Pro Glu Glu Glu Ala Glu Thr
                485                 490                 495

Glu Leu Lys Ala Ser Ala Met Ile Ala Ala Ile Arg Asp Ala Lys Ser
                500                 505                 510

Ala Asn Ser Ala Lys Ser Ala Arg Asp Val Ala Val Gly Ala Gly
                515                 520                 525

Val Ser Ile Leu Leu Val Asp His Glu Asp Ser Phe Val His Thr Leu
530                 535                 540

Ala Asn Tyr Phe Arg Gln Thr Gly Ala Ser Val Thr Thr Val Arg Thr
545                 550                 555                 560

Pro Val Ala Glu Glu Ile Phe Asp Arg Val Lys Pro Asp Leu Val Val
                565                 570                 575

Leu Ser Pro Gly Pro Gly Thr Pro Lys Asp Phe Asp Cys Lys Ala Thr
                580                 585                 590

Ile Lys Lys Ala Arg Ala Arg Asp Leu Pro Ile Phe Gly Val Cys Leu
                595                 600                 605

Gly Leu Gln Ala Leu Ala Glu Ala Tyr Gly Gly Asp Leu Arg Gln Leu
                610                 615                 620

Ala Ile Pro Met His Gly Lys Pro Ser Arg Ile Arg Val Leu Glu Pro
625                 630                 635                 640

Gly Ile Val Phe Ser Gly Leu Gly Lys Glu Val Thr Val Gly Arg Tyr
                645                 650                 655

His Ser Ile Phe Ala Asp Pro Ser Asn Leu Pro Arg Glu Phe Val Ile
                660                 665                 670

Thr Ala Glu Ser Glu Asp Gly Thr Ile Met Gly Ile Glu His Ser Lys
                675                 680                 685

Glu Pro Val Ala Ala Val Gln Phe His Pro Glu Ser Ile Met Thr Leu
                690                 695                 700

Gly Gly Asp Ala Gly Met Arg Met Ile Glu Asn Val Val Ala His Leu
705                 710                 715                 720

Ala Lys Arg Ala Lys Thr Lys Ala Ala
```

-continued

725

<210> SEQ ID NO 213
<211> LENGTH: 13596
<212> TYPE: DNA
<213> ORGANISM: Artificial Sequence
<220> FEATURE:
<223> OTHER INFORMATION: pMON68065;Figure 48; the expression vector for
      Zm-ASA2-CTP +18::AgroAS(S51C) mutant allele

<400> SEQUENCE: 213

| | | | | |
|---|---|---|---|---|
| gcgccaaatc | gtgaagtttc | tcatctaagc | ccccatttgg acgtgaatgt agacacgtcg | 60 |
| aaataaagat | ttccgaatta | gaataatttg | tttattgctt tcgcctataa atacgacgga | 120 |
| tcgtaatttg | tcgttttatc | aaaatgtact | ttcattttat aataacgctg cggacatcta | 180 |
| cattttgaa | ttgaaaaaaa | attggtaatt | actctttctt tttctccata ttgaccatca | 240 |
| tactcattgc | tgatccatgt | agatttcccg | gacatgaagc catttacaat tgaatatatc | 300 |
| ctgccgccgc | tgccgctttg | cacccggtgg | agcttgcatg ttggtttcta cgcagaactg | 360 |
| agccggttag | gcagataatt | tccattgaga | actgagccat gtgcaccttc cccccaacac | 420 |
| ggtgagcgac | gggcaacgg | agtgatccac | atgggacttt tcctagcttg gctgccattt | 480 |
| ttggggtgag | gccgttcgcg | gccgaggggc | gcagcccctg gggggatggg aggcccgcgt | 540 |
| tagcgggccg | ggagggttcg | agaaggggg | gcacccccct tcggcgtgcg cggtcacgcg | 600 |
| cacagggcgc | agccctggtt | aaaaacaagg | tttataaata ttggtttaaa agcaggttaa | 660 |
| aagacaggtt | agcggtggcc | gaaaaacggg | cggaaaccct tgcaaatgct ggattttctg | 720 |
| cctgtggaca | gcccctcaaa | tgtcaatagg | tgcgcccctc atctgtcagc actctgcccc | 780 |
| tcaagtgtca | aggatcgcgc | ccctcatctg | tcagtagtcg cgcccctcaa gtgtcaatac | 840 |
| cgcagggcac | ttatccccag | gcttgtccac | atcatctgtg ggaaactcgc gtaaaatcag | 900 |
| gcgttttcgc | cgatttgcga | ggctggccag | ctccacgtcg ccggccgaaa tcgagcctgc | 960 |
| ccctcatctg | tcaacgccgc | gccgggtgag | tcggcccctc aagtgtcaac gtccgcccct | 1020 |
| catctgtcag | tgagggccaa | gttttccgcg | aggtatccac aacgccggcg gccggccgcg | 1080 |
| gtgtctcgca | cacggcttcg | acggcgtttc | tggcgcgttt gcagggccat agacggccgc | 1140 |
| cagcccagcg | gcgagggcaa | ccagcccggt | gagcgtcgga aagggtcgat cgaccgatgc | 1200 |
| ccttgagagc | cttcaaccca | gtcagctcct | tccggtgggc gcggggcatg actatcgtcg | 1260 |
| ccgcacttat | gactgtcttc | tttatcatgc | aactcgtagg acaggtgccg gcagcgctct | 1320 |
| gggtcatttt | cggcgaggac | cgctttcgct | ggagcgcgac gatgatcggc ctgtcgcttg | 1380 |
| cggtattcgg | aatcttgcac | gccctcgctc | aagccttcgt cactggtccc gccaccaaac | 1440 |
| gtttcggcga | gaagcaggcc | attatcgccg | gcatggcggc cgacgcgctg ggctacgtct | 1500 |
| tgctggcgtt | cgcgacgcga | ggctggatgg | ccttccccat tatgattctt ctcgcttccg | 1560 |
| gcggcatcgg | gatgcccgcg | ttgcaggcca | tgctgtccag gcaggtagat gacgaccatc | 1620 |
| agggacagct | tcaaggatcg | ctcgcggctc | ttaccagcct aacttcgatc attggaccgc | 1680 |
| tgatcgtcac | ggcgatttat | gccgcctcgg | cgagcacatg gaacgggttg gcatggattg | 1740 |
| taggcgccgc | cctataccttg | gtctgcctcc | ccgcgttgcg tcgcggtgca tggagccggg | 1800 |
| ccacctcgac | ctgaatggaa | gccggcggca | cctcgctaac ggattcacca ctccaagaat | 1860 |
| tggagccaat | caattcttgc | ggagaactgt | gaatgcgcaa accaaccctt ggcagaacat | 1920 |
| atccatcgcg | tccgccatct | ccagcagccg | cacgcggcgc atctcgggca gcgttgggtc | 1980 |
| ctggccacgg | gtgcgcatga | tcgtgctcct | gtcgttgagg acccggctag gctggcgggg | 2040 |

```
ttgccttact ggttagcaga atgaatcacc gatacgcgag cgaacgtgaa gcgactgctg    2100
ctgcaaaacg tctgcgacct gagcaacaac atgaatggtc ttcggtttcc gtgtttcgta    2160
aagtctggaa acgcggaagt cagcgccctg caccattatg ttccggatct gcatcgcagg    2220
atgctgctgg ctaccctgtg gaacacctac atctgtatta acgaagcgct ggcattgacc    2280
ctgagtgatt tttctctggt cccgccgcat ccataccgcc agttgtttac cctcacaacg    2340
ttccagtaac cgggcatgtt catcatcagt aacccgtatc gtgagcatcc tctctcgttt    2400
catcggtatc attaccccca tgaacagaaa tccccttac acggaggcat cagtgaccaa     2460
acaggaaaaa accgcccttta acatggcccg ctttatcaga agccagacat taacgcttct   2520
ggagaaactc aacagctgg acgcggatga acaggcagac atctgtgaat cgcttcacga    2580
ccacgctgat gagctttacc gcagctgcct cgcgcgtttc ggtgatgacg gtgaaaacct    2640
ctgacacatg cagctcccgg agacggtcac agcttgtctg taagcggatg ccgggagcag    2700
acaagcccgt cagggcgcgt cagcgggtgt tggcgggtgt cggggcgcag ccatgaccca    2760
gtcacgtagc gatagcggag tgtatactgg cttaactatg cggcatcaga gcagattgta    2820
ctgagagtgc accatatgcg gtgtgaaata ccgcacagat gcgtaaggag aaaataccgc    2880
atcaggcgct cttccgcttc ctcgctcact gactcgctgc gctcggtcgt tcggctgcgg    2940
cgagcggtat cagctcactc aaaggcggta atacggttat ccacagaatc aggggataac    3000
gcaggaaaga acatgtgagc aaaaggccag caaaaggcca ggaaccgtaa aaaggccgcg    3060
ttgctggcgt ttttccatag gctccgcccc cctgacgagc atcacaaaaa tcgacgctca    3120
agtcagaggt ggcgaaaccc gacaggacta taaagatacc aggcgtttcc ccctggaagc    3180
tccctcgtgc gctctcctgt tccgaccctg ccgcttaccg gatacctgtc cgcctttctc    3240
ccttcgggaa gcgtggcgct ttctcatagc tcacgctgta ggtatctcag ttcggtgtag    3300
gtcgttcgct ccaagctggg ctgtgtgcac gaaccccccg ttcagcccga ccgctgcgcc    3360
ttatccggta actatcgtct tgagtccaac ccggtaagac acgacttatc gccactggca    3420
gcagccactg gtaacaggat tagcagagcg aggtatgtag cggtgctac agagttcttg      3480 aagtggtggc ctaactacgg ctacactaga aggacagtat ttggtatctg cgctctgctg    3540
aagccagtta ccttcggaaa aagagttggt agctcttgat ccggcaaaca aaccaccgct    3600
ggtagcggtg gtttttttgt ttgcaagcag cagattacgc gcagaaaaaa aggatctcaa    3660
gaagatcctt tgatcttttc tacggggtct gacgctcagt ggaacgaaaa ctcacgttaa    3720
gggattttgg tcatgagatt atcaaaaagg atcttcacct agatcctttt aaattaaaaa    3780
tgaagtttta aatcaatcta agtatatat gagtaaactt ggtctgacag ttaccaatgc     3840
ttaatcagtg aggcacctat ctcagcgatc tgtctatttc gttcatccat agttgcctga    3900
ctccccgtcg tgtagataac tacgatacgg gagggcttac catctggccc cagtgctgca    3960
atgataccgc gagacccacg ctcaccggct ccagatttat cagcaataaa ccagccagcc    4020
ggaagggccg agcgcagaag tggtcctgca actttatccg cctccatcca gtctattaat    4080
tgttgccggg aagctagagt aagtagttcg ccagttaata gtttgcgcaa cgttgttgcc    4140
attgctgcag gtcgggagca caggatgacg cctaacaatt cattcaagcc gacaccgctt    4200
cgcggcgcgg cttaattcag gagttaaaca tcatgaggga agcggtgatc gccgaagtat    4260
cgactcaact atcagaggta gttggcgtca tcgagcgcca tctcgaaccg acgttgctgg    4320
ccgtacattt gtacggctcc gcagtggatg gcggcctgaa gccacacagt gatattgatt    4380
tgctggttac ggtgaccgta aggcttgatg aaacaacgcg gcgagctttg atcaacgacc    4440
```

-continued

```
ttttggaaac ttcggcttcc cctggagaga gcgagattct ccgcgctgta gaagtcacca      4500
ttgttgtgca cgacgacatc attccgtggc gttatccagc taagcgcgaa ctgcaatttg      4560
gagaatggca gcgcaatgac attcttgcag gtatcttcga gccagccacg atcgacattg      4620
atctggctat cttgctgaca aaagcaagag aacatagcgt tgccttggta ggtccagcgg      4680
cggaggaact ctttgatccg gttcctgaac aggatctatt tgaggcgcta aatgaaacct      4740
taacgctatg gaactcgccg cccgactggg ctggcgatga gcgaaatgta gtgcttacgt      4800
tgtcccgcat ttggtacagc gcagtaaccg gcaaaatcgc gccgaaggat gtcgctgccg      4860
actgggcaat ggagcgcctg ccggcccagt atcagcccgt catacttgaa gctaggcagg      4920
cttatcttgg acaagaagat cgcttggcct cgcgcgcaga tcagttggaa gaatttgttc      4980
actacgtgaa aggcgagatc accaaggtag tcggcaaata atgtctaaca attcgttcaa      5040
gccgacgccg cttcgcggcg cggcttaact caagcgttag atgctgcagg catcgtggtg      5100
tcacgctcgt cgtttggtat ggcttcattc agctccggtt cccaacgatc aaggcgagtt      5160
acatgatccc ccatgttgtg caaaaaagcg gttagctcct tcggtcctcc gatcgaggat      5220
ttttcggcgc tgcgctacgt ccgcgaccgc gttgagggat caagccacag cagcccactc      5280
gaccttctag ccgacccaga cgagccaagg gatctttttg gaatgctgct ccgtcgtcag      5340
gctttccgac gtttgggtgg ttgaacagaa gtcattatcg cacggaatgc caagcactcc      5400
cgagggaaac cctgtggttg gcatgcacat acaaatggac gaacggataa accttttcac      5460 gccctttttaa atatccgatt attctaataa acgctctttt ctcttaggtt tacccgccaa      5520
tatatcctgt caaacactga tagtttaaac tgaaggcggg aaacgacaat ctgatcccca      5580
tcaagctagc ttctgcaggt cctgctcgag gtcactaagc aactaacttt gaggaatgag      5640
gtgatgatga attaactcac tccattccac aaaccaaaca aaaatttgag gagtgagaag      5700
atgattgact atctcattcc tcaaaccaaa cacctcaaat atatctgcta tcgggattgg      5760
cattcctgta tccctacgcc cgtgtaccc ctgtttagag aacctccaaa ggtataagat      5820
ggcgaagatt attgttgtct tgtctttcat catatatcga gtctttccct aggatattat      5880
tattggcaat gagcattaca cggttaatcg attgagagaa catgcatctc accttcagca      5940
aataattacg ataatccata ttttacgctt cgtaacttct catgagtttc gatatacaaa      6000
tttgttttct ggacacccta ccattcatcc tcttcggaga agagaggaag tgtcctcaat      6060
ttaaatatgt tgtcatgctg tagttcttca caaaatctca acaggtacca agcacattgt      6120
ttccacaaat tatattttag tcacaataaa tctatattat tattaatata ctaaaactat      6180
actgacgctc agatgctttt actagttctt gctagtatgt gatgtaggtc tacgtggacc      6240
agaaaatagt gagacacgga agacaaaaga agtaaaagag gcccggacta cggcccacat      6300
gagattcggc cccgccacct ccggcaacca gcggccgatc caacggcagt gcgcgcacac      6360
acacaacctc gtatatatcg ccgcgcggaa gcggcgcgac cgaggaagcc ttgtcctcga      6420
caccccctac acaggtgtcg cgctgccccc gacacgagtc ccgcatgcgt cccacgcggc      6480
cgcgccagat cccgcctccg cgcgttgcca cgccctctat aaacacccag ctctccctcg      6540
ccctcatcta cctcactcgt agtcgtagct caagcatcag cggcagcggc agcggcagga      6600
tctctgggca gcgtgcgcac gtggggtatc tagctcgctc tgctagccta ccaatcgaat      6660
tcctgcaggt cgactctaga ggatctaccg tcttcggtac gcgctcactc cgccctctgc      6720
ctttgttact gccacgtttc tctgaatgct ctcttgtgtg gtgattgctg agagtggttt      6780
agctggatct agaattacac tctgaaatcg tgttctgcct gtgctgatta cttgccgtcc      6840
```

```
tttgtagcag caaaatatag ggacatggta gtacgaaacg aagatagaac ctacacagca    6900
atacgagaaa tgtgtaattt ggtgcttagc ggtatttatt taagcacatg ttggtgttat    6960
agggcacttg gattcagaag tttgctgtta atttaggcac aggcttcata ctacatgggt    7020
caatagtata gggattcata ttataggcga tactataata atttgttcgt ctgcagagct    7080
tattatttgc caaaattaga tattcctatt ctgtttttgt ttgtgtgctg ttaaattgtt    7140
aacgcctgaa ggaataaata taaatgacga aattttgatg tttatctctg ctcctttatt    7200
gtgaccataa gtcaagatca gatgcacttg ttttaaatat tgttgtctga agaaataagt    7260
actgacagta ttttgatgca ttgatctgct tgtttgttgt aacaaaattt aaaaataaag    7320
agtttccttt ttgttgctct ccttacctcc tgatggtatc tagtatctac caactgacac    7380
tatattgctt ctctttacat acgtatcttg ctcgatgcct tctccctagt gttgaccagt    7440
gttactcaca tagtctttgc tcatttcatt gtaatgcaga taccaagcgg cctctagagg    7500
actccgatct atggaatccc tagccgccac ctccgtgttc gcgccctccc gcgtcgccgt    7560
cccggcggcg cgggccctgg ttagggcggg acggtggta ccaaccaggc ggacgagcag    7620
ccggagcgga accagcgggg tgaaatgctc tgctgccgtg acgccgcagg cgagcccagt    7680
gattagcagg agcgctgcgg cggccatggt aacgatcatt caggatgacg gagcggagac    7740
ctacgagacg aaaggcggca tccaggtcag ccgaaagcgc cggcccaccg attatgccaa    7800
cgccatcgat aattacatcg aaaagcttga ttcccatcgc ggcgcggttt tttcgtgcaa    7860
ctatgaatat ccgggccgtt acccccgctg ggatacggcc atcgtcgatc cgccgctcgg    7920
catttcctgt tttggccgca agatgtggat cgaagcctat aatggccgcg gcgaagtgct    7980
gctcgatttc attacggaaa agctgaaggc gacacccgat ctcaccctcg gcgcttcctc    8040
gacccgccgg ctcgatctta ccgtcaacga accggaccgt gtcttcaccg aagaagaacg    8100
ctcgaaaatc ccgacggtct tcaccgctct cagagccatc gtcgacctct tctattcgag    8160
cgcggattcg gccatcggcc tgttcggtgc cttcggttac gatctcgcct tccagttcga    8220
cgcgatcaag ctttcgctgg cgcgtccgga agaccagcgt gacatggtgc tgtttctgcc    8280
cgatgaaatc ctcgtcgttg atcactattc cgccaaggcc tggatcgacc gttacgattt    8340
cgagaaggac ggcatgacga cggacggcaa atcctccgac attaccccg atcccttcaa    8400 gaccaccgat accatcccgc caagggcga tcaccgtccc ggcgaatatt ccgagcttgt    8460
ggtgaaggcc aaggaaagct ccgccgcgg cgacctgttc gaggtcgttc ccggccagaa    8520
attcatggag cgttgcgaaa gcaatccgtc ggcgatttcc cgccgcctga aggcgatcaa    8580
cccgtcgccc tattccttct tcatcaatct cggcgatcag gaatatctgg tcggcgcctc    8640
gccggaaatg ttcgtgcgcg tctccggccg tcgcatcgag acctgcccga tatcaggcac    8700
catcaagcgc ggcgacgatc cgattgccga cagcgagcag attttgaaac tgctcaactc    8760
gaaaaaggac gaatccgaac tgaccatgtg ctcggacgtg accgcaacg acaagagccg    8820 cgtctgcgag ccgggttcgg tgaaggtcat tggccgccgc cagatcgaga tgtattcacg    8880
cctcatccac accgtcgatc acatcgaagg ccgcctgcgc gacgatatgg acgcctttga    8940
cggtttcctc agccacgcct gggccgtcac cgtcaccggt gcaccaaagc tgtgggccat    9000
gcgcttcatc gaaggtcatg aaaagagccc gcgcgcctgg tatggcggtg cgatcggcat    9060
ggtcggcttc aacggcgaca tgaataccgg cctgacgctg cgcaccatcc ggatcaagga    9120
cggtattgcc gaagtgcgcg ccggcgcgac cctgctcaat gattccaacc gcaggaaga    9180 agaagccgaa accgaactga aggcctccgc catgatatca gccattcgtg acgcaaaagg    9240
```

```
caccaactct gccgccacca agcgtgatgc cgccaaagtc ggcaccggcg tcaagatcct    9300
gctcgtcgac cacgaagaca gcttcgtgca cacgctggcg aattatttcc gccagacggg    9360
cgcgacggtc tcgaccgtca gatcaccggt cgcagccgac gtgttcgatc gcttccagcc    9420
ggacctcgtt gtcctgtcgc ccggacccgg cagcccgacg gatttcgact gcaaggcaac    9480
gatcaaggcc gcccgcgccc gcgatctgcc gatcttcggc gtttgcctcg gtctgcaggc    9540
attggcagaa gcctatggcg gcgagctgcg ccagcttgct gtgcccatgc acggcaagcc    9600
ttcgcgcatc cgcgtgctgg aacccggcct cgtcttctcc ggtctcggca aggaagtcac    9660
ggtcggtcgt taccattcga tcttcgccga tcccgccacc ctgccgcgtg atttcatcat    9720
caccgcagaa agcgaggacg gcacgatcat gggcatcgaa cacgccaagg aaccggtggc    9780
cgccgttcag ttccacccgg aatcgatcat gacgctcgga caggacgcgg gcatgcggat    9840
gatcgagaat gtcgtggtgc atctgacccg caaggcgaag accaaggccg cgtgatggcg    9900
ctcgatgaca cggttatatc actagtgcgg ccatcggatc cgttggcaat gcggataaag    9960
aataactaaa taaataaata aataaattgc aagcaattgc gttgctgcta tgtactgtaa   10020
aagtttctta taatatcagt tctgaatgct aaggacatcc ctcaagatgg tctttctatt   10080
tttgtgttcc cgttccaatg tactgttggt atcctcttgg agattcatca atatgagaaa   10140
acagagaatg gacaaccctc ccttatctta tggctcgagc ggccgctcta gaactagtgg   10200 atcccccccct taattaaggg ggctgcagga attcataact tcgtataatg tatgctatac   10260
gaagttatgt ttcgaggtca ttcatatgct tgagaagaga gtcggatag tccaaaataa    10320 aacaaggta agattacctg gtcaaaagtg aaaacatcag ttaaaggtg gtataaagta     10380 aaatatcggt aataaaggt ggcccaaagt gaaatttact cttttctact attataaaaa    10440
ttgaggatgt ttttgtcggt actttgatac gtcattttg tatgaattgg ttttaagtt     10500 tattcgctttt tggaaatgca tatctgtatt tgagtcgggt tttaagttcg tttgcttttg   10560
taaatacaga gggatttgta taagaaatat ctttagaaaa acccatatgc taatttgaca   10620
taatttttga gaaaaatata tattcaggcg aattctcaca atgaacaata ataagattaa   10680
aatagctttc ccccgttgca gcgcatgggt atttttttcta gtaaaaataa aagataaact   10740
tagactcaaa acatttacaa aaacaacccc taaagttcct aaagcccaaa gtgctatcca   10800
cgatccatag caagcccagc ccaacccaac ccaacccaac ccaccccagt ccagccaact   10860
ggacaatagt ctccacaccc ccccactatc accgtgagtt gtccgcacgc accgcacgtc   10920
tcgcagccaa aaaaaaaaag aaagaaaaaa aagaaaaaga aaaacagca ggtgggtccg    10980 ggtcgtgggg gccggaaacg cgaggaggat cgcgagccag cgacgaggcc ggccctccct   11040
ccgcttccaa agaaacgccc cccatcgcca ctatatacat acccccccct ctcctcccat   11100
ccccccaacc ctaccaccac caccaccacc acctccacct cctcccccct cgctgccgga   11160
cgacgagctc ctccccccctc cccctccgcc gccgccgcgc cggtaaccac cccgcccctc   11220
tcctctttct ttctccgttt ttttttccgt ctcggtctcg atctttggcc ttggtagttt   11280
gggtgggcga gaggcggctt cgtgcgcgcc cagatcggtg cgcgggaggg gcgggatctc   11340
gcggctgggg ctctcgccgg cgtggatccg gcccggatct cgcggggaat ggggctctcg   11400
gatgtagatc tgcgatccgc cgttgttggg ggagatgatg gggggtttaa aatttccgcc   11460
gtgctaaaca agatcaggaa gaggggaaaa gggcactatg gtttatattt ttatatattt   11520
ctgctgcttc gtcaggctta gatgtgctag atctttcttt cttcttttg tgggtagaat     11580 ttgaatccct cagcattgtt catcggtagt ttttcttttc atgatttgtg acaaatgcag   11640
```

```
cctcgtgcgg agcttttttg taggtagaag tgatcaacca tggcgcaagt tagcagaatc    11700
tgcaatggtg tgcagaaccc atctcttatc tccaatctct cgaaatccag tcaacgcaaa    11760
tctcccttat cggtttctct gaagacgcag cagcatccac gagcttatcc gatttcgtcg    11820
tcgtggggat tgaagaagag tgggatgacg ttaattggct ctgagcttcg tcctcttaag    11880
gtcatgtctt ctgtttccac ggcgtgcatg cttcacggtg caagcagccg gcccgcaacc    11940
gcccgcaaat cctctggcct ttccggaacc gtccgcattc ccggcgacaa gtcgatctcc    12000
caccggtcct tcatgttcgg cggtctcgcg agcggtgaaa cgcgcatcac cggccttctg    12060
gaaggcgagg acgtcatcaa tacgggcaag gccatgcagg cgatgggcgc ccgcatccgt    12120
aaggaaggcg acacctggat catcgatggc gtcggcaatg gcggcctcct ggcgcctgag    12180
gcgccgctcg atttcggcaa tgccgccacg ggctgccgcc tgacgatggg cctcgtcggg    12240
gtctacgatt tcgacagcac cttcatcggc gacgcctcgc tcacaaagcg cccgatgggc    12300
cgcgtgttga acccgctgcg cgaaatgggc gtgcaggtga atcggaagga cggtgaccgt    12360
cttcccgtta ccttgcgcgg gccgaagacg ccgacgccga tcacctaccg cgtgccgatg    12420
gcctccgcac aggtgaagtc cgccgtgctg ctcgccggcc tcaacacgcc cggcatcacg    12480
acggtcatcg agccgatcat gacgcgcgat catacggaaa agatgctgca gggctttggc    12540
gccaaccttc ccgtcgagac ggatgcggac ggcgtgcgca ccatccgcct ggaaggccgc    12600
ggcaagctca ccggccaagt catcgacgtg ccgggcgacc cgtcctcgac ggccttcccg    12660
ctggttgcgg ccctgcttgt tccgggctcc gacgtcacca tcctcaacgt gctgatgaac    12720
cccacccgca ccggcctcat cctgacgctg caggaaatgg gcgccgacat cgaagtcatc    12780
aacccgcgcc ttgccggcgg cgaagacgtg cggacctgc gcgttcgctc ctccacgctg    12840
aagggcgtca cggtgccgga agaccgcgcg ccttcgatga tcgacgaata tccgattctc    12900
gctgtcgccg ccgccttcgc ggaaggggcg accgtgatga acggtctgga agaactccgc    12960
gtcaaggaaa gcgaccgcct ctcggccgtc gccaatggcc tcaagctcaa tggcgtggat    13020
tgcgatgagg gcgagacgtc gctcgtcgtg cgtggccgcc ctgacggcaa ggggctcggc    13080
aacgcctcgg gcgccgccgt cgccacccat ctcgatcacc gcatcgccat gagcttcctc    13140
gtcatgggcc tcgtgtcgga aaaccctgtc acggtggacg atgccacgat gatcgccacg    13200
agcttcccgg agttcatgga cctgatggcc gggctgggcg cgaagatcga actctccgat    13260
acgaaggctg cctgatgagc tcgaattccc gatcgttcaa acatttggca ataaagtttc    13320
ttaagattga atcctgttgc cggtcttgcg atgattatca tataatttct gttgaattac    13380
gttaagcatg taataattaa catgtaatgc atgacgttat ttatgagatg gttttttatg    13440
attagagtcc cgcaattata catttaatac gcgatagaaa acaaaatata gcgcgcaaac    13500
taggataaat tatcgcgcgc ggtgtcatct atgttactag atcggggata acgatcaagc    13560
tataacttcg tataatgtat gctatacgaa gttatc                              13596
```

<210> SEQ ID NO 214
<211> LENGTH: 13559
<212> TYPE: DNA
<213> ORGANISM: Artificial Sequence
<220> FEATURE:
<223> OTHER INFORMATION: pMON68066;Figure 49;the expression vector for
      Zm-ASA2-CTP +18::AgroAS(S51C)-nno

<400> SEQUENCE: 214

```
gcgccaaatc gtgaagtttc tcatctaagc ccccatttgg acgtgaatgt agacacgtcg     60
```

```
aaataaagat ttccgaatta gaataatttg tttattgctt tcgcctataa atacgacgga    120
tcgtaatttg tcgttttatc aaaatgtact ttcattttat aataacgctg cggacatcta    180 cattttgaa ttgaaaaaaa attggtaatt actctttctt tttctccata ttgaccatca     240
tactcattgc tgatccatgt agatttcccg gacatgaagc catttacaat tgaatatatc    300
ctgccgccgc tgccgctttg cacccggtgg agcttgcatg ttggtttcta cgcagaactg    360
agccggttag gcagataatt tccattgaga actgagccat gtgcaccttc ccccaacac     420 ggtgagcgac ggggcaacgg agtgatccac atgggacttt tcctagcttg gctgccattt    480 ttgggggtgag ccgttcgcg gccgaggggc gcagcccctg ggggatggg aggcccgcgt     540 tagcgggccg ggagggttcg agaagggggg gcaccccct tcggcgtgcg cggtcacgcg     600
cacagggcgc agccctggtt aaaaacaagg tttataaata ttggtttaaa agcaggttaa    660
aagacaggtt agcggtggcc gaaaaacggg cggaaaccct tgcaaatgct ggattttctg    720
cctgtggaca gcccctcaaa tgtcaatagg tgcgcccctc atctgtcagc actctgcccc    780
tcaagtgtca aggatcgcgc ccctcatctg tcagtagtcg cgcccctcaa gtgtcaatac    840
cgcagggcac ttatcccag gcttgtccac atcatctgtg ggaaactcgc gtaaaatcag     900
gcgttttcgc cgatttgcga ggctggccag ctccacgtcg ccggccgaaa tcgagcctgc    960
ccctcatctg tcaacgccgc gccgggtgag tcggcccctc aagtgtcaac gtccgccct    1020 catctgtcag tgagggccaa gttttccgcg aggtatccac aacgccggcg gccggccgcg   1080
gtgtctcgca cacggcttcg acggcgtttc tggcgcgttt gcagggccat agacggccgc   1140
cagcccagcg gcgagggcaa ccagcccggt gagcgtcgga aagggtcgat cgaccgatgc   1200
ccttgagagc cttcaaccca gtcagctcct tccggtgggc gcggggcatg actatcgtcg   1260
ccgcacttat gactgtcttc tttatcatgc aactcgtagg acaggtgccg gcagcgctct   1320
gggtcatttt cggcgaggac cgctttcgct ggagcgcgac gatgatcggc ctgtcgcttg   1380
cggtattcgg aatcttgcac gccctcgctc aagccttcgt cactggtccc gccaccaaac   1440
gtttcggcga gaagcaggcc attatcgccg gcatggcggc cgacgcgctg ggctacgtct   1500
tgctggcgtt cgcgacgcga ggctggatgg ccttcccat tatgattctt ctcgcttccg    1560
gcggcatcgg gatgcccgcg ttgcaggcca tgctgtccag gcaggtagat gacgaccatc   1620
agggacagct tcaaggatcg ctcgcggctc ttaccagcct aacttcgatc attgaccgc    1680 tgatcgtcac ggcgatttat gccgcctcgg cgagcacatg gaacggggttg catggattg    1740 taggcgccgc cctataccgt gtctgcctcc ccgcgttgcg tcgcggtgca tggagccggg   1800
ccacctcgac ctgaatggaa gccggcggca cctcgctaac ggattcacca ctccaagaat   1860
tggagccaat caattcttgc ggagaactgt gaatgcgcaa accaacccctt ggcagaacat   1920 atccatcgcg tccgccatct ccagcagccg cacgcggcgc atctcgggca gcgttgggtc   1980
ctggccacgg gtgcgcatga tcgtgctcct gtcgttgagg acccggctag gctggcgggg   2040
ttgccttact ggttagcaga atgaatcacc gatacgcgag cgaacgtgaa gcgactgctg   2100
ctgcaaaacg tctgcgacct gagcaacaac atgaatggtc ttcggttcc gtgtttcgta   2160 aagtctggaa acgcggaagt cagcgccctg caccattatg ttccggatct gcatcgcagg   2220
atgctgctgg ctaccctgtg gaacacctac atctgtatta acgaagcgct ggcattgacc   2280
ctgagtgatt tttctctggt cccgccgcat ccataccgcc agttgtttac cctcacaacg   2340
ttccagtaac cggcatgtt catcatcagt aaccccgtatc gtgagcatcc tctctcgttt    2400
catcggtatc attaccccca tgaacagaaa tcccccttac acggaggcat cagtgaccaa   2460
```

```
acaggaaaaa accgcccttta acatggcccg ctttatcaga agccagacat taacgcttct    2520
ggagaaactc aacgagctgg acgcggatga acaggcagac atctgtgaat cgcttcacga    2580
ccacgctgat gagctttacc gcagctgcct cgcgcgtttc ggtgatgacg gtgaaaacct    2640
ctgacacatg cagctcccgg agacggtcac agcttgtctg taagcggatg ccgggagcag    2700
acaagcccgt cagggcgcgt cagcgggtgt tggcgggtgt cggggcgcag ccatgaccca    2760
gtcacgtagc gatagcggag tgtatactgg cttaactatg cggcatcaga gcagattgta    2820
ctgagagtgc accatatgcg gtgtgaaata ccgcacagat gcgtaaggag aaaataccgc    2880
atcaggcgct cttccgcttc ctcgctcact gactcgctgc gctcggtcgt tcggctgcgg    2940
cgagcggtat cagctcactc aaaggcggta atacggttat ccacagaatc aggggataac    3000
gcaggaaaga acatgtgagc aaaaggccag caaaaggcca ggaaccgtaa aaaggccgcg    3060
ttgctggcgt ttttccatag gctccgcccc cctgacgagc atcacaaaaa tcgacgctca    3120
agtcagaggt ggcgaaaccc gacaggacta taaagatacc aggcgtttcc ccctggaagc    3180
tccctcgtgc gctctcctgt tccgaccctg ccgcttaccg gatacctgtc cgcctttctc    3240
ccttcgggaa gcgtggcgct ttctcatagc tcacgctgta ggtatctcag ttcggtgtag    3300
gtcgttcgct ccaagctggg ctgtgtgcac gaaccccccg ttcagcccga ccgctgcgcc    3360
ttatccggta actatcgtct tgagtccaac ccggtaagac acgacttatc gccactggca    3420
gcagccactg gtaacaggat tagcagagcg aggtatgtag gcggtgctac agagttcttg    3480
aagtggtggc ctaactacgg ctacactaga aggacagtat ttggtatctg cgctctgctg    3540
aagccagtta ccttcggaaa aagagttggt agctcttgat ccggcaaaca aaccaccgct    3600
ggtagcggtg ttttttttgt ttgcaagcag cagattacgc gcagaaaaaa aggatctcaa    3660
gaagatcctt tgatcttttc tacggggtct gacgctcagt ggaacgaaaa ctcacgttaa    3720
gggattttgg tcatgagatt atcaaaaagg atcttcacct agatcctttt aaattaaaaa    3780
tgaagtttta aatcaatcta agtatatat gagtaaactt ggtctgacag ttaccaatgc    3840
ttaatcagtg aggcacctat ctcagcgatc tgtctatttc gttcatccat agttgcctga    3900
ctccccgtcg tgtagataac tacgatacgg gagggcttac catctggccc cagtgctgca    3960
atgataccgc gagacccacg ctcaccggct ccagatttat cagcaataaa ccagccagcc    4020
ggaagggccg agcgcagaag tggtcctgca actttatccg cctccatcca gtctattaat    4080
tgttgccggg aagctagagt aagtagttcg ccagttaata gtttgcgcaa cgttgttgcc    4140
attgctgcag gtcgggagca caggatgacg cctaacaatt cattcaagcc gacaccgctt    4200
cgcggcgcgg cttaattcag gagttaaaca tcatgaggga agcggtgatc gccgaagtat    4260
cgactcaact atcagaggta gttggcgtca tcgagcgcca tctcgaaccg acgttgctgg    4320
ccgtacattt gtacggctcc gcagtggatg gcggcctgaa gccacacagt gatattgatt    4380
tgctggttac ggtgaccgta aggcttgatg aaacaacgcg gcgagctttg atcaacgacc    4440
ttttggaaac ttcggcttcc cctggagaga gcgagattct ccgcgctgta gaagtcacca    4500
ttgttgtgca cgacgacatc attccgtggc gttatccagc taagcgcgaa ctgcaatttg    4560
gagaatggca gcgcaatgac attcttgcag gtatcttcga gccagccacg atcgacattg    4620
atctggctat cttgctgaca aaagcaagag aacatagcgt tgccttggta ggtccagcgg    4680
cggaggaact cttttgatccg gttcctgaac aggatctatt tgaggcgcta aatgaaacct    4740
taacgctatg gaactcgccg cccgactggg ctggcgatga gcgaaatgta gtgcttacgt    4800
tgtcccgcat ttggtacagc gcagtaaccg gcaaaatcgc gccgaaggat gtcgctgccg    4860
```

```
actgggcaat ggagcgcctg ccggcccagt atcagcccgt catacttgaa gctaggcagg    4920
cttatcttgg acaagaagat cgcttggcct cgcgcgcaga tcagttggaa gaatttgttc    4980
actacgtgaa aggcgagatc accaaggtag tcggcaaata atgtctaaca attcgttcaa    5040
gccgacgccg cttcgcggcg cggcttaact caagcgttag atgctgcagg catcgtggtg    5100
tcacgctcgt cgtttggtat ggcttcattc agctccggtt cccaacgatc aaggcgagtt    5160
acatgatccc ccatgttgtg caaaaaagcg gttagctcct tcggtcctcc gatcgaggat    5220
ttttcggcgc tgcgctacgt ccgcgaccgc gttgagggat caagccacag cagcccactc    5280
gaccttctag ccgacccaga cgagccaagg gatcttttg gaatgctgct ccgtcgtcag    5340
gctttccgac gtttgggtgg ttgaacagaa gtcattatcg cacggaatgc caagcactcc    5400
cgagggaac cctgtggttg gcatgcacat acaaatggac gaacggataa acctttcac     5460
gccctttaa atatccgatt attctaataa acgctctttt ctcttaggtt tacccgccaa    5520
tatatcctgt caaacactga tagttttaaac tgaaggcggg aaacgacaat ctgatcccca    5580
tcaagctagc ttctgcaggt cctgctcgag gtcactaagc aactaacttt gaggaatgag    5640
gtgatgatga attaactcac tccattccac aaaccaaaca aaaatttgag gagtgagaag    5700
atgattgact atctcattcc tcaaaccaaa cacctcaaat atatctgcta tcgggattgg    5760
cattcctgta tccctacgcc cgtgtacccc ctgtttagag aacctccaaa ggtataagat    5820
ggcgaagatt attgttgtct tgtctttcat catatatcga gtctttccct aggatattat    5880
tattggcaat gagcattaca cggttaatcg attgagagaa catgcatctc accttcagca    5940
aataattacg ataatccata ttttacgctt cgtaacttct catgagtttc gatatacaaa    6000
tttgttttct ggacaccta ccattcatcc tcttcggaga agagaggaag tgtcctcaat    6060
ttaaatatgt tgtcatgctg tagttcttca caaaatctca acaggtacca agcacattgt    6120
ttccacaaat tatattttag tcacaataaa tctatattat tattaatata ctaaaactat    6180
actgacgctc agatgctttt actagttctt gctagtatgt gatgtaggtc tacgtggacc    6240
agaaatagt gagacacgga agacaaaaga agtaaaagag gcccggacta cggcccacat     6300
gagattcggc cccgccacct ccggcaacca gcggccgatc caacggcagt gcgcgcacac    6360
acacaacctc gtatatatcg ccgcgcggaa gcggcgcgac cgaggaagcc ttgtcctcga    6420
cacccctac acaggtgtcg cgctgccccc gacacgagtc ccgcatgcgt cccacgcggc    6480
cgcgccagat cccgcctccg cgcgttgcca cgccctctat aaacacccag ctctccctcg    6540
ccctcatcta cctcactcgt agtcgtagct caagcatcag cggcagcggc agcggcagga    6600
tctctgggca gcgtgcgcac gtggggtatc tagctcgctc tgctagccta ccaatcgaat    6660
tcctgcaggt cgactctaga ggatctaccg tcttcggtac gcgctcactc cgccctctgc    6720
ctttgttact gccacgtttc tctgaatgct ctcttgtgtg gtgattgctg agagtggttt    6780
agctggatct agaattacac tctgaaatcg tgttctgcct gtgctgatta cttgccgtcc    6840
tttgtagcag caaaatatag ggacatggta gtacgaaacg aagatagaac ctacacagca    6900
atacgagaaa tgtgtaattt ggtgcttagc ggtatttatt taagcacatg ttggtgttat    6960
agggcacttg gattcagaag tttgctgtta atttaggcac aggcttcata ctacatgggt    7020
caatagtata gggattcata ttataggcga tactataata atttgttcgt ctgcagagct    7080
tattatttgc caaaattaga tattcctatt ctgttttgt ttgtgtgctg ttaaattgtt    7140
aacgcctgaa ggaataaata taatgacga aattttgatg tttatctctg ctcctttatt    7200
gtgaccataa gtcaagatca gatgcacttg tttaaatat tgttgtctga agaaataagt    7260
```

```
actgacagta ttttgatgca ttgatctgct tgtttgttgt aacaaaattt aaaaataaag   7320
agtttccttt ttgttgctct ccttacctcc tgatggtatc tagtatctac caactgacac   7380
tatattgctt ctctttacat acgtatcttg ctcgatgcct tctccctagt gttgaccagt   7440
gttactcaca tagtctttgc tcatttcatt gtaatgcaga taccaagcgg cctctagagg   7500
actccgatct atggaatccc tagccgccac ctccgtgttc gcgccctccc gcgtcgccgt   7560
cccggcggcg cgggccctgg ttagggcggg gacggtggta ccaaccaggc ggacgagcag   7620
ccggagcgga accagcgggg tgaaatgctc tgctgccgtg acgccgcagg cgagcccagt   7680
gattagcagg agcgctgcgg cggccatggt gaccatcatt caggacgacg cgctgagac    7740
ctacgagact aagggcggta tccaagtgag ccgtaagcgt aggcccactg actacgctaa   7800
cgccatcgac aactacatcg agaagctaga ctcccatcgc ggcgctgtgt tctcctgcaa   7860
ctacgaatac cctgggcgct acacgaggtg ggataccgcc atcgtcgatc ctccattggg   7920
catctcctgt tttgggcgta agatgtggat cgaggcgtac aacggccgtg gcgaagtctt   7980
gctggacttc atcacggaga agctcaaggc cacaccggac ctcaccctcg gcgcttcctc   8040
gacccgccgc ctcgacctta cggtcaacga gccggaccgc gtgttcaccg aggaagagcg   8100
tagcaagatc ccgactgtct tcaccgcgct cagagccatc gtggacctat tctactcttc   8160
tgcggacagc gccatcgggt tgttcggtgc cttcggttac gacctcgcgt tccagttcga   8220
cgccatcaag ctctcgctcg cgcggccgga ggaccagcga gacatggtgc tcttcctccc   8280
tgacgagatc ctggtcgtcg atcactattc cgcgaaggcg tggatcgacc ggtacgactt   8340
cgagaaggat ggcatgacca cggatggcaa gagcagcgac atcactcccg acccattcaa   8400
gaccaccgac accatccctc aaagggcga tcaccgccct ggcgagtatt ccgaactcgt    8460
ggtgaaggcc aaggaatcct tccggcgcgg cgatctgttt gaggtggttc ccggccaaaa   8520
gttcatggag aggtgcgagt cgaatccgtc tgcgatcagt cgccgactga aagcgatcaa   8580
cccgagcccg tattccttct tcatcaacct cggcgatcag gaatatctgg tcggagcctc   8640
acccgagatg ttcgtcaggg tctccggccg ccgatcgag acgtgcccaa tttccggaac    8700
catcaagcgc ggagatgacc cgatagccga ctctgagcag atcctgaaac tcttgaacag   8760
caagaaggac gagtccgagc tgactatgtg ctcagatgtg gaccgaaacg acaagtcacg   8820
tgtctgcgag cccggtagcg tcaaggtcat tggccgccgt cagatcgaga tgtactccag   8880
gctgattcac acgtcgatc atatcgaagg gcggctgcgc gacgatatgg acgcattcga   8940
cgggttcctc agtcacgcct gggccgttac tgtcaccgga gcgcctaagc tctgggctat   9000
gaggttcatc gagggccacg agaagagccc tagggcttgg tatggtggtg ccatcggcat   9060
ggttgggttc aacggcgaca tgaacaccgg gctgacgctc cggaccatca ggatcaaaga   9120
cggcattgcc gaggtgaggg ccggtgccac gcttctcaac gatagcaacc ctcaggagga   9180
agaggcggag accgagctga aagcctctgc gatgatctcc gcgattagag atgcaaaggg   9240
tacgaacagt gctgccacca agcgggacgc agccaaggtg ggcaccggcg tcaagatttt   9300
acttgtcgat cacgaggact ccttcgtgca cactctggcg aactacttcc gccagacagg   9360
cgcgacggtc tccaccgtta ggtcaccggt ggccgctgac gtgttcgata ggttccagcc   9420
cgaccttgtg gtgctctctc ccggtccgg ctcgccacg gacttcgact gcaaggccac     9480
cattaaggcc gccagggcca gggatctgcc aatcttcggc gtttgcctcg gcttcaggc    9540
attggcgag gcatcggtg gagagctgag gcagctcgcc gtcccgatgc acggaagcc      9600
atcccgcatc agagtcctgg agcccggcct cgtcttctcc ggtctcggga aggaggtcac   9660
```

```
ggtcggtcgg tatcattcga tcttcgccga tccggcaacc ctcccgcgcg acttcatcat    9720
aaccgccgag tcggaggacg gaacgatcat gggaatcgaa cacgccaagg agcccgtagc    9780
tgcggttcag ttccaccctg agtccatcat gaccctcggt caagatgcgg gtatgcggat    9840
gatcgagaat gtggtggttc acctcacccg caaggccaag accaaggcag catgataggg    9900
atccgttggc aatgcggata agaataact aaataaataa ataaataaat tgcaagcaat     9960
tgcgttgctg ctatgtactg taaaagtttc ttataatatc agttctgaat gctaaggaca   10020
tccctcaaga tggtctttct atttttgtgt tcccgttcca atgtactgtt ggtatcctct   10080
tggagattca tcaatatgag aaaacagaga atggacaacc ctcccttatc ttatggctcg   10140
agcggccgct ctagaactag tggatccccc ccttaattaa gggggctgca ggaattcata   10200
acttcgtata atgtatgcta tacgaagtta tgtttcgagg tcattcatat gcttgagaag   10260
agagtcggga tagtccaaaa taaaacaaag gtaagattac ctggtcaaaa gtgaaaacat   10320
cagttaaaag gtggtataaa gtaaaatatc ggtaataaaa ggtggcccaa agtgaaattt   10380
actcttttct actattataa aaattgagga tgttttgtc ggtactttga tacgtcattt    10440
ttgtatgaat tggttttaa gtttattcgc ttttggaaat gcatatctgt atttgagtcg    10500
ggttttaagt tcgtttgctt ttgtaaatac agagggattt gtataagaaa tatctttaga   10560
aaaacccata tgctaatttg acataatttt tgagaaaaat atatattcag gcgaattctc   10620
acaatgaaca ataataagat aaaatagct ttccccccgtt gcagcgcatg ggtattttt    10680
ctagtaaaaa taaagataa acttagactc aaaacattta caaaaacaac ccctaaagtt    10740
cctaaagccc aaagtgctat ccacgatcca tagcaagccc agcccaaccc aacccaaccc   10800
aacccacccc agtccagcca actggacaat agtctccaca cccccccact atcaccgtga   10860
gttgtccgca cgcaccgcac gtctcgcagc caaaaaaaaa aagaaagaaa aaaagaaaa    10920
agaaaaaaca gcaggtgggt ccgggtcgtg ggggccggaa acgcgaggag gatcgcgagc   10980
cagcgacgag gccggccctc cctccgcttc caaagaaacg cccccatcg ccactatata    11040
cataccccc cctctcctcc catccccca accctaccac caccaccacc accctcca      11100
cctcctcccc cctcgctgcc ggacgacgag ctcctcccc ctccccctcc gccgccgccg    11160
cgccggtaac caccccgccc ctctcctctt tctttctccg tttttttttc cgtctcggtc   11220
tcgatctttg gccttggtag tttggtggg cgagaggcgg cttcgtgcgc gcccagatcg    11280
gtgcgcggga ggggcgggat ctcgcggctg gggctctcgc cggcgtggat ccggcccgga   11340
tctcgcgggg aatggggctc tcggatgtag atctgcgatc cgccgttgtt gggggagatg   11400
atgggggtt taaaatttcc gccgtgctaa acaagatcag gaagagggga aaagggcact    11460
atggtttata ttttatata tttctgctgc ttcgtcaggc ttagatgtgc tagatctttc    11520
tttcttcttt ttgtgggtag aatttgaatc cctcagcatt gttcatcggt agttttctt    11580
ttcatgattt gtgacaaatg cagcctcgtg cggagctttt ttgtaggtag aagtgatcaa   11640
ccatggcgca agttagcaga atctgcaatg gtgtgcagaa cccatctctt atctccaatc   11700
tctcgaaatc cagtcaacgc aaatctccct tatcggtttc tctgaagacg cagcagcatc   11760
cacgagctta tccgatttcg tcgtcgtggg gattgaagaa gagtgggatg acgttaattg   11820
gctctgagct tcgtcctctt aaggtcatgt cttctgtttc cacggcgtgc atgcttcacg   11880
gtgcaagcag ccggcccgca accgcccgca atcctctgg cctttccgga accgtccgca    11940
ttcccggcga caagtcgatc tcccaccggt ccttcatgtt cggcggtctc gcagcggtg    12000
aaacgcgcat caccggcctt ctggaaggcg aggacgtcat caatacgggc aaggccatgc   12060
```

-continued

```
aggcgatggg cgcccgcatc cgtaaggaag gcgacacctg gatcatcgat ggcgtcggca    12120
atggcggcct cctggcgcct gaggcgccgc tcgatttcgg caatgccgcc acgggctgcc    12180
gcctgacgat gggcctcgtc ggggtctacg atttcgacag caccttcatc ggcgacgcct    12240
cgctcacaaa gcgcccgatg ggccgcgtgt tgaacccgct cgcgcgaaatg ggcgtgcagg   12300
tgaaatcgga agacggtgac cgtcttcccg ttaccttgcg cgggccgaag acgccgacgc    12360
cgatcaccta ccgcgtgccg atggcctccg cacaggtgaa gtccgccgtg ctgctcgccg    12420
gcctcaacac gcccggcatc acgacggtca tcgagccgat catgacgcgc gatcatacgg    12480
aaaagatgct gcagggcttt ggcgccaacc ttaccgtcga cggatgcg gacggcgtgc     12540
gcaccatccg cctggaaggc cgcggcaagc tcaccggcca agtcatcgac gtgccgggcg    12600
acccgtcctc gacggccttc ccgctggttg cggccctgct tgttccgggc tccgacgtca   12660
ccatcctcaa cgtgctgatg aaccccaccc gcaccggcct catcctgacg ctgcaggaaa    12720
tgggcgccga catcgaagtc atcaaccccg gccttgccgg cggcgaagac gtggcggacc    12780
tgcgcgttcg ctcctccacg ctgaagggcg tcacggtgcc ggaagaccgc gcgccttcga    12840
tgatcgacga atatccgatt ctcgctgtcg ccgccgcctt cgcggaaggg gcgaccgtga    12900
tgaacggtct ggaagaactc cgcgtcaagg aaagcgaccg cctctcggcc gtcgccaatg    12960
gcctcaagct caatgcgtg gattgcgatg agggcgagac gtcgctcgtc gtgcgtggcc     13020
gccctgacgg caaggggctc ggcaacgcct cgggcgccgc cgtcgccacc catctcgatc    13080
accgcatcgc catgagcttc ctcgtcatgg gcctcgtgtc ggaaaaccct gtcacggtgg    13140
acgatgccac gatgatcgcc acgagcttcc cggagttcat ggacctgatg gccgggctgg    13200
gcgcgaagat cgaactctcc gatacgaagg ctgcctgatg agctcgaatt cccgatcgtt    13260
caaacatttg gcaataaagt ttcttaagat tgaatcctgt tgccggtctt gcgatgatta    13320
tcatataatt tctgttgaat tacgttaagc atgtaataat taacatgtaa tgcatgacgt    13380
tatttatgag atgggttttt atgattagag tcccgcaatt atacatttaa tacgcgatag    13440
aaaacaaaat atagcgcgca aactaggata aattatcgcg cgcggtgtca tctatgttac    13500
tagatcgggg ataacgatca agctataact tcgtataatg tatgctatac gaagttatc    13559
```

<210> SEQ ID NO 215
<211> LENGTH: 13905
<212> TYPE: DNA
<213> ORGANISM: Artificial Sequence
<220> FEATURE:
<223> OTHER INFORMATION: pMON69757;Figure 33;the expression vector for
      the construct containing the AgroAS(F298W) mutant allele

<400> SEQUENCE: 215

```
gtcctccgat cgaggatttt tcggcgctgc gctacgtccg cgaccgcgtt gagggatcaa      60
gccacagcag cccactcgac cttctagccg acccagacga gccaagggat cttttttggaa    120
tgctgctccg tcgtcaggct ttccgacgtt tgggtggttg aacagaagtc attatcgcac     180
ggaatgccaa gcactcccga ggggaaccct gtggttggca tgcacataca aatggacgaa    240
cggataaacc ttttcacgcc cttttaaata tccgattatt ctaataaacg ctcttttctc     300
ttaggtttac ccgccaatat atcctgtcaa acactgatag tttaaactga aggcgggaaa    360
cgacaatctg atccccatca agctagcttc tgcaggtcct gctcgaggtc actaagcaac    420
taactttgag gaatgaggtg atgatgaatt aactcactcc attccacaaa ccaaacaaaa    480
atttgaggag tgagaagatg attgactatc tcattcctca aaccaaacac ctcaaatata    540
tctgctatcg ggattggcat tcctgtatcc ctacgccgt gtacccctg tttagagaac     600
```

| | | |
|---|---|---|
| ctccaaaggt ataagatggc gaagattatt gttgtcttgt ctttcatcat atatcgagtc | 660 | |
| tttccctagg atattattat tggcaatgag cattacacgg ttaatcgatt gagagaacat | 720 | |
| gcatctcacc ttcagcaaat aattacgata atccatattt tacgcttcgt aacttctcat | 780 | |
| gagtttcgat atacaaattt gttttctgga caccctacca ttcatcctct tcggagaaga | 840 | |
| gaggaagtgt cctcaattta aatatgttgt catgctgtag ttcttcacaa aatctcaaca | 900 | |
| ggtaccaagc acattgtttc cacaaattat attttagtca caataaatct atattattat | 960 | |
| taatatacta aaactatact gacgctcaga tgcttttact agttcttgct agtatgtgat | 1020 | |
| gtaggtctac gtggaccaga aaatagtgag acacggaaga caaagaagt aaaagaggcc | 1080 | |
| cggactacgg cccacatgag attcggcccc gccacctccg gcaaccagcg gccgatccaa | 1140 | |
| cggcagtgcg cgcacacaca caacctcgta tatatcgccg cgcggaagcg gcgcgaccga | 1200 | |
| ggaagccttg tcctcgacac cccctacaca ggtgtcgcgc tgcccccgac acgagtcccg | 1260 | |
| catgcgtccc acgcggccgc gccagatccc gcctccgcgc gttgccacgc cctctataaa | 1320 | |
| cacccagctc tccctcgccc tcatctacct cactcgtagt cgtagctcaa gcatcagcgg | 1380 | |
| cagcggcagc ggcaggatct ctgggcagcg tgcgcacgtg gggtatctag ctcgctctgc | 1440 | |
| tagcctacca atcgaattcc tgcaggtcga ctctagagga tctaccgtct tcggtacgcg | 1500 | |
| ctcactccgc cctctgcctt tgttactgcc acgtttctct gaatgctctc ttgtgtggtg | 1560 | |
| attgctgaga gtggtttagc tggatctaga attacactct gaaatcgtgt tctgcctgtg | 1620 | |
| ctgattactt gccgtccttt gtagcagcaa aatatagga catggtagta cgaaacgaag | 1680 | |
| atagaaccta cacagcaata cgagaaatgt gtaatttggt gcttagcggt atttatttaa | 1740 | |
| gcacatgttg gtgttatagg gcacttggat tcagaagttt gctgttaatt taggcacagg | 1800 | |
| cttcatacta catgggtcaa tagtataggg attcatatta taggcgatac tataataatt | 1860 | |
| tgttcgtctg cagagcttat tatttgccaa aattagatat tcctattctg tttttgtttg | 1920 | |
| tgtgctgtta aattgttaac gcctgaagga ataaatataa atgacgaaat tttgatgttt | 1980 | |
| atctctgctc ctttattgtg accataagtc aagatcagat gcacttgttt taaatattgt | 2040 | |
| tgtctgaaga aataagtact gacagtattt tgatgcattg atctgcttgt ttgttgtaac | 2100 | |
| aaaatttaaa aataaagagt ttccttttg ttgctctcct tacctcctga tggtatctag | 2160 | |
| tatctaccaa ctgacactat attgcttctc tttacatacg tatcttgctc gatgccttct | 2220 | |
| ccctagtgtt gaccagtgtt actcacatag tctttgctca tttcattgta atgcagatac | 2280 | |
| caagcggcct ctagaggact ccgatctatg gaatccctag ccgccacctc cgtgttcgcg | 2340 | |
| ccctcccgcg tcgccgtccc ggcggcgcgg gccctggtta gggcgnggac ggtggtacca | 2400 | |
| accaggcgga cgagcagccg gagcggaacc agcggggtga aatgctctgc tgccgtgacg | 2460 | |
| ccgcaggcga gcccagtgat tagcaggagc gctgcggcgg ccatggtaac gatcattcag | 2520 | |
| gatgacggag cggagaccta cgagacgaaa ggcggcatcc aggtcagccg aaagcgccgg | 2580 | |
| cccaccgatt atgccaacgc catcgataat tacatcgaaa agcttgattc ccatcgcggc | 2640 | |
| gcggtttttt cgtccaacta tgaatatccg ggccgttaca cccgctggga tacggccatc | 2700 | |
| gtcgatccgc cgctcggcat ttcctgtttt ggccgcaaga tgtggatcga agcctataat | 2760 | |
| ggccgcggcg aagtgctgct cgatttcatt acggaaaagc tgaaggcgac acccgatctc | 2820 | |
| accctcggcg cttcctcgac ccgccggctc gatcttaccg tcaacgaacc ggaccgtgtc | 2880 | |
| ttcaccgaag aagaacgctc gaaaatcccg acggtcttca ccgctctcag agccatcgtc | 2940 | |
| gacctcttct attcgagcgc ggattcggcc atcggcctgt tcggtgcctt cggttacgat | 3000 | |

```
ctcgccttcc agttcgacgc gatcaagctt tcgctggcgc gtccggaaga ccagcgtgac    3060
atggtgctgt ttctgcccga tgaaatcctc gtcgttgatc actattccgc caaggcctgg    3120
atcgaccgtt acgatttcga gaaggacggc atgacgacgg acggcaaatc ctccgacatt    3180 accccgatc ccttcaagac caccgatacc atcccgccca agggcgatca ccgtcccggc    3240
gaatattccg agcttgtggt gaaggccaag gaaagcttcc gccgcggcga cctgttcgag    3300
gtcgttcccg gccagaaatt catggagcgt tgcgaaagca atccgtcggc gatttcccgc    3360
cgcctgaagg cgatcaaccc gtcgccctat tcctggttca tcaatctcgg cgatcaggaa    3420
tatctggtcg gcgcctcgcc ggaaatgttc gtgcgcgtct ccggccgtcg catcgagacc    3480
tgcccgatat caggcaccat caagcgcggc gacgatccga ttgccgacag cgagcagatt    3540
ttgaaactgc tcaactcgaa aaaggacgaa tccgaactga ccatgtgctc ggacgtggac    3600
cgcaacgaca gagccgcgt ctgcgagccg ggttcggtga aggtcattgg ccgccgccag    3660
atcgagatgt attcacgcct catccacacc gtcgatcaca tcgaaggccg cctgcgcgac    3720
gatatggacg cctttgacgg tttcctcagc cacgcctggg ccgtcaccgt caccggtgca    3780
ccaaagctgt gggccatgcg cttcatcgaa ggtcatgaaa agagcccgcg cgcctggtat    3840
ggcggtgcga tcggcatggt cggcttcaac ggcgacatga ataccggcct gacgctgcgc    3900
accatccgga tcaaggacgg tattgccgaa gtgcgcgccg gcgcgaccct gctcaatgat    3960
tccaacccgc aggaagaaga agccgaaacc gaactgaagg cctccgccat gatatcagcc    4020
attcgtgacg caaaaggcac caactctgcc gccaccaagc gtgatgccgc caaagtcggc    4080
accggcgtca agatcctgct cgtcgaccac gaagacagct tcgtgcacac gctggcgaat    4140
tatttccgcc agacgggcgc gacggtctcg accgtcagat caccggtcgc agccgacgtg    4200
ttcgatcgct tccagccgga cctcgttgtc ctgtcgcccg gacccggcag cccgacggat    4260
ttcgactgca aggcaacgat caaggccgcc cgcgcccgcg atctgccgat cttcggcgtt    4320
tgcctcggtc tgcaggcatt ggcagaagcc tatggcggcg agctgcgcca gcttgctgtg    4380
cccatgcacg gcaagccttc gcgcatccgc gtgctggaac ccggcctcgt cttctccggt    4440
ctcggcaagg aagtcacggt cggtcgttac cattcgatct tcgccgatcc cgccaccctg    4500
ccgcgtgatt tcatcatcac cgcagaaagc gaggacggca cgatcatggg catcgaacac    4560
gccaaggaac cggtggccgc cgttcagttc cacccggaat cgatcatgac gctcggacag    4620
gacgcgggca tgcggatgat cgagaatgtc gtggtgcatc tgacccgcaa ggcgaagacc    4680
aaggccgcgt gatggcgctc gatgacacgg ttatatcact agtgcggcca tcggatccgg    4740
ggatcgatga gctaagctag ctatatcatc aatttatgta ttacacataa tatcgcactc    4800 agtcttt cat ctacggcaat gtaccagctg atataatcag ttattgaaat atttctgaat    4860
ttaaacttgc atcaataaat ttatgttttt gcttggacta taatacctga cttgttattt    4920
tatcaataaa tatttaaact atatttcttt caagatatca ttctttacaa gtatacgtgt    4980
ttaaattgaa taccataaat ttttattttt caaatacatg taaaattatg aaatgggagt    5040
ggtggcgacc gagctcaagc acacttcaat tcctataacg gaccaaatcg caaaaattat    5100
aataacatat tatttcatcc tggattaaaa gaaagtcacc ggggattatt ttgtgacgcc    5160
gattacatac ggcgacaata aagacattgg aaatcgtagt acatattgga atacactgat    5220
tatattaatg atgaatacat actttaatat ccttacgtag gatcgatccg aatttcgacc    5280
tcgagcggcc gctctagaac tagtggatcc ccccttaat taaggggct gcaggaattc    5340 ataacttcgt ataatgtatg ctatacgaag ttatgtttcg aggtcattca tatgcttgag    5400
```

-continued

```
aagagagtcg ggatagtcca aaataaaaca aaggtaagat tacctggtca aaagtgaaaa    5460
catcagttaa aaggtggtat aaagtaaaat atcggtaata aaaggtggcc caaagtgaaa    5520
tttactcttt tctactatta taaaaattga ggatgttttt gtcggtactt tgatacgtca    5580 ttttttgtatg aattggtttt taagtttatt cgcttttgga aatgcatatc tgtatttgag   5640
tcgggtttta agttcgtttg cttttgtaaa tacagaggga tttgtataag aaatatcttt    5700
agaaaaaccc atatgctaat ttgacataat ttttgagaaa aatatatatt caggcgaatt    5760
ctcacaatga acaataataa gattaaaata gctttccccc gttgcagcgc atgggtattt    5820
tttctagtaa aaataaaaga taaacttaga ctcaaaacat ttacaaaaac aaccctaaa     5880 gttcctaaag cccaaagtgc tatccacgat ccatagcaag cccagcccaa cccaacccaa    5940
cccaacccac cccagtccag ccaactggac aatagtctcc acaccccccc actatcaccg    6000
tgagttgtcc gcacgcaccg cacgtctcgc agccaaaaaa aaaagaaag aaaaaaaaga     6060 aaagaaaaa acagcaggtg ggtccgggtc gtggggccg gaaacgcgag gaggatcgcg      6120
agccagcgac gaggccggcc ctccctccgc ttccaaagaa cgcccccca tcgccactat     6180 atacataccc ccccctctcc tcccatcccc caaccctac caccaccacc accaccacct     6240
ccacctcctc ccccctcgct gccggacgac gagctcctcc ccctccccc tccgccgccg    6300 ccgcgccggt aaccacccg cccctctcct ctttctttct ccgttttttt ttccgtctcg     6360
gtctcgatct ttggccttgg tagtttgggt gggcgagagg cggcttcgtg cgcgcccaga    6420
tcggtgcgcg ggaggggcgg gatctcgcgg ctggggctct cgccggcgtg gatccggccc   6480
ggatctcgcg gggaatgggg ctctcggatg tagatctgcg atccgccgtt gttggggag    6540 atgatggggg gtttaaaatt tccgccgtgc taaacaagat caggaagagg ggaaaagggc    6600
actatggttt atatttttat atatttctgc tgcttcgtca ggcttagatg tgctagatct    6660
ttctttcttc ttttttgtggg tagaatttga atccctcagc attgttcatc ggtagttttt    6720
cttttcatga tttgtgacaa atgcagcctc gtgcggagct tttttgtagg tagaagtgat    6780
caaccatggc gcaagttagc agaatctgca atggtgtgca gaacccatct cttatctcca   6840
atctctcgaa atccagtcaa cgcaaatctc ccttatcggt ttctctgaag acgcagcagc    6900
atccacgagc ttatccgatt tcgtcgtcgt ggggattgaa gaagagtggg atgacgttaa   6960
ttggctctga gcttcgtcct cttaaggtca tgtcttctgt ttccacggcg tgcatgcttc    7020
acggtgcaag cagccggccc gcaaccgccc gcaaatcctc tggcctttcc ggaaccgtcc    7080
gcattcccgg cgacaagtcg atctcccacc ggtccttcat gttcggcggt ctcgcgagcg    7140
gtgaaacgcg catcaccggc cttctggaag gcgaggacgt catcaatacg ggcaaggcca    7200
tgcaggcgat gggcgcccgc atccgtaagg aaggcgacac ctggatcatc gatggcgtcg    7260
gcaatggcgg cctcctggcg cctgaggcgc cgctcgattt cggcaatgcc gccacgggct    7320
gccgcctgac gatgggcctc gtcggggtct acgatttcga cagcaccttc atcggcgacg    7380
cctcgctcac aaagcgcccg atgggccgcg tgttgaaccc gctgcgcgaa atggcgtgc    7440 aggtgaaatc ggaagacggt gaccgtcttc ccgttaccct gcgcgggccg aagacgccga    7500
cgccgatcac ctaccgcgtg ccgatggcct ccgcacaggt gaagtccgcc gtgctgctcg    7560
ccggcctcaa cacgcccggc atcacgacgg tcatcgagcc gatcatgacg cgcgatcata    7620
cggaaaagat gctgcagggc tttggcgcca accttaccgt cgagacggat gcggacggcg    7680
tgcgcaccat ccgcctggaa ggccgcgca agctcaccgg ccaagtcatc gacgtgccgg     7740 gcgaccgtc ctcgacggcc ttcccgctgg ttgcggccct gcttgttccg ggctccgacg     7800
```

```
tcaccatcct caacgtgctg atgaaccccca cccgcaccgg cctcatcctg acgctgcagg   7860
aaatgggcgc cgacatcgaa gtcatcaacc cgcgccttgc cggcggcgaa gacgtggcgg   7920
acctgcgcgt tcgctcctcc acgctgaagg gcgtcacggt gccggaagac cgcgcgcctt   7980
cgatgatcga cgaatatccg attctcgctg tcgccgccgc cttcgcggaa ggggcgaccg   8040
tgatgaacgg tctggaagaa ctccgcgtca aggaaagcga ccgcctctcg gccgtcgcca   8100
atggcctcaa gctcaatggc gtggattgcg atgagggcga cgtcgctc gtcgtgcgtg   8160 gccgccctga cggcaagggg ctcggcaacg cctcggcgc cgccgtcgcc acccatctcg   8220
atcaccgcat cgccatgagc ttcctcgtca tgggcctcgt gtcggaaaac cctgtcacgg   8280
tggacgatgc cacgatgatc gccacgagct tcccggagtt catggacctg atggccgggc   8340
tgggcgcgaa gatcgaactc tccgatacga aggctgcctg atgagctcga attcccgatc   8400
gttcaaacat ttggcaataa agtttcttaa gattgaatcc tgttgccggt cttgcgatga   8460
ttatcatata atttctgttg aattacgtta agcatgtaat aattaacatg taatgcatga   8520
cgttatttat gagatgggtt tttatgatta gagtcccgca attatacatt taatacgcga   8580
tagaaaacaa aatatagcgc gcaaactagg ataaattatc gcgcgcggtg tcatctatgt   8640
tactagatcg gggataacga tcaagctata acttcgtata atgtatgcta tacgaagtta   8700
tcgcgccaaa tcgtgaagtt tctcatccaa gccccccattt ggacgtgaat gtagacacgt   8760
cgaaataaag atttccgaat tagaataatt tgtttattgc tttcgcctat aaatacgacg   8820
gatcgtaatt tgtcgttta tcaaaatgta ctttcattt ataataacgc tgcggacatc   8880 tacattttg aattgaaaaa aaattggtaa ttactctttc tttttctcca tattgaccat   8940
catactcatt gctgatccat gtagatttcc cggacatgaa gccatttaca attgaatata   9000
tcctgccgcc gctgccgctt tgcacccggt ggagcttgca tgttggttc tacgcagaac   9060 tgagccggtt aggcagataa tttccattga gaactgagcc atgtgcacct cccccccaac   9120
acggtgagcg acgggcaac ggagtgatcc acatgggact tttcctagct tggctgccat   9180
ttttggggtg aggccgttcg cggccgaggg gcgcagcccc tggggggatg ggaggcccgc   9240
gttagcgggc cgggagggtt cgagaagggg gggcaccccc cttcggcgtg cgcggtcacg   9300
cgcacagggc gcagccctgg ttaaaaacaa ggtttataaa tattggttta aaagcaggtt   9360
aaaagacagg ttagcggtgg ccgaaaaacg ggcggaaacc cttgcaaatg ctggatttc   9420 tgcctgtgga cagcccctca aatgtcaata ggtgcgcccc tcatctgtca gcactctgcc   9480
cctcaagtgt caaggatcgc gcccctcatc tgtcagtagt cgcgcccctc aagtgtcaat   9540
accgcagggc acttatcccc aggcttgtcc acatcatctg tgggaaactc gcgtaaaatc   9600
aggcgttttc gccgatttgc gaggctggcc agctccacgt cgccggccga aatcgagcct   9660
gcccctcatc tgtcaacgcc gcgccgggtg agtcggcccc tcaagtgtca acgtccgccc   9720
ctcatctgtc agtgagggcc aagttttccg cgaggtatcc acaacgccgg cggccggccg   9780
cggtgtctcg cacacggctt cgacggcgtt tctggcgcgt ttgcagggcc atagacggcc   9840
gccagcccag cggcgagggc aaccagcccg gtgagcgtcg gaaagggtcg atcgaccgat   9900
gcccttgaga gccttcaacc cagtcagctc cttccggtgg gcgcggggca tgactatcgt   9960
cgccgcactt atgactgtct tctttatcat gcaactcgta ggacaggtgc cggcagcgct   10020
ctgggtcatt ttcggcgagg accgctttcg ctggagcgcg acgatgatcg gcctgtcgct   10080
tgcggtattc ggaatcttgc acgccctcgc tcaagccttc gtcactggtc ccgccaccaa   10140
acgtttcggc gagaagcagg ccattatcgc cggcatggcg gccgacgcgc tgggctacgt   10200
```

```
cttgctggcg ttcgcgacgc gaggctggat ggccttcccc attatgattc ttctcgcttc   10260
cggcggcatc gggatgcccg cgttgcaggc catgctgtcc aggcaggtag atgacgacca   10320
tcagggacag cttcaaggat cgctcgcggc tcttaccagc ctaacttcga tcattggacc   10380
gctgatcgtc acggcgattt atgccgcctc ggcgagcaca tggaacgggt tggcatggat   10440
tgtaggcgcc gccctatacc ttgtctgcct ccccgcgttg cgtcgcggtg catggagccg   10500
ggccacctcg acctgaatgg aagccggcgg cacctcgcta acggattcac cactccaaga   10560
attggagcca atcaattctt gcggagaact gtgaatgcgc aaaccaaccc ttggcagaac   10620
atatccatcg cgtccgccat ctccagcagc cgcacgcggc gcatctcggg cagcgttggg   10680
tcctggccac gggtgcgcat gatcgtgctc ctgtcgttga ggaccgggct aggctggcgg   10740
ggttgcctta ctggttagca gaatgaatca ccgatacgcg agcgaacgtg aagcgactgc   10800
tgctgcaaaa cgtctgcgac ctgagcaaca acatgaatgg tcttcggttt ccgtgtttcg   10860
taaagtctgg aaacgcggaa gtcagcgccc tgcaccatta tgttccggat ctgcatcgca   10920
ggatgctgct ggctaccctg tggaacacct acatctgtat taacgaagcg ctggcattga   10980
ccctgagtga ttttctctg gtcccgccgc atccataccg ccagttgttt accctcacaa   11040
cgttccagta accgggcatg ttcatcatca gtaacccgta tcgtgagcat cctctctcgt   11100
ttcatcggta tcattacccc catgaacaga aatccccctt acacggaggc atcagtgacc   11160
aaacaggaaa aaaccgccct taacatggcc cgctttatca gaagccagac attaacgctt   11220
ctggagaaac tcaacgagct ggacgcggat gaacaggcag acatctgtga atcgcttcac   11280
gaccacgctg atgagcttta ccgcagctgc ctcgcgcgtt tcggtgatga cggtgaaaac   11340
ctctgacaca tgcagctccc ggagacggtc acagcttgtc tgtaagcgga tgccgggagc   11400
agacaagccc gtcagggcgc gtcagcgggt gttggcgggt gtcggggcgc agccatgacc   11460
cagtcacgta gcgatagcgg agtgtatact ggcttaacta gcggcatca gagcagattg   11520 tactgagagt gcaccatatg cggtgtgaaa taccgcacag atgcgtaagg agaaaatacc   11580
gcatcaggcg ctcttccgct tcctcgctca ctgactcgct gcgctcggtc gttcggctgc   11640
ggcgagcggt atcagctcac tcaaaggcgg taatacggtt atccacagaa tcaggggata   11700
acgcaggaaa gaacatgtga gcaaaaggcc agcaaaaggc caggaaccgt aaaaaggccg   11760
cgttgctggc gttttttcat aggctccgcc ccctgacga gcatcacaaa aatcgacgct   11820
caagtcagag gtggcgaaac ccgacaggac tataaagata ccaggcgttt ccccctggaa   11880
gctccctcgt gcgctctcct gttccgaccc tgccgcttac cggatacctg tccgcctttc   11940
tcccttcggg aagcgtggcg ctttctcata gctcacgctg taggtatctc agttcggtgt   12000
aggtcgttcg ctccaagctg ggctgtgtgc acgaaccccc cgttcagccc gaccgctgcg   12060
ccttatccgg taactatcgt cttgagtcca acccggtaag acacgactta tcgccactgg   12120
cagcagccac tggtaacagg attagcagag cgaggtatgt aggcggtgct acagagttct   12180
tgaagtggtg gcctaactac ggctacacta aaggacagt attggtatc tgcgctctgc   12240 tgaagccagt taccttcgga aaagagttg gtagctcttg atccggcaaa caaaccaccg   12300
ctggtagcgg tggttttttt gtttgcaagc agcagattac gcgcagaaaa aaaggatctc   12360
aagaagatcc tttgatcttt tctacggggt ctgacgctca gtggaacgaa aactcacgtt   12420
aagggatttt ggtcatgaga ttatcaaaaa ggatcttcac ctagatcctt ttaaattaaa   12480
aatgaagttt taaatcaatc taagtatat atgagtaaac ttggtctgac agttaccaat   12540
gcttaatcag tgaggcacct atctcagcga tctgtctatt tcgttcatcc atagttgcct   12600
```

```
gactccccgt cgtgtagata actacgatac gggagggctt accatctggc cccagtgctg    12660
caatgatacc gcgagaccca cgctcaccgg ctccagattt atcagcaata aaccagccag    12720
ccggaagggc cgagcgcaga agtggtcctg caactttatc cgcctccatc cagtctatta    12780
attgttgccg ggaagctaga gtaagtagtt cgccagttaa tagtttgcgc aacgttgttg    12840
ccattgctgc aggtcgggag cacaggatga cgcctaacaa ttcattcaag ccgacaccgc    12900
ttcgcggcgc ggcttaattc aggagttaaa catcatgagg gaagcggtga tcgccgaagt    12960
atcgactcaa ctatcagagg tagttggcgt catcgagcgc catctcgaac cgacgttgct    13020
ggccgtacat ttgtacggct ccgcagtgga tggcggcctg aagccacaca gtgatattga    13080
tttgctggtt acggtgaccg taaggcttga tgaaacaacg cggcgagctt tgatcaacga    13140
ccttttggaa acttcggctt ccctggaga gagcgagatt ctccgcgctg tagaagtcac     13200
cattgttgtg cacgacgaca tcattccgtg gcgttatcca gctaagcgcg aactgcaatt    13260
tggagaatgg cagcgcaatg acattcttgc aggtatcttc gagccagcca cgatcgacat    13320
tgatctggct atcttgctga caaaagcaag agaacatagc gttgccttgg taggtccagc    13380
ggcggaggaa ctctttgatc cggttcctga acaggatcta tttgaggcgc taaatgaaac    13440
cttaacgcta tggaactcgc cgcccgactg gctggcgat gagcgaaatg tagtgcttac     13500
gttgtcccgc atttggtaca gcgcagtaac cggcaaaatc gcgccgaagg atgtcgctgc    13560
cgactgggca atggagcgcc tgccggccca gtatcagccc gtcatacttg aagctaggca    13620
ggcttatctt ggacaagaag atcgcttggc ctcgcgcgca gatcagttgg aagaatttgt    13680
tcactacgtg aaaggcgaga tcaccaaggt agtcggcaaa taatgtctaa caattcgttc    13740
aagccgacgc cgcttcgcgg cgcggcttaa ctcaagcgtt agatgctgca ggcatcgtgg    13800
tgtcacgctc gtcgtttggt atggcttcat tcagctccgg ttcccaacga tcaaggcgag    13860
ttacatgatc ccccatgttg tgcaaaaaag cggttagctc cttcg                    13905
```

<210> SEQ ID NO 216
<211> LENGTH: 13905
<212> TYPE: DNA
<213> ORGANISM: Artificial Sequence
<220> FEATURE:
<223> OTHER INFORMATION: pMON69770;Figure 37;the expression vector for
      the construct containing the AgroAS(S51C) non-optimized allele

<400> SEQUENCE: 216

```
tcgaggattt ttcggcgctg cgctacgtcc gcgaccgcgt tgagggatca agccacagca      60
gcccactcga ccttctagcc gacccagacg agccaaggga tcttttttgga atgctgctcc    120 gtcgtcaggc tttccgacgt ttgggtggtt gaacagaagt cattatcgca cggaatgcca    180
agcactcccg agggggaacc ctgtggttggc atgcacatac aaatggacga acggataaac    240
cttttcacgc cctttaaat atccgattat tctaataaac gctctttttct cttaggttta    300 cccgccaata tatcctgtca aacactgata gtttaaactg aaggcgggaa acgacaatct    360
gatccccatc aagctagctt ctgcaggtcc tgctcgaggt cactaagcaa ctaactttga    420
ggaatgaggt gatgatgaat taactcactc cattccacaa accaaacaaa atttgagga     480 gtgagaagat gattgactat ctcattcctc aaaccaaaca cctcaaatat atctgctatc    540
gggattggca ttcctgtatc cctacgcccg tgtaccccct gtttagagaa cctccaaagg    600
tataagatgg cgaagattat tgttgtcttg tctttcatca tatatcgagt ctttccctag    660
gatattatta ttggcaatga gcattacacg gttaatcgat tgagagaaca tgcatctcac    720
```

```
cttcagcaaa taattacgat aatccatatt ttacgcttcg taacttctca tgagtttcga    780
tatacaaatt tgttttctgg acaccctacc attcatcctc ttcggagaag agaggaagtg    840
tcctcaattt aaatatgttg tcatgctgta gttcttcaca aaatctcaac aggtaccaag    900
cacattgttt ccacaaatta tattttagtc acaataaatc tatattatta ttaatatact    960
aaaactatac tgacgctcag atgcttttac tagttcttgc tagtatgtga tgtaggtcta   1020
cgtggaccag aaaatagtga gacacggaag acaaaagaag taaagaggc ccggactacg    1080
gcccacatga gattcggccc cgccacctcc ggcaaccagc ggccgatcca acggcagtgc   1140
gcgcacacac acaacctcgt atatatcgcc gcgcggaagc ggcgcgaccg aggaagcctt   1200
gtcctcgaca cccctacac aggtgtcgcg ctgcccccga cacgagtccc gcatgcgtcc    1260
cacgcggccg cgccagatcc cgcctccgcg cgttgccacg ccctctataa acacccagct   1320
ctccctcgcc ctcatctacc tcactcgtag tcgtagctca agcatcagcg gcagcggcag   1380
cggcaggatc tctgggcagc gtgcgcacgt ggggtatcta gctcgctctg ctagcctacc   1440
aatcgaattc ctgcaggtcg actctagagg atctaccgtc ttcggtacgc gctcactccg   1500
ccctctgcct ttgttactgc cacgtttctc tgaatgctct cttgtgtggt gattgctgag   1560
agtggtttag ctggatctag aattacactc tgaaatcgtg ttctgcctgt gctgattact   1620
tgccgtcctt tgtagcagca aaatataggg acatggtagt acgaaacgaa gatagaacct   1680
acacagcaat acgagaaatg tgtaatttgg tgcttagcgg tatttattta agcacatgtt   1740
ggtgttatag ggcacttgga ttcagaagtt tgctgttaat ttaggcacag gcttcatact   1800
acatgggtca atagtatagg gattcatatt ataggcgata ctataataat ttgttcgtct   1860
gcagagctta ttatttgcca aaattagata ttcctattct gttttttgttt gtgtgctgtt   1920
aaattgttaa cgcctgaagg aataaatata aatgacgaaa ttttgatgtt tatctctgct   1980
cctttattgt gaccataagt caagatcaga tgcacttgtt ttaaatattg ttgtctgaag   2040
aaataagtac tgacagtatt ttgatgcatt gatctgcttg tttgttgtaa caaaatttaa   2100
aaataaagag tttcctttt gttgctctcc ttacctcctg atggtatcta gtatctacca   2160
actgacacta tattgcttct ctttacatac gtatcttgct cgatgccttc tccctagtgt   2220
tgaccagtgt tactcacata gtctttgctc atttcattgt aatgcagata ccaagcggcc   2280
tctagaggac tccgatctat ggaatcccta gccgccacct ccgtgttcgc gccctcccgc   2340
gtcgccgtcc cggcggcgcg ggccctggtt agggcgggga cggtggtacc aaccaggcgg   2400
acgagcagcc ggagcggaac cagcggggtg aaatgctctg ctgccgtgac gccgcaggcg   2460
agcccagtga ttagcaggag cgctgcggcg gccatggtaa cgatcattca ggatgacgga   2520
gcggagacct acgagacgaa aggcggcatc caggtcagcc gaaagcgccg gcccaccgat   2580
tatgccaacg ccatcgataa ttacatcgaa aagcttgatt cccatcgcgg cgcggttttt   2640
tcgtgcaact atgaatatcc gggccgttac acccgctggg atacggccat cgtcgatccg   2700
ccgctcggca tttcctgttt tggccgcaag atgtggatcg aagcctataa tggccgcggc   2760
gaagtgctgc tcgatttcat tacgaaaaag ctgaaggcga caccgatct caccctcggc   2820
gcttcctcga cccgccggct cgatcttacc gtcaacgaac cggaccgtgt cttcaccgaa   2880
gaagaacgct cgaaaatccc gacggtcttc accgctctca gagccatcgt cgacctcttc   2940
tattcgagcg cggattcggc catcggcctg ttcggtgcct tcggttacga tctcgccttc   3000
cagttcgacg cgatcaagct ttcgctggcg cgtccggaag accagcgtga catggtgctg   3060
tttctgcccg atgaaatcct cgtcgttgat cactattccg ccaaggcctg gatcgaccgt   3120
```

| | |
|---|---|
| tacgatttcg agaaggacgg catgacgacg gacggcaaat cctccgacat taccccccgat | 3180 |
| cccttcaaga ccaccgatac catcccgccc aagggcgatc accgtcccgg cgaatattcc | 3240 |
| gagcttgtgg tgaaggccaa ggaaagcttc cgccgcggcg acctgttcga ggtcgttccc | 3300 |
| ggccagaaat tcatggagcg ttgcgaaagc aatccgtcgg cgatttcccg ccgcctgaag | 3360 |
| gcgatcaacc cgtcgcccta ttccttcttc atcaatctcg gcgatcagga atatctggtc | 3420 |
| ggcgcctcgc cggaaatgtt cgtgcgcgtc tccggccgtc gcatcgagac ctgcccgata | 3480 |
| tcaggcacca tcaagcgcgg cgacgatccg attgccgaca gcgagcagat tttgaaactg | 3540 |
| ctcaactcga aaaaggacga atccgaactg accatgtgct cggacgtgga ccgcaacgac | 3600 |
| aagagccgcg tctgcgagcc gggttcggtg aaggtcattg gccgccgcca gatcgagatg | 3660 |
| tattcacgcc tcatccacac cgtcgatcac atcgaaggcc gcctgcgcga cgatatggac | 3720 |
| gcctttgacg gtttcctcag ccacgcctgg gccgtcaccg tcaccggtgc accaaagctg | 3780 |
| tgggccatgc gcttcatcga aggtcatgaa aagagcccgc gcgcctggta tggcggtgcg | 3840 |
| atcggcatgg tcggcttcaa cggcgacatg aataccggcc tgacgctgcg caccatccgg | 3900 |
| atcaaggacg gtattgccga agtgcgcgcc ggcgcgaccc tgctcaatga ttccaacccg | 3960 |
| caggaagaag aagccgaaac cgaactgaag gcctccgcca tgatatcagc cattcgtgac | 4020 |
| gcaaaaggca ccaactctgc cgccaccaag cgtgatgccg ccaaagtcgg caccggcgtc | 4080 |
| aagatcctgc tcgtcgacca cgaagacagc ttcgtgcaca cgctggcgaa ttatttccgc | 4140 |
| cagacgggcg cgacggtctc gaccgtcaga tcaccggtcg cagccgacgt gttcgatcgc | 4200 |
| ttccagccgg acctcgttgt cctgtcgccc ggacccggca gccgacgga tttcgactgc | 4260 |
| aaggcaacga tcaaggccgc ccgcgcccgc gatctgccga tcttcggcgt ttgcctcggt | 4320 |
| ctgcaggcat tggcagaagc ctatggcggc gagctgcgcc agcttgctgt gcccatgcac | 4380 |
| ggcaagcctt cgcgcatccg cgtgctggaa cccggcctcg tcttctccgg tctcggcaag | 4440 |
| gaagtcacgg tcggtcgtta ccattcgatc ttcgccgatc ccgccaccct gccgcgtgat | 4500 |
| ttcatcatca ccgcagaaag cgaggacggc acgatcatgg gcatcgaaca cgccaaggaa | 4560 |
| ccggtggccg ccgttcagtt ccaccccgaa tcgatcatga cgctcggaca ggacgcgggc | 4620 |
| atgcggatga tcgagaatgt cgtggtgcat ctgacccgca aggcgaagac caaggccgcg | 4680 |
| tgatggcgct cgatgacacg gttatatcac tagtgcggcc atcggatccg gggatcgatg | 4740 |
| agctaagcta gctatatcat caatttatgt attacacata atatcgcact cagtctttca | 4800 |
| tctacggcaa tgtaccagct gatataatca gttattgaaa tatttctgaa tttaaacttg | 4860 |
| catcaataaa tttatgtttt tgcttggact ataatacctg acttgttatt ttatcaataa | 4920 |
| atatttaaac tatatttctt tcaagatatc attctttaca agtatacgtg tttaaattga | 4980 |
| ataccataaa ttttatttt tcaaatacat gtaaaattat gaaatgggag tggtggcgac | 5040 |
| cgagctcaag cacacttcaa ttcctataac ggaccaaatc gcaaaaatta taataacata | 5100 |
| ttatttcatc ctggattaaa agaaagtcac cggggattat tttgtgacgc cgattacata | 5160 |
| cggcgacaat aaagacattg gaaatcgtag tacatattgg aatacactga ttatattaat | 5220 |
| gatgaataca tactttaata tccttacgta ggatcgatcc gaatttcgac ctcgagcggc | 5280 |
| cgctctagaa ctagtggatc cccccttaa ttaggggc tgcaggaatt cataacttcg | 5340 |
| tataatgtat gctatacgaa gttatgtttc gaggtcattc atatgcttga agagagtc | 5400 |
| gggatagtcc aaaataaaac aaaggtaaga ttacctggtc aaaagtgaaa acatcagtta | 5460 |
| aaaggtggta taaagtaaaa tatcggtaat aaaaggtggc ccaaagtgaa atttactctt | 5520 |

-continued

```
ttctactatt ataaaaattg aggatgtttt tgtcggtact ttgatacgtc attttttgtat    5580
gaattggttt ttaagtttat tcgcttttgg aaatgcatat ctgtatttga gtcgggtttt    5640
aagttcgttt gcttttgtaa atacagaggg atttgtataa gaaatatctt tagaaaaacc    5700
catatgctaa tttgacataa ttttttgagaa aaatatatat tcaggcgaat tctcacaatg    5760
aacaataata agattaaaat agctttcccc cgttgcagcg catgggtatt ttttctagta    5820
aaaataaaag ataaacttag actcaaaaca tttacaaaaa caaccccctaa agttcctaaa    5880
gcccaaagtg ctatccacga tccatagcaa gcccagccca acccaaccca acccaaccca    5940
ccccagtcca gccaactgga caatagtctc cacacccccc cactatcacc gtgagttgtc    6000
cgcacgcacc gcacgtctcg cagccaaaaa aaaaagaaa gaaaaaaaag aaaaagaaaa    6060
aacagcaggt gggtccgggt cgtggggggcc ggaaacgcga ggaggatcgc gagccagcga    6120
cgaggccggc cctccctccg cttccaaaga aacgccccccc atcgccacta tatacatacc    6180
ccccctctc ctcccatccc cccaaaccta ccaccaccac caccaccacc tccacctcct    6240
ccccctcgc tgccggacga cgagctcctc ccccctcccc ctccgccgcc gccgcgccgg    6300
taaccacccc gcccctctcc tctttctttc tccgttttt tttccgtctc ggtctcgatc    6360
tttggccttg gtagtttggg tgggcgagag gcggcttcgt gcgcgcccag atcggtgcgc    6420
gggaggggcg ggatctcgcg gctgggggctc tcgccggcgt ggatccggcc cggatctcgc    6480
ggggaatggg gctctcggat gtagatctgc gatccgccgt tgttggggga gatgatgggg    6540
ggtttaaaat ttccgccgtg ctaaacaaga tcaggaagag gggaaaaggg cactatggtt    6600
tatatttta tatatttctg ctgcttcgtc aggcttagat gtgctagatc tttcttctt    6660
cttttttgtgg gtagaatttg aatccctcag cattgttcat cggtagtttt tcttttcatg    6720
atttgtgaca aatgcagcct cgtgcggagc ttttttgtag gtagaagtga tcaaccatgg    6780
cgcaagttag cagaatctgc aatggtgtgc agaacccatc tcttatctcc aatctctcga    6840
aatccagtca acgcaaatct cccttatcgg ttttctgaa gacgcagcag catccacgag    6900
cttatccgat ttcgtcgtcg tggggattga agaagagtgg gatgacgtta attggctctg    6960
agcttcgtcc tcttaaggtc atgtcttctg ttttccacggc gtgcatgctt cacggtgcaa    7020
gcagccggcc cgcaaccgcc cgcaaatcct ctggccttttc cggaaccgtc cgcattcccg    7080
gcgacaagtc gatctcccac cggtccttca tgttcggcgg tctcgcgagc ggtgaaacgc    7140
gcatcaccgg ccttctggaa ggcgaggacg tcatcaatac gggcaaggcc atgcaggcga    7200
tgggcgcccg catccgtaag gaaggcgaca cctggatcat cgatggcgtc ggcaatggcg    7260
gcctcctggc gcctgaggcg ccgctcgatt tcggcaatgc cgccacgggc tgccgcctga    7320
cgatgggcct cgtcggggtc tacgatttcg acagcacctt catcggcgac gcctcgctca    7380
caaagcgccc gatgggccgc gtgttgaacc cgctgcgcga aatgggcgtg caggtgaaat    7440
cggaagacgg tgaccgtctt cccgttacct tgcgcgggcc gaagacgccg acgccgatca    7500
cctaccgcgt gccgatggcc tccgcacagg tgaagtccgc cgtgctgctc gccggcctca    7560
acacgcccgg catcacgacg gtcatcgagc cgatcatgac gcgcgatcat acggaaaaga    7620
tgctgcaggg cttttggcgcc aaccttaccg tcgagacgga tgcggacggc gtgcgcacca    7680
tccgcctgga aggccgcggc aagctcaccg gccaagtcat cgacgtgccg ggcgacccgt    7740
cctcgacggc cttcccgctg gttgcggccc tgcttgttcc gggctccgac gtcaccatcc    7800
tcaacgtgct gatgaacccc acccgcaccg gcctcatcct gacgctgcag gaaatgggcg    7860
ccgacatcga agtcatcaac ccgcgccttg ccggcggcga agacgtggcg gacctgcgcg    7920
```

```
ttcgctcctc cacgctgaag ggcgtcacgg tgccggaaga ccgcgcgcct tcgatgatcg    7980
acgaatatcc gattctcgct gtcgccgccg ccttcgcgga aggggcgacc gtgatgaacg    8040
gtctggaaga actccgcgtc aaggaaagcg accgcctctc ggccgtcgcc aatggcctca    8100
agctcaatgg cgtggattgc gatgagggcg agacgtcgct cgtcgtgcgt ggccgccctg    8160
acggcaaggg gctcggcaac gcctcgggcg ccgccgtcgc cacccatctc gatcaccgca    8220
tcgccatgag cttcctcgtc atgggcctcg tgtcggaaaa ccctgtcacg gtggacgatg    8280
ccacgatgat cgccacgagc ttcccggagt tcatggacct gatggccggg ctgggcgcga    8340
agatcgaact ctccgatacg aaggctgcct gatgagctcg aattcccgat cgttcaaaca    8400
tttggcaata aagtttctta agattgaatc ctgttgccgg tcttgcgatg attatcatat    8460
aatttctgtt gaattacgtt aagcatgtaa taattaacat gtaatgcatg acgttattta    8520
tgagatgggt ttttatgatt agagtcccgc aattatacat ttaatacgcg atagaaaaca    8580
aaatatagcg cgcaaactag gataaattat cgcgcgcggt gtcatctatg ttactagatc    8640
ggggataacg atcaagctat aacttcgtat aatgtatgct atacgaagtt atcgcgccaa    8700
atcgtgaagt ttctcatcta agcccccatt tggacgtgaa tgtagacacg tcgaaataaa    8760
gatttccgaa ttagaataat ttgtttattg ctttcgccta taaatacgac ggatcgtaat    8820
ttgtcgtttt atcaaaatgt actttcattt tataataacg ctgcggacat ctacattttt    8880
gaattgaaaa aaaattggta attactcttt cttttctcc  atattgacca tcatactcat    8940
tgctgatcca tgtagatttc ccggacatga agccatttac aattgaatat atcctgccgc    9000
cgctgccgct ttgcacccgg tggagcttgc atgttggttt ctacgcagaa ctgagccggt    9060
taggcagata atttccattg agaactgagc catgtgcacc ttccccccaa cacggtgagc    9120
gacgggcaa  cggagtgatc cacatgggac ttttcctagc ttggctgcca tttttggggt    9180
gaggccgttc gcggccgagg ggcgcagccc ctgggggat  gggaggcccg cgttagcggg    9240
ccgggagggt tcgagaaggg ggggcacccc ccttcggcgt gcgcggtcac gcgcacaggg    9300
cgcagccctg gttaaaaaca aggtttataa atattggttt aaaagcaggt taaaagacag    9360
gttagcggtg gccgaaaaac gggcggaaac ccttgcaaat gctggatttt ctgcctgtgg    9420
acagcccctc aaatgtcaat aggtgcgccc ctcatctgtc agcactctgc ccctcaagtg    9480
tcaaggatcg cgcccctcat ctgtcagtag tcgcgcccct caagtgtcaa taccgcaggg    9540
cacttatccc caggcttgtc cacatcatct gtgggaaact cgcgtaaaat caggcgtttt    9600
cgccgatttg cgaggctggc cagctccacg tcgccggccg aaatcgagcc tgcccctcat    9660
ctgtcaacgc cgcgccgggt gagtcggccc ctcaagtgtc aacgtccgcc cctcatctgt    9720
cagtgagggc caagttttcc gcgaggtatc cacaacgccg cggccggcc  gcggtgtctc    9780
gcacacggct tcgacggcgt ttctggcgcg tttgcagggc catagacggc cgccagccca    9840
gcggcgaggg caaccagccc ggtgagcgtc ggaaagggtc gatcgaccga tgcccttgag    9900
agccttcaac ccagtcagct ccttccggtg ggcgcgggc  atgactatcg tcgccgcact    9960
tatgactgtc ttctttatca tgcaactcgt aggacaggtg ccggcagcgc tctgggtcat   10020
tttcggcgag gaccgctttc gctggagcgc gacgatgatc ggcctgtcgc ttgcggtatt   10080
cggaatcttg cacgccctcg ctcaagcctt cgtcactggt cccgccacca aacgtttcgg   10140
cgagaagcag gccattatcg ccggcatggc ggccgacgcg ctgggctacg tcttgctggc   10200
gttcgcgacg cgaggctgga tggccttccc cattatgatt cttctcgctt ccggcggcat   10260
cgggatgccc gcgttgcagg ccatgctgtc caggcaggta gatgacgacc atcagggaca   10320
```

```
gcttcaagga tcgctcgcgg ctcttaccag cctaacttcg atcattggac cgctgatcgt   10380
cacggcgatt tatgccgcct cggcgagcac atggaacggg ttggcatgga ttgtaggcgc   10440
cgccctatac cttgtctgcc tccccgcgtt gcgtcgcggt gcatggagcc gggccacctc   10500
gacctgaatg gaagccggcg gcacctcgct aacggattca ccactccaag aattggagcc   10560
aatcaattct tgcggagaac tgtgaatgcg caaaccaacc cttggcagaa catatccatc   10620
gcgtccgcca tctccagcag ccgcacgcgg cgcatctcgg gcagcgttgg gtcctggcca   10680
cgggtgcgca tgatcgtgct cctgtcgttg aggacccggc taggctggcg gggttgcctt   10740
actggttagc agaatgaatc accgatacgc gagcgaacgt gaagcgactg ctgctgcaaa   10800
acgtctgcga cctgagcaac aacatgaatg gtcttcggtt ccgtgtttc gtaaagtctg    10860 gaaacgcgga agtcagcgcc ctgcaccatt atgttccgga tctgcatcgc aggatgctgc   10920
tggctaccct gtggaacacc tacatctgta ttaacgaagc gctggcattg accctgagtg   10980 attttctct ggtcccgccg catccatacc gccagttgtt taccctcaca acgttccagt    11040 aacgggcat gttcatcatc agtaacccgt atcgtgagca tcctctctcg tttcatcggt    11100
atcattaccc ccatgaacag aaatcccct tacacgaggg catcagtgac caaacaggaa    11160 aaaccgccc ttaacatggc ccgctttatc agaagccaga cattaacgct tctggagaaa    11220
ctcaacgagc tggacgcgga tgaacaggca gacatctgtg aatcgcttca cgaccacgct   11280
gatgagcttt accgcagctg cctcgcgcgt ttcggtgatg acggtgaaaa cctctgacac   11340
atgcagctcc cggagacggt cacagcttgt ctgtaagcgg atgccgggag cagacaagcc   11400
cgtcagggcg cgtcagcggg tgttggcggg tgtcggggcg cagccatgac ccagtcacgt   11460
agcgatagcg gagtgtatac tggcttaact atgcggcatc agagcagatt gtactgagag   11520
tgcaccatat gcggtgtgaa ataccgcaca gatgcgtaag gagaaaatac cgcatcaggc   11580
gctcttccgc ttcctcgctc actgactcgc tgcgctcggt cgttcggctg cggcgagcgg   11640
tatcagctca ctcaaaggcg gtaatacggt tatccacaga atcaggggat aacgcaggaa   11700
agaacatgtg agcaaaaggc cagcaaaagg ccaggaaccg taaaaaggcc gcgttgctgg   11760 cgttttttcca taggctccgc cccctgacg agcatcacaa aaatcgacgc tcaagtcaga   11820
ggtggcgaaa cccgacagga ctataaagat accaggcgtt tccccctgga agctccctcg   11880
tgcgctctcc tgttccgacc ctgccgctta ccggatacct gtccgccttt ctcccttcgg   11940
gaagcgtggc gctttctcat agctcacgct gtaggtatct cagttcggtg taggtcgttc   12000
gctccaagct gggctgtgtg cacgaacccc ccgttcagcc cgaccgctgc gccttatccg   12060
gtaactatcg tcttgagtcc aacccggtaa gacacgactt atcgccactg gcagcagcca   12120
ctggtaacag gattagcaga gcgaggtatg taggcggtgc tacagagttc ttgaagtggt   12180
ggcctaacta cggctacact agaaggacag tatttggtat ctgcgctctg ctgaagccag   12240
ttaccttcgg aaaaagagtt ggtagctctt gatccggcaa acaaaccacc gctggtagcg   12300
gtggtttttt tgtttgcaag cagcagatta cgcgcagaaa aaaggatctc aagaagatc    12360 ctttgatctt ttctacgggg tctgacgctc agtggaacga aaactcacgt taagggattt   12420
tggtcatgag attatcaaaa aggatcttca cctagatcct tttaaattaa aatgaagtt    12480 ttaaatcaat ctaaagtata tatgagtaaa cttggtctga cagttaccaa tgcttaatca   12540
gtgaggcacc tatctcagcg atctgtctat ttcgttcatc catagttgcc tgactccccg   12600
tcgtgtagat aactacgata cgggagggct taccatctgg ccccagtgct gcaatgatac   12660
cgcgagaccc acgctcaccg gctccagatt tatcagcaat aaaccagcca gccggaaggg   12720
```

```
ccgagcgcag aagtggtcct gcaactttat ccgcctccat ccagtctatt aattgttgcc   12780
gggaagctag agtaagtagt tcgccagtta atagtttgcg caacgttgtt gccattgctg   12840
caggtcggga gcacaggatg acgcctaaca attcattcaa gccgacaccg cttcgcggcg   12900
cggcttaatt caggagttaa acatcatgag ggaagcggtg atcgccgaag tatcgactca   12960
actatcagag gtagttggcg tcatcgagcg ccatctcgaa ccgacgttgc tggccgtaca   13020
tttgtacggc tccgcagtgg atggcggcct gaagccacac agtgatattg atttgctggt   13080
tacggtgacc gtaaggcttg atgaaacaac gcggcgagct ttgatcaacg accttttgga   13140
aacttcggct tcccctggag agagcgagat tctccgcgct gtagaagtca ccattgttgt   13200
gcacgacgac atcattccgt ggcgttatcc agctaagcgc gaactgcaat tggagaatg    13260 gcagcgcaat gacattcttg caggtatctt cgagccagcc acgatcgaca ttgatctggc   13320
tatcttgctg acaaaagcaa gagaacatag cgttgccttg gtaggtccag cggcggagga   13380
actctttgat ccggttcctg aacaggatct atttgaggcg ctaaatgaaa ccttaacgct   13440
atggaactcg ccgcccgact gggctggcga tgagcgaaat gtagtgctta cgttgtcccg   13500
catttggtac agcgcagtaa ccggcaaaat cgcgccgaag gatgtcgctg ccgactgggc   13560
aatggagcgc ctgccggccc agtatcagcc cgtcatactt gaagctaggc aggcttatct   13620
tggacaagaa gatcgcttgg cctcgcgcgc agatcagttg gaagaatttg ttcactacgt   13680
gaaaggcgag atcaccaagg tagtcggcaa ataatgtcta acaattcgtt caagccgacg   13740
ccgcttcgcg gcgcggctta actcaagcgt tagatgctgc aggcatcgtg gtgtcacgct   13800
cgtcgtttgg tatggcttca ttcagctccg gttcccaacg atcaaggcga gttacatgat   13860
cccccatgtt gtgcaaaaaa gcggttagct ccttcggtcc tccga                    13905
```

<210> SEQ ID NO 217
<211> LENGTH: 13905
<212> TYPE: DNA
<213> ORGANISM: Artificial Sequence
<220> FEATURE:
<223> OTHER INFORMATION: pMON69768;Figure 36;the expression vector for the construct containing the AgroAS(S51F) mutant allele

<400> SEQUENCE: 217

```
tcgaggattt ttcggcgctg cgctacgtcc gcgaccgcgt tgagggatca agccacagca     60
gcccactcga ccttctagcc gacccagacg agccaaggga tcttttttgga atgctgctcc   120 gtcgtcaggc tttccgacgt ttgggtggtt gaacagaagt cattatcgca cggaatgcca   180
agcactcccg aggggaaccc tgtggttggc atgcacatac aaatggacga acggataaac   240
cttttcacgc ccttttaaat atccgattat tctaataaac gctcttttct cttaggttta   300
cccgccaata tatcctgtca aacactgata gtttaaactg aaggcgggaa acgacaatct   360
gatccccatc aagctagctt ctgcaggtcc tgctcgaggt cactaagcaa ctaactttga   420
ggaatgaggt gatgatgaat taactcactc cattccacaa accaaacaaa aatttgagga   480
gtgagaagat gattgactat ctcattcctc aaaccaaaca cctcaaatat atctgctatc   540
gggattggca ttcctgtatc cctacgcccg tgtaccccct gtttagagaa cctccaaagg   600
tataagatgg cgaagattat tgttgtcttg tctttcatca tatatcgagt ctttccctag   660
gatattatta ttggcaatga gcattacacg gttaatcgat tgagagaaca tgcatctcac   720
cttcagcaaa taattacgat aatccatatt ttacgcttcg taacttctca tgagtttcga   780
tatacaaatt tgttttctgg acaccctacc attcatcctc ttcggagaag agaggaagtg   840
tcctcaattt aaatatgttg tcatgctgta gttcttcaca aaatctcaac aggtaccaag   900
```

| | |
|---|---|
| cacattgttt ccacaaatta tattttagtc acaataaatc tatattatta ttaatatact | 960 |
| aaaactatac tgacgctcag atgcttttac tagttcttgc tagtatgtga tgtaggtcta | 1020 |
| cgtggaccag aaaatagtga gacacggaag acaaaagaag taaaagaggc ccggactacg | 1080 |
| gcccacatga gattcggccc cgccacctcc ggcaaccagc ggccgatcca acggcagtgc | 1140 |
| gcgcacacac acaacctcgt atatatcgcc gcgcggaagc ggcgcgaccg aggaagcctt | 1200 |
| gtcctcgaca cccctacac aggtgtcgcg ctgcccccga cacgagtccc gcatgcgtcc | 1260 |
| cacgcggccg cgccagatcc cgcctccgcg cgttgccacg ccctctataa acacccagct | 1320 |
| ctccctcgcc ctcatctacc tcactcgtag tcgtagctca agcatcagcg gcagcggcag | 1380 |
| cggcaggatc tctgggcagc gtgcgcacgt ggggtatcta gctcgctctg ctagcctacc | 1440 |
| aatcgaattc ctgcaggtcg actctagagg atctaccgtc ttcggtacgc gctcactccg | 1500 |
| ccctctgcct ttgttactgc cacgtttctc tgaatgctct cttgtgtggt gattgctgag | 1560 |
| agtggtttag ctggatctag aattacactc tgaaatcgtg ttctgcctgt gctgattact | 1620 |
| tgccgtcctt tgtagcagca aaatataggg acatggtagt acgaaacgaa gatagaacct | 1680 |
| acacagcaat acgagaaatg tgtaatttgg tgcttagcgg tatttattta agcacatgtt | 1740 |
| ggtgttatag ggcacttgga ttcagaagtt tgctgttaat ttaggcacag gcttcatact | 1800 |
| acatgggtca atagtatagg gattcatatt ataggcgata ctataataat ttgttcgtct | 1860 |
| gcagagctta ttatttgcca aaattagata ttcctattct gtttttgttt gtgtgctgtt | 1920 |
| aaattgttaa cgcctgaagg aataaatata aatgacgaaa ttttgatgtt tatctctgct | 1980 |
| cctttattgt gaccataagt caagatcaga tgcacttgtt ttaaatattg ttgtctgaag | 2040 |
| aaataagtac tgacagtatt ttgatgcatt gatctgcttg tttgttgtaa caaaatttaa | 2100 |
| aaataaagag tttccttttt gttgctctcc ttacctcctg atggtatcta gtatctacca | 2160 |
| actgacacta tattgcttct ctttacatac gtatcttgct cgatgccttc tccctagtgt | 2220 |
| tgaccagtgt tactcacata gtctttgctc atttcattgt aatgcagata ccaagcggcc | 2280 |
| tctagaggac tccgatctat ggaatcccta gccgccacct ccgtgttcgc gccctcccgc | 2340 |
| gtcgccgtcc cggcggcgcg ggccctggtt agggcgggga cggtggtacc aaccaggcgg | 2400 |
| acgagcagcc ggagcggaac cagcggggtg aaatgctctg ctgccgtgac gccgcaggcg | 2460 |
| agcccagtga ttagcaggag cgctgcggcg gccatggtaa cgatcattca ggatgacgga | 2520 |
| gcggagacct acgagacgaa aggcggcatc caggtcagcc gaaagcgccg gcccaccgat | 2580 |
| tatgccaacg ccatcgataa ttacatcgaa aagcttgatt cccatcgcgg cgcggttttt | 2640 |
| tcgttcaact atgaatatcc gggccgttac accgctggg atacggccat cgtcgatccg | 2700 |
| ccgctcggca tttcctgttt tggccgcaag atgtggatcg aagcctataa tggccgcggc | 2760 |
| gaagtgctgc tcgatttcat tacgaaaag ctgaaggcga cacccgatct caccctcggc | 2820 |
| gcttcctcga cccgccggct cgatcttacc gtcaacgaac cggaccgtgt cttcaccgaa | 2880 |
| gaagaacgct cgaaaatccc gacggtcttc accgctctca gagccatcgt cgacctcttc | 2940 |
| tattcgagcg cggattcggc catcggcctg ttcggtgcct tcggttacga tctcgccttc | 3000 |
| cagttcgacg cgatcaagct ttcgctggcg cgtccggaag accagcgtga catggtgctg | 3060 |
| tttctgcccg atgaaatcct cgtcgttgat cactattccg ccaaggcctg gatcgaccgt | 3120 |
| tacgatttcg agaaggacgg catgacgacg gacggcaaat cctccgacat taccccgat | 3180 |
| cccttcaaga ccaccgatac catcccgccc aagggcgatc accgtcccgg cgaatattcc | 3240 |
| gagcttgtgg tgaaggccaa ggaaagcttc cgccgcggcg acctgttcga ggtcgttccc | 3300 |

-continued

```
ggccagaaat tcatggagcg ttgcgaaagc aatccgtcgg cgatttcccg ccgcctgaag    3360
gcgatcaacc cgtcgcccta ttccttcttc atcaatctcg gcgatcagga atatctggtc    3420
ggcgcctcgc cggaaatgtt cgtgcgcgtc tccggccgtc gcatcgagac ctgcccgata    3480
tcaggcacca tcaagcgcgg cgacgatccg attgccgaca gcgagcagat tttgaaactg    3540
ctcaactcga aaaggacga atccgaactg accatgtgct cggacgtgga ccgcaacgac     3600
aagagccgcg tctgcgagcc gggttcggtg aaggtcattg gccgccgcca gatcgagatg    3660
tattcacgcc tcatccacac cgtcgatcac atcgaaggcc gcctgcgcga cgatatggac    3720
gcctttgacg gtttcctcag ccacgcctgg gccgtcaccg tcaccggtgc accaaagctg    3780
tgggccatgc gcttcatcga aggtcatgaa aagagcccgc gcgcctggta tggcggtgcg    3840
atcggcatgg tcggcttcaa cggcgacatg aataccggcc tgacgctgcg caccatccgg    3900
atcaaggacg gtattgccga agtgcgcgcc ggcgcgaccc tgctcaatga ttccaacccg    3960
caggaagaag aagccgaaac cgaactgaag gcctccgcca tgatatcagc cattcgtgac    4020
gcaaaaggca ccaactctgc cgccaccaag cgtgatgccg ccaaagtcgg caccggcgtc    4080
aagatcctgc tcgtcgacca cgaagacagc ttcgtgcaca cgctggcgaa ttatttccgc    4140
cagacgggcg cgacggtctc gaccgtcaga tcaccggtcg cagccgacgt gttcgatcgc    4200
ttccagccgg acctcgttgt cctgtcgccc ggacccggca gcccgacgga tttcgactgc    4260
aaggcaacga tcaaggccgc ccgcgcccgc gatctgccga tcttcggcgt ttgcctcggt    4320
ctgcaggcat tggcagaagc ctatggcggc gagctgcgcc agcttgctgt gcccatgcac    4380
ggcaagcctt cgcgcatccg cgtgctggaa cccggcctcg tcttctccgg tctcggcaag    4440
gaagtcacgg tcggtcgtta ccattcgatc ttcgccgatc ccgccaccct gccgcgtgat    4500
ttcatcatca ccgcagaaag cgaggacggc acgatcatgg gcatcgaaca cgccaaggaa    4560
ccggtggccg ccgttcagtt ccacccgaaa tcgatcatga cgctcggaca ggacgcgggc    4620
atgcggatga tcgagaatgt cgtggtgcat ctgacccgca aggcgaagac caaggccgcg    4680
tgatggcgct cgatgacacg gttatatcac tagtgcggcc atcggatccg ggatcgatg     4740 agctaagcta gctatatcat caatttatgt attacacata atatcgcact cagtctttca    4800
tctacggcaa tgtaccagct gatataatca gttattgaaa tatttctgaa tttaaacttg    4860
catcaataaa tttatgtttt tgcttggact ataatacctg acttgttatt ttatcaataa    4920
atatttaaac tatatttctt tcaagatatc attctttaca agtatacgtg tttaaattga    4980
ataccataaa ttttattttt tcaaatacat gtaaaattat gaaatgggag tggtggcgac    5040
cgagctcaag cacacttcaa ttcctataac ggaccaaatc gcaaaaatta taataacata    5100
ttatttcatc ctggattaaa agaaagtcac cggggattat tttgtgacgc cgattacata    5160
cggcgacaat aaagacattg gaaatcgtag tacatattgg aatacactga ttatattaat    5220
gatgaataca tactttaata tccttacgta ggatcgatcc gaatttcgac ctcgagcggc    5280
cgctctagaa ctagtggatc ccccccttaa ttaaggggc tgcaggaatt cataacttcg     5340
tataatgtat gctatacgaa gttatgtttc gaggtcattc atatgcttga aagagagtc     5400 gggatagtcc aaaataaaac aaaggtaaga ttacctggtc aaaagtgaaa acatcagtta    5460
aaaggtggta taaagtaaaa tatcggtaat aaaaggtggc ccaaagtgaa atttactctt    5520
ttctactatt ataaaaattg aggatgtttt tgtcggtact tgatacgtc attttttgtat    5580 gaattggttt ttaagtttat tcgcttttgg aaatgcatat ctgtatttga gtcgggtttt    5640
aagttcgttt gcttttgtaa atacagaggg atttgtataa gaaatatctt tagaaaaacc    5700
```

```
catatgctaa ttttgacataa tttttgagaa aaatatatat tcaggcgaat tctcacaatg   5760
aacaataata agattaaaat agctttcccc cgttgcagcg catgggtatt ttttctagta   5820
aaaataaaag ataaacttag actcaaaaca tttacaaaaa caacccctaa agttcctaaa   5880
gcccaaagtg ctatccacga tccatagcaa gcccagccca acccaaccca acccaaccca   5940
ccccagtcca gccaactgga caatagtctc cacaccccccc cactatcacc gtgagttgtc   6000
cgcacgcacc gcacgtctcg cagccaaaaa aaaaagaaaa gaaaaaaaag aaaaagaaaa   6060
aacagcaggt gggtccgggt cgtgggggcc ggaaacgcga ggaggatcgc gagccagcga   6120
cgaggccggc cctccctccg cttccaaaga aacgcccccc atcgccacta tatacatacc   6180 ccccctctc ctcccatccc cccaaccta ccaccaccac caccaccacc tccacctcct   6240
cccccctcgc tgccggacga cgagctcctc ccccctcccc ctccgccgcc gccgcgccgg   6300
taaccacccc gcccctctcc tctttctttc tccgttttt tttccgtctc ggtctcgatc   6360
tttggccttg gtagtttggg tgggcgagag gcggcttcgt gcgcgcccag atcggtgcgc   6420
gggaggggcg ggatctcgcg gctggggctc tcgccggcgt ggatccggcc cggatctcgc   6480
ggggaatggg gctctcggat gtagatctgc gatccgccgt tgttggggga gatgatgggg   6540
ggtttaaaat ttccgccgtg ctaaacaaga tcaggaagag gggaaaaggg cactatggtt   6600
tatattttta tatatttctg ctgcttcgtc aggcttagat gtgctagatc tttcttctt   6660 cttttttgtgg gtagaatttg aatccctcag cattgttcat cggtagtttt tcttttcatg   6720
atttgtgaca aatgcagcct cgtgcggagc tttttttgtag gtagaagtga tcaaccatgg   6780
cgcaagttag cagaatctgc aatggtgtgc agaacccatc tcttatctcc aatctctcga   6840
aatccagtca acgcaaatct cccttatcgg tttctctgaa gacgcagcag catccacgag   6900
cttatccgat ttcgtcgtcg tggggattga agaagagtgg gatgacgtta attggctctg   6960
agcttcgtcc tcttaaggtc atgtcttctg tttccacggc gtgcatgctt cacggtgcaa   7020
gcagccggcc cgcaaccgcc cgcaaatcct ctggcctttc cggaaccgtc cgcattcccg   7080
gcgacaagtc gatctcccac cggtccttca tgttcggcgg tctcgcgagc ggtgaaacgc   7140
gcatcaccgg ccttctggaa ggcgaggacg tcatcaatac gggcaaggcc atgcaggcga   7200
tgggcgcccg catccgtaag gaaggcgaca cctggatcat cgatggcgtc ggcaatggcg   7260
gcctcctggc gcctgaggcg ccgctcgatt tcggcaatgc cgccacgggc tgccgcctga   7320
cgatgggcct cgtcggggtc tacgatttcg acagcacctt catcggcgac gcctcgctca   7380
caaagcgccc gatgggccgc gtgttgaacc cgctgcgcga aatgggcgtg caggtgaaat   7440
cggaagacgg tgaccgtctt cccgttacct tgcgcgggcc gaagacgccg acgccgatca   7500
cctaccgcgt gccgatggcc tccgcacagg tgaagtccgc cgtgctgctc gccggcctca   7560
acacgcccgg catcacgacg gtcatcgagc cgatcatgac gcgcgatcat acggaaaaga   7620
tgctgcaggg cttttggcgcc aaccttaccg tcgagacgga tgcggacggc gtgcgcacca   7680
tccgcctgga aggccgcggc aagctcaccg gccaagtcat cgacgtgccg ggcgacccgt   7740
cctcgacggc cttcccgctg gttgcggccc tgcttgttcc gggctccgac gtcaccatcc   7800
tcaacgtgct gatgaacccc acccgcaccg gcctcatcct gacgctgcag gaaatgggcg   7860
ccgacatcga agtcatcaac ccgcgccttg ccggcggcga agacgtggcg gacctgcgcg   7920
ttcgctcctc cacgctgaag ggcgtcacgg tgccggaaga ccgcgcgcct tcgatgatcg   7980
acgaatatcc gattctcgct gtcgccgcg ccttcgcgga aggggcgacc gtgatgaacg   8040
gtctggaaga actccgcgtc aaggaaagcg accgcctctc ggccgtcgcc aatggcctca   8100
```

```
agctcaatgg cgtggattgc gatgagggcg agacgtcgct cgtcgtgcgt ggccgccctg    8160
acggcaaggg gctcggcaac gcctcgggcg ccgccgtcgc cacccatctc gatcaccgca    8220
tcgccatgag cttcctcgtc atgggcctcg tgtcggaaaa ccctgtcacg gtggacgatg    8280
ccacgatgat cgccacgagc ttcccggagt tcatggacct gatggccggg ctgggcgcga    8340
agatcgaact ctccgatacg aaggctgcct gatgagctcg aattcccgat cgttcaaaca    8400
tttggcaata aagtttctta agattgaatc ctgttgccgg tcttgcgatg attatcatat    8460
aatttctgtt gaattacgtt aagcatgtaa taattaacat gtaatgcatg acgttattta    8520
tgagatgggt ttttatgatt agagtcccgc aattatacat ttaatacgcg atagaaaaca    8580
aaatatagcg cgcaaactag gataaattat cgcgcgcggt gtcatctatg ttactagatc    8640
ggggataacg atcaagctat aacttcgtat aatgtatgct atacgaagtt atcgcgccaa    8700
atcgtgaagt ttctcatcta agcccccatt tggacgtgaa tgtagacacg tcgaaataaa    8760
gatttccgaa ttagaataat ttgttttattg ctttcgccta taaatacgac ggatcgtaat    8820
ttgtcgtttt atcaaaatgt actttcattt tataataacg ctgcggacat ctacattttt    8880
gaattgaaaa aaaattggta attactcttt cttttttctcc atattgacca tcatactcat    8940
tgctgatcca tgtagatttc ccggacatga agccatttac aattgaatat atcctgccgc    9000
cgctgccgct ttgcacccgg tggagcttgc atgttggttt ctacgcagaa ctgagccggt    9060
taggcagata atttccattg agaactgagc catgtgcacc ttcccccccaa cacggtgagc    9120
gacggggcaa cggagtgatc cacatgggac ttttcctagc ttggctgcca tttttggggt    9180
gaggccgttc gcggccgagg ggcgcagccc ctggggggat gggaggcccg cgttagcggg    9240
ccgggagggt tcgagaaggg ggggcacccc ccttcggcgt gcgcggtcac gcgcacaggg    9300
cgcagccctg gttaaaaaca aggtttataa atattggttt aaaagcaggt taaaagacag    9360
gttagcggtg gccgaaaaac gggcggaaac ccttgcaaat gctggatttt ctgcctgtgg    9420
acagcccctc aaatgtcaat aggtgcgccc ctcatctgtc agcactctgc ccctcaagtg    9480
tcaaggatcg cgcccctcat ctgtcagtag tcgcgcccct caagtgtcaa taccgcaggg    9540
cacttatccc caggcttgtc cacatcatct gtgggaaact cgcgtaaaat caggcgtttt    9600
cgccgatttg cgaggctggc cagctccacg tcgccggccg aaatcgagcc tgcccctcat    9660
ctgtcaacgc cgcgccgggt gagtcggccc ctcaagtgtc aacgtccgcc cctcatctgt    9720
cagtgagggc caagttttcc gcgaggtatc cacaacgccg gcggccggcc gcggtgtctc    9780
gcacacggct tcgacggcgt ttctggcgcg tttgcagggc catagacggc cgccagccca    9840
gcggcgaggg caaccagccc ggtgagcgtc ggaaagggtc gatcgaccga tgcccttgag    9900
agccttcaac ccagtcagct ccttccggtg ggcgcggggc atgactatcg tcgccgcact    9960
tatgactgtc ttctttatca tgcaactcgt aggacaggtg ccggcagcgc tctgggtcat   10020
tttcggcgag gaccgctttc gctggagcgc gacgatgatc ggcctgtcgc ttgcggtatt   10080
cggaatcttg cacgccctcg ctcaagcctt cgtcactggt cccgccacca aacgtttcgg   10140
cgagaagcag gccattatcg ccggcatggc ggccgacgcg ctgggctacg tcttgctggc   10200
gttcgcgacg cgaggctgga tggccttccc cattatgatt cttctcgctt ccggcggcat   10260
cgggatgccc gcgttgcagg ccatgctgtc caggcaggta gatgacgacc atcagggaca   10320
gcttcaagga tcgctcgcgg ctcttaccag cctaacttcg atcattggac cgctgatcgt   10380
cacggcgatt tatgccgcct cggcgagcac atggaacggg ttggcatgga ttgtaggcgc   10440
cgccctatac cttgtctgcc tccccgcgtt gcgtcgcggt gcatggagcc gggccacctc   10500
```

```
gacctgaatg gaagccggcg gcacctcgct aacggattca ccactccaag aattggagcc   10560
aatcaattct tgcggagaac tgtgaatgcg caaaccaacc cttggcagaa catatccatc   10620
gcgtccgcca tctccagcag ccgcacgcgg cgcatctcgg gcagcgttgg gtcctggcca   10680
cgggtgcgca tgatcgtgct cctgtcgttg aggacccggc taggctggcg gggttgcctt   10740
actggttagc agaatgaatc accgatacgc gagcgaacgt gaagcgactg ctgctgcaaa   10800
acgtctgcga cctgagcaac aacatgaatg gtcttcggtt ccgtgtttc gtaaagtctg    10860
gaaacgcgga gtcagcgcc ctgcaccatt atgttccgga tctgcatcgc aggatgctgc    10920
tggctaccct gtggaacacc tacatctgta ttaacgaagc gctggcattg accctgagtg   10980
attttctct ggtcccgccg catccatacc gccagttgtt taccctcaca cgttccagt     11040
aacgggcat gttcatcatc agtaacccgt atcgtgagca tcctctctcg tttcatcggt    11100
atcattaccc ccatgaacag aaatcccct tacacggagg catcagtgac caaacaggaa    11160
aaaaccgccc ttaacatggc ccgctttatc agaagccaga cattaacgct tctggagaaa   11220
ctcaacgagc tggacgcgga tgaacaggca gacatctgtg aatcgcttca cgaccacgct   11280
gatgagcttt accgcagctg cctcgcgcgt ttcggtgatg acggtgaaaa cctctgacac   11340
atgcagctcc cggagacggt cacagcttgt ctgtaagcgg atgccgggag cagacaagcc   11400
cgtcagggcg cgtcagcggg tgttggcggg tgtcggggcg cagccatgac ccagtcacgt   11460
agcgatagcg gagtgtatac tggcttaact atgcggcatc agagcagatt gtactgagag   11520
tgcaccatat gcggtgtgaa ataccgcaca gatgcgtaag gagaaaatac cgcatcaggc   11580
gctcttccgc ttcctcgctc actgactcgc tgcgctcggt cgttcggctg cggcgagcgg   11640
tatcagctca ctcaaaggcg gtaatacggt tatccacaga atcaggggat aacgcaggaa   11700
agaacatgtg agcaaaaggc cagcaaaagg ccaggaaccg taaaaaggcc gcgttgctgg   11760
cgtttttcca taggctccgc ccccctgacg agcatcacaa aaatcgacgc tcaagtcaga   11820
ggtggcgaaa cccgacagga ctataaagat accaggcgtt tcccctggaa gctccctcg    11880
tgcgctctcc tgttccgacc ctgccgctta ccggatacct gtccgccttt ctcccttcgg   11940
gaagcgtggc gctttctcat agctcacgct gtaggtatct cagttcggtg taggtcgttc   12000
gctccaagct gggctgtgtg cacgaacccc ccgttcagcc cgaccgctgc gccttatccg   12060
gtaactatcg tcttgagtcc aacccggtaa gacacgactt atcgccactg gcagcagcca   12120
ctggtaacag gattagcaga gcgaggtatg taggcggtgc tacagagttc ttgaagtggt   12180
ggcctaacta cggctacact agaaggacag tatttggtat ctgcgctctg ctgaagccag   12240
ttaccttcgg aaaaagagtt ggtagctctt gatccggcaa acaaaccacc gctggtagcg   12300
gtggtttttt tgtttgcaag cagcagatta cgcgcagaaa aaaaggatct caagaagatc   12360
ctttgatctt ttctacgggg tctgacgctc agtggaacga aaactcacgt taagggattt   12420
tggtcatgag attatcaaaa aggatcttca cctagatcct ttaaattaa aaatgaagtt    12480
ttaaatcaat ctaaagtata tatgagtaaa cttggtctga cagttaccaa tgcttaatca   12540
gtgaggcacc tatctcagcg atctgtctat ttcgttcatc catagttgcc tgactccccg   12600
tcgtgtagat aactacgata cgggagggct taccatctgg ccccagtgct gcaatgatac   12660
cgcgagaccc acgctcaccg gctccagatt tatcagcaat aaaccagcca gccggaaggg   12720
ccgagcgcag aagtggtcct gcaactttat ccgcctccat ccagtctatt aattgttgcc   12780
gggaagctag agtaagtagt tcgccagtta atagtttgcg caacgttgtt gccattgctg   12840
caggtcggga gcacaggatg acgcctaaca attcattcaa gccgacaccg cttcgcggcg   12900
```

-continued

```
cggcttaatt caggagttaa acatcatgag ggaagcggtg atcgccgaag tatcgactca    12960
actatcagag gtagttggcg tcatcgagcg ccatctcgaa ccgacgttgc tggccgtaca    13020
tttgtacggc tccgcagtgg atggcggcct gaagccacac agtgatattg atttgctggt    13080
tacggtgacc gtaaggcttg atgaaacaac gcggcgagct ttgatcaacg accttttgga    13140
aacttcggct tccctggag agagcgagat tctccgcgct gtagaagtca ccattgttgt     13200
gcacgacgac atcattccgt ggcgttatcc agctaagcgc gaactgcaat ttggagaatg    13260
gcagcgcaat gacattcttg caggtatctt cgagccagcc acgatcgaca ttgatctggc    13320
tatcttgctg acaaaagcaa gagaacatag cgttgccttg gtaggtccag cggcggagga    13380
actctttgat ccggttcctg aacaggatct atttgaggcg ctaaatgaaa ccttaacgct    13440
atggaactcg ccgcccgact gggctggcga tgagcgaaat gtagtgctta cgttgtcccg    13500
catttggtac agcgcagtaa ccggcaaaat cgcgccgaag gatgtcgctg ccgactgggc    13560
aatggagcgc ctgccggccc agtatcagcc cgtcatactt gaagctaggc aggcttatct    13620
tggacaagaa gatcgcttgg cctcgcgcgc agatcagttg gaagaatttg ttcactacgt    13680
gaaaggcgag atcaccaagg tagtcggcaa ataatgtcta acaattcgtt caagccgacg    13740
ccgcttcgcg gcgcggctta actcaagcgt tagatgctgc aggcatcgtg gtgtcacgct    13800
cgtcgtttgg tatggcttca ttcagctccg gttcccaacg atcaaggcga gttacatgat    13860 ccccccatgtt gtgcaaaaaa gcggttagct ccttcggtcc tccga                  13905
```

<210> SEQ ID NO 218
<211> LENGTH: 13888
<212> TYPE: DNA
<213> ORGANISM: Artificial Sequence
<220> FEATURE:
<223> OTHER INFORMATION: pMON78850;Figure 47;the expression vector for the construct containing the Rhizobium meliloti anthranilate synthase wild type allele

<400> SEQUENCE: 218

```
ccaaatcgtg aagtttctca tctaagcccc catttggacg tgaatgtaga cacgtcgaaa      60
taaagatttc cgaattagaa taatttgttt attgcttttcg cctataaata cgacggatcg     120
taatttgtcg ttttatcaaa atgtactttc attttataat aacgctgcgg acatctacat      180
ttttgaattg aaaaaaaatt ggtaattact ctttcttttt ctccatattg accatcatac      240
tcattgctga tccatgtaga tttcccggac atgaagccat ttacaattga atatatcctg      300
ccgccgctgc cgctttgcac ccggtggagc ttgcatgttg gtttctacgc agaactgagc      360
cggttaggca gataatttcc attgagaact gagccatgtg caccttcccc ccaacacggt      420
gagcgacggg gcaacggagt gatccacatg ggacttttcc tagcttggct gccattttg       480 gggtgaggcc gttcgcggcc gaggggcgca gccctgggg ggatgggagg cccgcgttag       540
cgggccggga gggttcgaga agggggggca ccccccttcg gcgtgcgcgg tcacgcgcac      600
agggcgcagc cctggttaaa aacaaggttt ataaatattg gtttaaaagc aggttaaaag      660
acaggttagc ggtggccgaa aaacgggcgg aaaccccttgc aaatgctgga ttttctgcct    720
gtggacagcc cctcaaatgt caataggtgc gcccctcatc tgtcagcact ctgcccctca      780
agtgtcaagg atcgcgcccc tcatctgtca gtagtcgcgc ccctcaagtg tcaataccgc      840
agggcactta tccccaggct tgtccacatc atctgtggga aactcgcgta aaatcaggcg      900
ttttcgccga tttgcgaggc tggccagctc cacgtcgccg gccgaaatcg agcctgcccc      960
tcatctgtca acgccgcgcc gggtgagtcg gccctcaag tgtcaacgtc cgcccctcat     1020
```

-continued

```
ctgtcagtga gggccaagtt ttccgcgagg tatccacaac gccggcggcc ggccgcggtg    1080
tctcgcacac ggcttcgacg gcgtttctgg cgcgtttgca gggccataga cggccgccag    1140
cccagcggcg agggcaacca gcccggtgag cgtcggaaag ggtcgatcga ccgatgccct    1200
tgagagcctt caacccagtc agctccttcc ggtgggcgcg gggcatgact atcgtcgccg    1260
cacttatgac tgtcttcttt atcatgcaac tcgtaggaca ggtgccggca gcgctctggg    1320
tcattttcgg cgaggaccgc tttcgctgga gcgcgacgat gatcggcctg tcgcttgcgg    1380
tattcggaat cttgcacgcc ctcgctcaag ccttcgtcac tggtcccgcc accaaacgtt    1440
tcggcgagaa gcaggccatt atcgccggca tggcggccga cgcgctgggc tacgtcttgc    1500
tggcgttcgc gacgcgaggc tggatggcct tccccattat gattcttctc gcttccggcg    1560
gcatcgggat gcccgcgttg caggccatgc tgtccaggca ggtagatgac gaccatcagg    1620
gacagcttca aggatcgctc gcggctctta ccagcctaac ttcgatcatt ggaccgctga    1680
tcgtcacggc gatttatgcc gcctcggcga gcacatggaa cggggttggca tggattgtag    1740 gcgccgccct ataccttgtc tgcctccccg cgttgcgtcg cggtgcatgg agccgggcca    1800
cctcgacctg aatggaagcc ggcggcacct cgctaacgga ttcaccactc caagaattgg    1860
agccaatcaa ttcttgcgga gaactgtgaa tgcgcaaacc aaccctttggc agaacatatc    1920 catcgcgtcc gccatctcca gcagccgcac gcggcgcatc tcgggcagcg ttgggtcctg    1980
gccacgggtg cgcatgatcg tgctcctgtc gttgaggacc cggctaggct ggcggggttg    2040
ccttactggt tagcagaatg aatcaccgat acgcgagcga acgtgaagcg actgctgctg    2100
caaaacgtct gcgacctgag caacaacatg aatggtcttc ggtttccgtg tttcgtaaag    2160
tctggaaacg cggaagtcag cgccctgcac cattatgttc cggatctgca tcgcaggatg    2220
ctgctggcta ccctgtggaa cacctacatc tgtattaacg aagcgctggc attgaccctg    2280
agtgattttt ctctggtccc gccgcatcca taccgccagt tgtttaccct cacaacgttc    2340
cagtaaccgg gcatgttcat catcagtaac ccgtatcgtg agcatcctct ctcgtttcat    2400
cggtatcatt accccatga acagaaatcc cccttacacg gaggcatcag tgaccaaaca    2460
ggaaaaaacc gcccttaaca tggcccgctt tatcagaagc cagacattaa cgcttctgga    2520
gaaactcaac gagctggacg cggatgaaca ggcagacatc tgtgaatcgc ttcacgacca    2580
cgctgatgag ctttaccgca gctgcctcgc gcgtttcggt gatgacggtg aaaacctctg    2640
acacatgcag ctcccggaga cggtcacagc ttgtctgtaa gcggatgccg ggagcagaca    2700
agcccgtcag ggcgcgtcag cgggtgttgg cgggtgtcgg ggcgcagcca tgacccagtc    2760
acgtagcgat agcggagtgt atactggctt aactatgcgg catcagagca gattgtactg    2820
agagtgcacc atatgcggtg tgaaataccg cacagatgcg taaggagaaa ataccgcatc    2880
aggcgctctt ccgcttcctc gctcactgac tcgctgcgct cggtcgttcg gctgcggcga    2940
gcggtatcag ctcactcaaa ggcggtaata cggttatcca cagaatcagg ggataacgca    3000
ggaaagaaca tgtgagcaaa aggccagcaa aaggccagga accgtaaaaa ggccgcgttg    3060
ctggcgtttt tccataggct ccgccccct gacgagcatc acaaaaatcg acgctcaagt    3120
cagaggtggc gaaacccgac aggactataa agataccagg cgtttccccc tggaagctcc    3180
ctcgtgcgct ctcctgttcc gaccctgccg cttaccggat acctgtccgc ctttctccct    3240
tcgggaagcg tggcgctttc tcatagctca cgctgtaggt atctcagttc ggtgtaggtc    3300
gttcgctcca agctgggctg tgtgcacgaa ccccccgttc agcccgaccg ctgcgcctta    3360
tccggtaact atcgtcttga gtccaacccg gtaagacacg acttatcgcc actggcagca    3420
```

```
gccactggta acaggattag cagagcgagg tatgtaggcg gtgctacaga gttcttgaag      3480
tggtggccta actacggcta cactagaagg acagtatttg gtatctgcgc tctgctgaag      3540
ccagttacct tcggaaaaag agttggtagc tcttgatccg gcaaacaaac caccgctggt      3600
agcggtggtt ttttgtttg caagcagcag attacgcgca gaaaaaagg atctcaagaa        3660 gatcctttga tcttttctac ggggtctgac gctcagtgga acgaaaactc acgttaaggg      3720
attttggtca tgagattatc aaaaaggatc ttcacctaga tccttttaaa ttaaaaatga      3780
agttttaaat caatctaaag tatatatgag taaacttggt ctgacagtta ccaatgctta      3840
atcagtgagg cacctatctc agcgatctgt ctatttcgtt catccatagt tgcctgactc      3900
cccgtcgtgt agataactac gatacgggag ggcttaccat ctggccccag tgctgcaatg      3960
ataccgcgag acccacgctc accggctcca gatttatcag caataaacca gccagccgga      4020
agggccgagc gcagaagtgg tcctgcaact ttatccgcct ccatccagtc tattaattgt      4080
tgccgggaag ctagagtaag tagttcgcca gttaatagtt tgcgcaacgt tgttgccatt      4140
gctgcaggtc gggagcacag gatgacgcct aacaattcat tcaagccgac accgcttcgc      4200
ggcgcggctt aattcaggag ttaaacatca tgagggaagc ggtgatcgcc gaagtatcga      4260
ctcaactatc agaggtagtt ggcgtcatcg agcgccatct cgaaccgacg ttgctggccg      4320
tacatttgta cggctccgca gtggatggcg gcctgaagcc acacagtgat attgatttgc      4380
tggttacggt gaccgtaagg cttgatgaaa caacgcggcg agctttgatc aacgaccttt      4440
tggaaacttc ggcttcccct ggagagagcg agattctccg cgctgtagaa gtcaccattg      4500
ttgtgcacga cgacatcatt ccgtggcgtt atccagctaa gcgcgaactg caatttggag      4560
aatggcagcg caatgacatt cttgcaggta tcttcgagcc agccacgatc gacattgatc      4620
tggctatctt gctgacaaaa gcaagagaac atagcgttgc cttggtaggt ccagcggcgg      4680
aggaactctt tgatccggtt cctgaacagg atctatttga ggcgctaaat gaaaccttaa      4740
cgctatggaa ctcgccgccc gactgggctg gcgatgagcg aaatgtagtg cttacgttgt      4800
cccgcatttg gtacagcgca gtaaccggca aaatcgcgcc gaaggatgtc gctgccgact      4860
gggcaatgga gcgcctgccg gcccagtatc agcccgtcat acttgaagct aggcaggctt      4920
atcttggaca agaagatcgc ttggcctcgc gcgcagatca gttggaagaa tttgttcact      4980
acgtgaaagg cgagatcacc aaggtagtcg gcaaataatg tctaacaatt cgttcaagcc      5040
gacgccgctt cgcggcgcgg cttaactcaa gcgttagatg ctgcaggcat cgtggtgtca      5100
cgctcgtcgt ttggtatggc ttcattcagc tccggttccc aacgatcaag gcgagttaca      5160
tgatccccca tgttgtgcaa aaaagcggtt agctccttcg gtcctccgat cgaggatttt      5220
tcggcgctgc gctacgtccg cgaccgcgtt gagggatcaa gccacagcag cccactcgac      5280
cttctagccg acccagacga gccaagggat cttttttggaa tgctgctccg tcgtcaggct      5340
ttccgacgtt tgggtggttg aacagaagtc attatcgcac ggaatgccaa gcactcccga      5400
ggggaaccct gtggttggca tgcacataca aatggacgaa cggataaacc ttttcacgcc      5460
cttttaaata tccgattatt ctaataaacg ctctttctc ttaggtttac ccgccaatat       5520
atcctgtcaa acactgatag tttaaactga aggcgggaaa cgacaatctg atccccatca     5580
agctagcttc tgcaggtcct gctcgaggtc actaagcaac taactttgag gaatgaggtg     5640
atgatgaatt aactcactcc attccacaaa ccaaacaaaa atttgaggag tgagaagatg     5700
attgactatc tcattcctca aaccaaacac ctcaaatata tctgctatcg ggattggcat      5760
tcctgtatcc ctacgcccgt gtacccctg tttagagaac ctccaaaggt ataagatggc       5820
```

```
gaagattatt gttgtcttgt ctttcatcat atatcgagtc tttccctagg atattattat    5880
tggcaatgag cattacacgg ttaatcgatt gagagaacat gcatctcacc ttcagcaaat    5940
aattacgata atccatattt tacgcttcgt aacttctcat gagtttcgat atacaaattt    6000
gttttctgga caccctacca ttcatcctct tcggagaaga gaggaagtgt cctcaattta    6060
aatatgttgt catgctgtag ttcttcacaa aatctcaaca ggtaccaagc acattgtttc    6120
cacaaattat attttagtca caataaatct atattattat taatatacta aaactatact    6180
gacgctcaga tgcttttact agttcttgct agtatgtgat gtaggtctac gtggaccaga    6240
aaatagtgag acacggaaga caaaagaagt aaaagaggcc cggactacgg cccacatgag    6300
attcggcccc gccacctccg gcaaccagcg gccgatccaa cggcagtgcg cgcacacaca    6360
caacctcgta tatatcgccg cgcggaagcg gcgcgaccga ggaagccttg tcctcgacac    6420
cccctacaca ggtgtcgcgc tgcccccgac acgagtcccg catgcgtccc acgcggccgc    6480
gccagatccc gcctccgcgc gttgccacgc cctctataaa cacccagctc tccctcgccc    6540
tcatctacct cactcgtagt cgtagctcaa gcatcagcgg cagcggcagc ggcaggatct    6600
ctgggcagcg tgcgcacgtg gggtatctag ctcgctctgc tagcctacca atcgaattcc    6660
tgcaggtcga ctctagagga tctaccgtct tcggtacgcg ctcactccgc cctctgcctt    6720
tgttactgcc acgtttctct gaatgctctc ttgtgtggtg attgctgaga gtggtttagc    6780
tggatctaga attacactct gaaatcgtgt tctgcctgtg ctgattactt gccgtccttt    6840
gtagcagcaa aatataggga catggtagta cgaaacgaag atagaaccta cacagcaata    6900
cgagaaatgt gtaatttggt gcttagcggt atttatttaa gcacatgttg gtgttatagg    6960
gcacttggat tcagaagttt gctgttaatt taggcacagg cttcatacta catgggtcaa    7020
tagtataggg attcatatta taggcgatac tataataatt tgttcgtctg cagagcttat    7080
tatttgccaa aattagatat tcctattctg tttttgtttg tgtgctgtta aattgttaac    7140
gcctgaagga ataaatataa atgacgaaat tttgatgttt atctctgctc ctttattgtg    7200
accataagtc aagatcagat gcacttgttt taaatattgt tgtctgaaga aataagtact    7260
gacagtattt tgatgcattg atctgcttgt ttgttgtaac aaaatttaaa aataaagagt    7320 ttccttttg ttgctctcct tacctcctga tggtatctag tatctaccaa ctgacactat    7380
attgcttctc tttacatacg tatcttgctc gatgccttct ccctagtgtt gaccagtgtt    7440
actcacatag tctttgctca tttcattgta atgcagatac caagcggcct ctagaggatc    7500
tccctagagg atctccagat ctatggaatc cctagccgcc acctccgtgt tcgcgccctc    7560
ccgcgtcgcc gtcccggcgg cgcgggccct ggttagggcg gggacggtgg taccaaccag    7620
gcggacgagc agccggagcg gaaccagcgg ggtgaaatgc tctgctgccg tgacgccgca    7680
ggcgagccca gtgattagca ggagcgctgc ggcggccatg gcagcggtaa ttctggaaga    7740
cggcgcggag agttatacca cgaagggtgg catcgtcgtc acccgcaggc ggcgtgaggc    7800
atcctacagc gacgcgatcg ccggttatgt cgaccggctg gacgaacgcc gcggcgcggt    7860
cttttcctcg aactacgaat atcccggccg ctatacccgc tgggacactg cggtggtcga    7920
cccgccgctt gccatctcct ccttcggtcg ctcgctctgg atcgaagcct ataacgaacg    7980
cggcgaagtg ctgctggcgc tgatcgccga ggatctgaag tccgttgccg acatcacgct    8040
cggctcactt gccgcccgcc gcctcgacct caccatcaac gagcccgatc gtgtcttcac    8100
cgaggaagag cggtcgaaga tgccgacggt cttttacggtt cttcgcgcgg tgacgaacct    8160
cttccactcg gaggaggact cgaacctcgg cctctatggc gccttcggct acgacctcgc    8220
```

```
cttccagttc gatgcgatcg aactgaagct ttcgcgtccg gacgaccagc gcgacatggt    8280
tctctttctg ccggacgaga tccttgtggt cgatcactat gcggccaagg cctggatcga    8340
ccgctacgat ttcgccaggg agaacctttc gaccgagggc aaggcagcgg acattgctcc    8400
cgagccgttc cgcagcgtcg acagcatccc gccgcacggg gatcaccgcc cgggcgaata    8460
tgccgagctc gtcgtcaagg cgaaggaaag cttccgtcgc ggcgatcttt tcgaagtggt    8520
gccggggcag aaattctacg agcgctgcga aagccgcccg tccgagattt ccaaccggct    8580
gaaggcgatc aatccgtcgc cctattcctt cttcatcaat ctcggcaacc aggaatatct    8640
cgtcggtgct tcgccggaga tgttcgtgcg cgtttccggc cggcgcatcg agacctgccc    8700
gatctccggt acgatcaagc gcggcgacga tccgatcgcc gacagcgagc agatcctgaa    8760
gctcttgaac tcgaagaagg acgagtccga gctcaccatg tgctcggacg tcgaccgcaa    8820
cgacaagagc cgggtctgcg tgccgggctc ggtcaaggtg atcggccggc gtcagatcga    8880
gatgtattcg cggctgatcc acacggtcga tcacatcgag gggcgcctgc gcgacgatat    8940
ggacgccttc gacgggttcc tcagccacgc ctgggcggtg accgttaccg gcgcgccaaa    9000
gctctgggcc atgcgcttca tcgagagcca cgagaagagc ccgcgtgcct ggtatggcgg    9060
cgcgatcggc atggtcggct tcaacggcga catgaatacc gggctgacct tgcgtaccat    9120
ccgcatcaag gacgggatcg ccgaggtgag ggcgggtgcg acgctcctct atgattccaa    9180
tccggaagaa gaagaagccg aaaccgaact gaaggcctct gccatgattg cagccatccg    9240
cgacgcgaaa tccgcaaaca gcgccaaatc cgcgcgcgat gtcgccgccg tcggcgccgg    9300
agtcagcatc ctgctcgtcg atcacgagga cagcttcgtc catccctcg cgaactactt    9360
ccgccagacc ggcgcgtccg tcaccaccgt gcgcacgccg gtggccgagg aaatcttcga    9420
ccgggtcaag ccggacctcg tcgtgctttc gcccggtccc ggcaccccga aggacttcga    9480
ctgcaaggcg acgatcaaga ggcgcgggc gcgggacctg ccgatcttcg gcgtctgcct    9540
ggggctgcag gcgctcgcgg aggcctatgg cggcgacctt cgtcaactgg cgatcccgat    9600
gcatgggaag ccctcgcgca tccgcgtgct cgaacccggc atcgtcttct ccggcctcgg    9660
caaggaggtg acggtcgggc gctatcattc gattttcgcc gatccgtcca acctgccgcg    9720
cgaattcgtg atcacggccg aaagcgaaga tggtacgatc atgggcatcg aacacagcaa    9780
ggagccggtg gcggccgtgc agttccatcc ggaatcgatc atgacgctgg gcggcgacgc    9840
cggcatgcgg atgatcgaga acgtggttgc ccatctcgcc aagcgggcga agaccaaggc    9900
agcctgaact agatcggatc cggggatcga tgagctaagc tagctatatc atcaatttat    9960
gtattacaca taatatcgca ctcagtcttt catctacggc aatgtaccag ctgatataat   10020
cagttattga aatatttctg aatttaaact tgcatcaata aatttatgtt tttgcttgga   10080
ctataatacc tgacttgtta ttttatcaat aaatatttaa actatatttc tttcaagata   10140
tcattcttta caagtatacg tgtttaaatt gaataccata aatttttatt tttcaaatac   10200
atgtaaaatt atgaaatggg agtggtggcg accgagctca agcacacttc aattcctata   10260
acggaccaaa tcgcaaaaat tataataaca tattatttca tcctggatta aaagaaagtc   10320
accgggatt attttgtgac gccgattaca tacggcgaca ataaagacat tggaaatcgt   10380
agtacatatt ggaatacact gattatatta atgatgaata catactttaa tatccttacg   10440
taggatcgat ccgaatttcg acctcgagcg gccgctctag aactagtgga tcccccctt   10500
aattaagggg gctgcaggaa ttcataactt cgtataatgt atgctatacg aagttatgtt   10560
tcgaggtcat tcatatgctt gagaagagag tcgggatagt ccaaaataaa acaaaggtaa   10620
```

```
gattacctgg tcaaaagtga aaacatcagt taaaaggtgg tataaagtaa aatatcggta   10680
ataaaaggtg gcccaaagtg aaatttactc ttttctacta ttataaaaat tgaggatgtt   10740
tttgtcggta ctttgatacg tcattttgt atgaattggt ttttaagttt attcgctttt    10800
ggaaatgcat atctgtattt gagtcgggtt ttaagttcgt ttgcttttgt aaatacagag   10860
ggatttgtat aagaaatatc tttagaaaaa cccatatgct aatttgacat aattttgag    10920 aaaaatatat attcaggcga attctcacaa tgaacaataa taagattaaa atagctttcc   10980
cccgttgcag cgcatgggta ttttttctag taaaaataaa agataaactt agactcaaaa   11040
catttacaaa aacaacccct aaagttccta aagcccaaag tgctatccac gatccatagc   11100
aagcccagcc caacccaacc caacccaacc cacccagtc cagccaactg gacaatagtc     11160
tccacacccc cccactatca ccgtgagttg tccgcacgca ccgcacgtct cgcagccaaa   11220 aaaaaaaga aagaaaaaaa agaaaagaa aaaacagcag gtgggtccgg gtcgtgggg      11280 ccggaaacgc gaggaggatc gcgagccagc gacgaggccg gccctccctc cgcttccaaa   11340
gaaacgcccc ccatcgccac tatatacata ccccccctc tcctcccatc ccccaaccc     11400 taccaccacc accaccacca cctccacctc ctccccctc gctgccggac gacgagctcc    11460
tcccccctcc ccctccgccg ccgccgcgcc ggtaaccacc ccgcccctct cctctttctt   11520
tctccgtttt ttttccgtc tcggtctcga tctttggcct tggtagtttg ggtgggcgag    11580
aggcggcttc gtgcgcgccc agatcggtgc gcgggagggg cgggatctcg cggctggggc   11640
tctcgccggc gtggatccgg cccgatctc gcgggaatg gggctctcgg atgtagatct     11700
gcgatccgcc gttgttgggg gagatgatgg ggggtttaaa atttccgccg tgctaaacaa   11760
gatcaggaag aggggaaaag ggcactatgg tttatatttt tatatatttc tgctgcttcg   11820
tcaggcttag atgtgctaga tcttttcttc ttcttttgt gggtagaatt tgaatccctc    11880
agcattgttc atcggtagtt tttcttttca tgatttgtga caaatgcagc ctcgtgcgga   11940
gcttttttgt aggtagaagt gatcaaccat ggcgcaagtt agcagaatct gcaatggtgt   12000
gcagaaccca tctcttatct ccaatctctc gaaatccagt caacgcaaat ctcccttatc   12060
ggtttctctg aagacgcagc agcatccacg agcttatccg atttcgtcgt cgtggggatt   12120
gaagaagagt gggatgacgt taattggctc tgagcttcgt cctcttaagg tcatgtcttc   12180
tgtttccacg gcgtgcatgc ttcacggtgc aagcagccgg cccgcaaccg cccgcaaatc   12240
ctctggcctt tccggaaccg tccgcattcc cggcgacaag tcgatctccc accggtcctt   12300
catgttcggc ggtctcgcga gcggtgaaac gcgcatcacc ggccttctgg aaggcgagga   12360
cgtcatcaat acgggcaagg ccatgcaggc gatgggcgcc cgcatccgta aggaaggcga   12420
cacctggatc atcgatggcg tcggcaatgg cggcctcctg gcgcctgagg cgccgctcga   12480
tttcggcaat gccgccacgg gctgccgcct gacgatgggc ctcgtcgggg tctacgattt   12540
cgacagcacc ttcatcggcg acgcctcgct cacaaagcgc ccgatgggcc gcgtgttgaa   12600
cccgctgcgc gaaatgggcg tgcaggtgaa atcggaagac ggtgaccgtc ttcccgttac   12660
cttgcgcggg ccgaagacgc cgacgccgat cacctaccgc gtgccgatgg cctccgcaca   12720
ggtgaagtcc gccgtgctgc tcgccggcct caacacgccc ggcatcacga cggtcatcga   12780
gccgatcatg acgcgcgatc atacggaaaa gatgctgcag ggctttggcg ccaaccttac   12840
cgtcgagacg gatgcggacg gcgtgcgcac catccgcctg gaaggccgcg gcaagctcac   12900
cggccaagtc atcgacgtgc cgggcgaccc gtcctcgacg gccttcccgc tggttgcggc   12960
cctgcttgtt ccgggctccg acgtcaccat cctcaacgtg ctgatgaacc ccacccgcac   13020
```

| | | | | |
|---|---|---|---|---|
| cggcctcatc | ctgacgctgc | aggaaatggg | cgccgacatc | gaagtcatca acccgcgcct | 13080 |
| tgccggcggc | gaagacgtgg | cggacctgcg | cgttcgctcc | tccacgctga agggcgtcac | 13140 |
| ggtgccggaa | gaccgcgcgc | cttcgatgat | cgacgaatat | ccgattctcg ctgtcgccgc | 13200 |
| cgccttcgcg | gaagggcga | ccgtgatgaa | cggtctggaa | gaactccgcg tcaaggaaag | 13260 |
| cgaccgcctc | tcggccgtcg | ccaatggcct | caagctcaat | ggcgtggatt gcgatgaggg | 13320 |
| cgagacgtcg | ctcgtcgtgc | gtggccgccc | tgacggcaag | gggctcggca cgcctcggg | 13380 |
| cgccgccgtc | gccacccatc | tcgatcaccg | catcgccatg | agcttcctcg tcatgggcct | 13440 |
| cgtgtcggaa | aaccctgtca | cggtggacga | tgccacgatg | atcgccacga gcttcccgga | 13500 |
| gttcatggac | ctgatggccg | ggctgggcgc | gaagatcgaa | ctctccgata cgaaggctgc | 13560 |
| ctgatgagct | cgaattcccg | atcgttcaaa | catttggcaa | taaagtttct taagattgaa | 13620 |
| tcctgttgcc | ggtcttgcga | tgattatcat | ataatttctg | ttgaattacg ttaagcatgt | 13680 |
| aataattaac | atgtaatgca | tgacgttatt | tatgagatgg | gtttttatga ttagagtccc | 13740 |
| gcaattatac | atttaatacg | cgatagaaaa | caaaatatag | cgcgcaaact aggataaatt | 13800 |
| atcgcgcgcg | gtgtcatcta | tgttactaga | tcggggataa | cgatcaagct ataacttcgt | 13860 |
| ataatgtatg | ctatacgaag | ttatcgcg | | | 13888 |

<210> SEQ ID NO 219
<211> LENGTH: 13888
<212> TYPE: DNA
<213> ORGANISM: Artificial Sequence
<220> FEATURE:
<223> OTHER INFORMATION: pMON78851;Figure 48;the expression vector for the construct containing the Rhizobium meliloti anthranilate synthase S51C allele

<400> SEQUENCE: 219

| | | | | |
|---|---|---|---|---|
| ccaaatcgtg | aagtttctca | tctaagcccc | catttggacg | tgaatgtaga cacgtcgaaa | 60 |
| taaagatttc | cgaattagaa | taatttgttt | attgctttcg | cctataaata cgacggatcg | 120 |
| taatttgtcg | ttttatcaaa | atgtactttc | attttataat | aacgctgcgg acatctacat | 180 |
| ttttgaattg | aaaaaaaatt | ggtaattact | cttcttttt | ctccatattg accatcatac | 240 |
| tcattgctga | tccatgtaga | tttcccggac | atgaagccat | ttacaattga atatatcctg | 300 |
| ccgccgctgc | cgcttttgcac | ccggtggagc | ttgcatgttg | gttctacgc agaactgagc | 360 |
| cggttaggca | gataatttcc | attgagaact | gagccatgtg | caccttcccc caacacggt | 420 |
| gagcgacggg | gcaacggagt | gatccacatg | ggactttttcc | tagcttggct gccattttg | 480 |
| gggtgaggcc | gttcgcggcc | gaggggcgca | gcccctgggg | ggatgggagg cccgcgttag | 540 |
| cgggccggga | gggttcgaga | aggggggca | ccccccttcg | gcgtgcgcgg tcacgcgcac | 600 |
| agggcgcagc | cctggttaaa | aacaaggttt | ataaatattg | gtttaaaagc aggttaaaag | 660 |
| acaggttagc | ggtggccgaa | aaacgggcgg | aaacccttgc | aaatgctgga ttttctgcct | 720 |
| gtggacagcc | cctcaaatgt | caataggtgc | gcccctcatc | tgtcagcact ctgcccctca | 780 |
| agtgtcaagg | atcgcgcccc | tcatctgtca | gtagtcgcgc | ccctcaagtg tcaataccgc | 840 |
| agggcactta | tccccaggct | tgtccacatc | atctgtggga | aactcgcgta aaatcaggcg | 900 |
| ttttcgccga | tttgcgaggc | tggccagctc | cacgtcgccg | gccgaaatcg agcctgcccc | 960 |
| tcatctgtca | acgccgcgcc | gggtgagtcg | gcccctcaag | tgtcaacgtc cgcccctcat | 1020 |
| ctgtcagtga | gggccaagtt | ttccgcgagg | tatccacaac | gccggcggcc ggccgcggtg | 1080 |
| tctcgcacac | ggcttcgacg | gcgtttctgg | cgcgtttgca | gggccataga cggccgccag | 1140 |

```
cccagcggcg agggcaacca gcccggtgag cgtcggaaag ggtcgatcga ccgatgccct   1200
tgagagcctt caacccagtc agctccttcc ggtgggcgcg gggcatgact atcgtcgccg   1260
cacttatgac tgtcttcttt atcatgcaac tcgtaggaca ggtgccggca gcgctctggg   1320
tcattttcgg cgaggaccgc tttcgctgga gcgcgacgat gatcggcctg tcgcttgcgg   1380
tattcggaat cttgcacgcc ctcgctcaag ccttcgtcac tggtcccgcc accaaacgtt   1440
tcggcgagaa gcaggccatt atcgccggca tggcggccga cgcgctgggc tacgtcttgc   1500
tggcgttcgc gacgcgaggc tggatggcct tccccattat gattcttctc gcttccggcg   1560
gcatcgggat gcccgcgttg caggccatgc tgtccaggca ggtagatgac gaccatcagg   1620
gacagcttca aggatcgctc gcggctctta ccagcctaac ttcgatcatt ggaccgctga   1680
tcgtcacggc gatttatgcc gcctcggcga gcacatggaa cgggttggca tggattgtag   1740
gcgccgccct ataccttgtc tgcctccccg cgttgcgtcg cggtgcatgg agccgggcca   1800
cctcgacctg aatggaagcc ggcggcacct cgctaacgga ttcaccactc caagaattgg   1860
agccaatcaa ttcttgcgga gaactgtgaa tgcgcaaacc aaccccttggc agaacatatc   1920 catcgcgtcc gccatctcca gcagccgcac gcggcgcatc tcgggcagcg ttgggtcctg   1980
gccacgggtg cgcatgatcg tgctcctgtc gttgaggacc cggctaggct ggcggggttg   2040
ccttactggt tagcagaatg aatcaccgat acgcgagcga acgtgaagcg actgctgctg   2100
caaaacgtct gcgacctgag caacaacatg aatggtcttc ggtttccgtg tttcgtaaag   2160
tctggaaacg cggaagtcag cgccctgcac cattatgttc cggatctgca tcgcaggatg   2220
ctgctggcta ccctgtggaa cacctacatc tgtattaacg aagcgctggc attgaccctg   2280
agtgattttt ctctggtccc gccgcatcca taccgccagt tgtttaccct cacaacgttc   2340
cagtaaccgg gcatgttcat catcagtaac ccgtatcgtg agcatcctct ctcgtttcat   2400
cggtatcatt accccccatga acagaaatcc cccttacacg gaggcatcag tgaccaaaca   2460
ggaaaaaacc gcccttaaca tggcccgctt tatcagaagc cagacattaa cgcttctgga   2520
gaaactcaac gagctggacg cggatgaaca ggcagacatc tgtgaatcgc ttcacgacca   2580
cgctgatgag ctttaccgca gctgcctcgc gcgtttcggt gatgacggtg aaaacctctg   2640
acacatgcag ctcccggaga cggtcacagc ttgtctgtaa gcggatgccg ggagcagaca   2700
agcccgtcag ggcgcgtcag cgggtgttgg cgggtgtcgg ggcgcagcca tgacccagtc   2760
acgtagcgat agcggagtgt atactggctt aactatgcgg catcagagca gattgtactg   2820
agagtgcacc atatgcggtg tgaaataccg cacagatgcg taaggagaaa ataccgcatc   2880
aggcgctctt ccgcttcctc gctcactgac tcgctgcgct cggtcgttcg gctgcggcga   2940
gcggtatcag ctcactcaaa ggcggtaata cggttatcca cagaatcagg ggataacgca   3000
ggaaagaaca tgtgagcaaa aggccagcaa aaggccagga accgtaaaaa ggccgcgttg   3060
ctggcgtttt tccataggct ccgcccccct gacgagcatc acaaaaatcg acgctcaagt   3120
cagaggtggc gaaacccgac aggactataa agataccagg cgtttccccc tggaagctcc   3180
ctcgtgcgct ctcctgttcc gaccctgccg cttaccggat acctgtccgc ctttctccct   3240
tcgggaagcg tggcgctttc tcatagctca cgctgtaggt atctcagttc ggtgtaggtc   3300
gttcgctcca agctgggctg tgtgcacgaa ccccccgttc agcccgaccg ctgcgcctta   3360
tccggtaact atcgtcttga gtccaacccg gtaagacacg acttatcgcc actggcagca   3420
gccactggta acaggattag cagagcgagg tatgtaggcg gtgctacaga gttcttgaag   3480
tggtggccta actacggcta cactagaagg acagtatttg gtatctgcgc tctgctgaag   3540
```

```
ccagttacct tcggaaaaag agttggtagc tcttgatccg gcaaacaaac caccgctggt   3600
agcggtggtt ttttttgtttg caagcagcag attacgcgca gaaaaaaagg atctcaagaa   3660
gatcctttga tcttttctac ggggtctgac gctcagtgga acgaaaactc acgttaaggg   3720
attttggtca tgagattatc aaaaaggatc ttcacctaga tccttttaaa ttaaaaatga   3780
agttttaaat caatctaaag tatatatgag taaacttggt ctgacagtta ccaatgctta   3840
atcagtgagg cacctatctc agcgatctgt ctatttcgtt catccatagt tgcctgactc   3900
cccgtcgtgt agataactac gatacgggag ggcttaccat ctggcccag tgctgcaatg    3960 ataccgcgag acccacgctc accggctcca gatttatcag caataaacca gccagccgga   4020
agggccgagc gcagaagtgg tcctgcaact ttatccgcct ccatccagtc tattaattgt   4080
tgccgggaag ctagagtaag tagttcgcca gttaatagtt tgcgcaacgt tgttgccatt   4140
gctgcaggtc gggagcacag gatgacgcct aacaattcat tcaagccgac accgcttcgc   4200
ggcgcggctt aattcaggag ttaaacatca tgagggaagc ggtgatcgcc gaagtatcga   4260
ctcaactatc agaggtagtt ggcgtcatcg agcgccatct cgaaccgacg ttgctggccg   4320
tacatttgta cggctccgca gtggatggcg gcctgaagcc acacagtgat attgatttgc   4380
tggttacggt gaccgtaagg cttgatgaaa caacgcggcg agctttgatc aacgaccttt   4440
tggaaacttc ggcttcccct ggagagagcg agattctccg cgctgtagaa gtcaccattg   4500
ttgtgcacga cgacatcatt ccgtggcgtt atccagctaa gcgcgaactg caatttggag   4560
aatggcagcg caatgacatt cttgcaggta tcttcgagcc agccacgatc gacattgatc   4620
tggctatctt gctgacaaaa gcaagagaac atagcgttgc cttggtaggt ccagcggcgg   4680
aggaactctt tgatccggtt cctgaacagg atctatttga ggcgctaaat gaaaccttaa   4740
cgctatggaa ctcgccgccc gactgggctg gcgatgagcg aaatgtagtg cttacgttgt   4800
cccgcatttg gtacagcgca gtaaccggca aaatcgcgcc gaaggatgtc gctgccgact   4860
gggcaatgga gcgcctgccg gcccagtatc agcccgtcat acttgaagct aggcaggctt   4920
atcttggaca agaagatcgc ttggcctcgc gcgcagatca gttggaagaa tttgttcact   4980
acgtgaaagg cgagatcacc aaggtagtcg gcaaataatg tctaacaatt cgttcaagcc   5040
gacgccgctt cgcggcgcgg cttaactcaa gcgttagatg ctgcaggcat cgtggtgtca   5100
cgctcgtcgt ttggtatggc ttcattcagc tccggttccc aacgatcaag gcgagttaca   5160
tgatccccca tgttgtgcaa aaaagcggtt agctccttcg gtcctccgat cgaggatttt   5220
tcggcgctgc gctacgtccg cgaccgcgtt gagggatcaa gccacagcag cccactcgac   5280
cttctagccg acccagacga gccaaggat cttttttggaa tgctgctccg tcgtcaggct   5340
ttccgacgtt tgggtggttg aacagaagtc attatcgcac ggaatgccaa gcactcccga   5400
ggggaaccct gtggttggca tgcacataca aatggacgaa cggataaacc ttttcacgcc   5460
cttttaaata tccgattatt ctaataaacg ctcttttctc ttaggtttac ccgccaatat   5520
atcctgtcaa acactgatag tttaaactga aggcgggaaa cgacaatctg atccccatca   5580
agctagcttc tgcaggtcct gctcgaggtc actaagcaac taactttgag gaatgaggtg   5640
atgatgaatt aactcactcc attccacaaa ccaaacaaaa atttgaggag tgagaagatg   5700
attgactatc tcattcctca aaccaaacac ctcaaatata tctgctatcg ggattggcat   5760
tcctgtatcc ctacgcccgt gtaccccctg tttagagaac ctccaaaggt ataagatggc   5820
gaagattatt gttgtcttgt cttthcatcat atatcgagtc tttccctagg atattattat   5880
tggcaatgag cattacacgg ttaatcgatt gagagaacat gcatctcacc ttcagcaaat   5940
```

```
aattacgata atccatattt tacgcttcgt aacttctcat gagtttcgat atacaaattt    6000
gttttctgga caccctacca ttcatcctct tcggagaaga gaggaagtgt cctcaattta    6060
aatatgttgt catgctgtag ttcttcacaa aatctcaaca ggtaccaagc acattgtttc    6120
cacaaattat attttagtca caataaatct atattattat taatatacta aaactatact    6180
gacgctcaga tgcttttact agttcttgct agtatgtgat gtaggtctac gtggaccaga    6240
aaatagtgag acacggaaga caaaagaagt aaaagaggcc cggactacgg cccacatgag    6300
attcggcccc gccacctccg gcaaccagcg gccgatccaa cggcagtgcg cgcacacaca    6360
caacctcgta tatatcgccg cgcggaagcg gcgcgaccga ggaagccttg tcctcgacac    6420
cccctacaca ggtgtcgcgc tgcccccgac acgagtcccg catgcgtccc acgcggccgc    6480
gccagatccc gcctccgcgc gttgccacgc cctctataaa cacccagctc tccctcgccc    6540
tcatctacct cactcgtagt cgtagctcaa gcatcagcgg cagcggcagc ggcaggatct    6600
ctgggcagcg tgcgcacgtg gggtatctag ctcgctctgc tagcctacca atcgaattcc    6660
tgcaggtcga ctctagagga tctaccgtct tcggtacgcg ctcactccgc cctctgcctt    6720
tgttactgcc acgtttctct gaatgctctc ttgtgtggtg attgctgaga gtggtttagc    6780
tggatctaga attacactct gaaatcgtgt tctgcctgtg ctgattactt gccgtccttt    6840
gtagcagcaa aatataggga catggtagta cgaaacgaag atagaaccta cacagcaata    6900
cgagaaatgt gtaatttggt gcttagcggt atttatttaa gcacatgttg gtgttatagg    6960
gcacttggat tcagaagttt gctgttaatt taggcacagg cttcatacta catgggtcaa    7020
tagtataggg attcatatta taggcgatac tataataatt tgttcgtctg cagagcttat    7080
tatttgccaa aattagatat tcctattctg tttttgtttg tgtgctgtta aattgttaac    7140
gcctgaagga ataaatataa atgacgaaat tttgatgttt atctctgctc ctttattgtg    7200
accataagtc aagatcagat gcacttgttt taaatattgt tgtctgaaga aataagtact    7260
gacagtattt tgatgcattg atctgcttgt ttgttgtaac aaaatttaaa aataaagagt    7320 ttccttttg ttgctctcct tacctcctga tggtatctag tatctaccaa ctgacactat    7380
attgcttctc tttacatacg tatcttgctc gatgccttct ccctagtgtt gaccagtgtt    7440
actcacatag tctttgctca tttcattgta atgcagatac caagcggcct ctagaggatc    7500
tccctagagg atctccagat ctatggaatc cctagccgcc acctccgtgt tcgcgccctc    7560
ccgcgtcgcc gtcccggcgg cgcgggcccT ggttagggcg gggacggtgg taccaaccag    7620
gcggacgagc agccggagcg gaaccagcgg ggtgaaatgc tctgctgccg tgacgccgca    7680
ggcgagccca gtgattagca ggagcgctgc ggcggccatg gcagcggtaa ttctggaaga    7740
cggcgcggag agttatacca cgaagggtgg catcgtcgtc acccgcaggc ggcgtgaggc    7800
atcctacagc gacgcgatcg ccggttatgt cgaccggctg gacgaacgcc gcggcgcggt    7860
cttttcctgc aactacgaat atcccggccg ctatacccgc tgggacactg cggtggtcga    7920
cccgccgctt gccatctcct ccttcggtcg ctcgctctgg atcgaagcct ataacgaacg    7980
cggcgaagtg ctgctggcgc tgatcgccga ggatctgaag tccgttgccg acatcacgct    8040
cggctcactt gccgcccgcc gcctcgacct caccatcaac gagcccgatc gtgtcttcac    8100
cgaggaagag cggtcgaaga tgccgacggt ctttacggtt cttcgcgcgg tgacgaacct    8160
cttccactcg gaggaggact cgaacctcgg cctctatggc gccttcggct acgacctcgc    8220
cttccagttc gatgcgatcg aactgaagct ttcgcgtccg gacgaccagc gcgacatggt    8280
tctctttctg ccggacgaga tccttgtggt cgatcactat gcggccaagg cctggatcga    8340
```

```
ccgctacgat tcgccaggg agaacctttc gaccgagggc aaggcagcgg acattgctcc    8400
cgagccgttc cgcagcgtcg acagcatccc gccgcacggg gatcaccgcc cgggcgaata    8460
tgccgagctc gtcgtcaagg cgaaggaaag cttccgtcgc ggcgatcttt tcgaagtggt    8520
gccggggcag aaattctacg agcgctgcga aagccgcccg tccgagattt ccaaccggct    8580
gaaggcgatc aatccgtcgc cctattcctt cttcatcaat ctcggcaacc aggaatatct    8640
cgtcggtgct tcgccggaga tgttcgtgcg cgtttccggc cggcgcatcg agacctgccc    8700
gatctccggt acgatcaagc gcggcgacga tccgatcgcc gacagcgagc agatcctgaa    8760
gctcttgaac tcgaagaagg acgagtccga gctcaccatg tgctcggacg tcgaccgcaa    8820
cgacaagagc cgggtctgcg tgccgggctc ggtcaaggtg atcggccggc gtcagatcga    8880
gatgtattcg cggctgatcc acacggtcga tcacatcgag gggcgcctgc gcgacgatat    8940
ggacgccttc gacgggttcc tcagccacgc ctgggcggtg accgttaccg gcgcgccaaa    9000
gctctgggcc atgcgcttca tcgagagcca cgagaagagc ccgcgtgcct ggtatggcgg    9060
cgcgatcggc atggtcggct tcaacggcga catgaatacc gggctgacct tgcgtaccat    9120
ccgcatcaag gacgggatcg ccgaggtgag ggcgggtgcg acgctcctct atgattccaa    9180
tccggaagaa gaagaagccg aaaccgaact gaaggcctct gccatgattg cagccatccg    9240
cgacgcgaaa tccgcaaaca cgccaaatc gcgcgcgat gtcgccgccg tcggcgccgg    9300
agtcagcatc ctgctcgtcg atcacgagga cagcttcgtc catccctcg cgaactactt    9360
ccgccagacc ggcgcgtccg tcaccaccgt gcgcacgccg gtggccgagg aaatcttcga    9420
ccgggtcaag ccggacctcg tcgtgctttc gcccggtccc ggcaccccga aggacttcga    9480
ctgcaaggcg acgatcaaga aggcgcggc gcgggacctg ccgatcttcg gcgtctgcct    9540
ggggctgcag gcgctcgcgg aggcctatgg cggcgacctt cgtcaactgg cgatcccgat    9600
gcatgggaag ccctcgcgca tccgcgtgct cgaacccggc atcgtcttct ccggcctcgg    9660
caaggaggtg acggtcgggc gctatcattc gattttcgcc gatccgtcca acctgccgcg    9720
cgaattcgtg atcacggccg aaagcgaaga tggtacgatc atgggcatcg aacacagcaa    9780
ggagccggtg gcggccgtgc agttccatcc ggaatcgatc atgacgctgg gcggcgacgc    9840
cggcatgcgg atgatcgaga acgtggttgc ccatctcgcc aagcgggcga agaccaaggc    9900
agcctgaact agatcggatc cggggatcga tgagctaagc tagctatatc atcaatttat    9960
gtattacaca taatatcgca ctcagtcttt catctacggc aatgtaccag ctgatataat   10020
cagttattga aatatttctg aatttaaact tgcatcaata aatttatgtt tttgcttgga   10080
ctataatacc tgacttgtta ttttatcaat aaatatttaa actatatttc tttcaagata   10140
tcattcttta caagtatacg tgtttaaatt gaataccata aattttatt tttcaaatac   10200
atgtaaaatt atgaaatggg agtggtggcg accgagctca agcacacttc aattcctata   10260
acggaccaaa tcgcaaaaat tataataaca tattatttca tcctggatta aagaaagtc   10320
accgggatt attttgtgac gccgattaca tacggcgaca ataaagacat tggaaatcgt   10380
agtacatatt ggaatacact gattatatta atgatgaata catactttaa tatccttacg   10440
taggatcgat ccgaatttcg acctcgagcg gccgctctag aactagtgga tccccccctt   10500
aattaagggg gctgcaggaa ttcataactt cgtataatgt atgctatacg aagttatgtt   10560
tcgaggtcat tcatatgctt gagaagagag tcgggatagt ccaaaataaa acaaaggtaa   10620
gattacctgc tcaaaagtga aaacatcagt taaaggtgg tataaagtaa aatatcggta   10680
ataaaaggtg gcccaaagtg aaatttactc ttttctacta ttataaaaat tgaggatgtt   10740
```

-continued

```
tttgtcggta ctttgatacg tcattttgt atgaattggt ttttaagttt attcgctttt    10800
ggaaatgcat atctgtattt gagtcgggtt ttaagttcgt ttgcttttgt aaatacagag    10860
ggatttgtat aagaaatatc tttagaaaaa cccatatgct aatttgacat aattttgag    10920 aaaatatat attcaggcga attctcacaa tgaacaataa taagattaaa atagctttcc    10980
cccgttgcag cgcatgggta tttttctag taaaaataaa agataaactt agactcaaaa    11040
catttacaaa aacaacccct aaagttccta aagcccaaag tgctatccac gatccatagc    11100
aagcccagcc caacccaacc caacccaacc caccccagtc cagccaactg gacaatagtc    11160
tccacacccc cccactatca ccgtgagttg tccgcacgca ccgcacgtct cgcagccaaa    11220
aaaaaaaaga aagaaaaaaa agaaaaagaa aaaacagcag gtgggtccgg gtcgtggggg    11280
ccggaaacgc gaggaggatc gcgagccagc gacgaggccg gccctccctc cgcttccaaa    11340
gaaacgcccc ccatcgccac tatatacata ccccccctc tcctcccatc ccccaaccc    11400 taccaccacc accaccacca cctccacctc ctccccctc gctgccggac gacgagctcc    11460 tccccctcc cctccgccg ccgccgcgcc ggtaaccacc ccgcccctct cctctttctt    11520
tctccgtttt tttttccgtc tcggtctcga tctttggcct tggtagtttg ggtgggcgag    11580
aggcggcttc gtgcgcgccc agatcggtgc gcgggagggg cgggatctcg cggctggggc    11640
tctcgccggc gtggatccgg cccggatctc gcggggaatg gggctctcgg atgtagatct    11700
gcgatccgcc gttgttgggg gagatgatgg ggggtttaaa atttccgccg tgctaaacaa    11760
gatcaggaag aggggaaaag ggcactatgg tttatatttt tatatatttc tgctgcttcg    11820
tcaggcttag atgtgctaga tcttctttc ttcttttgt gggtagaatt tgaatccctc    11880
agcattgttc atcggtagtt tttcttttca tgatttgtga caaatgcagc ctcgtgcgga    11940
gcttttttgt aggtagaagt gatcaaccat ggcgcaagtt agcagaatct gcaatggtgt    12000
gcagaaccca tctcttatct ccaatctctc gaaatccagt caacgcaaat ctcccttatc    12060
ggtttctctg aagacgcagc agcatccacg agcttatccg atttcgtcgt cgtggggatt    12120
gaagaagagt gggatgacgt taattggctc tgagcttcgt cctcttaagg tcatgtcttc    12180
tgtttccacg gcgtgcatgc ttcacggtgc aagcagccgg cccgcaaccg cccgcaaatc    12240
ctctggcctt tccggaaccg tccgcattcc cggcgacaag tcgatctccc accggtcctt    12300
catgttcggc ggtctcgcga gcggtgaaac gcgcatcacc ggccttctgg aaggcgagga    12360
cgtcatcaat acgggcaagg ccatgcaggc gatgggcgcc cgcatccgta aggaaggcga    12420
cacctggatc atcgatggcg tcggcaatgg cggcctcctg gcgcctgagg cgccgctcga    12480
tttcggcaat gccgccacgg gctgccgcct gacgatgggc ctcgtcgggg tctacgattt    12540
cgacagcacc ttcatcggcg acgcctcgct cacaaagcgc ccgatgggcc gcgtgttgaa    12600
cccgctgcgc gaaatgggcg tgcaggtgaa atcggaagac ggtgaccgtc ttcccgttac    12660
cttgcgcggg ccgaagacgc cgacgccgat cacctaccgc gtgccgatgg cctccgcaca    12720
ggtgaagtcc gccgtgctgc tcgccggcct caacacgccc ggcatcacga cggtcatcga    12780
gccgatcatg acgcgcgatc atacggaaaa gatgctgcag ggctttggcg ccaaccttac    12840
cgtcgagacg gatgcggacg gcgtgcgcac catccgcctg gaaggccgcg gcaagctcac    12900
cggccaagtc atcgacgtgc cgggcgaccc gtcctcgacg gccttcccgc tggttgcggc    12960
cctgcttgtt ccgggctccg acgtcaccat cctcaacgtg ctgatgaacc ccacccgcac    13020
cggcctcatc ctgacgctgc aggaaatggg cgccgacatc gaagtcatca acccgcgcct    13080
tgccggcggc gaagacgtgg cggacctgcg cgttcgctcc tccacgctga agggcgtcac    13140
```

| | |
|---|---|
| ggtgccggaa gaccgcgcgc cttcgatgat cgacgaatat ccgattctcg ctgtcgccgc | 13200 |
| cgccttcgcg gaagggggcga ccgtgatgaa cggtctggaa gaactccgcg tcaaggaaag | 13260 |
| cgaccgcctc tcggccgtcg ccaatggcct caagctcaat ggcgtggatt gcgatgaggg | 13320 |
| cgagacgtcg ctcgtcgtgc gtggccgccc tgacggcaag gggctcggca acgcctcggg | 13380 |
| cgccgccgtc gccacccatc tcgatcaccg catcgccatg agcttcctcg tcatgggcct | 13440 |
| cgtgtcggaa aaccctgtca cggtggacga tgccacgatg atcgccacga gcttcccgga | 13500 |
| gttcatggac ctgatggccg ggctgggcgc gaagatcgaa ctctccgata cgaaggctgc | 13560 |
| ctgatgagct cgaattcccg atcgttcaaa catttggcaa taaagtttct taagattgaa | 13620 |
| tcctgttgcc ggtcttgcga tgattatcat ataatttctg ttgaattacg ttaagcatgt | 13680 |
| aataattaac atgtaatgca tgacgttatt tatgagatgg gtttttatga ttagagtccc | 13740 |
| gcaattatac atttaatacg cgatagaaaa caaaatatag cgcgcaaact aggataaatt | 13800 |
| atcgcgcgcg gtgtcatcta tgttactaga tcggggataa cgatcaagct ataacttcgt | 13860 |
| ataatgtatg ctatacgaag ttatcgcg | 13888 |

<210> SEQ ID NO 220
<211> LENGTH: 866
<212> TYPE: DNA
<213> ORGANISM: Hordeum vulgare

<400> SEQUENCE: 220

| | |
|---|---|
| ggtttacata tttaaaggaa aaaatgttca tcgattttaa aaaaaagttc ataccttttca | 60 |
| aaaacgttca tcaattttt taaaaagttc actaaaaatg aaaaaaagtt catccaattt | 120 |
| aaaaaaagtt cattaatttt ttataaattt caataaattt gaaaaaactt cataaaattc | 180 |
| aacaaaagtt cattgaagtg aaaaaagctc ataaatcttt aaaaagtgca tccattttca | 240 |
| aaagatgtt catcaaaatt caatatagtt caccaatatt caaaaaagtt cattaatctt | 300 |
| aaaaaatatt cgctaaaatt taaaaaatgt ttatcaatat ttaaacggcg tctagatgag | 360 |
| ccggtctatt tacaaacacc ataggcgcca attaacaaaa atgcacgtta gatcacgtct | 420 |
| acggcgtcaa ataggaaatg cccatcggcc ttactattaa gagttgtttt ggttatcctt | 480 |
| taggatttat gctgtgggct ggacttaaca caaaacccac agccatggta ggccggaatc | 540 |
| tattattcag ctcacaaacg atgttctact caaaagaaga aaaaaatctg ttgtcagaaa | 600 |
| aagagaacaa aaaaggctca cgaacatgcc gcggctcgca caggtggccg tgagcttctg | 660 |
| aatgacttgg ccacccggca tgtccactgc cccctagac ggtgtgggtg ggtggacagg | 720 |
| tcaagcgcat tgaacaaggt caccctgcgt tctgccacga ggccaactgc gtggccctca | 780 |
| tgcaacgcgc cttgctgcca cttctacaca cgccctcgcc ggccgaccgc tgctataaaa | 840 |
| gcagctcccc gttgcgtcct cgacgg | 866 |

<210> SEQ ID NO 221
<211> LENGTH: 392
<212> TYPE: DNA
<213> ORGANISM: Zea mays

<400> SEQUENCE: 221

| | |
|---|---|
| gatctcgtca attttccct tttgtaattt tgtaatttat aatttacttt cctgtatgct | 60 |
| tctaactctg tcgtttttaaa attttaataa aatttcagta ggggcttgcc cctcctgtcc | 120 |
| tataaaaaaa agttgacgtg aatagatttc attaagaggt tggatgttag tgggatgaca | 180 |
| tgactattag taggacgaga tgatgtggaa agttagtggg agatgatatg gatagttttt | 240 |

```
gctttcatcg aaaggttgga agttagtatg atgacatggc taatatagat acatagatat    300
agactaccaa catggctgca tgcccccaag ctctcccact atatatatct ctggtagcac    360
atcatcccaa ttcacaatgc ttacaaaaac cc                                  392
```

<210> SEQ ID NO 222
<211> LENGTH: 1041
<212> TYPE: DNA
<213> ORGANISM: Zea mays

<400> SEQUENCE: 222

```
gtcccgcgtc aatattatta aaaaactcct acatttcttt ataatcaacc cgcactctta     60
taatctcttc tctactacta taataagaga gtttatgtac aaaataaggt gaaattatgt    120
ataagtgttc tggatattgg ttgttggctc catattcaca caacctaatc aatagaaaac    180
atatgtttta ttaaaacaaa atttatcata tatcatatat atatatatac atatatatat    240
atatatatat aaaccgtagc aatgcacggg catataacta gtgcaactta atacatgtgt    300
gtattaagat gaataagagg gtatccaaat aaaaaacttg ttcgcttacg tctggatcga    360
aagggggttgg aaacgattaa atctcttcct agtcaaaatt gaatagaagg agatttaatc    420
tctcccaatc cccttcgatc atccaggtgc aaccgtataa gtcctaaagt ggtgaggaac    480
acgaaacaac catgcattgg catgtaaagc tccaagaatt tgttgtatcc ttaacaactc    540
acagaacatc aaccaaaatt gcacgtcaag ggtattgggt aagaaacaat caaacaaatc    600
ctctctgtgt gcaaagaaac acggtgagtc atgccgagat catactcatc tgatatacat    660
gcttacagct cacaagacat tacaaacaac tcatattgca ttacaaagat cgtttcatga    720
aaaataaaat aggccggaca ggacaaaaat ccttgacgtg taaagtaaat ttacaacaaa    780
aaaaaagcca tatgtcaagc taaatctaat tcgttttacg tagatcaaca acctgtagaa    840
ggcaacaaaa ctgagccacg cagaagtaca gaatgattcc agatgaacca tcgacgtgct    900
acgtaaagag agtgacgagt catatacatt tggcaagaaa ccatgaagct gcctacagcc    960
gtctcggtgg cataagaaca caagaaattg tgttaattaa tcaaagctat aaataacgct   1020
cgcatgcctg tgcacttctc c                                             1041
```

<210> SEQ ID NO 223
<211> LENGTH: 1401
<212> TYPE: DNA
<213> ORGANISM: Zea mays

<400> SEQUENCE: 223

```
aagcttgccg agtgccatcc ttggacactc gataaagtat attttatttt ttttattttg     60
ccaaccaaac ttttgtggt atgttcctac actatgtaga tctacatgta ccattttggc    120
acaattacat atttacaaaa atgttttcta taaatattag atttagttcg tttatttgaa    180
tttcttcgga aaattcacat ttaaactgca agtcactcga acatggaaaa accgtgcatg    240
caaaataaat gatatgcatg ttatctagca caagttacga ccgatttcag aagcagacca    300
gaatcttcaa gcaccatgct cactaaacat gaccgtgaac ttgttatcta gttgtttaaa    360
aattgtataa aacacaaata aagtcagaaa ttaatgaaac ttgtccacat gtcatgatat    420
catatataga ggttgtgata aaaatttgat aatgtttcgg taaagttgtg acgtactatg    480
tgtagaaacc taagtgacct acacataaaa tcatagagtt tcaatgtagt tcactcgaca    540
aagactttgt caagtgtccg ataaaaagta ctcgacaaag aagccgttgt cgatgtactg    600
ttcgtcgaga tctctttgtc gagtgtcaca ctaggcaaag tctttacgga gtgttttca    660
```

```
ggctttgaca ctcggcaaag cgctcgattc cagtagtgac agtaatttgc atcaaaaata    720
gctgagagat ttaggccccg tttcaatctc acgggataaa gtttagcttc ctgctaaact    780
ttagctatat gaattgaagt gctaaagttt agtttcaatt accaccatta gctctcctgt    840
ttagattaca aatggctaaa agtagctaaa aaatagctgc taaagtttat ctcgcgagat    900
tgaaacaggg ccttaaaatg agtcaactaa tagaccaact aattattagc tattagtcgt    960
tagcttcttt aatctaagct aaaaccaact aatagcttat ttgttgaatt acaattagct   1020
caacggaatt ctctgttttt ctaaaaaaaa actgcccctc tcttacagca aattgtccgc   1080
tgcccgtcgt ccagatacaa tgaacgtacc tagtaggaac tcttttacac gctcggtcgc   1140
tcgccgcgga tcggagtccc cggaacacga caccactgtg gaacacgaca agtctgctc   1200 agaggcggcc acaccctggc gtgcaccgag ccggagcccg gataagcacg gtaaggagag   1260
tacggcggga cgtggcgacc cgtgtgtctg ctgccacgca gccttcctcc acgtagccgc   1320
gcggccgcgc cacgtaccag ggcccggcgc tggtataaat gcgcgccacc tccgctttag   1380
ttctgcatac agccaaccca a                                             1401

<210> SEQ ID NO 224
<211> LENGTH: 1805
<212> TYPE: DNA
<213> ORGANISM: Coix lacryma-jobi

<400> SEQUENCE: 224
ggcggaagtt ttgcggcgga gctccggtcg gtgttggaga agacgaccac agcggtggcg     60
ttacggttca ccggagtagg ctagcgaggg ctcaacgaaa gctcaggagg cggcgggatc    120
agaagcacgg ccaatttggc cgtagacggc gtaacgacgg cgaggtgtgg aagcggagct    180
tggcgatttc agaggagcag aggaggaaaa cggggatggt accggcgatg aggaggctta    240
tatagccggc caaggacctg gggcgaaggg cacgtcaaag gcggtcacca cagtgcaagc    300
aggaggtggc ctggtggcgt ggcatggtcg gcagaggata cggcggtgtg gcggccgacg    360
agcagagcac gactctgctc tgatattttt tcccctccgg ttactgttca ccagagaaca    420
tctagatctt cttttcccta tttctccaaa aacattatac aacaggaaaa actcccaaca    480
tgaaagttgt tccaaaaatt aggacctaca actttcattt aaggagcaca accaaaatct    540
gcctagattt taaaatcaca ttttgaattt gaaaaacatt caaacttgaa ttcaaaatta    600
cttttgaatt ttctgaacga cttcaaattt tatcaatata aaagttgttc ctcattaaat    660
tatctacaac tttgtttttg gtcatatatc caaattgtgc ttaattttga aactaaaaaa    720
gggataaaac taggttttgg gaattgattt tcaatttgaa accaaatcaa acttgttttc    780
caaatcactt cagattctct ttagtaactt gaaaatctat cttaataaaa gttgtttctt    840
ttaatcctct ctacaacttt gattaaaaga cccaagtcta attctttta gttttgaaa    900 tctagtttag gggtcaaatt cagggtttga aacatttcaa atttattcaa aattttgtac    960
agaaacttta aaactttga ataccaaagt tgtacatctc aacaagagct acaactttgc   1020
ttttgaaatc attttgaaat ttgacatact ttttgactta ttaaaaggg acaaaaaga   1080 gagatttaaa aaccaaggtt ttctcacttg ccctatcatg taacaccaaa catctcaatc   1140
aagccacata tatcaaaac atggaaatca acactcaaaa acatacaaca ctcttgtcaa   1200
acatacaaag catcatattt atgccttaaa cataaaaaca tgaaatgctt ttatgccatg   1260
atgccagatg attatgcata ctaaacaact taattaaaat tttaattaat gtttaacacc   1320 agggggtgtta cattaggcaa ttagtccatg ccaaacattt ctattgcatc cagagaccag   1380
```

```
aatagctttt tttttaatat ttaaccaaaa aaagaagaaa atgaggtgaa tgaatgggcc   1440
gacgggcaca taaactattg catggaccca gactattgaa ggcccgctaa tgttgagaca   1500
cggaacgcaa aaggaaaaga gggcccagac tacggcccac gcgtgggatt cggcccggcc   1560
acctccggca accagcggct catcatccaa cgccactacg ccagggcgtt cgtccacaac   1620
ctcctcgtac atatcgccgg gcggaagcgg cgcgaccgcg caagcgcaag cttgtcctcg   1680
acagcccgca caggtgtcgc gcggcccgg acacgagtcc cgcatgcgcc ccacgcggcc    1740
gcgccaggtc ccgcctcccc gcatcccac gccctctata aaccccgcgc tctccctggc    1800
cctcg                                                               1805

<210> SEQ ID NO 225
<211> LENGTH: 232
<212> TYPE: DNA
<213> ORGANISM: Oryza sativa

<400> SEQUENCE: 225
gttggcaatg cggataaaga ataactaaat aaataaataa ataaattgca agcaattgcg   60
ttgctgctat gtactgtaaa agtttcttat aatatcagtt ctgaatgcta aggacatccc  120
tcaagatggt ctttctattt ttgtgttccc gttccaatgt actgttggta tcctcttgga  180
gattcatcaa tatgagaaaa cagagaatgg acaaccctcc cttatcttat gg          232

<210> SEQ ID NO 226
<211> LENGTH: 24
<212> TYPE: DNA
<213> ORGANISM: Artificial Sequence
<220> FEATURE:
<223> OTHER INFORMATION: primer

<400> SEQUENCE: 226
atgagtataa gaatgctgtt ctgc                                          24

<210> SEQ ID NO 227
<211> LENGTH: 21
<212> TYPE: DNA
<213> ORGANISM: Artificial Sequence
<220> FEATURE:
<223> OTHER INFORMATION: primer

<400> SEQUENCE: 227
gcacactgtt tttcacttaa c                                             21

<210> SEQ ID NO 228
<211> LENGTH: 24
<212> TYPE: DNA
<213> ORGANISM: Artificial Sequence
<220> FEATURE:
<223> OTHER INFORMATION: primer

<400> SEQUENCE: 228
tcgcgcccct caagtgtcaa tacc                                          24

<210> SEQ ID NO 229
<211> LENGTH: 24
<212> TYPE: DNA
<213> ORGANISM: Artificial Sequence
<220> FEATURE:
<223> OTHER INFORMATION: primer

<400> SEQUENCE: 229
caccgcctac atacctcgct ctgc                                          24
```

```
<210> SEQ ID NO 230
<211> LENGTH: 16
<212> TYPE: DNA
<213> ORGANISM: Artificial Sequence
<220> FEATURE:
<223> OTHER INFORMATION: primer

<400> SEQUENCE: 230
ggacagcccc tcaaat                                                     16

<210> SEQ ID NO 231
<211> LENGTH: 20
<212> TYPE: DNA
<213> ORGANISM: Artificial Sequence
<220> FEATURE:
<223> OTHER INFORMATION: primer

<400> SEQUENCE: 231
cctacatacc tcgctctgct                                                 20
```

US 8,138,393 B2

PRODUCTION OF HIGH TRYPTOPHAN MAIZE BY CHLOROPLAST TARGETED EXPRESSION OF ANTHRANILATE SYNTHASE

This application claims the priority of U.S. Provisional Patent Application Ser. No. 60/837,200, filed Aug. 11, 2006, the entire disclosure of which is specifically incorporated herein by reference.

BACKGROUND OF THE INVENTION

1. Field of the Invention

The invention relates to methods and compositions for expressing and localizing anthranilate synthase in plant cells.

2. Description of Related Art

In maize, anthranilate synthase exists as a two-subunit enzyme which catalyzes the first reaction branching from the aromatic amino acid pathway to the biosynthesis of tryptophan in the chloroplast. It has been shown to be an important enzyme in the regulation of tryptophan production in plants. Anderson et al. (U.S. Pat. No. 6,118,047) demonstrated that over expression of a tryptophan-insensitive α-subunit of anthranilate synthase from maize led to an increased level of tryptophan in transgenic maize plants. Recently, it has been shown that monomeric forms of anthranilate synthases from prokaryotic sources are capable of increasing tryptophan levels in transgenic soybeans and corn (U.S. patent application Ser. Nos. 10/138,927, issued as U.S. Pat. No. 7,217,865, and Ser. No. 10/430,011, published as U.S. patent application Publication 20030213010).

Most proteins which participate in the biosynthetic pathways within the chloroplast are nuclear-encoded and are synthesized in the cytosol. Correct targeting of these proteins to the plastids is thus essential for their biosynthetic function. In most cases, this targeting is achieved by the presence of an N-terminal extension, called a chloroplast transit peptide (CTP) or plastid transit peptide. Transgenes from bacterial sources must have a sequence encoding a CTP sequence fused to a sequence encoding an expressed polypeptide if the expressed polypeptide is to be compartmentalized in the chloroplast. Accordingly, transport of an exogenous polypeptide to a chloroplast is accomplished by means of operably linking a polynucleotide sequence encoding a CTP sequence to the 5' region of a polynucleotide encoding the exogenous polypeptide.

For many purposes in the manipulation and transformation of plant cells with a monomeric anthranilate synthase, it will be desirable that the gene that is introduced into the plant cell results in a product that is translocated to the plastid and functions in the plastid. Not all CTPs, however, are able to accomplish this translocation with equal efficacy. The identification of efficient and effective CTPs for successful expression and localization of anthranilate synthase in monocotyledonous plants, and in particular maize plants, is needed in the art.

SUMMARY OF THE INVENTION

In one aspect, the present invention provides polynucleotides encoding polypeptides comprising chloroplast transit peptides (CTPs) fused to monomeric anthranilate synthases (AS), wherein the chloroplast transit peptides are capable of compartmentalizing the anthranilate synthase in the plastid fraction of a plant cell. When such anthranilate synthase nucleic acids are expressed in a transgenic plant, elevated levels of tryptophan can be achieved within the cells of the plant. In one embodiment of the present invention, expression vectors and constructs containing these polynucleotides are provided. The recombinant plant cells that contain such expression vectors and constructs are also part of the present invention. The transgenic plant cells, seeds and feed products obtained by the expression of proteins using the sequences, constructs and methods of the present invention are further considered part of the invention.

In another aspect, the present invention provides methods for increasing the free tryptophan content in monocotyledonous plants. In one embodiment, the method comprises transforming a monocotyledonous plant with a polynucleotide encoding a polypeptide comprising a chloroplast transit peptide fused to a monomeric anthranilate synthase, wherein the chloroplast transit peptide functions to localize or compartmentalize the anthranilate synthase activity in the plastid of the plant cell.

In yet another aspect, the invention provides novel isolated polynucleotides encoding monomeric anthranilate synthases from *Agrobacterium* and *Sinorhizobium* sources. In one embodiment aspect of the present invention, expression vectors comprising these novel polynucleotides are provided. In yet other embodiments, host cells, transgenic plant cells, transgenic plants, seeds from the transgenic plants and resulting feed products containing these expression vectors are also considered part of the present invention.

DETAILED DESCRIPTION OF THE INVENTION

Figure 1:
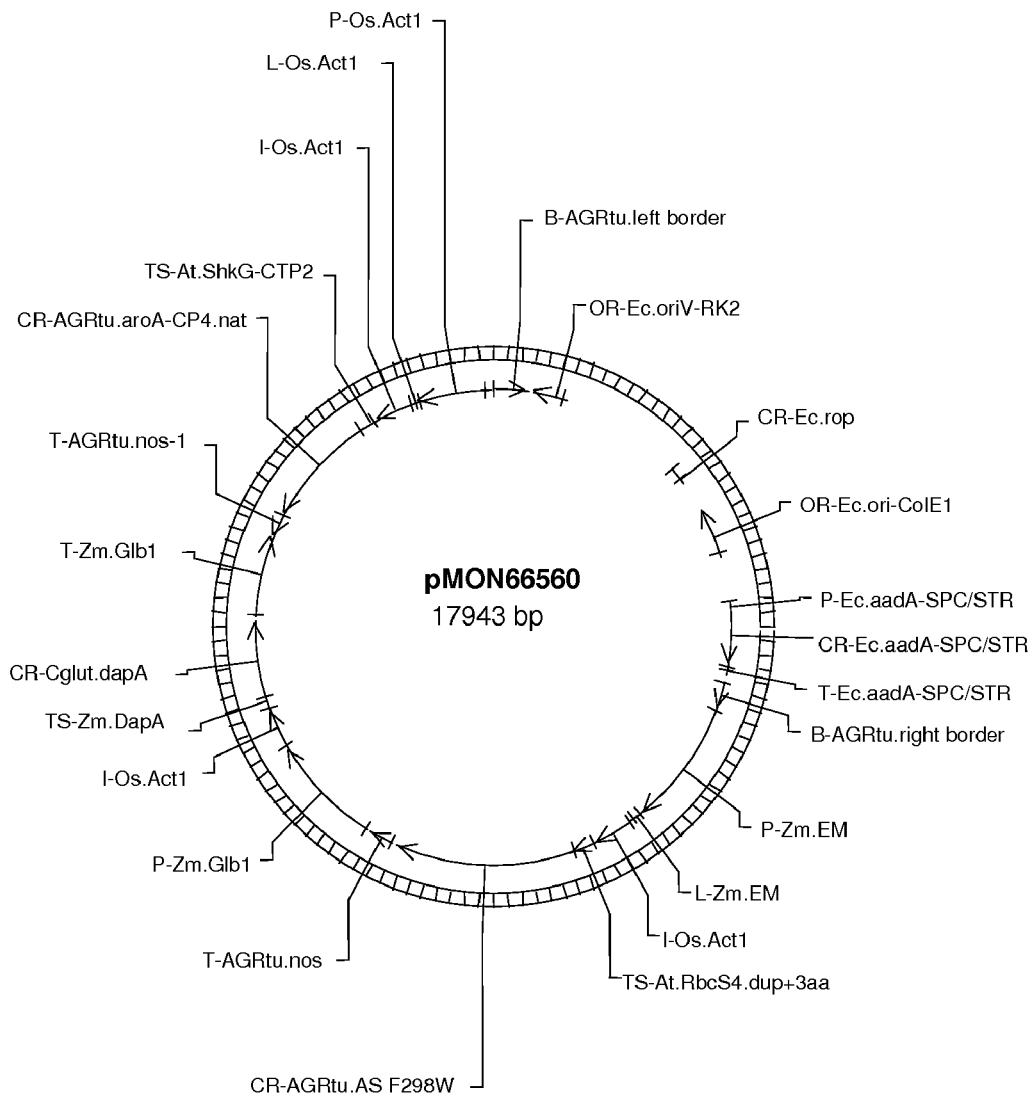
FIG. 1 depicts a restriction map of plasmid pMON66560

In accordance with the invention, compositions are provided for expressing and transporting a monomeric anthranilate synthase to the plastids of a plant cell. The invention in particular provides novel polynucleotide sequences that will find use in increasing the free tryptophan content in the cells of transformed plants. Additionally, novel polynucleotides encoding monomeric anthranilate synthase polypeptides from *Agrobacterium* and *Sinorhizobium* are provided.

The invention provides polynucleotides encoding polypeptides comprising chloroplast transit peptides (CTPs) fused to monomeric anthranilate synthases (AS), wherein the chloroplast transit peptides are capable of compartmentalizing the anthranilate synthase in the plastid fraction of a plant cell. When such anthranilate synthase nucleic acids are expressed in a transgenic plant, elevated levels of tryptophan can be achieved within the cells of the plant. In one aspect of the present invention, expression vectors and constructs containing these polynucleotides are provided. The recombinant plant cells that contain such expression vectors and constructs are also part of the present invention. The transgenic plant cells, seeds and feed products obtained by the expression of proteins using the sequences, constructs and methods of the present invention are also considered part of the invention.

In yet another aspect of the present invention, a method of increasing the free tryptophan content in monocotyledonous plants is provided. In one embodiment the method comprises transforming a monocotyledonous plant with a polynucleotide encoding a polypeptide comprising a chloroplast transit peptide fused to a monomeric anthranilate synthase, wherein the chloroplast transit peptide is capable of compartmentalizing the anthranilate synthase activity in the plastid of the plant cell.

The present invention is additionally directed to novel isolated polynucleotides encoding monomeric anthranilate synthases from *Agrobacterium* and *Sinorhizobium* sources. In one aspect of the present invention, expression vectors comprising these novel polynucleotides are provided. In yet other embodiments, host cells, transgenic plant cells, transgenic plants, seeds from the transgenic plants and resulting feed products containing these expression vectors are also considered part of the present invention.

A transgenic plant or seed that shows a desired trait, for example, increased tryptophan levels of the present invention, comprises a particular exogenous DNA inserted into the genome of the transgenic plant that imparts the desired trait. The trait being a measurable change from the naturally occurring trait in a control plant, for example, a plant or seed of substantially the same genotype that lacks that particular exogenous DNA. The enhanced desired trait may be measured by comparing the trait in a transgenic plant or seed with the particular exogenous DNA associated with the enhanced desired trait to the trait in a control plant or seed. "High tryptophan maize" therefore refers to a corn (maize) plant with increased tryptophan levels in any plant part, preferably a seed; the seed may also be referred to herein as a kernel or a grain.

Anthranilate synthase (AS; EC 4.1.3.27) catalyzes the first reaction branching from the aromatic amino acid pathway to the biosynthesis of tryptophan in plants, fungi, and bacteria. In plants, the chemical processes for the biosynthesis of tryptophan are compartmentalized in the chloroplast. Since anthranilate synthase is a nuclear-encoded protein that is synthesized in the cytosol, it must be transported by some means into the chloroplast to participate in the biosynthesis of tryptophan. Additionally, the endogenous anthranilate synthase that is native to wild type or nontransgenic plants is sensitive to feedback inhibition by the accumulation of tryptophan during the biosynthetic process. In this way, the tryptophan content of nontransgenic plant cells is limited to a relatively low level. For example, in nontransgenic corn, tryptophan levels are typically less than 25 parts per million (ppm) in the seed of the plant; usually in the 8 to 10 ppm range. The present invention provides novel polynucleotides encoding feedback-insensitive monomeric anthranilate synthase polypeptides from *Agrobacterium* and *Sinorhizobium* which are fused to a chloroplast transit peptide capable of targeting the anthranilate synthase to the plastids. The present invention further provides DNA constructs and seeds that contain at least one of the plant expression cassettes of the DNA constructs of the present inventions in its genome, wherein the seed has a higher tryptophan content than seeds not containing the construct.

Increased tryptophan may be exhibited in the plant cell by accumulation of increased amounts (greater than 25 ppm) of the amino acid in the kernel and may be measured by any suitable method, such as that of mass spectrophotometry or high performance liquid chromatography, of appropriately extracted tissue. A transgenic corn kernel of the present invention with increased tryptophan is especially useful as a feed or food product, a meal or meal product, or protein products, or source of other products processed from the kernel that contain a higher tryptophan content than nontransgenic kernels of a similar variety.

Any of the plants or parts thereof of the present invention may be processed to produce a feed (e.g. silage), meal, protein or oil preparation. A particularly preferred plant part for this purpose is a seed. In a preferred embodiment the feed, meal, protein or oil preparation is designed for use in feeding farm animals (livestock). Methods to produce feed, meal, protein and oil preparations are known in the art, for example, U.S. Pat. Nos. 4,957,748; 5,100,679; 5,219,596; 5,936,069; 6,005,076; 6,146,669; and 6,156,227, herein incorporated by reference in their entirety. In a preferred embodiment, the protein preparation is a high protein preparation. The high protein preparation preferably has a protein content of greater than 5% w/v, more preferably 10% w/v, and even more preferably 15% w/v.

Isolated Polynucleotides and Polypeptides

The present invention provides, in one embodiment, isolated polynucleotides encoding chloroplast transit peptides (CTPs; plastid transit peptides) fused to monomeric anthranilate synthases. The term "plastid" means a class of plant cell organelles comprising proplastids, leucoplasts, amyloplasts, chromoplasts, and chloroplasts. In the context of the present invention, the phrase "transit peptide" means a polypeptide that directs the transport of a nuclear encoded protein to a plastid. Typically, the CTP or transit peptide sequence is located at the N-terminus of a polypeptide.

Polynucleotides encoding monomeric anthranilate synthases, and polynucleotides encoding CTPs or plastid transit peptides are "isolated" in that they have been substantially separated or purified away from other nucleic acid sequences with which the nucleic acid is normally associated in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids. The term "substantially purified", as used herein, refers to a molecule separated from other molecules normally associated with it in its native state. More preferably, a substantially purified molecule is the predominant species present in a preparation. A substantially purified molecule may be greater than 60% free, preferably 75% free, more preferably 90% free from the other molecules (exclusive of solvent) present in the natural mixture. The term "substantially purified" is not intended to encompass molecules present in their native state. Such isolated polynucleotides can also be "recombinant" in that they have been combined with exogenous polynucleotides. For example, a recombinant DNA molecule can be an isolated polynucleotide that is operably linked to an exogenous promoter, or to a promoter that is endogenous to the host cell.

As used herein, an "exogenous" polynucleotide is a DNA sequence that has been introduced into a host cell, and that is preferably not identical to any DNA sequence present in the cell in its native, untransformed state. An "endogenous" or "native" polynucleotide is a DNA sequence that is naturally present in a host cell or organism. Likewise, an "exogenous" polypeptide is a protein sequence that is encoded by an isolated DNA that has been introduced into a host cell, and that is preferably not identical to any DNA sequence present in the cell in its native, untransformed state. An "endogenous" or "native" polypeptide is a protein that is naturally present in a host cell or organism.

Of particular interest are polypeptides representing CTP sequences of the present invention which are capable of correctly compartmentalizing the monomeric anthranilate synthase polypeptide in the plastid of the transformed plant cell. The CTP sequence may be derived from a gene encoding a plastid-targeted protein from maize or from other plant species including, but not limited to, *Ruta graveolens*, *Oryza sativa*, and *Arabidopsis thaliana*. Chloroplast transit peptide sequences are known in the art and include the targeting sequences of *Arabidopsis thaliana* ribulose-1,5-bisphosphate carboxylase (rubisco) small subunit 1 (At-CTP1; Silva-Filho et al. (1996); Schnell et al. (1991); *Arabidopsis thaliana* 5-(enolpyruvyl)shikimate-3-phosphate synthase (At-CTP2; Archer et al. (1990); *Zea mays* anthranilate synthase-alpha 1 (Zm-ASA1-CTP) and alpha 2 (Zm-ASA2-CTP) subunits; *Zea mays* dihydrodipicolinate synthase (Zm-DHDPS-CTP); *Oyza sativa* ADP glucose pyrophosphorylase (Os-Waxy (Os-Wx)-CTP; and *Ruta graveolens* anthranilate synthase alpha subunit (Rm-ASA short-CTP and Rg-ASA long-CTP). For descriptions of the use of chloroplast transit peptides see U.S. Pat. Nos. 5,188,642 and 5,728,925, both of which are incorporated herein by reference.

Exemplary isolated polynucleotides encoding chloroplast transit peptides (CTPs) of the invention include DNAs comprising the following nucleotide SEQ ID NOs:

SEQ ID NO: 1: Nucleic acid sequence encoding At-CTP2 (C/M) (*Arabidopsis thaliana* 5-(enolpyruvyl) shikimate-3-phosphate synthase) with modified cleavage site (C/M);

SEQ ID NO:2: Nucleic acid sequence encoding At-CTP2 (E/K) with native cleavage site (E/K);

SEQ ID NO:3: Nucleic acid sequence encoding At-CTP2 (E/K)+10 amino acids from mature *Arabidopsis* EPSPS synthase;

SEQ ID NO:4: Nucleic acid sequence encoding At-CTP2 (E/K)+5 amino acids from mature *Arabidopsis* EPSPS synthase;

SEQ ID NO:5: Nucleic acid sequence encoding Zm-ASA1-CTP (*Zea mays* anthranilate synthase α1 subunit);

SEQ ID NO:6: Nucleic acid sequence encoding Zm-ASA1-CTP+20 amino acids from mature *Zea mays* anthranilate synthase α1 subunit;

SEQ ID NO:7: Nucleic acid sequence encoding Zm-ASA2-CTP (*Zea mays* anthranilate synthase α2 subunit);

SEQ ID NO:8: Zm-ASA2-CTP+5 amino acids from mature *Zea mays* anthranilate synthase α2 subunit;

SEQ ID NO:9: Nucleic acid sequence encoding Zm-ASA2-CTP+18 amino acids from mature *Zea mays* anthranilate synthase α2 subunit;

SEQ ID NO:10: Nucleic acid sequence encoding Os-Wx-CTP (*Oryza sativa* ADP glucose pyrophosphorylase);

SEQ ID NO:11: Nucleic acid sequence encoding Os-Wx-CTP+5 amino acids from mature *Oryza sativa* ADP glucose pyrophosphorylase;

SEQ ID NO:12: Nucleic acid sequence encoding Os-Wx-CTP+20 amino acids from mature *Oryza sativa* ADP glucose pyrophosphorylase;

SEQ ID NO:13: Nucleic acid sequence encoding Rg-AS short-CTP (*Ruta graveolens* anthranilate synthase α subunit; Met1 to Ser72);

SEQ ID NO:14: Nucleic acid sequence encoding Rg-AS long-CTP (*Ruta graveolens* anthranilate synthase α subunit; Met1 to Ser92);

SEQ ID NO:15: Nucleic acid sequence encoding Zm-DH-DPS-CTP (*Zea mays* dihydrodipicolinate synthase);

SEQ ID NO:16: Zm-DHDPS-CTP+9 amino acids from mature *Zea mays* dihydrodipicolinate synthase;

SEQ ID NO:17: Nucleic acid sequence encoding Zm-DH-DPS-CTP+20 amino acids from mature *Zea mays* dihydrodipicolinate synthase;

SEQ ID NO:18: Nucleic acid sequence encoding Zm-DH-DPS-CTP+3 amino acids from mature *Zea mays* dihydrodipicolinate synthase; and SEQ ID NO:19: Nucleic acid sequence encoding *Arabidopsis thaliana* rubisco small subunit gene chloroplast transit peptide, CTP 1.

The present invention also contemplates any isolated nucleic acid encoding a chloroplast transit peptide (CTP) comprising, for example, any one of the following amino acid sequences:

SEQ ID NO:20: At-CTP2(C/M) (*Arabidopsis thaliana* 5-(enolpyruvyl) shikimate-3-phosphate synthase) with modified cleavage site (C/M);

SEQ ID NO:21: At-CTP2(E/K) with native cleavage site (E/K);

SEQ ID NO:22 At-CTP2(E/K)+10 amino acids from mature *Arabidopsis* EPSPS synthase;

SEQ ID NO:23 At-CTP2(E/K)+5 amino acids from mature *Arabidopsis* EPSPS synthase;

SEQ ID NO:24 Zm-ASA1-CTP (*Zea mays* anthranilate synthase α1 subunit);

SEQ ID NO:25 Zm-ASA1-CTP+20 amino acids from mature *Zea mays* anthranilate synthase α1 subunit;

SEQ ID NO:26 Zm-ASA2-CTP (*Zea mays* anthranilate synthase α2 subunit);

SEQ ID NO:27 Zm-ASA2-CTP+5 amino acids from mature *Zea mays* anthranilate synthase α2 subunit;

SEQ ID NO:28 Zm-ASA2-CTP+18 amino acids from mature *Zea mays* anthranilate synthase α2 subunit;

SEQ ID NO:29 Os-Wx-CTP (*Oryza sativa* ADP glucose pyrophosphorylase);

SEQ ID NO:30 Os-Wx-CTP+5 amino acids from mature *Oryza sativa* ADP glucose pyrophosphorylase;

SEQ ID NO:31 Os-Wx-CTP+20 amino acids from mature *Oryza sativa* ADP glucose pyrophosphorylase;

SEQ ID NO:32 Rg-AS short-CTP (*Ruta graveolens* anthranilate synthase α subunit; Met1 to Ser72);

SEQ ID NO:33 Rg-AS long-CTP (*Ruta graveolens* anthranilate synthase α subunit; Met1 to Ser92);

SEQ ID NO:34 Zm-DHDPS-CTP (*Zea mays* dihydrodipicolinate synthase)

SEQ ID NO:35 Zm-DHDPS-CTP+9 amino acids from mature *Zea mays* dihydrodipicolinate synthase;

SEQ ID NO:36 Zm-DHDPS-CTP+20 amino acids from mature *Zea mays* dihydrodipicolinate synthase;

SEQ ID NO:37 Zm-DHDPS-CTP+3 amino acids from mature *Zea mays* dihydrodipicolinate synthase; and SEQ ID NO:38 *Arabidopsis thaliana* rubisco small subunit gene, CTP1.

Isolated polynucleotides encoding chloroplast transit peptides (CTPs) of the invention fused to green fluorescent protein (GFP), to anthranilate synthases, or to anthranilate synthase fused to GFP include DNAs comprising the following nucleotide SEQ ID NOs:

SEQ ID NO:39 Nucleic acid sequence encoding At-CTP2 fused to green fluorescent protein (GFP);

SEQ ID NO:40 Nucleic acid sequence encoding Zm-ASA2-CTP fused to green fluorescent protein (GFP);

SEQ ID NO:41 Nucleic acid sequence encoding Os-Wx-CTP fused to green fluorescent protein (GFP);

SEQ ID NO:42 Nucleic acid sequence encoding Rg-AS short-CTP fused to green fluorescent protein (GFP);

SEQ ID NO:43 Nucleic acid sequence encoding Zm-DH-DPS-CTP fused to green fluorescent protein (GFP);

SEQ ID NO:44 Nucleic acid sequence encoding Zm-DH-DPS-CTP+5 amino acids from mature *Zea mays* dihydrodipicolinate synthase fused to GFP;

SEQ ID NO:45 Nucleic acid sequence encoding At-CTP2 with native cleavage site E/K fused to *Rhizobium meliloti* anthranilate synthase;

SEQ ID NO:46 Nucleic acid sequence encoding At-CTP2+ 10 amino acids from mature *Arabidopsis* EPSPS synthase fused to *Rhizobium meliloti* anthranilate synthase;

SEQ ID NO:47 Nucleic acid sequence encoding Zm-ASA2-CTP fused to *Rhizobium meliloti* anthranilate synthase;

SEQ ID NO:48 Nucleic acid sequence encoding Zm-ASA2-CTP+18 amino acids from mature *Zea mays* anthranilate synthase α2 subunit fused to *Rhizobium meliloti* anthranilate synthase; and SEQ ID NO:49 Nucleic acid sequence encoding Zm-ASA2-CTP+18 amino acids from mature *Zea mays* anthranilate synthase α2 subunit (the first 65 amino acids encoded by the Zm-ASA2 gene) fused to *Agrobacterium tumefaciens* monomeric anthranilate synthase fused to green fluorescent protein.

Sequences representative of chloroplast transit peptides (CTPs) of the invention fused to green fluorescent protein (GFP) or anthranilate synthases include amino acids comprising the following polypeptide SEQ ID NOs:

SEQ ID NO:50 At-CTP2 fused to green fluorescent protein (GFP);

SEQ ID NO:51 Zm-ASA2-CTP fused to green fluorescent protein (GFP);

SEQ ID NO:52 Os-Wx-CTP fused to green fluorescent protein (GFP);

SEQ ID NO:53 Rg-AS short-CTP fused to green fluorescent protein (GFP);

SEQ ID NO:54 Zm-DHDPS-CTP fused to green fluorescent protein (GFP);

SEQ ID NO:55 Zm-DHDPS-CTP+5 amino acids from mature *Zea mays* dihydrodipicolinate synthase fused to GFP;

SEQ ID NO:56 At-CTP2 with native cleavage site E/K fused to *Rhizobium meliloti* anthranilate synthase;

SEQ ID NO:57 At-CTP2+10 amino acids from mature *Arabidopsis* EPSPS synthase fused to *Rhizobium meliloti* anthranilate synthase;

SEQ ID NO:58 Zm-ASA2-CTP fused to *Rhizobium meliloti* anthranilate synthase;

SEQ ID NO:59 Zm-ASA2-CTP+18 amino acids from mature *Zea mays* anthranilate synthase α2 subunit fused to *Rhizobium meliloti* anthranilate synthase; and SEQ ID NO:60 Zm-ASA2-CTP+18 amino acids from mature *Zea mays* anthranilate synthase α2 subunit (the first 65 amino acids encoded by the Zm-ASA2 gene) fused to *Agrobacterium tumefaciens* monomeric anthranilate synthase fused to green fluorescent protein.

Certain oligonucleotides are also useful for the practice of the present invention, for example, oligonucleotides comprising SEQ ID NOs: 61-198 are useful in the construction of transfection vectors for transient protoplast assays; and oligonucleotides comprising SEQ ID NOs: 226-231 are useful as PCR primers.

Another aspect of the present invention relates to isolated monomeric anthranilate synthases (AS) and fragments thereof; and their use in methods for obtaining plants that produce elevated levels of free L-tryptophan. Overproduction of free L-tryptophan in transgenic plants containing such polypeptides results from the introduction and expression of a nucleic acid encoding anthranilate synthase, or a domain thereof. Such anthranilate synthase nucleic acids include wild type or mutant α-domains, or monomeric forms of anthranilate synthase. A monomeric form of anthranilate synthase comprises at least two anthranilate synthase domains in a single polypeptide chain, e.g., an α-domain linked to a β-domain.

Native plant anthranilate synthases are generally quite sensitive to feedback inhibition by L-tryptophan and analogs thereof. Such inhibition constitutes a key mechanism for regulating the tryptophan synthetic pathway. Therefore, an anthranilate synthase or a domain thereof that is highly active, more efficient or that is inhibited to a lesser extent by tryptophan or an analog thereof will likely produce elevated levels of tryptophan. According to the invention, the anthranilate synthases from *Agrobacterium tumefaciens* and *Sinorhizobium meliloti* are particularly useful for producing high levels of tryptophan. Isolated monomeric anthranilate synthases of the present invention additionally include deregulated forms and fragments thereof. Such deregulated forms include the S5C allele of *Sinorhizobium* as described herein; the F298W, V48F, V48Y, S51F and S51C alleles of *Agrobacterium* anthranilate synthase, as described in U.S. patent application 2003097677; and the codon-optimized form of the *Agrobacterium* anthranilate synthase S51C allele as described in U.S. patent application Ser. No. 11/503,532, entitled "High Tryptophan Maize", each of which are herein incorporated by reference in their entirety. These alleles are deregulated for feedback inhibition from tryptophan.

To generate high levels of tryptophan in a plant or a selected host cell, the selected anthranilate synthase nucleic acid is isolated and may be manipulated in vitro to include regulatory signals required for gene expression in plant cells or other cell types. Because the tryptophan biosynthetic pathway in plants is reported to be present within plastids, the exogenous anthranilate synthase nucleic acids are either introduced into plastids or are modified by adding a nucleic acid segment encoding an amino-terminal plastid transit peptide. Such a plastid transit peptide can direct the anthranilate synthase gene product into plastids.

In order to alter the biosynthesis of tryptophan, the nucleic acid encoding an anthranilate synthase activity must be introduced into plant cells or other host cells and these transformed cells identified, either directly or indirectly. An entire anthranilate synthase or a useful portion or domain thereof can be used. The anthranilate synthase is stably incorporated into the plant cell genome. The transcriptional signals controlling expression of the anthranilate synthase must be recognized by and be functional within the plant cells or other host cells. That is, the anthranilate synthase must be transcribed into messenger RNA (mRNA), and the mRNA must be stable in the plant cell nucleus and be transported intact to the cytoplasm for translation. The anthranilate synthase mRNA must have appropriate translational signals to be recognized and properly translated by plant cell ribosomes. The polypeptide gene product must substantially escape proteolytic attack in the cytoplasm, be transported into the correct cellular compartment (e.g. a plastid) and be able to assume a three-dimensional conformation that will confer enzymatic activity. The anthranilate synthase must further be able to function in the biosynthesis of tryptophan and its derivatives; that is, it must be localized near the native plant enzymes catalyzing the flanking steps in biosynthesis (presumably in a plastid) in order to obtain the required substrates and to pass on the appropriate product.

Even if all these conditions are met, successful overproduction of tryptophan is not a predictable event. The expression of some transgenes may be negatively affected by nearby chromosomal elements. If the high level of tryptophan is achieved by mutation to reduce feedback inhibition, there may be other control mechanisms compensating for the reduced regulation at the anthranilate synthase step. There may be mechanisms that increase the rate of breakdown of the accumulated amino acids. Tryptophan and related amino acids must also be overproduced at levels that are not toxic to the plant. Finally, the introduced trait must be stable and heritable in order to permit commercial development and use.

Isolation and identification of polynucleotides encoding anthranilate synthases is described in U.S. patent application Ser. Nos. 10/138,927, published as U.S. patent application Publication 20030097677 and issued as U.S. Pat. No. 7,217,865; and Ser. No. 10/430,011, published as U.S. patent application Publication 20030213010, which are herein incorporated by reference in their entirety.

Exemplary isolated DNAs encoding anthranilate synthases of the present invention include DNAs comprising the following nucleotide SEQ ID NOs:

SEQ ID NO: 199 *Agrobacterium tumefaciens* wild type anthranilate synthase;

SEQ ID NO: 201 *Agrobacterium tumefaciens* F298W mutant allele;

SEQ ID NO: 203 *Agrobacterium tumefaciens* S51F mutant allele;

SEQ ID NO: 205 *Agrobacterium tumefaciens* S51C mutant allele;

SEQ ID NO: 207 *Agrobacterium tumefaciens* codon-optimized S51C mutant allele;

SEQ ID NO: 209 *Sinorhizobium meliloti* anthranilate synthase wild type; and

SEQ ID NO: 211 *Sinorhizobium meliloti* anthranilate synthase S51C mutant allele.

The present invention also contemplates any isolated nucleic acid encoding an anthranilate synthase comprising, for example, any one of the following amino acid sequences:

SEQ ID NO: 200 *Agrobacterium tumefaciens* wild type anthranilate synthase;

SEQ ID NO: 202 *Agrobacterium tumefaciens* F298W mutant;

SEQ ID NO: 204 *Agrobacterium tumefaciens* S51F mutant;

SEQ ID NO: 206 *Agrobacterium tumefaciens* S51C mutant;

SEQ ID NO: 208 *Agrobacterium tumefaciens* codon-optimized S5C mutant;

SEQ ID NO: 210 *Sinorhizobium meliloti* anthranilate synthase wild type;

SEQ ID NO: 212 *Sinorhizobium meliloti* anthranilate synthase S5C mutant.

As used herein with respect to anthranilate synthase, the term "monomeric" means that two or more anthranilate synthase domains are incorporated in a functional manner into a single polypeptide chain. The monomeric anthranilate synthase may be assembled in vivo into a dimeric form. Monomeric anthranilate synthase polynucleotides and polypeptides can be isolated from various organisms such as *Agrobacterium tumefaciens*, *Anabaena* M22983, *Azospirillum brasilense*, *Brucella melitensis*, *Euglena gracilis*, *Mesorhizobium loti*, *Nostoc* sp. PCC7120 or *Rhizobium meliloti* (*Sinorhizobium meliloti*). Alternatively, monomeric anthranilate synthase nucleic acids and polypeptides can be constructed from a combination of domains selected from any convenient monomeric or multimeric anthranilate synthase gene. Such organisms include, for example, *Agrobacterium tumefaciens*, *Anabaena* M22983, *Arabidopsis thaliana*, *Azospirillum brasilense*, *Brucella melitensis*, *Mesorhizobium loti*, *Nostoc* sp. PCC7120, *Rhizobium meliloti* (*Sinorhizobium meliloti*), *Rhodopseudomonas palustris*, *Ruta graveolens*, *Sulfolobus solfataricus*, *Salmonella typhimurium*, *Serratia marcescens*, soybean, rice, cotton, maize, or any gene encoding a subunit or domain of anthranilate synthase. Nucleic acids encoding the selected domains can be linked recombinantly. For example, a nucleic acid encoding the C-terminus of an α-domain can be linked to a nucleic acid encoding the N-terminus of the β-domain, or vice versa, by forming a phosphodiester bond. As an alternative, such single domain polypeptides can be linked chemically. For example, the α-domain can be linked via its C-terminus to the N-terminus of the β-domain, or vice versa, by forming a peptide bond.

As used herein, an anthranilate synthase that is "deregulated to feedback inhibition by tryptophan" is an anthranilate synthase that retains greater than about 10% more activity than a corresponding "wild-type" or native susceptible anthranilate synthase, when the deregulated and "wild type" anthranilate synthases are exposed to equivalent amounts of tryptophan or an amino acid analog of tryptophan. Preferably the deregulated anthranilate synthase retains greater than about 20% more activity than a corresponding "wild-type" or native susceptible anthranilate synthase.

Fragments and variants of the polypeptides are also considered to be a part of the present invention. A fragment is a variant polypeptide that has an amino acid sequence that is entirely the same as part but not all of the amino acid sequence of the previously described polypeptides. The fragments can be "free-standing" or comprised within a larger polypeptide of that the fragment forms a part or a region, most preferably as a single continuous region. Preferred fragments are biologically active fragments that are those fragments that mediate activities of the polypeptides of the invention, including those with similar activity or improved activity or with a decreased activity. Also included are those fragments that are antigenic or immunogenic in an animal, for the purpose of generating antibodies useful in a detection method, for example, an enzyme-linked immunosorbent assay.

Variants of the polypeptides also include polypeptides that vary from the sequences set forth in the Sequence Listing by conservative amino acid substitutions, substitution of a residue by another with like characteristics. In general, such substitutions are among Ala, Val, Leu and Ile; between Ser and Thr; between Asp and Glu; between Asn and Gln; between Lys and Arg; or between Phe and Tyr. Particularly preferred are variants in which 5 to 10; 1 to 5; 1 to 3 or one amino acid(s) are substituted, deleted, or added, in any combination.

Functional anthranilate synthase DNA sequences and functional anthranilate synthase polypeptides that exhibit 80%, more preferably 85%, even more preferably 90% to 95% and most preferably 96% to 99%, sequence identity to the DNA sequences and amino acid sequences explicitly described herein are also within the scope of the present invention. For example, 85% amino acid identity means that 85% of the amino acids are identical when the 2 sequences are aligned for maximum matching. Gaps (in either of the 2 sequences being matched) are allowed in maximizing matching; gap lengths of 5 or less are preferred with 2 or less being more preferred.

The polynucleotides of the present invention can be used, for example, in the construction of recombinant expression vectors useful for the transformation of plant host cells, as further discussed herein.

Plant Transformation Vectors

Of interest in the present invention, is the use of the polynucleotide sequences, or polynucleotides, in recombinant expression vectors to direct the transcription and translation of the polynucleotide sequences encoding monomeric AS fused to a CTP in a plant host cell.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

The term "operably linked" refers to a functional linkage between a promoter and a second sequence, wherein the promoter initiates and mediates transcription of DNA sequences corresponding to the second sequence. As used herein, "operably linked" also refers to a functional linkage between 2 or more distinct nucleotide sequences such that the nucleic acid sequences being linked are contiguous and, where necessary to join two protein coding regions, contiguous and in the same reading frame. For example, operably linking the CTP-coding sequences with the nucleotide sequence encoding a monomeric anthranilate synthase may require the manipulation of one or more of the DNA sequences, such as a convenient restriction site or a linker sequence that may permit better recognition of the amino-terminal transit sequence.

Such polynucleotides can be amplified using cDNA, mRNA or genomic DNA as a template and appropriate oligonucleotide primers according to standard PCR amplification techniques. Alternatively, they can be synthesized using standard synthetic techniques, such as an automated DNA synthesizer.

An expression vector minimally comprises a polynucleotide sequence which encodes a polypeptide that is expressed in a host cell. Typically, an expression vector is placed under the control of certain regulatory elements including promoters, tissue specific regulatory elements, and enhancers. Such an expression vector is said to be "operably linked to" the regulatory elements.

The expression vectors of the present invention generally comprise a promoter, functional in a plant cell, operably linked to a nucleic acid sequence encoding an anthranilate synthase, fused to a chloroplast transit peptide (CTP) of the present invention and a transcriptional termination region functional in a plant host cell.

Exemplary expression vectors of the present invention include DNAs having the following SEQ ID NOs:

SEQ ID NO: 213, nucleic acid sequence encoding pMON68065, the expression vector for Zm-ASA2-CTP+18:: AgroAS(S51C) non-optimized mutant allele;

SEQ ID NO: 214, nucleic acid sequence encoding pMON68066, the expression vector for Zm-ASA2-CTP+18:: AgroAS(S51C) non-native optimized (nno) mutant allele;

SEQ ID NO: 215, nucleic acid sequence encoding pMON69757, the expression vector for the construct containing the AgroAS(F298W) mutant allele;

SEQ ID NO: 216, nucleic acid sequence encoding pMON69770, the expression vector for the construct containing the AgroAS(S51C) non-optimized mutant allele with an alternate 3' UTR;

SEQ ID NO: 217, nucleic acid sequence encoding pMON69768, the expression vector for the construct containing the AgroAS(51F) mutant allele;

SEQ ID NO: 218, nucleic acid sequence encoding pMON78850, the expression vector for the construct containing the *Rhizobium meliloti* anthranilate synthase wild type allele;

SEQ ID NO: 219, nucleic acid sequence encoding pMON78851, the expression vector for the construct containing the *Rhizobium meliloti* anthranilate synthase S51C allele.

By "host cell" is meant a cell that contains a vector and supports the replication, and/or transcription or transcription and translation (expression) of the expression construct. Host cells for use in the present invention can be monocotyledonous plant cells or bacterial cells. An example of a bacterial host cell of the present invention is *Agrobacterium*. In a preferred embodiment, host cells are maize cells.

As used herein, a "transgenic plant" is a plant having an exogenous polynucleotide stably introduced into its genome, for example, the nuclear or plastid polynucleotides from another organism.

The terms "seeds" and "kernels" are understood to be equivalent in meaning. The term kernel is frequently used in describing the seed of a corn or rice plant. In all plants the seed is the mature ovule consisting of a seed coat, embryo, aleurone, and an endosperm.

Of particular interest is the use of the polynucleotides of the present invention for the preparation of recombinant expression vectors to encode a monomeric AS fused with a CTP in a host plant cell, wherein the CTP directs the localization of the AS to the plastid fraction of the plant host cell. Plant expression constructs generally comprise a promoter functional in a plant host cell operably linked to a nucleic acid sequence of the present invention and a transcriptional termination region functional in a plant host cell.

As used herein "promoter" means a region of DNA sequence that is essential for the initiation of transcription of RNA from DNA. Promoters are located upstream of DNA to be transcribed and have regions that act as binding sites for RNA polymerase and have regions that work with other factors to promote RNA transcription. More specifically, basal promoters in plants comprise canonical regions associated with the initiation of transcription, such as CAAT and TATA boxes. In the present invention, preferred promoter molecules and 5' UTR molecules allow for transcription in seed cells or tissues at a rate or level greater than in other cells and tissues of the plant. Those skilled in the art will recognize that there are a number of constitutive and tissue specific promoters that are functional in plant cells, and have been described in the literature. For example, promoters are described in U.S. Pat. No. 6,437,217 (maize RS81 promoter); U.S. Pat. No. 5,641, 876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142 and 5,530,196 (35S promoter); U.S. Pat. No. 6,433,252 (maize L3 oleosin promoter, P-Zm.L3); U.S. Pat. No. 6,429,357 (rice actin 2 promoter as well as a rice actin 2 intron); U.S. Pat. No. 5,837,848 (root specific promoter); U.S. Pat. No. 6,294,714 (light inducible promoters); U.S. Pat. No. 6,140,078 (salt inducible promoters); U.S. Pat. No. 6,252,138 (pathogen inducible promoters); U.S. Pat. No. 6,175,060 (phosphorus deficiency inducible promoters); U.S. Pat. No. 6,635,806 (gamma-coixin promoter, P-Cl.Gcx); U.S. patent application Ser. No. 10/732,721 (maize embryo-specific promoter ZmEM; emb5); U.S. Pat. No. 7,151,204 (maize chloroplast aldolase promoter); SEQ ID NO: 220 (Barley Per1 promoter); SEQ ID NO: 221 (maize B32 promoter); SEQ ID NO: 222 (maize Z27 promoter); SEQ ID NO: 223 (maize Globulin 1 promoter; Belanger and Kriz, 1991); and SEQ ID NO: 224 (coixin L-3 promoter), all of which are incorporated herein by reference.

Constitutive promoters such as the CaMV35S promoter derived from the cauliflower mosaic virus (U.S. Pat. Nos. 5,858,741 and 5,322,938) or the FMV35S promoter derived from figwort mosaic virus (U.S. Pat. No. 5,378,619) yield high levels of expression in most plant organs. Enhanced or duplicated versions of the CaMV35S and FMV35S promoters are useful in the practice of this invention, for example the enhanced CaMV35S (e35S) (Odell, et al., 1985); U.S. Pat. No. 5,378,619). In addition, it may also be preferred to bring about expression of the protein of interest in specific tissues of the plant, such as leaf, stem, root, tuber, seed endosperm, seed embryos, fruit, etc., and the promoter chosen should have the desired tissue and developmental specificity.

Regulatory transcript termination regions may be provided in plant expression vectors of the present invention as well. Transcript termination regions may be provided by the gene sequence of the endogenous anthranilate synthase or a convenient transcription termination region derived from a different gene source. These transcription termination regions are commonly referred to as 3' untranslated regions or 3' UTRs. Examples of 3' UTR regions are the nopaline synthase 3' region (nos 3'; Fraley et al., 1983), the wheat heat shock protein, hsp17 (T-Ta.Hsp17), the 3' region of the glutelin gene of Oryza sativa (Os-gt1; SEQ ID NO: 225), a 3' UTR from a zein gene, such as Z27 3' UTR (Lopes et al., 1995), maize globulin 1 (T-Zm.Glb1), and T-Ps.RbcS2:E9 (pea rubisco small subunit), those disclosed in WO0011200A2 and other 3' UTRs known in the art which can be tested and used in combination with an anthranilate synthase coding region fused to a chloroplast transit peptide. The skilled artisan will recognize that any convenient transcript termination region that is capable of terminating transcription in a monocot plant cell may be employed in the constructs of the present invention.

Moreover, transcription enhancers or duplications of enhancers can be used to increase expression from a particular promoter. Examples of such enhancers include, but are not limited to a maize hsp70 intron (also referred to as Zm.DnaK) (U.S. Pat. No. 5,424,412 Brown, et al.), the Adh intron1 (Callis et al., 1987), a rice actin intron (McElroy et al., 1991; U.S. Pat. No. 5,641,876), sucrose synthase intron (Vasil et al., 1989), a TMV omega element (Gallie et al., 1999), and the CaMV 35S enhancer or an octopine synthase enhancer (U.S. Pat. No. 5,290,924). As the DNA sequence between the transcription initiation site and the start of the coding sequence, i.e., the untranslated leader sequence, can influence gene expression, one may also wish to employ a particular leader sequence. Any leader sequence available to one of skill in the art may be employed. Preferred leader sequences direct optimum levels of expression of the attached gene, for example, by increasing or maintaining mRNA stability and/or by preventing inappropriate initiation of translation (Joshi, 1987).

The choice of such sequences is at the discretion of those of skill in the art. Sequences that are derived from genes that are highly expressed in monocots, and in particular maize and rice, are contemplated.

Assays to determine the efficiency by which the isolated CTP sequences of the invention target a protein of interest to a plastid are well known in the art. By way of example, a reporter gene such as β-glucuronidase (GUS), chloramphenicol acetyl transferase (CAT), or green fluorescent protein (GFP) may be operably linked to the CTP sequence. This gene fusion is placed behind the control of a suitable promoter, ligated into a transformation vector, and transformed into a plant cell. Following an adequate period of time for expression and localization into the plastid, the plastid fraction is extracted and reporter activity assayed. The ability of the isolated CTP sequences to target and deliver the reporter protein to the plastid is thus evaluated and compared to other known CTP sequences; see Silva-Filho et al. (1996).

Plant Cell Transformation

A plant cell, tissue, organ, or plant into which the recombinant expression vector of the present invention has been introduced is considered transformed, transfected, or transgenic. A transgenic or transformed plant cell or plant also includes progeny of the plant cell or plant and progeny produced from a breeding program employing such a transgenic plant as a parent in a cross and exhibiting an altered phenotype resulting from the presence of an introduced nucleic acid sequence.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, the term "plant" includes reference to whole plants, plant organs (for example, leaves, stems, roots, etc.), seeds, and plant cells and progeny of same. Plant cell, as used herein includes, without limitation, seed suspension cultures, embryos, meristematic regions, callus tissue, leaves, roots, shoots, gametophytes, sporophytes, pollen, and microspores. The class of plants that can be used in the methods of the present invention is generally monocotyledonous plants. A preferred plant of the present invention is maize.

As used herein, "transgenic plant" includes reference to a plant that comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression vector. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic.

Thus a plant having within its cells a heterologous polynucleotide is referred to herein as a transgenic plant. The heterologous polynucleotide can be either stably integrated into the genome, or can be extra-chromosomal. Preferably, the polynucleotides of the present invention are stably integrated into the genome such that the polynucleotides are passed on to successive generations. The polynucleotides are integrated into the genome alone or as part of a recombinant expression vector.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species, or, if from the same species, is substantially modified from its original form by deliberate human intervention.

The particular methods used for the transformation of the host plant cell are not critical to the present invention. The transformation of the plant is preferably permanent, i.e., by integration of the introduced expression constructs into the host plant genome, so that the introduced constructs are passed onto successive plant generations. The skilled artisan will recognize that a wide variety of transformation techniques exist in the art. Any technique that is suitable for the target host plant can be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to, calcium-phosphate-DNA co-precipitation, electroporation, microinjection, *Agrobacterium* infection, liposomes or microprojectile transformation (i.e., the gene gun).

With respect to microprojectile bombardment (U.S. Pat. Nos. 5,550,318; 5,538,880; and 5,610,042; each of which is specifically incorporated herein by reference in its entirety), particles are coated with polynucleotides and delivered into cells by a propelling force. Exemplary particles include those comprised of tungsten, platinum, and preferably, gold. A useful method for delivering DNA into plant cells by particle acceleration is the Biolistics® Particle Delivery System (Bio-Rad, Hercules, Calif.), which can be used to propel particles coated with DNA or cells through a screen, such as a stainless steel or NYTEX screen, onto a filter surface covered with monocot plant cells cultured in suspension. Microprojectile bombardment techniques are widely applicable, and may be used to transform virtually any plant species. Examples of species that have been transformed by microprojectile bombardment include monocot species such as corn (PCT Publication WO95/06128), barley, wheat (U.S. Pat. No. 5,563,055, incorporated herein by reference in its entirety), rice, oat, rye, sugarcane, and sorghum; as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety) The skilled artisan can refer to the literature for details and select suitable techniques for use in the methods of the present invention.

Normally, included with the expression vector of the present invention will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where *Agrobacterium* is used for plant cell transformation, a vector may be used that may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cells and gall.

In some instances where *Agrobacterium* is used as the vehicle for transforming host plant cells, the expression or transcription construct bordered by the T-DNA border region(s) will be inserted into a broad host range vector capable of replication in *E. coli* and *Agrobacterium*, there being broad host range vectors described in the literature. Commonly used is pRK2 or derivatives thereof. See, for example, Ditta et al. (1980) and EPA 0 120 515, that are incorporated herein by reference. Alternatively, one may insert the sequences to be expressed in plant cells into a vector containing separate replication sequences, one of which stabilizes the vector in *E. coli*, and the other in *Agrobacterium*. See, for example, McBride and Summerfelt (1990), wherein the pRiHRI (Jouanin et al., 1985) origin of replication is utilized and provides for added stability of the plant expression vectors in host *Agrobacterium* cells.

Included with the expression construct and the T-DNA will be one or more markers that allow for selection of transformed *Agrobacterium* and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed may be used to establish repetitive generations.

There are several possible ways to obtain the plant cells of this invention that contain multiple expression vectors. Any means for producing a plant comprising a vector or polynucleotide sequence of the present invention, and at least one other vector having another polynucleotide sequence encoding a separate enzyme are encompassed by the present invention. For example, the expression vector of the present invention can be used to transform a plant at the same time as the second construct either by inclusion of both expression vectors in a single plant transformation vector (plasmid) or by using separate plant transformation vectors, each of which express desired genes. The second vector can be introduced into a plant that has already been transformed with the first expression vector, or alternatively, transformed plants, one having the first construct and one having the second construct, can be crossed, using standard breeding techniques, to bring the constructs together in the same plant.

Methods

The present invention provides a method of increasing free tryptophan levels in a seed of a transgenic plant. In one embodiment, the method of increasing tryptophan comprises introducing into a plant cell a nucleic acid sequence encoding a monomeric anthranilate synthase operably linked to a CTP that is capable of targeting or localizing the monomeric anthranilate synthase to the chloroplast of the plant cell. The monomeric anthranilate synthase of the present invention is a deregulated form of the enzyme that is insensitive to feedback inhibition by tryptophan.

As used herein, "increased" or "elevated" levels of free tryptophan in a plant cell, plant tissue, plant part or plant are levels that are about 2 to 200 times, preferably about 5 to 150 times, and more preferably about 10 to 100 times, the levels found in an untransformed plant cell, plant tissue, plant part or plant, i.e., one where the genome has not been altered by the presence of a polynucleotide encoding a chloroplast transit peptide fused to a monomeric anthranilate synthase. For example, the levels of free L-tryptophan in a transformed plant seed are compared with those in an untransformed plant seed ("the starting material").

A further aspect of the present invention is to provide a relatively high throughput method for predicting the ability of a CTP to correctly compartmentalize a monomeric AS to the plastids of plant cells. The present invention provides a visualization method utilizing transient expression in maize protoplasts, or maize developing embryos, of a green fluorescent protein (GFP) fused with various monomeric AS and various CTPs. A GFP is capable of producing a green fluorescence, absorbing in the UV to blue range with a peak at 395 nm and emitting in the green range with a peak at 510 nm. This method allows for the visualization of the localization of the AS::GFP polypeptide. A result where greater than 50% of the localization is in the plastid would be a positive predictor of the ability of the CTP to successfully compartmentalize monomeric AS.

The present invention further provides a method of making a nutritionally enhanced corn feed product comprising processing a seed of a corn plant of the present invention into a meal, protein or oil.

Additionally, the present invention provides a method for detecting unique DNA sequences belonging to any of the CTP::AS sequence combinations described herein in a transgenic plant cell, or in a feed or meal product derived from such a transgenic plant cell. The genome of such a transgenic plant cell, or a feed or meal product derived from such a transgenic plant cell, produces an amplicon diagnostic for an expression vector containing any of the unique CTP::AS DNA sequences when tested in a DNA amplification method to amplify a DNA molecule from DNA extracted from such a transgenic plant cell, or a feed or meal product derived from such a transgenic plant cell. As used herein, an "amplicon" is a piece of DNA that has been synthesized using amplification techniques such as PCR or LCR. An "amplicon" is also understood in its common usage to be a PCR product.

The invention now being generally described, it will be more readily understood by reference to the following examples that are included for purposes of illustration only and are not intended to limit the present invention.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Localization of an Anthranilate Synthase Comprising a CTP1 Chloroplast Transit Peptide This example demonstrates that the protein product of a transgene encoding a CTP1 chloroplast transit peptide fused to the amino terminus of an *Agrobacterium* anthranilate synthase allele is not targeted efficiently to embryo plastids in transgenic maize.

The plant transformation vector pMON66560 (FIG. 1) encodes a fusion protein comprising the chloroplast transit peptide sequence from the *Arabidopsis rubisco* small subunit gene, CTP1 (encoded by SEQ ID NO: 19) fused to the amino-terminus of AgroAS(F298W (encoded by SEQ ID NO: 201), and driven by a maize embryo-specific promoter (ZmEM).

To isolate the plastid fraction from embryos of immature kernels from transgenic maize plants, several ears were harvested at 25-27 days after pollination (DAP). The homozygous F3 transgenic maize plants contained the plant transformation vector pMON66560 (FIG. 1).

Approximately 2.5 g of embryos were placed on ice as they were excised from kernels. The embryos were then rinsed 3 times in cold, sterile water, followed by a rinse in cold PIM buffer (20 mM Hepes/NaOH, 0.5M sorbitol, 10 mM KCl, 1 mM $MgCl_2$, 1 mM EDTA, 10 mM DTT, pH7.4). The embryos and subsequent fractions were kept cold during all isolation steps.

The embryos were then transferred to a petri dish containing 5 ml PIM, and chopped finely using single edge razor blades until the consistency of the chopped embryos resembled sand. The chopped embryos were filtered through 1 layer of Miracloth™ (Calbiochem Corporation, La Jolla, Calif.) into a 50 ml conical tube and brought to a total volume of 20 ml with PIM. A small aliquot of this filtered homogenate (designated fraction H) was stored at −80° C. prior to analysis. The filtered homogenate was then centrifuged at 750×g for 5 minutes to pellet the plastids. The supernatant was poured off, and a small aliquot (designated S1) stored at −80° C. An aliquot of 2.5 ml of PIM was then added to the pelleted plastids, and the pellets were resuspended using a small, soft-haired paint brush. After a small aliquot was removed and frozen (fraction designated P1), 2.5 ml of the resuspended pellets were layered onto each of two discontinuous Percoll gradients. The gradient tubes consisted of 6 ml 35% Percoll/PIM layered onto 3 ml 75% Percoll/PIM. The gradient tubes were then centrifuged for 8 minutes at 1000×g. The resulting plastid bands at the 35%/75% interface were collected and transferred to another 15 ml tube, and 5 ml 1×PIM was added to each tube. After centrifuging at 750×g for 5 minutes, the supernatant was removed, and both pellets were resuspended in 0.25 ml PIM. The resuspended pellet fraction containing the purified plastids was designated P2 and was stored at −80° C. prior to analysis.

The presence of the AS protein in the four isolated fractions (H, S1, P1 and P2) was analyzed by western blot analysis, using methods well known in the art. Briefly, the protein fractions were separated by SDS-PAGE on 4-12% Bio-Rad Criterion Bis-Tris gels (Bio-Rad Laboratories, Hercules, Calif.), loading 18 µg protein/lane. Following electrophoresis, the proteins were transferred to nitrocellulose, and duplicate blots were subjected to standard protocols for western blotting including blocking, primary antibody incubation (primary antibodies described below), washing, secondary antibody incubation (conjugated to horse radish peroxidase), washing, and chemiluminescent detection. The primary antibodies used in the blot analysis were raised in goat against (a) the anthranilate synthase α-2 subunit from maize, a known plastid localized protein; (b) pea glutamine synthetase 1 (GS1), a cytosolic form of glutamine synthase (GS) (Tingey et al., 1987); and (c) *Agrobacterium* anthranilate synthase. The antibodies, termed anti-maize AS(X, anti-pea GS1 and anti-Agro AS, respectively, were prepared using standard methodology known in the art.

Figure 2:
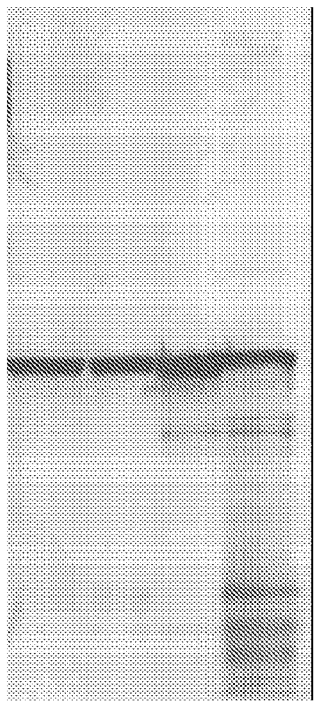
FIG. 2 depicts a western blot analysis of plastid fractions of transgenic corn cells containing the plant transformation vector pMON66560
Figure 2:
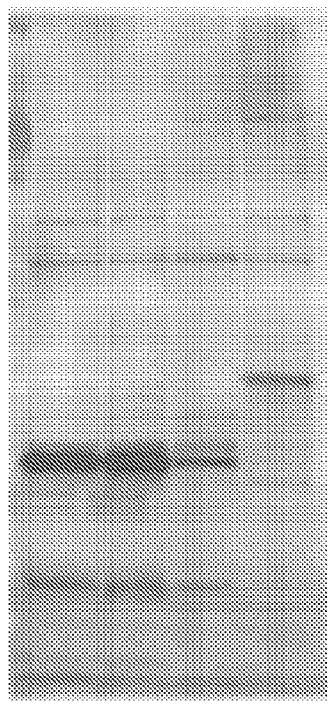
Figure 2:
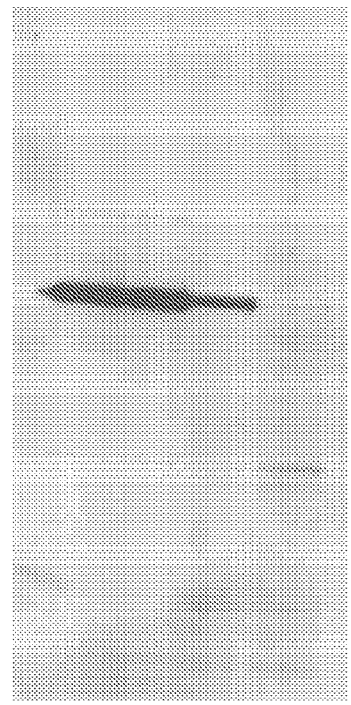

The results (FIG. 2) demonstrate that the anti-maize ASα antibody, while recognizing bands corresponding to maize anthranilate synthase α-2 subunit in all four fractions, was enriched in plastid fractions P1 and P2. In contrast, anti-pea GS1 antibody recognized a band corresponding to a protein of the expected size in fractions H and S1, a smaller amount of protein in the crude P1 plastid fraction, and barely detectable amounts in the purified plastids, P2 fraction. This pattern of partitioning of glutamine synthetase is consistent with its localization to the cytosol. Anti-Agro AS antibody recognized a protein of the expected size which displays a pattern that resembles the cytosolic marker GS1 in all 4 fractions, indicating it is also localized primarily in the cytosol, despite the fact that the coding sequence included the CTP1 sequence. The results indicate that CTP1 would not be useful in expression vectors for compartmentalizing the protein in the plastid of maize embryo cells. Additionally, the results suggest that not all chloroplast transit peptides have the ability to successfully localize a monomeric AS to the plastids of maize cells.

Example 2

Additional Transit Peptide Sequences for Localization of Anthranilate Synthase

This example describes the design of the various CTP sequences that were incorporated in the construction of the protoplast transfection vectors containing the maize anthranilate synthase-green fluorescent protein (Zm-AS::GFP) fusions and the control::GFP fusions detailed in Example 3; and which were evaluated in the transient expression assay systems which are described in Example 4.

TABLE 1

CTP variants

| CTP Name | SEQ ID NO: | Brief Description of CTP |
| --- | --- | --- |
| At-CTP2(C/M) | 1 | At-CTP2 (*Arabidopsis thaliana* 5-(enolpyruvyl) shikimate-3-phosphate synthase) with modified cleavage site (C/M) |
| At-CTP2(E/K) | 2 | At-CTP2 with native cleavage site (E/K) |
| At-CTP2(E/K) + 10 | 3 | At-CTP2 + 10 amino acids from mature *Arabidopsis* EPSPS synthase |
| At-CTP2(E/K) + 5 | 4 | At-CTP2 + 5 amino from mature *Arabidopsis* EPSPS synthase |
| Zm-ASA1-CTP | 5 | Zm-ASA1 CTP (*Zea mays* anthranilate synthase α1 subunit) |
| Zm-ASA1-CTP + 20 | 6 | Zm-ASA1 CTP + 20 amino acids from mature *Zea mays* anthranilate synthase α1 subunit |
| Zm-ASA2-CTP | 7 | Zm-ASA2 CTP (*Zea mays* anthranilate synthase α2 subunit) |
| Zm-ASA2-CTP + 5 | 8 | Zm-ASA2 CTP + 5 amino acids from mature *Zea mays* anthranilate synthase α2 subunit |
| Zm-ASA2-CTP + 18 | 9 | Zm-ASA2 CTP + 18 amino acids from mature *Zea mays* anthranilate synthase α2 subunit |
| Os-Wx-CTP | 10 | Os-Wx CTP (*Oryza sativa* ADP glucose pyrophosphorylase) |
| Os-Wx-CTP + 5 | 11 | Os-Wx CTP + 5 amino acids from mature *Oryza sativa* ADP glucose pyrophosphrylase |
| Os-Wx-CTP + 20 | 12 | Os-Wx CTP + 20 amino acids from mature *Oryza sativa* ADP glucose pyrophosphrylase |
| Rg-AS short-CTP | 13 | Rg-AS short-CTP (*Ruta graveolens* anthranilate synthase α subunit; Met1 to Ser72) |
| Rg-AS long-CTP | 14 | Rg-AS long-CTP (*Ruta graveolens* anthranilate synthase α subunit CTP; Met1 to Ser92) |
| Zm-DHDPS-CTP | 15 | Zm-DHDPS CTP (*Zea mays* dihydrodipicolinate synthase) |
| Zm-DHDPS-CTP + 9 | 16 | Zm-DHDPS CTP + 9 amino acids from mature *Zea mays* dihydrodipicolinate synthase |
| Zm-DHDPS-CTP + 20 | 17 | Zm-DHDPS CTP + 20 amino acids from mature *Zea mays* dihydrodipicolinate synthase |
| Zm-DHDPS-CTP + 3 | 18 | Zm-DHDPS CTP + 3 amino acids from mature *Zea mays* dihydrodipicolinate synthase |

Example 3

Construction of Transformation Vectors

This example describes the construction of the protoplast transfection vectors containing the maize anthranilate synthase::green fluorescent protein (Zm-AS::GFP) fusions and the control::GFP fusions that were used in the transient protoplast and embryo assays described in Example 4. Two general strategies were employed to construct these vectors.

Figure 3:
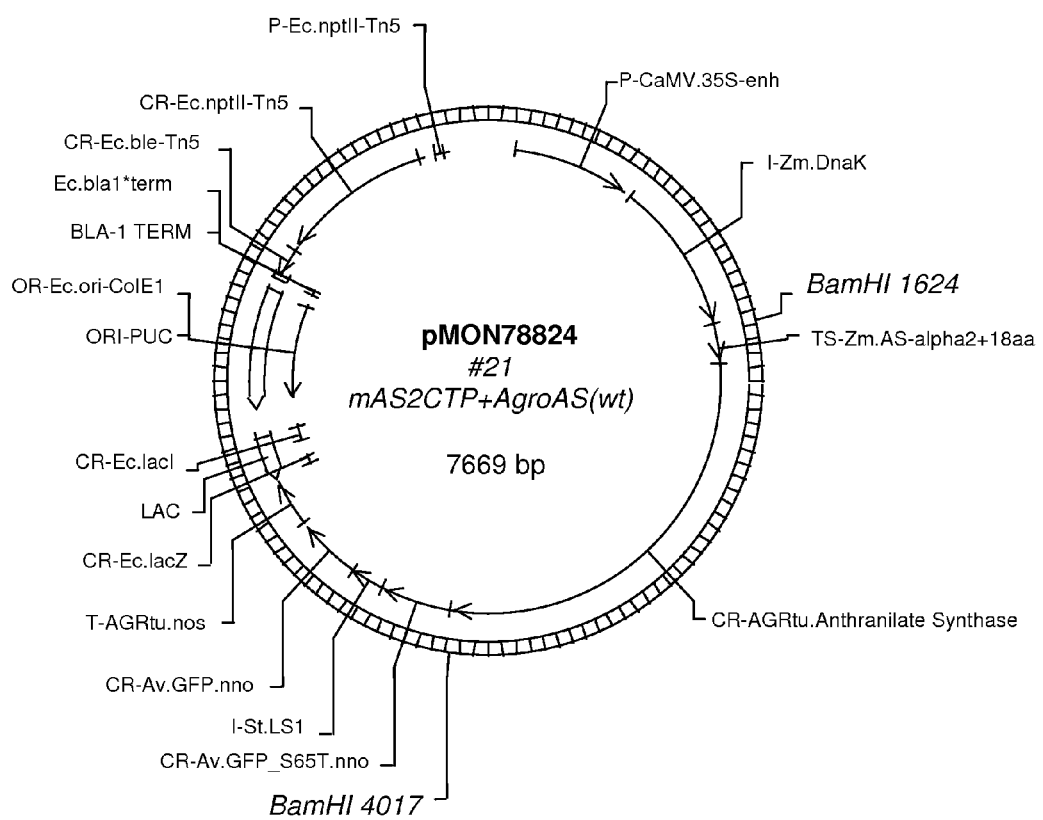
FIG. 3 depicts a restriction map of plasmid pMON78824

The first strategy involved PCR amplification of the CTP-AS coding sequence with the introduction of a restriction site to facilitate the addition of the GFP coding sequence. The first strategy is exemplified by the construction of pMON78824 (FIG. 3). The plasmid pMON78824 was constructed by PCR amplification of a DNA fragment containing the Zm-ASA2 CTP-coding sequence using the plasmid pMON66574 as a template. BamHI restriction sites were incorporated into the primers AS25 and AS 3' (SEQ ID NOs: 63 and 61, respectively) to allow insertion of the fragment in frame with the GFP coding sequence contained in the plasmid pMON30098. The PCR product was cloned into the pCRII vector (Invitrogen Corporation, Carlsbad, Calif.), according to manufacturer's instructions contained in the TA cloning kit (Invitrogen), resulting in plasmid pMON82553. The sequence integrity was confirmed by DNA sequencing using methodologies well known in the art.

The Zm-ASA2 CTP-fragment was then excised from pMON82553 using BamHI, and inserted into the BamHI site of the plasmid pMON30098 to create pMON78824. The resulting plasmid pMON78824 encoded a fusion protein (SEQ ID NO: 60) comprising: a) the first 65 amino acids encoded by the Zm-ASA2 gene; b) *Agrobacterium tumefaciens* monomeric anthranilate synthase; and c) the GFP coding region, all under the control of the e35S promoter.

Additional protoplast transformation vectors containing various GFP translational fusions were constructed in a similar manner using standard PCR and cloning methods, well known in the art. The transfection vector IDs (pMON number), general description of the fusion protein included in the transfection vector, PCR primers used, and PCR template are summarized in Table 2.

TABLE 2

Summary of the strategy 1 plasmid vectors constructed for protoplast transfection assays

| Transfection Vector ID | General description of fusion protein | PCR primers | SEQ ID NO: | PCR template |
|---|---|---|---|---|
| pMON30098 | Base vector provides GFP sequence for transfection vectors | n/a | | n/a |
| pMON79960 | CTP1::GFP | CTP1 5' | 61 | pMON66559 |
| | | CTP1 3' | 62 | |
| pMON79961 | CTP1::AgroAS(F298W)::GFP | CTP1 5' | 61 | pMON66559 |
| | | AS 3' | 63 | |
| pMON78818 | No CTP::AgroAS(F298W)::GFP | AS 5' | 64 | pMON79961 |
| | | AS 3' | 63 | |
| pMON78820 | Zm-ASA2(includes CTP)::GFP | AS25 | 65 | pMON64201 |
| | | AS23 | 66 | |
| pMON78822 | No CTP:mature Zm-ASA2::GFP | AS2MAT | 67 | pMON64201 |
| | | AS23 | 66 | |
| pMON78824 | Zm-ASA2-CTP + 18::AgroAS(wt)::GFP | AS25 | 65 | pMON66574 |
| | | AS 3' | 63 | |
| pMON78140 | Os-Wx-CTP::GFP | RW-5 | 68 | pMON66356 |
| | | RW-3 | 69 | |
| pMON78139 | Rg-AS short-CTP::GFP | Ruta-5 | 70 | pMON66575 |
| | | Ruta-3 | 71 | |
| pMON78143 | Rg-AS short-CTP::AgroAS(F298W)::GFP | Ruta XbaI | 72 | pMON66575 |
| | | AgroBsiWI | 73 | |
| pMON78142 | Rg-AS long-CTP::AgroAS(F298W)::GFP | Ruta XbaI | 72 | pMON66571 |
| | | AgroBsiWI | 73 | |
| pMON69763 | DHDPS + 3-CTP::AgroAS(F298W)::GFP | DHDPS-67146-5' | 74 | pMON67146 |
| | | DHDPS-67146-3' | 75 | |
| pMON69774 | At-CTP2(EK)::*Rhizobium meliloti* anthranilate synthase::GFP | 5'XbaI-CTP2-N1 | 76 | pMON78834 |
| | | 3'XbaI-CTP2-N1 | 77 | |
| pMON69775 | At-CTP2 + 10::*Rhizobium meliloti* anthranilate synthase::GFP | 3'XbaI-CTP2-N2 | 78 | pMON78834 |
| | | 3'XbaI-CTP2-N3 | 79 | |
| pMON69776 | Zm-ASA2-CTP::*Rhizobium meliloti* anthranilate synthase::GFP | 5'-XbaI-ZmAS2-N1 | 80 | pMON69754 |
| | | 3'-XbaI-ZmAS2-N1 | 81 | |
| pMON69777 | Zm-ASA2-CTP + 18::*Rhizobium meliloti* anthranilate synthase::GFP | 5'-XbaI-ZmAS1-N1 | 82 | pMON69754 |
| | | 3'-XbaI-ZmAS2-N2 | 83 | |

The second strategy used for protoplast transformation vector construction involved the assembly of sequences corresponding to various CTPs, and fusing these sequences to the N-terminal coding sequence of AgroAS(F298W) (SEQ ID NO: 201). The CTP coding sequences were generated using sets of overlapping primers in a PCR-based assembly reaction based on a method of Withers-Martinez et. al. (1999). An example of this second strategy is the generation of plasmid pMON78832 (FIG. 4) containing an expression vector encoding an At-CTP2::AgroAS(F298W)::GFP fusion protein.

The first step of this second strategy is to synthesize a shuttle vector containing the AgroAS(F298W) coding sequence that was modified for in-frame fusions to various CTPs to its N-terminus and GFP to its C-terminus. To this end, a PCR amplification reaction was done using pMON79961 as the template, and the oligonucleotide primers AS5A (SEQ ID NO: 84) and AS 3' (SEQ ID NO: 63), using methods well known in the art. The resulting 2.2 kb PCR-product, containing the AgroAS(F298W) coding sequence was agarose gel-purified, ligated into the pCRII vector, and transformed into competent E. coli cells using the Invitrogen TA cloning kit (Invitrogen). The resulting intermediate plasmid was named WDRAPP01.0005, and was sequenced to confirm the presence of the 2.2 kb PCR product. The 2.2 kb insert was then excised from plasmid WDRAPP01.0005 using BamHI and cloned into the BamHI site in the plasmid pBluescriptII SK+ to generate the plasmid pMON82554.

The second step of this second strategy involved the synthesis of At-CTP2-AgroAS(F298W) N-terminal coding sequence. To this end, the following 14 oligonucleotide primers, listed in Table 3, were prepared.

TABLE 3

Oligonucleotide Primers

| Oligo Name | SEQ ID NO: |
|---|---|
| At-CTP2-Agro N1-1 | SEQ ID NO: 85 |
| At-CTP2-Agro N1-2 | SEQ ID NO: 86 |
| At-CTP2-Agro N1-3 | SEQ ID NO: 87 |
| At-CTP2-Agro N1-4 | SEQ ID NO: 88 |
| At-CTP2-Agro N1-5 | SEQ ID NO: 89 |
| At-CTP2-Agro N1-6 | SEQ ID NO: 90 |
| At-CTP2-Agro N1-7 | SEQ ID NO: 91 |
| At-CTP2-Agro N1-8 | SEQ ID NO: 92 |
| At-CTP2-Agro N1-9 | SEQ ID NO: 93 |
| At-CTP2-Agro N1-10 | SEQ ID NO: 94 |
| At-CTP2-Agro N1-11 | SEQ ID NO: 95 |
| At-CTP2-Agro N1-12 | SEQ ID NO: 96 |
| At-CTP2-Agro N1-13 | SEQ ID NO: 97 |
| At-CTP2-Agro N1-14 | SEQ ID NO: 98 |

Figure 4:
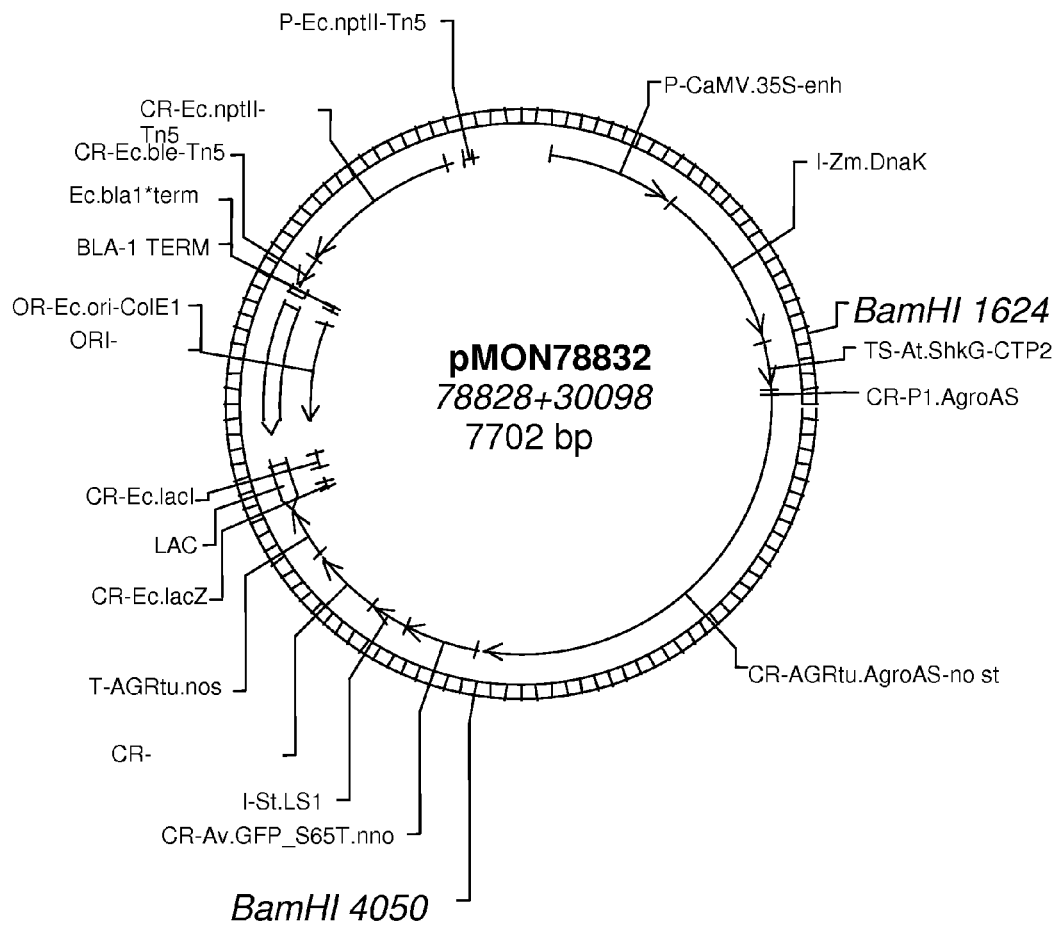
FIG. 4 depicts a restriction map of plasmid pMON78832
Figure 5:
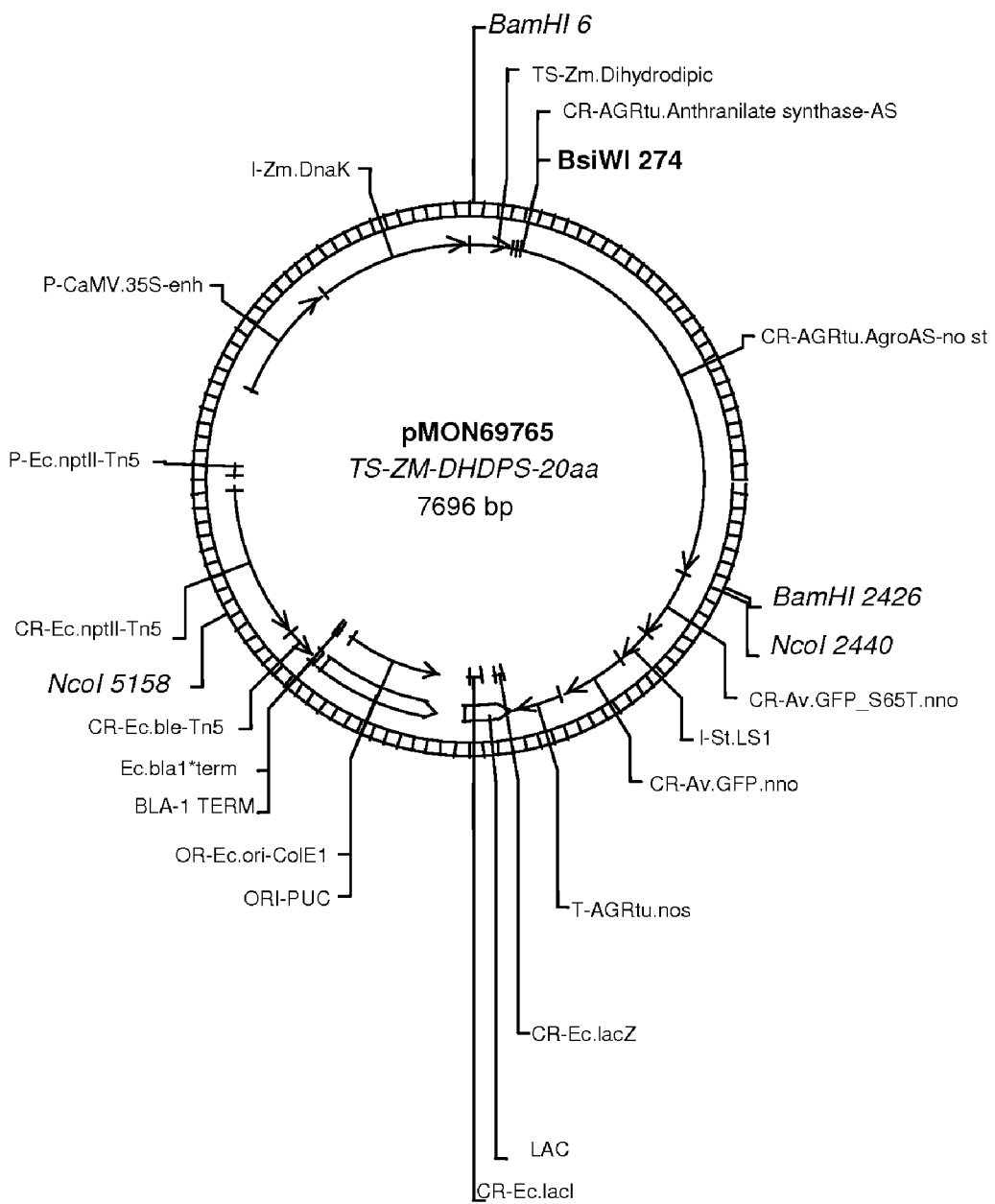
FIG. 5 depicts a restriction map of plasmid pMON69765

Stock solutions (100 μmoles/L) were made for each of the 14 oligonucleotides described in Table 5 by dissolving the requisite amounts in distilled water. An oligonucleotide mixture (At-CTP2 N1 oligo mix) was then prepared by combining 5 μl of each individual oligonucleotide solution. The PCR amplification was carried out using the following conditions:
Primary PCR
Mix 1:
1 microliter CTP2 N1 oligo mix
1 microliter 4 dNTP mix (Roche, 10 millimolar each)
23 microliter water
Mix 2:
6 microliters 25 mM MgCl$_2$
5 microliters PCR buffer (w/out MgCl$_2$)
0.75 microliters Expand Hi-Fi enzyme mix (Roche)
13.25 microliters water
Mix 1 and Mix 2 were combined in a thin-walled PCR tube and the PCR reaction was carried out as follows:
1) 94° C./2 min
2) 94° C./30 sec
3) 45° C./30 sec
4) 72° C./30 sec
5) Go to step 2 four more times
6) 72° C./2 min
7) 4° C./hold
Secondary PCR
Mix 3:
1 microliter of primary PCR reaction
1.5 microliter N1-1 oligo (10 picomoles/microliter)
1.5 microliter N1-14 oligo (10 picomoles/microliter)
1 microliter dNTP mix
20 microliter water
Mix 4:
6 microliters 25 mM MgCl$_2$
5 microliters PCR buffer (w/out MgCl$_2$)
0.75 microliters Expand Hi-Fi enzyme mix (Roche)
13.25 microliters water
Mix 1 and Mix 2 were combined in a thin-walled PCR tube and the PCR reaction was carried out as follows:
Mix 3 and Mix 4 were combined in a thin-walled PCR tube and the PCR reaction was carried out as follows:
1) 94° C./2 min
2) 94° C./30 sec
3) 55° C./30 sec
4) 72° C./30 sec
5) Go to step 2 24 more times
6) 72° C./2 min
7) 4° C./hold The resulting PCR product of the correct size (~0.3 kb) was agarose gel-purified and ligated into the pCRII vector (Invitrogen TA cloning kit, Invitrogen) as described above. After confirming the sequence, the plasmid was digested with NcoI and BsiWI, and cloned into pMON82554, replacing a fragment which had previously been removed at the NcoI and BsiWI site. The resulting intermediate plasmid was then digested with BamH1 to generate a fragment that was then cloned into pMON30098. This resulting plasmid vector comprised the e35S promoter::hsp70 intron::At-CTP2:AgroAS(F298W)::GFP::nos 3' UTR genetic elements (pMON78832; FIG. 4).

Several variants of each CTP were built in the manner described above by adding the DNA sequence of the corresponding mature protein that encodes 3 to 20 amino acids at the 3' end of the CTP. For each pCRII vector containing a CTP variant, the fragment between the NcoI and BSiWI restriction sites of the pCRII vector was subsequently removed from the vector and cloned between the NcoI and BsiWI sites of the pMON82554 shuttle vector as described above. Each of these vectors was subsequently digested with BamHI to generate a fragment that was then cloned into the BamHI site of pMON30098 as described above to provide the remaining genetic elements of the final plasmid vector. The final plasmid vectors containing these CTP variants fused to GFP and the remaining genetic elements of the vector are listed in Table 4 along with the primers that were used in their construction.

TABLE 4

Summary of the strategy 2 plasmid vectors constructed for protoplast transfection assays

| pMON | CTP::GFP variants | Primer Name | SEQ ID NO: |
|---|---|---|---|
| pMON78832 | At-CTP2(C/M)::AgroAS(F298W)::GFP | CTP2-N1-1 | 85 |
| | | CTP2-N1-2 | 86 |
| | | CTP2-N1-3 | 87 |

TABLE 4-continued

Summary of the strategy 2 plasmid vectors constructed for protoplast transfection assays

| pMON | CTP::GFP variants | Primer Name | SEQ ID NO: |
|---|---|---|---|
| | | CTP2-N1-4 | 88 |
| | | CTP2-N1-5 | 89 |
| | | CTP2-N1-6 | 90 |
| | | CTP2-N1-7 | 91 |
| | | CTP2-N1-8 | 92 |
| | | CTP2-N1-9 | 93 |
| | | CTP2-N1-10 | 94 |
| | | CTP2-N1-11 | 95 |
| | | CTP2-N1-12 | 96 |
| | | CTP2-N1-13 | 97 |
| | | CTP2-N1-14 | 98 |
| pMON78833 | At-CTP2(E/K)::AgroAS(F298W)::GFP | CTP2-N1-1 | 85 |
| | | CTP2-N1-2 | 86 |
| | | CTP2-N1-3 | 87 |
| | | CTP2-N1-4 | 88 |
| | | CTP2-N1-5 | 89 |
| | | CTP2-N2-6 | 99 |
| | | CTP2-N1-7 | 91 |
| | | CTP2-N1-8 | 92 |
| | | CTP2-N2-9 | 100 |
| | | CTP2-N1-10 | 94 |
| | | CTP2-N1-11 | 95 |
| | | CTP2-N1-12 | 96 |
| | | CTP2-N1-13 | 97 |
| | | CTP2-N1-14 | 98 |
| pMON78834 | At-CTP2 + 10::AgroAS(F298W)::GFP | CTP2-N1-1 | 85 |
| | | CTP2-N1-2 | 86 |
| | | CTP2-N1-3 | 87 |
| | | CTP2-N1-4 | 88 |
| | | CTP2-N1-5 | 89 |
| | | CTP2-N3-6A | 101 |
| | | CTP2-N3-6B | 102 |
| | | CTP2-N1-7 | 91 |
| | | CTP2-N1-8 | 92 |
| | | CTP2-N3-9A | 103 |
| | | CTP2-N3-9B | 104 |
| | | CTP2-N1-10 | 94 |
| | | CTP2-N1-11 | 95 |
| | | CTP2-N1-12 | 96 |
| | | CTP2-N1-13 | 97 |
| | | CTP2-N1-14 | 98 |
| pMON78835 | At-CTP2 + 5::AgroAS(F298W)::GFP | CTP2-N1-1 | 85 |
| | | CTP2-N1-2 | 86 |
| | | CTP2-N1-3 | 87 |
| | | CTP2-N1-4 | 88 |
| | | CTP2-N1-5 | 89 |
| | | CTP2-N4-6 | 105 |
| | | CTP2-N1-7 | 91 |
| | | CTP2-N1-8 | 92 |
| | | CTP2-N4-9 | 106 |
| | | CTP2-N1-10 | 94 |
| | | CTP2-N1-11 | 95 |
| | | CTP2-N1-12 | 96 |
| | | CTP2-N1-13 | 97 |
| | | CTP2-N1-14 | 98 |
| pMON78138 | Zm-ASA1-CTP::AgroAS(F298W)::GFP | ASA1-1-1T | 107 |
| | | ASA1-1-2T | 108 |
| | | ASA1-1-3T | 109 |
| | | CTP2-N1-7 | 91 |
| | | ASA1-1-5B | 110 |
| | | ASA1-1-4B | 111 |
| | | ASA1-1-3B | 112 |
| | | ASA1-1-2B | 113 |
| | | CTP2-N1-8 | 92 |
| pMON78141 | Zm-ASA1-CTP + 20::AgroAS(F298W)::GFP | ASA1-1-1T | 107 |
| | | ASA1-1-2T | 108 |
| | | ASA1-20-3T | 114 |
| | | ASA1-20-4T | 115 |
| | | CTP2-N1-7 | 91 |
| | | ASA1-1-5B | 110 |
| | | ASA1-1-4B | 111 |
| | | ASA1-1-3B | 112 |
| | | ASA1-20-3B | 116 |
| | | ASA1-20-2B | 117 |
| | | CTP2-N1-8 | 92 |

TABLE 4-continued

Summary of the strategy 2 plasmid vectors constructed for protoplast transfection assays

| pMON | CTP::GFP variants | Primer Name | SEQ ID NO: |
|---|---|---|---|
| pMON69760 | Zm-ASA2-CTP::AgroAS(F298W)::GFP | AS2-5'-1 | 118 |
| | | AS2-5'-41 | 119 |
| | | AS2-5'-81 | 120 |
| | | AS2-5'-121 | 121 |
| | | AS2-5'-161 | 122 |
| | | AS2-3'-208 | 123 |
| | | AS2-3'-168 | 124 |
| | | AS2-3'-128 | 125 |
| | | AS2-3'-88 | 126 |
| | | AS2-3'-48 | 127 |
| pMON69761 | Zm-ASA2-CTP + 5aa::AgroAS(F298W)::GFP | AS2-5'-161-5aa | 128 |
| | | AS2-3'-183-5aa | 129 |
| | | AS2-3'-153-5aa | 130 |
| pMON69762 | Zm-ASA2-CTP + 10aa::AgroAS(F298W)::GFP | AS2-5'-161-10aa | 131 |
| | | AS2-5'-196-10aa | 132 |
| | | AS2-3'-198-10aa | 133 |
| | | AS2-3'-163-10aa | 134 |
| pMON69771 | Zm-ASA2-CTP::GFP | AS2GFP-5' | 135 |
| | | AS2GFP-3' | 136 |
| pMON78135 | Os-Wx-CTP::AgroAS(F298W)::GFP | RW-CM-1T | 137 |
| | | RW-CM-2T | 138 |
| | | RW-CM-3T | 139 |
| | | RW-CM-4T | 140 |
| | | RW-CM-5T | 141 |
| | | RW-CM-6T | 142 |
| | | RW-CM-7T | 143 |
| | | RW-CM-8B | 144 |
| | | RW-CM-7B | 145 |
| | | RW-CM-6B | 146 |
| | | RW-CM-5B | 147 |
| | | RW-CM-4B | 148 |
| | | RW-CM-3B | 149 |
| | | RW-CM-2B | 150 |
| | | RW-CM-1B | 151 |
| pMON78136 | Os-Wx-CTP + 5::AgroAS(F298W)::GFP | RW-CM-1T | 137 |
| | | RW-CM-2T | 138 |
| | | RW-CM-3T | 139 |
| | | RW-CM-4T | 140 |
| | | RW-CM-5T | 141 |
| | | RW-CM-6T | 142 |
| | | RW-5-7T | 152 |
| | | RW-5-8T | 153 |
| | | RW-CM-8B | 144 |
| | | RW-CM-7B | 145 |
| | | RW-CM-6B | 146 |
| | | RW-CM-5B | 147 |
| | | RW-CM-4B | 148 |
| | | RW-CM-3B | 149 |
| | | RW-5-2B | 154 |
| | | RW-5-1B | 155 |
| pMON78137 | Os-Wx-CTP + 20::AgroAS(F298W)::GFP | RW-CM-1T | 137 |
| | | RW-CM-2T | 138 |
| | | RW-CM-3T | 139 |
| | | RW-CM-4T | 140 |
| | | RW-CM-5T | 141 |
| | | RW-CM-6T | 142 |
| | | RW-20-7T | 156 |
| | | RW-20-8T | 157 |
| | | RW-20-9T | 158 |
| | | RW-CM-8B | 144 |
| | | RW-CM-7B | 145 |
| | | RW-CM-6B | 146 |
| | | RW-CM-5B | 147 |
| | | RW-CM-4B | 148 |
| | | RW-CM-3B | 149 |
| | | RW-5-2B | 154 |
| | | RW-20-2B | 159 |
| | | RW-20-1B | 160 |
| pMON69758 | Zm-DHDPS-CTP::AgroAS(F298W)::GFP | DHDPS-5'-1 | 161 |
| | | DHDPS-5'-41 | 162 |
| | | DHDPS-5'-81 | 163 |
| | | DHDPS-5'-121 | 164 |
| | | DHDPS-5'-161 | 165 |
| | | DHDPS-3'-AgroAS | 166 |

TABLE 4-continued

Summary of the strategy 2 plasmid vectors constructed for protoplast transfection assays

| pMON | CTP::GFP variants | Primer Name | SEQ ID NO: |
|---|---|---|---|
| | | DHDPS-3'-184 | 167 |
| | | DHDPS-3'-140 | 168 |
| | | DHDPS-3'-99 | 169 |
| | | DHDPS-3'-59 | 170 |
| pMON69759 | Zm-DHDPS-CTP + 9aa:: AgroAS(F298W)::GFP | DHDPS-5'-161-9aa | 171 |
| | | DHDPS-5'-201-9aa | 172 |
| | | DHDPS-3'-216-9aa | 173 |
| | | DHDPS-3'-176-9aa | 174 |
| pMON69765 | Zm-DHDPS-CTP + 20aa:: AgroAS(F298W)::GFP | DHDPS-5'-201-20aa | 175 |
| | | DHDPS-5'-241-20aa | 176 |
| | | DHDPS-3'-249-20aa | 177 |
| | | DHDPS-3'-209-20aa | 178 |
| | | DHDPS-3'-169-20aa | 179 |
| pMON69764 | Zm-DHDPS-CTP + 5aa:: AgroAS(F298W)::GFP | DHDPS-5'-161-5aa | 180 |
| | | DHDPS-5'-201-5aa | 181 |
| | | DHDPS-3'-244-5aa | 182 |
| | | DHDPS-3'-204-5aa | 183 |
| | | DHDPS-3'-164-5aa | 184 |
| pMON69772 | Zm-DHDPS-CTP::GFP | DHDPSGFP-5' | 185 |
| | | DHDPSGFP-3' | 186 |
| pMON69766 | Zm-DHDPS-CTP + 5::GFP | DHDPS-N1 | 187 |
| | | DHDPS-N2 | 188 |
| | | DHDPS-N3 | 189 |
| | | DHDPS-N4 | 190 |
| | | DHDPS-N9 | 191 |
| | | DHDPS-N10 | 192 |
| | | DHDPS-N11 | 193 |
| | | DHDPS-N12 | 194 |
| | | DHDPS-N13 | 195 |
| | | DHDPS-N14 | 196 |
| | | DHDPS-N15 | 197 |
| | | DHDPS-N18 | 198 |

Example 4

Localization of AgroAS and Variants to Plastids

This example describes the two transient expression assay systems used to predict the abilities of different chloroplast transit peptides (CTPs) in plastid targeting of AS::GFP fusion proteins. These assays utilize the protoplast transfection vectors containing the anthranilate synthase-green fluorescent protein (AS::GFP) fusions and the fusions that were described in Example 3.

Two transient expression assay methods were developed to predict the localization of AS::GFP fusion proteins in maize cells. A medium throughput maize protoplast system was used to screen many different CTPs for their ability to target the AS::GFP fusion proteins to the plastids of etiolated maize leaf cells. A lower throughput system of expressing proteins in developing maize embryos was used to confirm the plastid localization pattern seen in the protoplast system. Data from these two assays were then used to predict the abilities of various CTPs in directing the localization of *Agrobacterium* and *Sinorhizobium* AS proteins in transgenic maize embryos.

All constructs tested in the transient assay systems were built with the same genetic elements in a common vector backbone which expressed each gene using the e35S promoter, hsp70 (DnaK) intron and nos 3'UTR.

To ensure that the transient assay systems were functioning correctly, control plasmids were constructed. The controls for cytosolic localization were the vectors containing GFP fusion with no CTP (pMON30098; Tables 2 and 5), AgroAS fusion to GFP (no CTP added) (pMON78818; Tables 2 and 5), and a truncated Zm-ASA2-CTP::GFP fusion lacking the Zm-ASA2-CTP (pMON78822; Tables 2 and 5). The controls used for plastid localization were maize ASA2 fused to GFP (pMON78820; Tables 2 and 5) and At-CTP2 fused to GFP (pMON53173; Table 5). Two additional controls were used to confirm the data from the transgenic plants; CTP1::GFP (pMON79960; Tables 2 and 5) and CTP1::AgroAS (F298W)::GFP (pMON79961; Tables 2 and 5). Localization patterns of GFP or GFP fusion proteins from each of these vectors are reported in Table 5. The data also confirmed the cell fractionation results as described in Example 1, indicating cytosolic localization of the CTP1::AgroAS(F298W)::GFP fusion protein and the inability of CTP1 to target the AgroAS(F298W) to the plastid.

In most of the experiments, an additional control was constructed for each CTP tested. These controls consisted of the tested CTP fused directly to GFP. For example, Zm-ASA2-CTP fused to GFP (pMON69771) to test the Zm-ASA2::AgroAS::GFP fusions. The methods for construction of all of the vectors tested are detailed in Example 3.

Several variations were made for each of the CTPs tested. These variations were distinguished by varying the number of N-terminal amino acids added to the CTP of the native host protein (Table 1). For example, in the Zm-ASA2-CTP series, the experimentally determined CTP fused directly to GFP was used, as well as two additional versions which included 5 and 18 amino acids from the N-terminus of the Zm-ASA2, isolated from the region of the amino-terminus of the mature *Zea mays* anthranilate synthase α2 subunit adjacent to the CTP. The constructs are denoted as Zm-ASA2-CTP+5 (SEQ ID NO: 8) and Zm-ASA2-CTP+18 (SEQ ID NO: 9) in Table 1.

As a primary test, the CTP constructs described in Table 1 were evaluated in an etiolated protoplast system. Leaf mesophyll protoplasts were prepared from etiolated maize seedlings using methods well known in the art (see for example Sheen, 1993).

The different vectors were electroporated into the protoplasts using methods well known in the art. Approximately 18 to 24 hours later, the protoplast cells were counted for GFP fluorescence using confocal microscopy. Briefly, microscopy was performed using a Zeiss Laser Scanning Microscope LSM510 META (Carl Zeiss MicroImaging, Inc., Thornwood, N.Y.) equipped with an Argon Ion laser, green and red Helium-Neon lasers, and a chameleon diode-pumped laser (Coherent Laser Division, Santa Clara, Calif.). Image acquisition and analysis was performed using LSM 5 Image Examiner, version 3.2.0.70 (Carl Zeiss MicroImaging, Inc., Thornwood, N.Y.). Image processing was performed using Adobe Photoshop CS, version 8.0 (Adobe Systems Incorporated, San Jose, Calif.). At least 50 cells for each construct were scored with respect to having GFP fluorescence in the; a) plastids only, b) cytosol only and c) both plastid and cytosol.

As a secondary test, a specific transient assay system was developed to evaluate constructs designed to be expressed in developing maize germ tissue. The constructs evaluated by this test were chosen based upon having a score in the protoplast system of 50% or greater of transformed cells containing plastid only localization. Additional control constructs, as detailed above, were also tested.

Embryos were isolated from surface-sterilized ears from the maize, e.g. Hill or an inbred parent, at approximately 14 days after pollination (DAP). About 20-30 embryos were placed on Petri plates containing N6 medium supplemented with 0.2M sorbitol+0.2M mannitol (Chu, 1978). Following four hours of incubation at room temperature, the embryos were bombarded with 0.6 μm gold particles coated with DNA using the Biolistic™ PDS-1000/He Particle Delivery System (Bio-Rad Corporation). The plates were bombarded twice at 9 cm from the stopping screen to the target shelf, with a rupture pressure of 1100 psi and a gap distance of 1 cm. Following bombardment, the embryos were incubated at 28° C. in the dark overnight before being analyzed by multiphoton confocal microscopy, as described above. At least 50 cells were counted per sample and scored as described for above for the protoplast system.

The results from the localization assays are shown in Table 5. The results indicate that based upon visualization, the following six CTPs effectively target AgroAS to the plastids in maize germ cells: Zm-ASA2-CTP+18 (SEQ ID NO: 9; the CTP component of pMON78824), Rg-AS long-CTP (SEQ ID NO: 14; the CTP component of pMON78142), Rg-AS short-CTP (SEQ ID NO: 13; the CTP component of pMON78143 and pMON78139), At-CTP2 (E/K) (SEQ ID NO: 2; the CTP component of pMON78833), At-CTP2 (E/K)+10 (SEQ ID NO: 3; the CTP component of pMON78834), and Zm-DHDPS-CTP+20 (SEQ ID NO: 17; the CTP component of pMON69765). The results also indicate that not all of the various CTPs assayed were positive for the ability to localize AS::GFP in either the protoplast or the embryo transient expression assays. These results corroborate the results described in Example 1, and indicate the need for identifying useful CTPs for successfully localizing monomeric AS proteins in the chloroplasts of monocotyledonous plants and therefore producing elevated tryptophan levels.

TABLE 5

Results of localization assays

| pMON ID | CTP::AgroAS::GFP variants | Protoplast % Plastid Loc | Embryo % Plastid Loc |
| --- | --- | --- | --- |
| 78832 | At-CTP2(C/M)::AgroAS(F298W)::GFP | 68.6 | Not tested |
| 78833 | At-CTP2(E/K)::AgroAS(F298W)::GFP | 64 | 79 |
| 78834 | At-CTP2 + 10::AgroAS(F298W)::GFP | 72 | 35 |
| 78835 | At-CTP2 + 5::AgroAS(F298W)::GFP | 60.6 | Not tested |
| 53173 | Control: At-CTP2::GFP | >80 | 80 |
| 78138 | Zm-ASA1-CTP::AgroAS(F298W)::GFP | 0 | Not tested |
| 78141 | Zm-ASA1-CTP + 20::AgroAS(F298W)::GFP | 0 | Not tested |
| 69760 | Zm-ASA2-CTP::AgroAS(F298W)::GFP | 0 | Not tested |
| 69761 | Zm-ASA2-CTP + 5::AgroAS(F298W)::GFP | 0 | Not tested |
| 78824 | Zm-ASA2-CTP + 18::AgroAS(wt)::GFP | 100 | 81 |
| 69771 | Control: Zm-ASA2-CTP::GFP | 15 | Not tested |
| 78135 | Os-Wx-CTP::AgroAS(F298W)::GFP | 0 | Not tested |
| 78136 | Os-Wx CTP + 5::AgroAS(F298W)::GFP | 0 | Not tested |
| 78137 | Os-Wx-CTP + 20::AgroAS(F298W)::GFP | 72 | Not tested |
| 78140 | Control: Os-Wx-CTP::GFP | 77 | Not tested |
| 78143 | Rg-AS short-CTP::AgroAS(F298W)::GFP | 87.3 | 54 |
| 78142 | Rg-AS long-CTP::AgroAS(F298W)::GFP | 88.6 | 55 |
| 78139 | Control: Rg-AS short-CTP::GFP | 77.3 | 67 |
| 69758 | Zm-DHDPS-CTP::AgroAS(F298W)::GFP | 0 | Not tested |
| 69759 | Zm-DHDPS-CTP + 9::AgroAS(F298W)::GFP | 3 | Not tested |
| 69765 | Zm-DHDPS-CTP + 20::AgroAS (F298W)::GFP | 71 | 91% in plastid and cytosol; 9% in cytosol only |
| 69763 | Zm-DHDPS-CTP + 3::AgroAS(F298W)::GFP | 0 | 33 |
| 69772 | Control: Zm-DHDPS-CTP::GFP | 0 | 10 |
| 69766 | Control: Zm-DHDPS-CTP + 5::GFP | 30 | Not tested |
| 69774 | At-CTP2(E/K)::*Rhizobium meliloti* anthranilate synthase::GFP | 64 | Not tested |

TABLE 5-continued

Results of localization assays

| pMON ID | CTP::AgroAS::GFP variants | Protoplast % Plastid Loc | Embryo % Plastid Loc |
|---|---|---|---|
| 69775 | At-CTP2 + 10::*Rhizobium meliloti* anthranilate synthase::GFP | 72.7 | Not tested |
| 69776 | Zm-ASA2-CTP::*Rhizobium meliloti* anthranilate synthase::GFP | 0 | Not tested |
| 69777 | Zm-ASA2-CTP + 18::*Rhizobium meliloti* anthranilate synthase::GFP | 70.7 | Not tested |
| 78818 | Control: No CTP::AgroAS(F298W)::GFP | 0 | 0 |
| 78820 | Control: Zm-ASA2(includes CTP)::GFP | 70.3 | 85 |
| 78822 | Control: No CTP::mature Zm-ASA2::GFP | * | Not tested |
| 79961 | Control: CTP1::AgroAS(F298W)::GFP | * | 0 |
| 30098 | Control: GFP | * | 0 |
| 79960 | Control: CTP1::GFP | ** | 44 |

* For these controls, no plastid localization was observed in the protoplast transient assay; the data was not quantified.
** For this control, plastid and cytosolic localization was observed but not quantified.

Example 5

Transformation Vectors and Maize Transformation

This example describes the construction of the transformation vectors containing nucleic acid sequences encoding the wild type (wt) and mutant alleles of both *Agrobacterium tumefaciens* and *Rhizobium meliloti* anthranilate synthase (AS) in combination with various chloroplast transport proteins. This example also provides a protocol for transformation of maize with the transformation vectors described herein.

Figure 6:
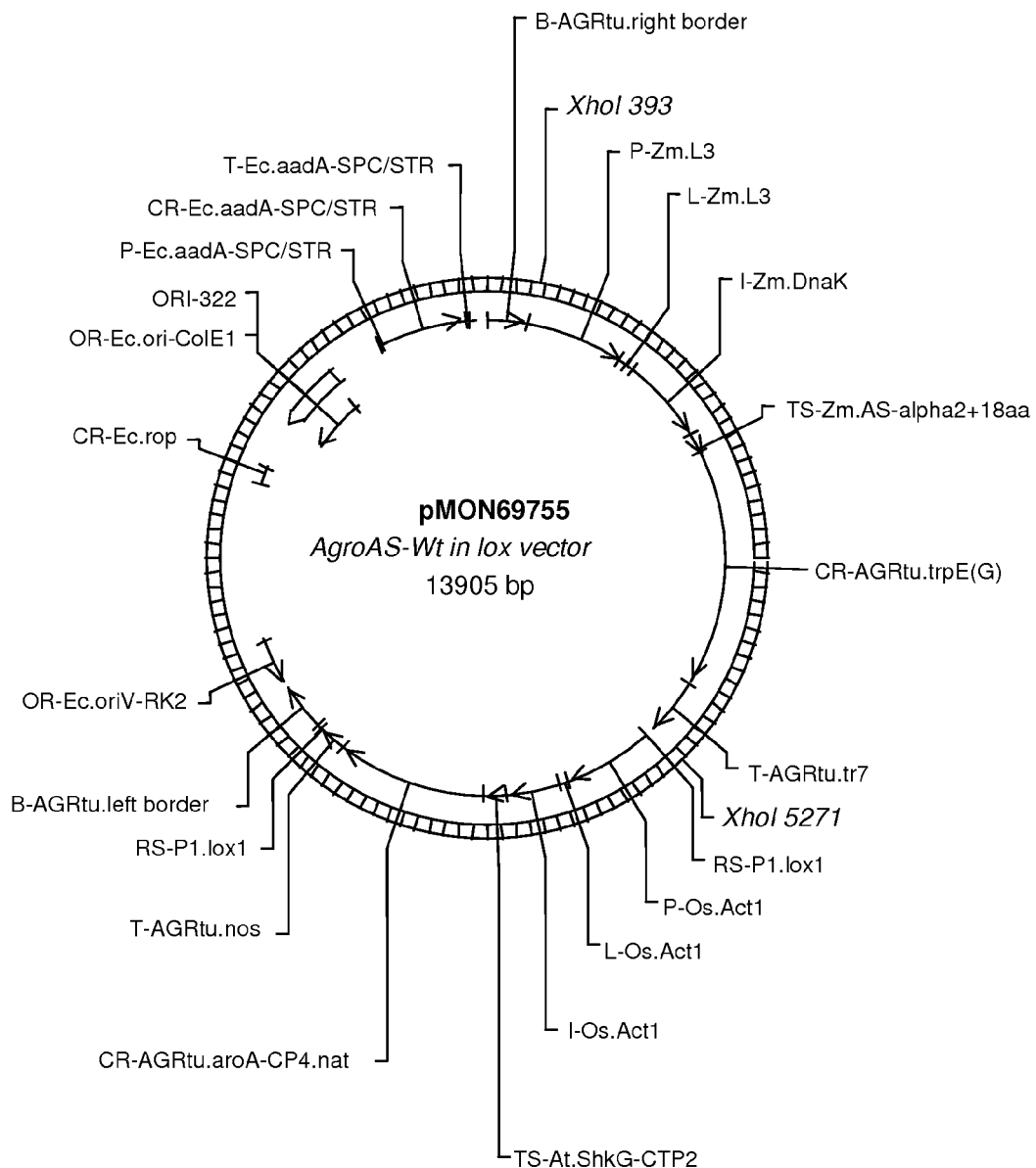
FIG. 6 depicts a restriction map of plasmid pMON69755

For the construction of transformation vectors containing the wild type *Agrobacterium tumefaciens* AS, the AS coding sequence was cut out of plasmid pMON66580 by digesting with XhoI, blunting the ends using mungbean nuclease, and then cutting with BglII to isolate a first fragment. To isolate a second fragment containing maize oleosin promoter, hsp70 intron, and Tr7-3'-UTR, the plasmid pMON69753 was cut with BglII and SmaI. These two fragments were ligated to generate pMON69754. To construct the final transformation vector containing the Zm-ASA2-CTP, pMON69754 was digested with XhoI, and the purified fragment containing maize oleosin promoter, hsp70 intron, Zm-ASA2-CTP fused to -wt, and Tr7-3'UTR was isolated. This fragment was then ligated in the vector pMON78808, which had also been digested with XhoI to generate the final transformation vector pMON69755 (FIG. 6).

For the construction of transformation vectors containing the AgroAS(F298W) mutant allele, pMON66869 was digested with StuI and RsrII to isolate a fragment containing part of the AgroAS(F298W) coding region. Similarly, pMON69754 was also digested with StuI and RsrII to isolate a fragment containing the maize oleosin promoter, hsp70 intron, part of the coding region and Tr7 3'-UTR. The resulting fragments were ligated to generate pMON69756. To construct final transformation vector, pMON69756 was digested with XhoI, and purified the fragment containing maize oleosin promoter, hsp70 intron, Zm-ASA2-CTP fused to AgroAS(F298W), and Tr7-3'UTR. This fragment was then ligated into the XhoI site of pMON78808, to generate pMON69757; SEQ ID NO: 215).

Transformation vectors containing the AgroAS(S51F) coding region (SEQ ID NO: 203) were similarly constructed. For example, the plasmid pMON69754, described above, was digested with BamHI and NcoI to remove the AgroAS coding region. The plasmid pMON58121 was also digested with BamHI and NcoI to isolate the AgroAS(S51F) mutant allele. The resulting fragments were then ligated to generate the intermediate plasmid pMON69767. The final transformation vector, pMON69768, was constructed as described above by digesting pMON69767 with XhoI, and ligating the fragments at the XhoI site of pMON78808.

An example of the construction of transformation vectors containing the AgroAS(S51C) allele is pMON68065. pMON68063 was digested with XhoI restriction enzyme, separated on 1.0% agarose gel, and the 4569 bp DNA fragment that corresponds to the *Zea mays* Oleosin promoter fused to the Zmhsp70 (Zm.DNAK) intron, the AgroAS (S51C) allele and the Os-gt1-3'UTR was isolated from the gel.

pMON78808 DNA was also cut with XhoI restriction enzyme, dephosphorylated using alkaline phosphatase enzyme (New England BioLabs Inc.), and the DNA was purified using a QIAGEN PCR purification kit (QIAGEN Inc.). The XhoI-digested DNA of pMON78808 and the 4569 bp XhoI-digested DNA fragment of pMON68063 were ligated together to generate pMON68065.

An example of the construction of transformation vectors containing the AgroAS(S51C) codon-optimized (AgroAS (S51C)-nno) allele is pMON68066. Codon optimization of the AgroAS(S51C) mutant allele was carried out as described in U.S. patent application Ser. No. 11/503,532, which is herein incorporated by reference). Codon-optimized AgroAS (S51C)-nno DNA was synthesized by the BLUE HERON BIOTECHNOLOGY group (Bothell, Wash., USA). The synthetic DNA was then digested with NcoI and BamHI restriction enzymes, separated on a 1.0% agarose gel, and the 2193 bp DNA fragment corresponding to the AgroAS(S51C)-nno was cut out from the gel and purified as described above. The DNA of pMON68063 was also cut with NcoI and BamHI restriction enzymes and separated on a 1.0% agarose gel. The isolated 5244 bp NcoI/BamHI-digested DNA fragment contains all the genetic elements described in pMON68063 except the AgroAS(S51C) mutant allele. Ligation reactions were carried out by mixing the DNA of the NcoI/BamHI-digested AgroAS(S51C)-nno DNA (2193 bp fragment) and pMON68063 (5244 bp DNA fragment), to generate pMON68064. pMON68064 was then cut with XhoI restriction enzyme, separated on a 1.0% agarose gel, and the 4532 bp DNA fragment that contains the *Zea mays* oleosin promoter fused to the hsp70 (Zm.DNAK) intron, the AgroAS (S51C)-nno and the Os-gt1-3'UTR was purified as described above. The DNA of pMON78808 DNA was also cut with XhoI restriction enzyme, dephosphorylated using alkaline phosphatase enzyme (New England BioLabs Inc., Beverly, Mass.), and purified using a QIAGEN PCR purification kit (QIAGEN Inc., Valencia, Calif.). Ligation reactions were carried out by mixing the dephosphorylated XhoI-cut pMON78808 DNA and the 4532 bp DNA fragment of pMON68064, to generate pMON68066.

Figure 7:
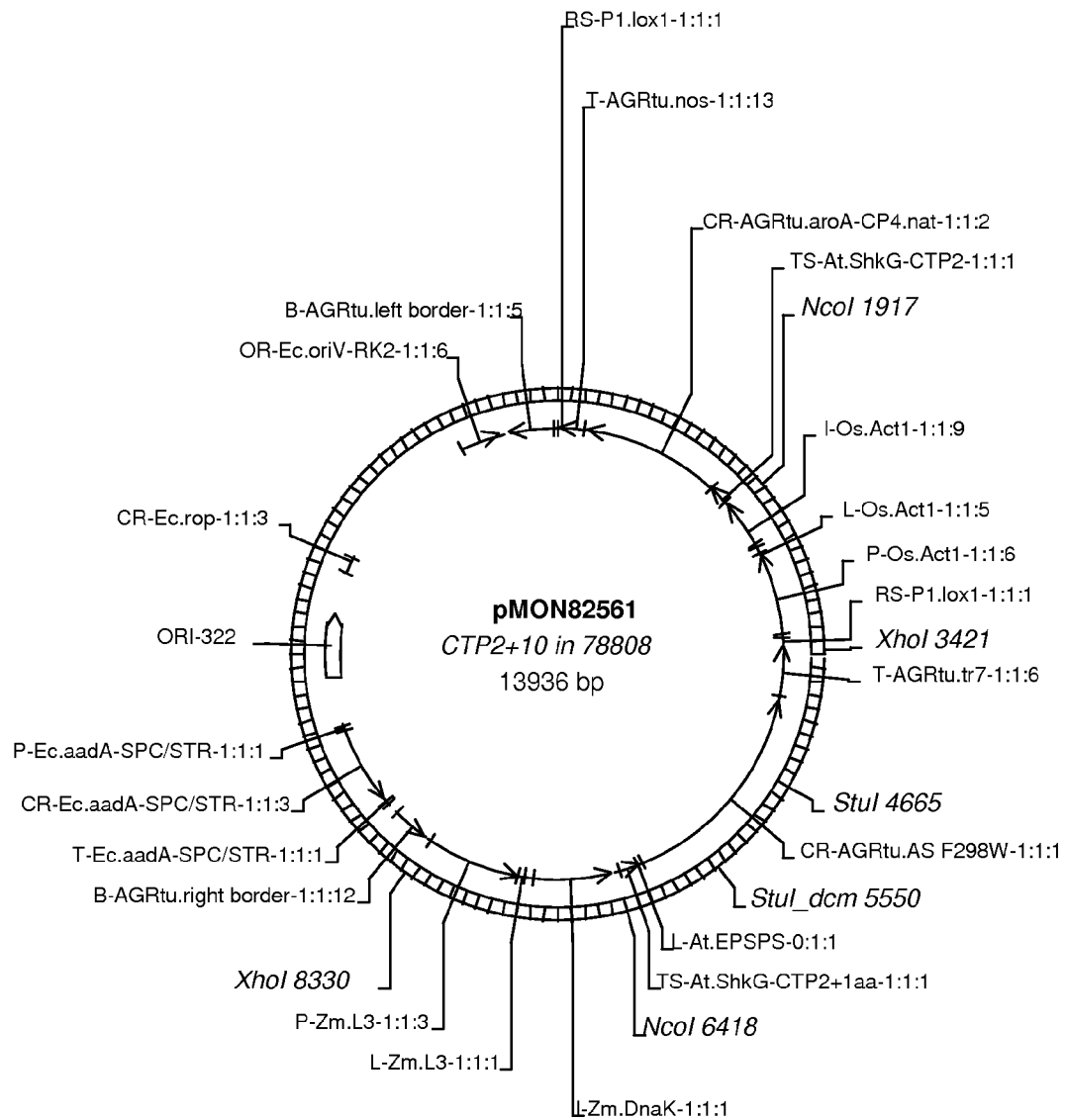
FIG. 7 depicts a restriction map of plasmid pMON82561
Figure 9:
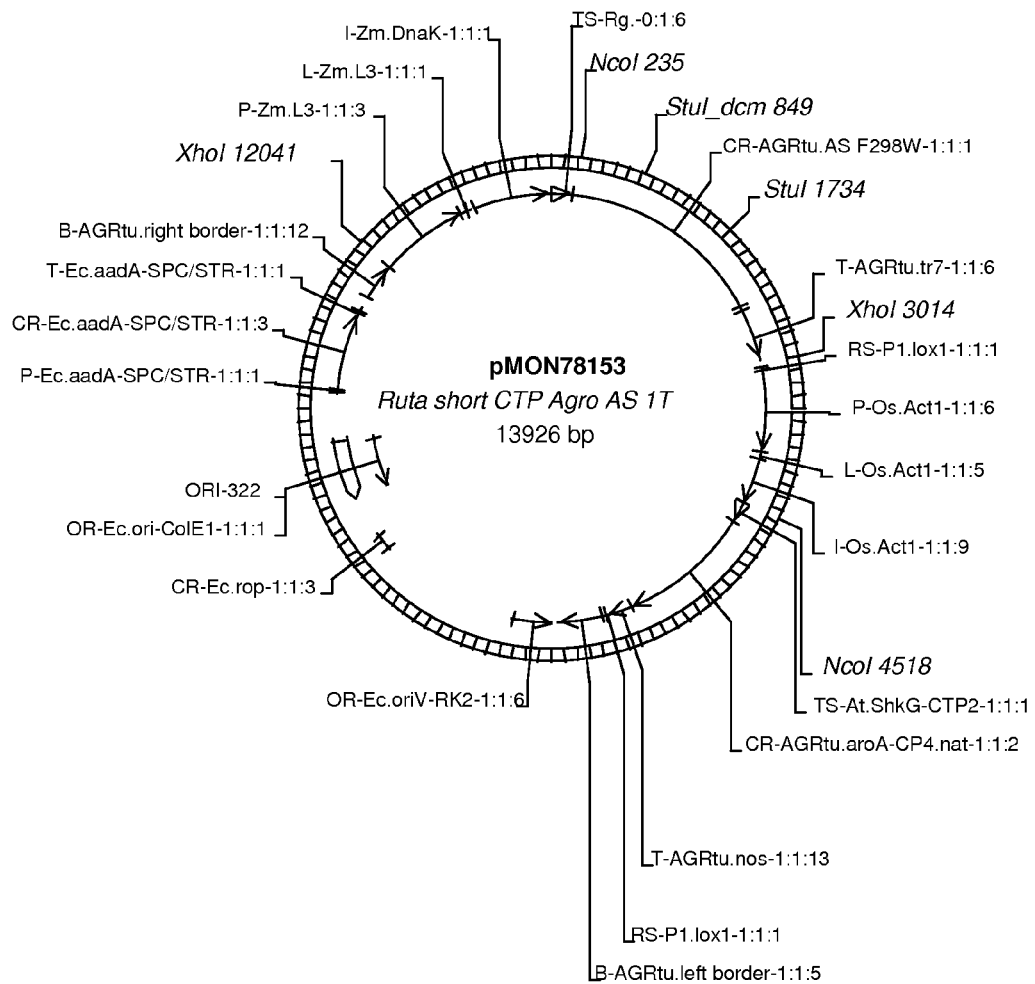
FIG. 9 depicts a restriction map of plasmid pMON78153
Figure 10:
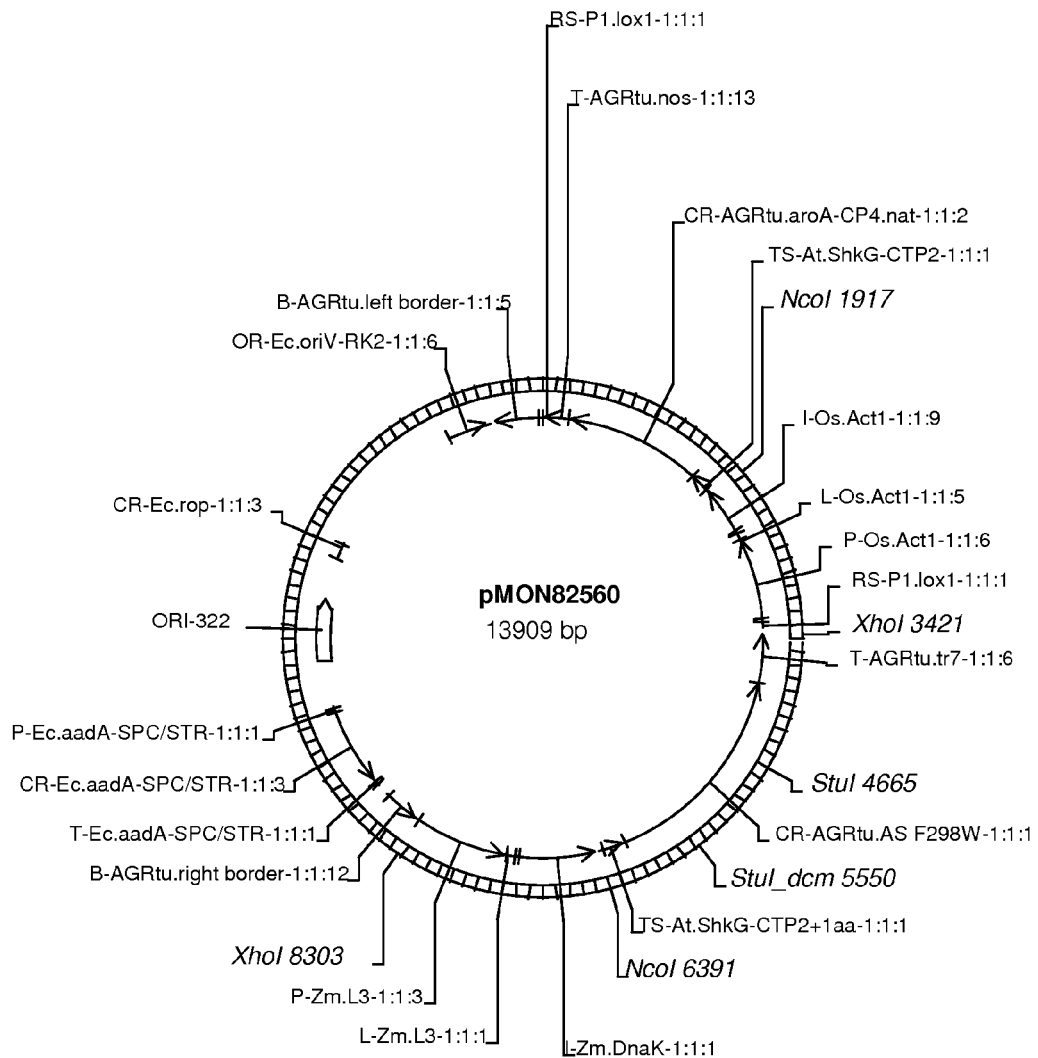
FIG. 10 depicts a restriction map of plasmid pMON82560
Figure 11:
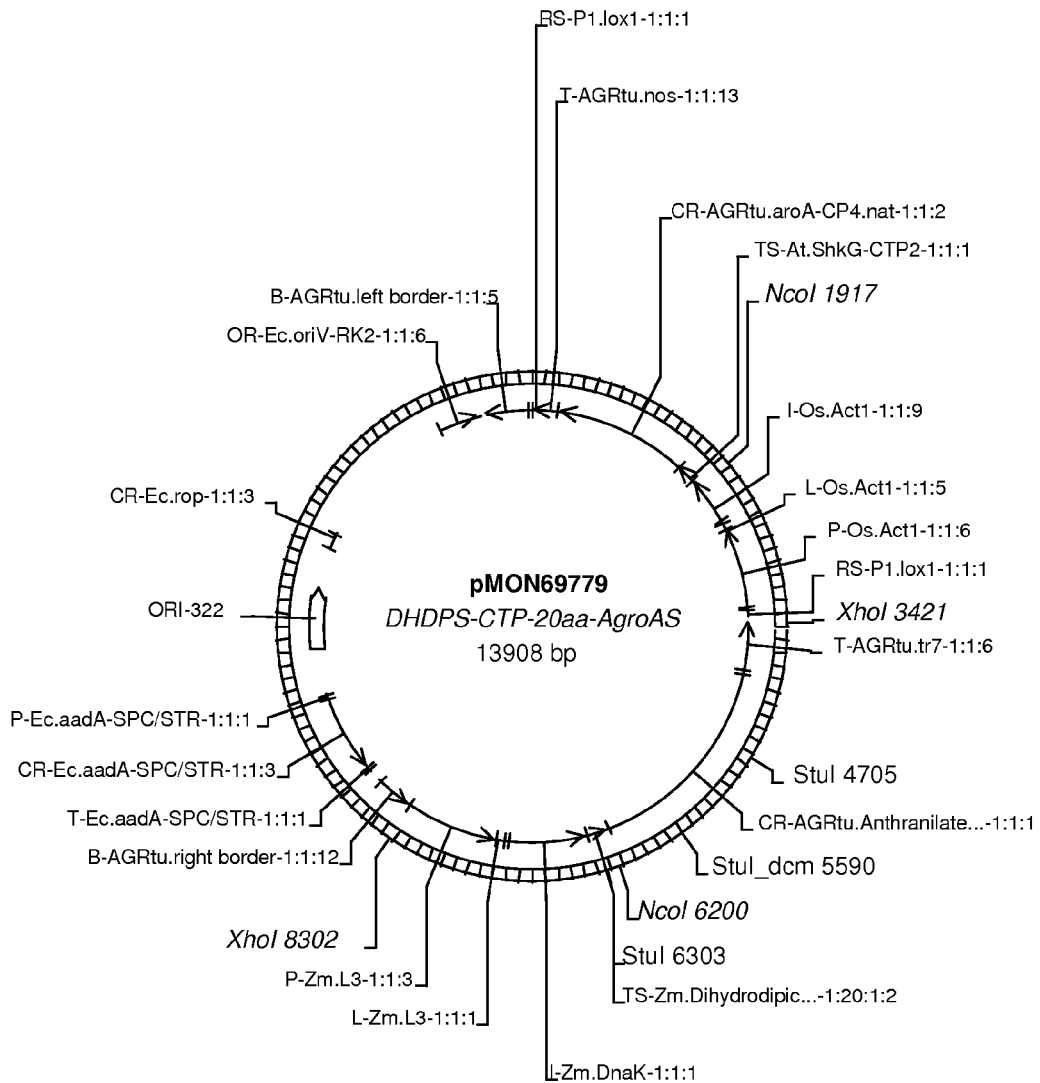
FIG. 11 depicts a restriction map of plasmid pMON69779
Figure 12:
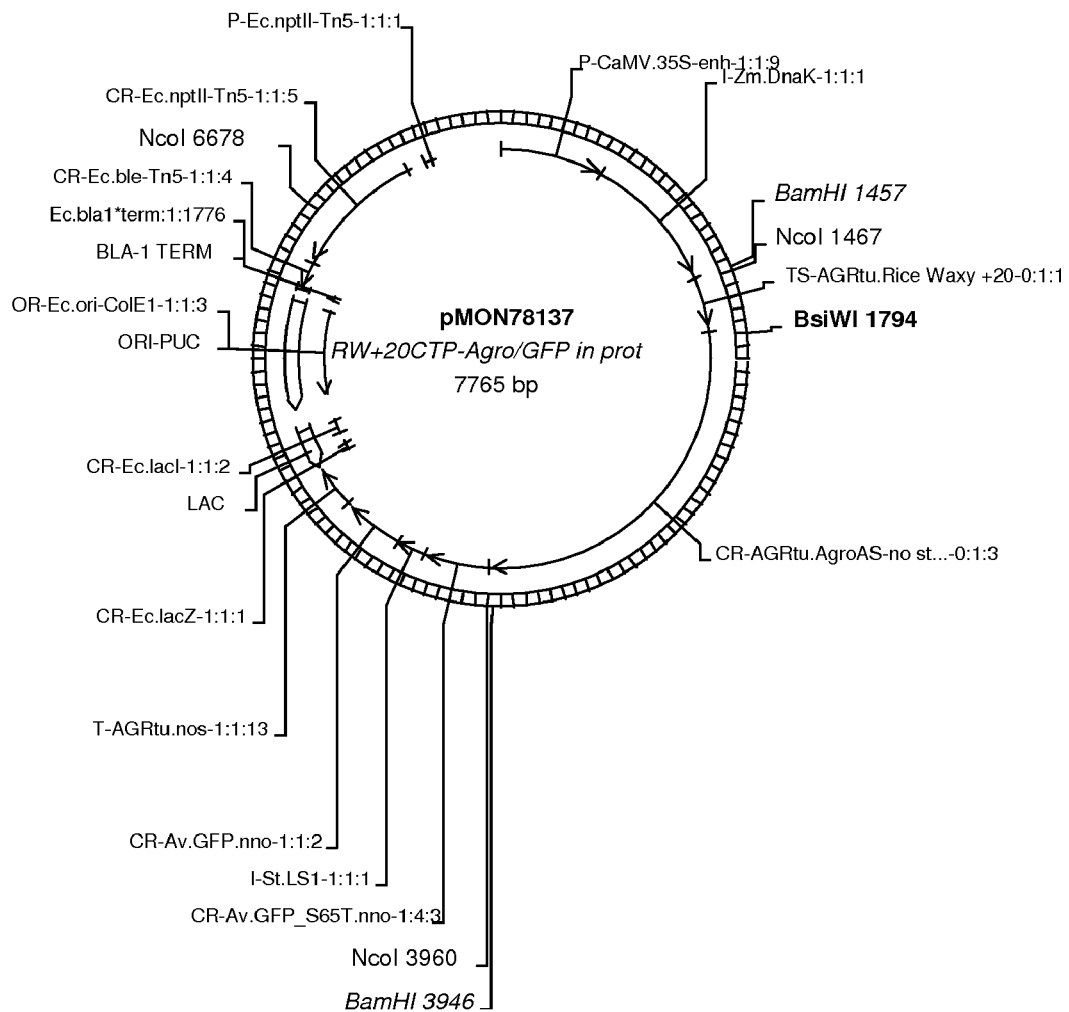
FIG. 12 depicts a restriction map of plasmid pMON78137
Figure 13:
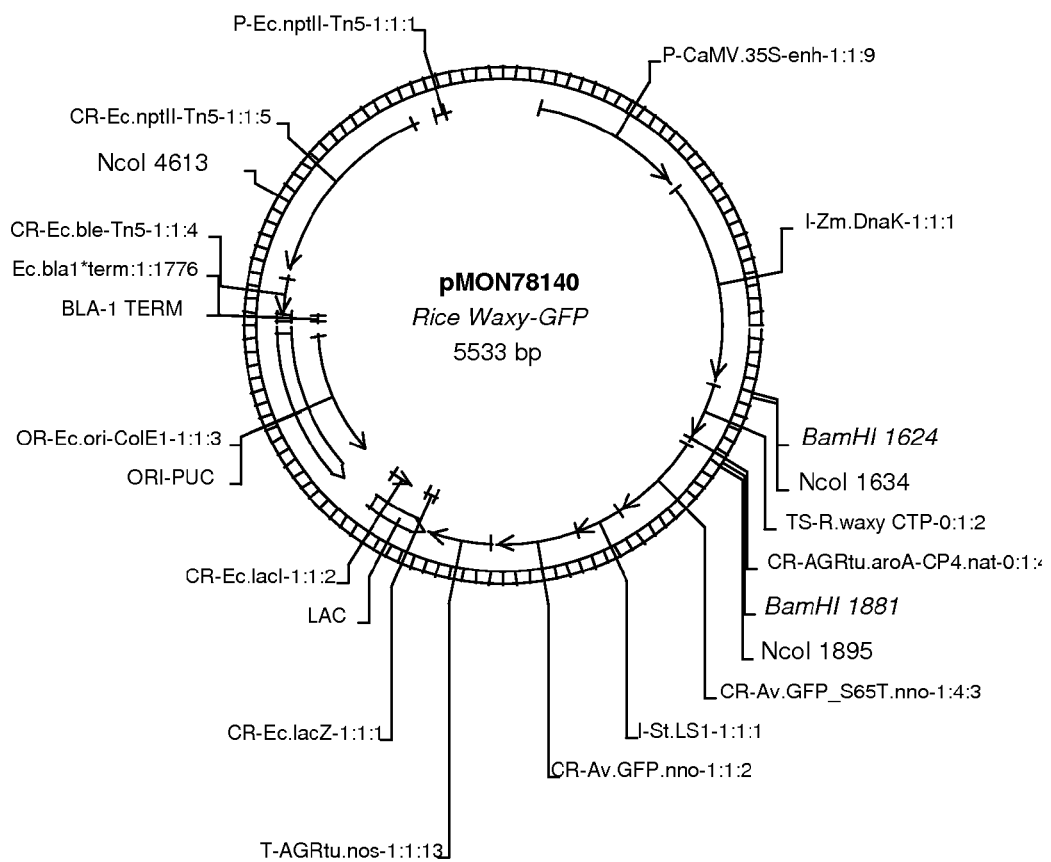
FIG. 13 depicts a restriction map of plasmid pMON78140
Figure 14:
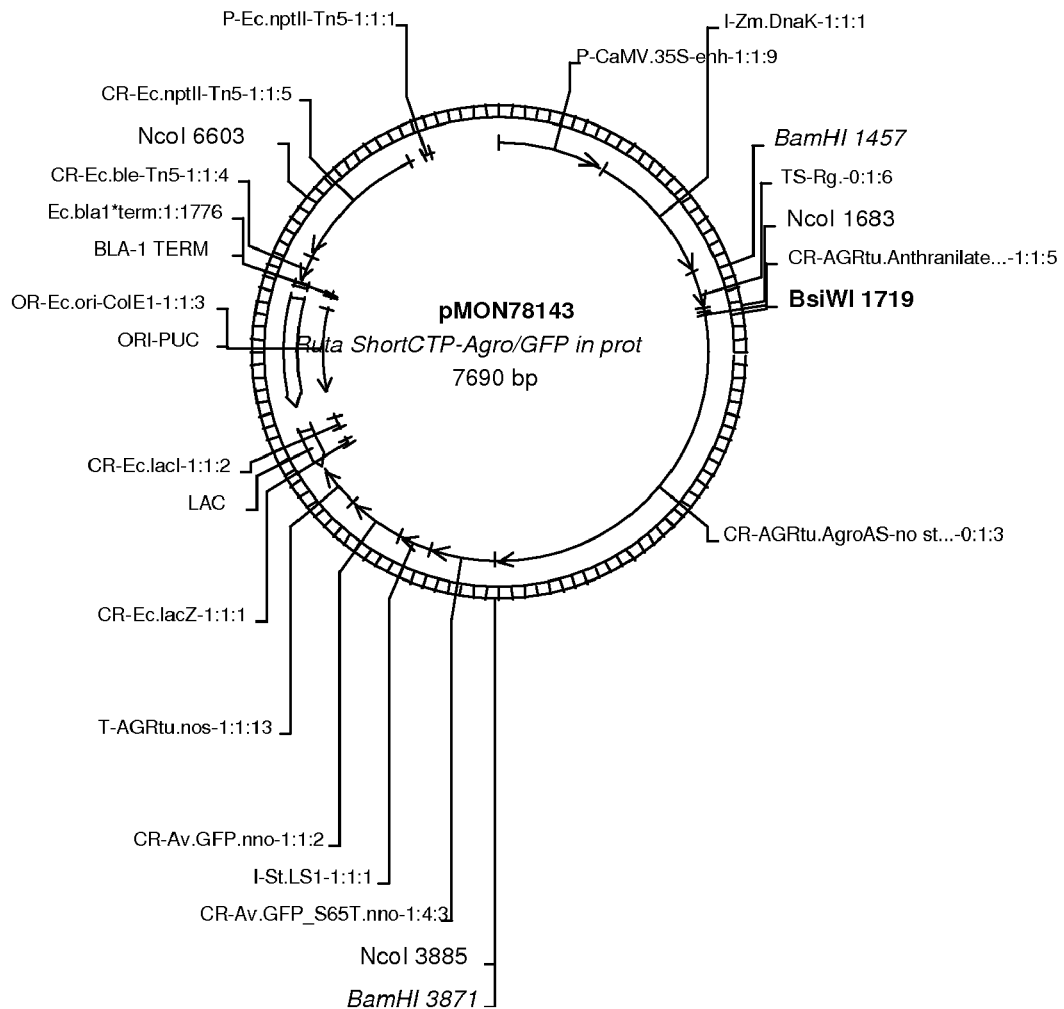
FIG. 14 depicts a restriction map of plasmid pMON78143
Figure 15:
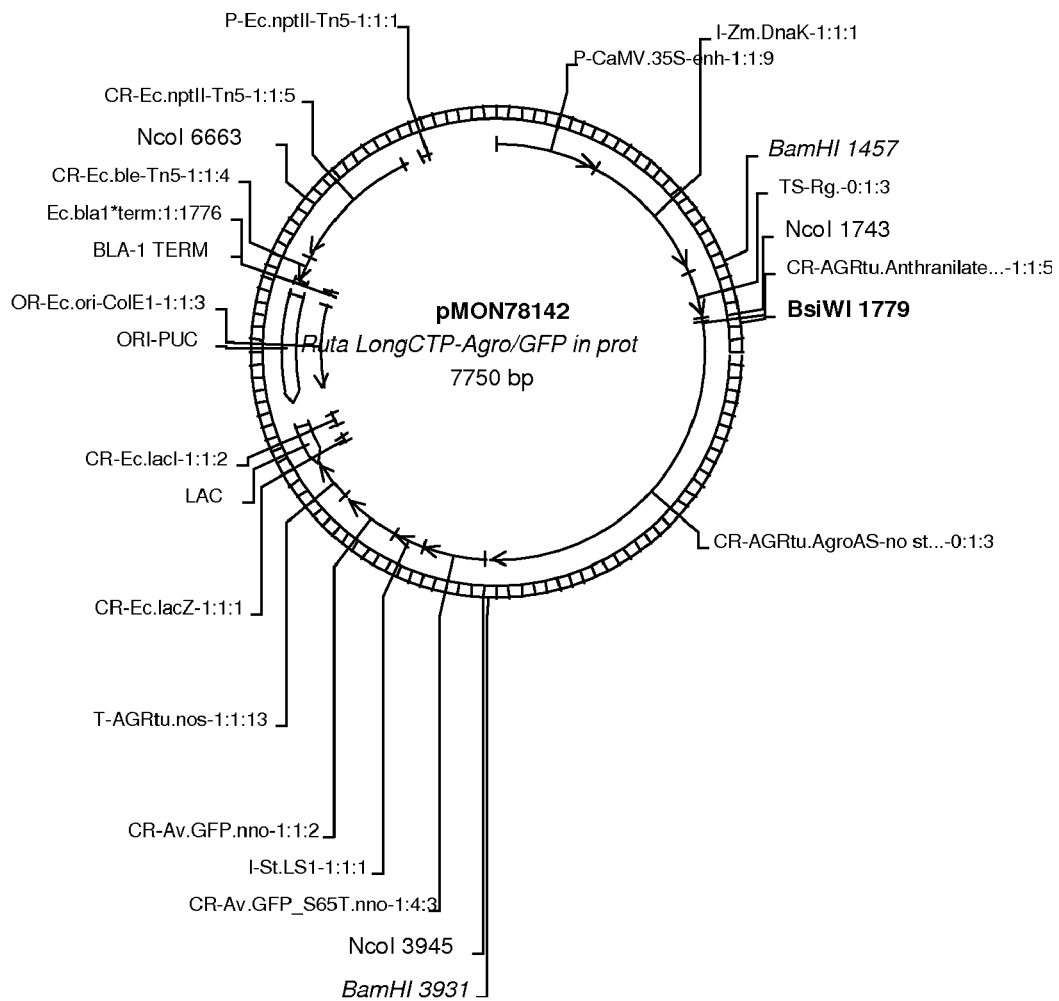
FIG. 15 depicts a restriction map of plasmid pMON78142
Figure 16:
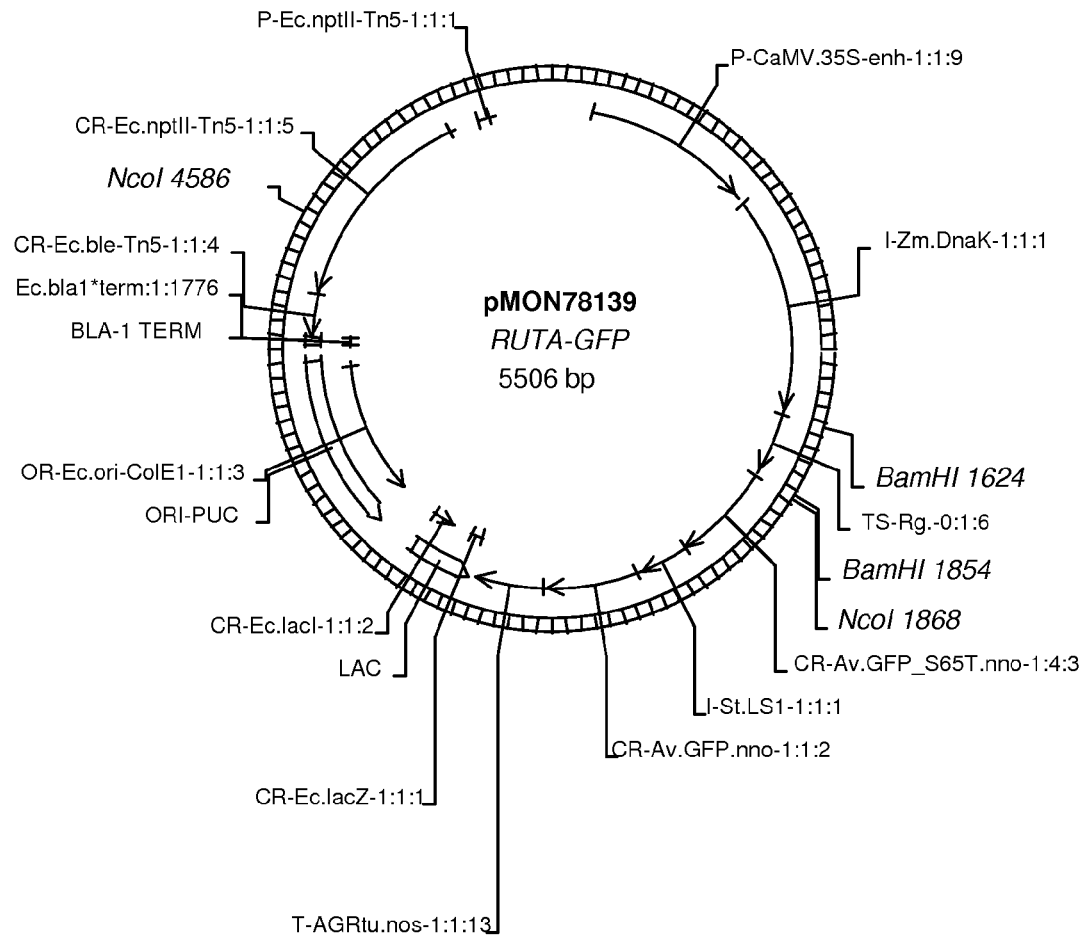
FIG. 16 depicts a restriction map of plasmid pMON78139
Figure 17:
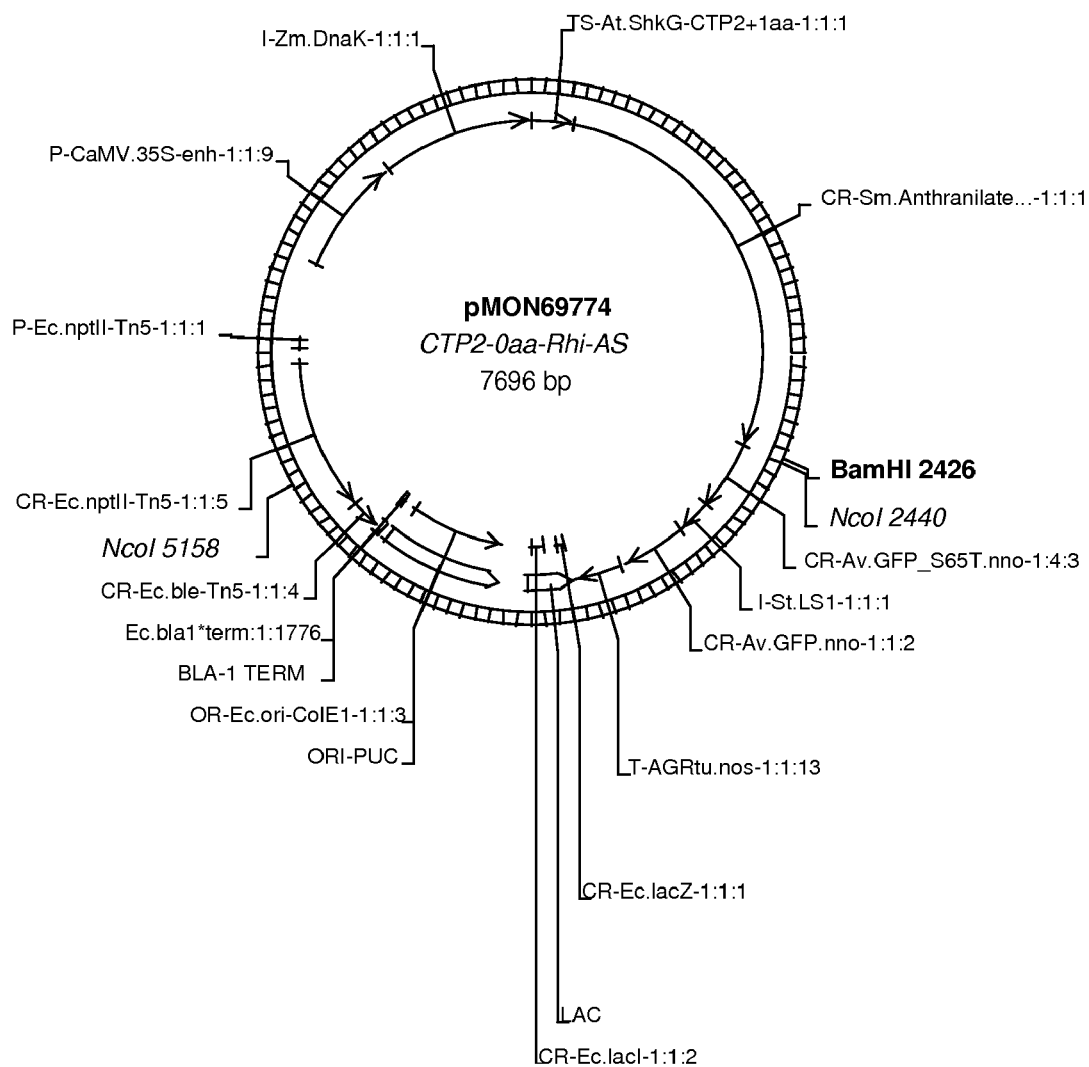
FIG. 17 depicts a restriction map of plasmid pMON69774
Figure 18:
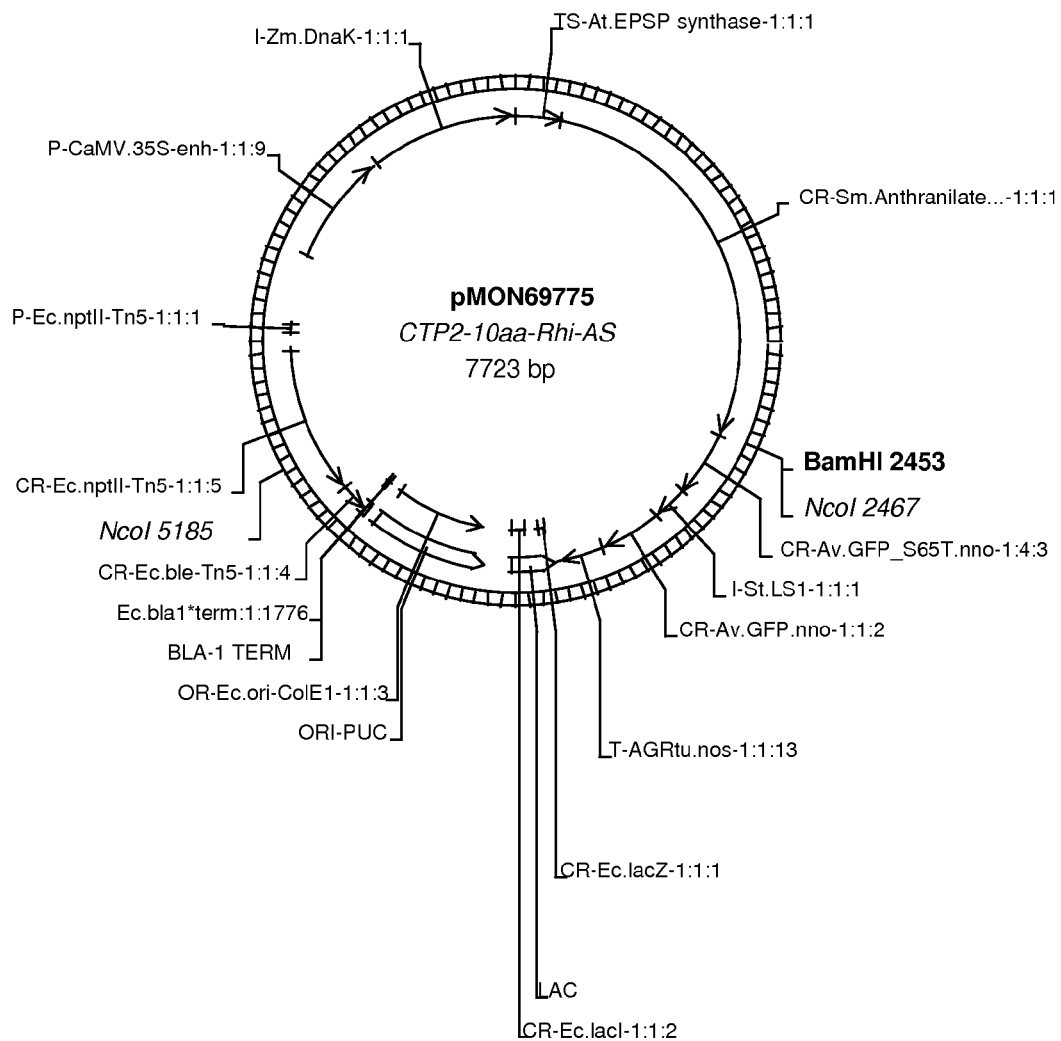
FIG. 18 depicts a restriction map of plasmid pMON69775
Figure 19:
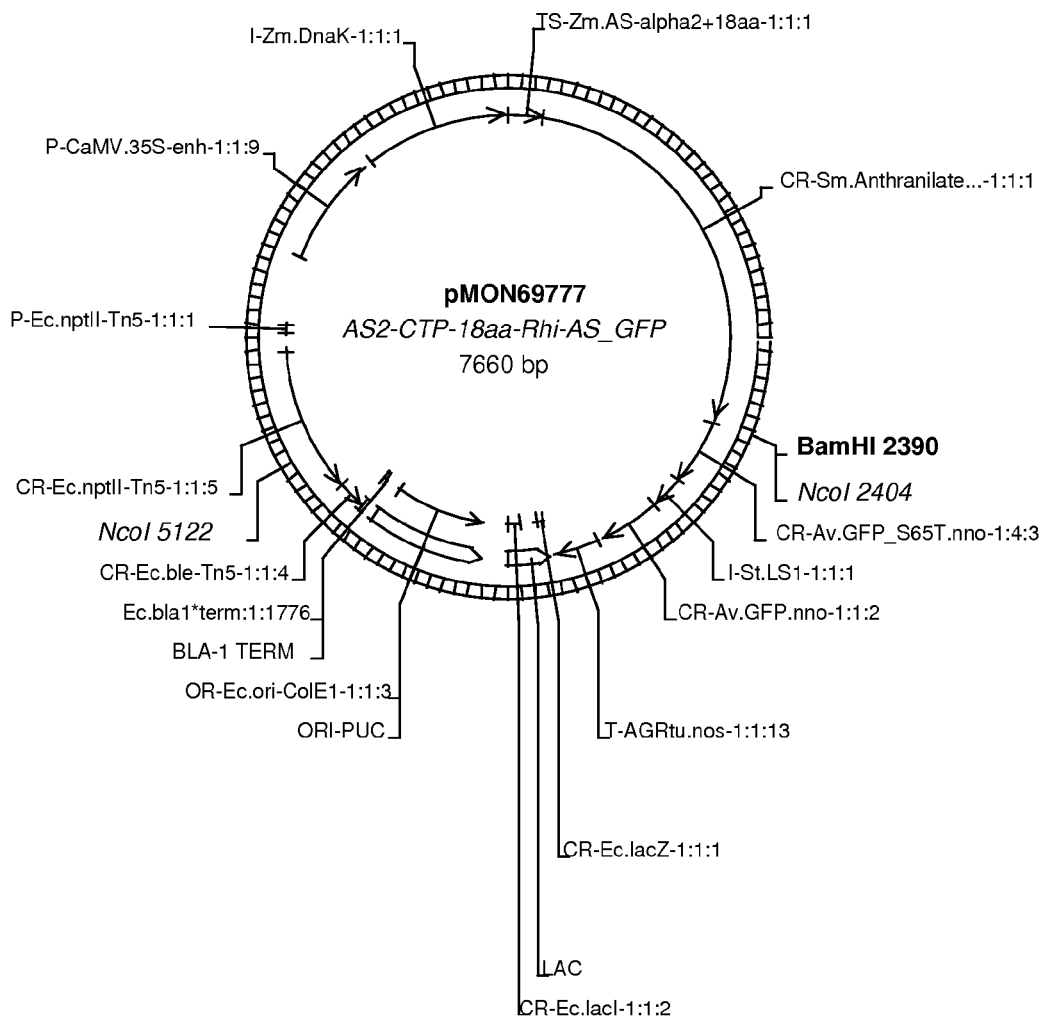
FIG. 19 depicts a restriction map of plasmid pMON69777

The plasmid pMON69769 was used as a base vector to generate various other transformation vectors including pMON82561 (FIG. 7), pMON78152 (FIG. 8), pMON78153 (FIG. 9), pMON82560 (FIG. 10), pMON69779 (FIG. 11), pMON78846, pMON78850, pMON78851, pMON68065, pMON69781, pMON94548, pMON94549, pMON97701, pMON97703 and pMON97705 using similar cloning strategies.

Transformation of Maize

The transformation vectors described above were transformed into maize essentially as described in U.S. patent application Publication 20050005327, which is herein incorporated by reference in its entirety. Briefly, ears containing immature embryos are harvested approximately 10 days after pollination and kept refrigerated at 4° C. until use (up to 5 days post-harvest). The preferred embryo size for this method of transformation is ~1.5-2.0 mm. This size is usually achieved 10 days after pollination inside the greenhouse with the growth conditions of an average temperature of 87° F., day length of 14 hours with supplemental lighting supplied by GE 1000 Watt High Pressure Sodium lamps.

Immature embryos are isolated from surface sterilized ears and directly dropped into the prepared *Agrobacterium* cell suspension in a 1.5-mL microcentrifuge tube. The isolation lasts continuously for approximately 5 to 60 minutes. Alternately, embryos are excised directly into inoculation medium (without *Agrobacterium* or acetosyringone) for 5-60 minutes and subsequently inoculated for 5-30 minutes with *Agrobacterium* cell suspension. After the *Agrobacterium* cell suspension is removed using a fine tipped sterile transfer pipette, the immature embryos are transferred onto a crn398 co-culture medium (Table 6). The embryos are then placed on the medium with the scutellum side facing up. The embryos are cultured in a dark incubator (23° C.) for approximately 14-48 hours.

The embryos are then transferred onto a callus induction medium (crn336, Table 6) which contains 0.1 mM glyphosate and 500 mg/L carbenicillin to inhibit *Agrobacterium* in Petri dishes (100 mm×25 mm). The cultures are incubated in a dark culture room/incubator at 30° C. for 2 weeks followed by an additional week in a dark culture room/incubator at 27° C. All the callus pieces are then transferred individually onto the first regeneration medium (crn335, Table 6) which contains 0.1 mM glyphosate and 250 mg/L carbenicillin. The cultures are grown on this medium in a 27° C. culture room with 16 hours light/8 hours dark photoperiod for 7 to 10 days. They are then transferred onto the second regeneration medium (crn333, Table 6) in Petri dishes (100 mm×25 mm) at 27° C. with 16 hours of light for approximately 2 to 3 weeks. All the callus pieces with regenerating shoots and living tissue are then transferred onto either fresh crn333 plates or crn334 PHYTATRAYs (Table 6) or directly transferred to sundae cups containing a rooting medium (crn366, Table 6) to grow further prior to being transferred to soil (approximately 1 to 3 weeks). The regeneration media (crn335, crn333 and crn334) all contain 250 mg/L carbenicillin and 0.1 mM glyphosate.

Plantlets are then transferred to soil, hardened off in a growth chamber at 27° C., 80% humidity, and low light intensity for approximately 1 to 2 weeks, and then transferred to a greenhouse and grown under standard greenhouse conditions. The resulting kernels are collected and analyzed as described below.

TABLE 6

Composition of media used in corn transformation (per Liter).

| Component | Co-culture media (crn398) | *Callus* induction media (crn336) | First regeneration media (crn335) | Second regeneration media (crn333 (plates)/crn334 (PHYTATRAYs)) | Rooting media (crn366) |
| --- | --- | --- | --- | --- | --- |
| MS salts | 2.17 g | 4.33 g | 4.33 g | 4.33 g | 2.17 g |
| Sucrose | 20 g | 30 g | 30 g | | 20 g |
| Maltose | | | | 20 g | |
| Glucose | 10 g | | | 10 g | |
| 1-Proline | 115 mg | 1.38 g | 1.38 g | | |
| Casamino Acids | | 0.5 g | 0.05 g | | |
| IBA (1 mg/mL stock) | | | | | 0.75 mL |
| 1-Asparagine | | | | 0.15 g | |
| Myo-inositol | | | | 0.1 g | |
| NAA (1 mg/mL stock) | | | | | 0.5 mL |
| Thiamine-HCl (0.5 mg/mL stock) | 1.0 mL | 1.0 mL | | | |
| 2,4-D (1 mg/mL stock) | 3.0 mL | 0.5 mL | | | |
| Silver Nitrate (2 mg/mL stock) | 1.7 mL | 1.7 mL | | | |
| MS Vitamins 100X | 10 mL | 10 mL | | | 5.0 mL |
| MS Fromm 1000X | | | 1.0 mL | 1.0 mL | |
| Carbenicillin (250 mg/mL) | | 2.0 mL | 1.0 mL | 1.0 mL | |
| Glyphosate (0.5M stock) | | 0.2 mL | 0.2 mL | 0.2 mL | 0.2 mL |

TABLE 6-continued

Composition of media used in corn transformation (per Liter).

| Component | Co-culture media (crn398) | *Callus* induction media (crn336) | First regeneration media (crn335) | Second regeneration media (crn333 (plates)/crn334 (PHYTATRAYs)) | Rooting media (crn366) |
|---|---|---|---|---|---|
| Phytagel | | 3.0 g | 3.0 g | 3.0 g | 3.0 g |
| BAP (0.5 mg/mL stock) | | 0.02 mL | 7.0 mL | | |
| Acetosyringone (1.0M) | 0.2 mL | | | | |
| Agarose Low EEO | 5.5 g | | | | |

Example 6

Methods for Immunolocalization of AS and Quantification of Tryptophan in Maize Kernels This example describes the analytical procedures used in immunolocalization studies and quantification of free tryptophan levels in kernels from maize events transformed with the CTP-constructs described in Example 5.

Figure 8:
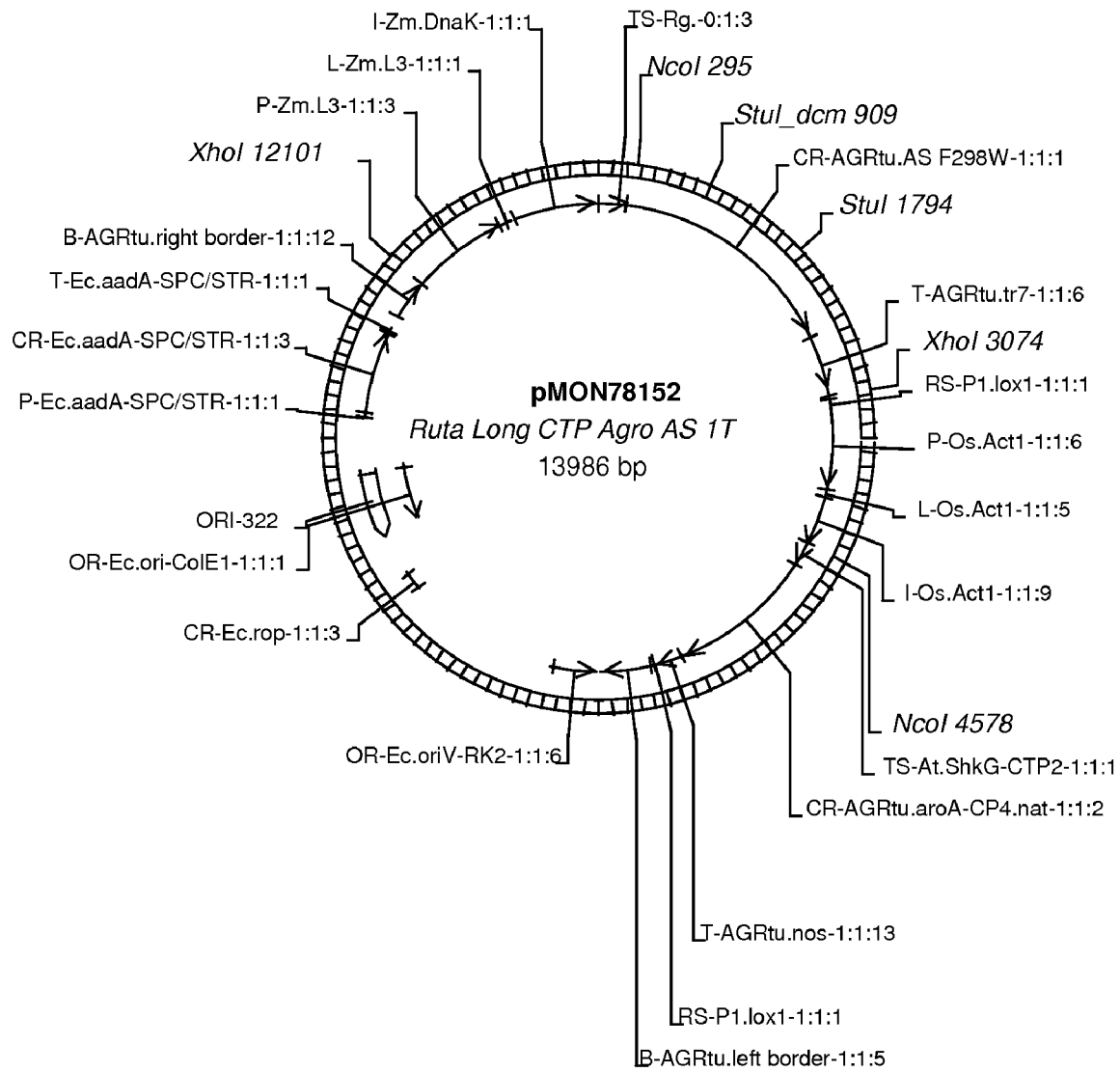
FIG. 8 depicts a restriction map of plasmid pMON78152

The kernels from F1 stage transgenic plants harboring different constructs were separately harvested at 26 DAP. These constructs included pMON69755 (FIG. 6), pMON69779 (FIG. 11), pMON82560 (FIG. 10), pMON82561 (FIG. 7), pMON78153 (FIG. 9) and pMON78152 (FIG. 8). Eight to ten embryos were isolated from each transgenic line of these constructs, fixed in 3.7% formaldehyde solution, and stored at 4° C., prior to being analyzed for the localization of the expressed proteins by the immunolabeling study described below.

Genomic DNA was also extracted from endosperm of these transgenic kernels using DNeaSy™ plant Kit (Cat. No. 69104, Qiagen, Waltham, Mass.). PCR amplifications were performed to identify the positive and negative kernels using the oligonucleotide primers maize AS2-5' and maize AS2-3' designated SEQ ID NO: 226 and SEQ ID NO: 227 respectively in the Sequence Listing.

The corn embryos described above were incubated in 500 µl 0.05% Triton X-100 for 30 minutes. Scutellum tissue sections were sliced into sections 20 µm thick using a Leica VT 1000S Vibrating-blade microtome (Leica Microsystems GmbH, Nussloch Germany) equipped with a sapphire knife, and then washed 3 times in PBS buffer (137 mM NaCl, 3 mM KCl, 8 mM $Na_2HPO_4$ and 1.5 mM $KH_2PO_4$) containing 10 mM glycine, for 10 minutes per wash.

The tissue sections were then incubated in enzymatic mixture (4% pectinase, 2% cellulase) for 40 minutes at 28° C. The tissues were then blocked with undiluted serum for 15 minutes, using goat serum (Sigma Cat. No. G-9023; Sigma Chemical Company, St. Louis, Mo.) for AgroAS detection and rabbit serum (Sigma R-9133) for maize AS. The tissue sections were then incubated overnight at 4° C., with gentle shaking, in either 1% rabbit anti-his AgroAS or goat anti-maize AS in PBS buffer.

Following the overnight incubation, the tissues were washed in PBS buffer containing 10 mM glycine for 20 minutes and incubated again in the respective undiluted serums for 15 minutes at room temperature. The tissues were then incubated in the dark with Alexa-conjugate secondary antibody for 2 hours at room temperature. The dilution factors were 1:1000 for AlexaFluor® 532 (Molecular Probes, Inc., Eugene, Oreg.) goat anti-rabbit-conjugate secondary antibody for AgroAS protein and 1:1000 AlexaFluor® 488 (Molecular Probes, Inc.) rabbit anti-goat for Zm AS protein. Following the incubation, the tissues were washed 3 times in PBS containing 10 mM glycine for 10 minutes per wash. The tissues were then counterstained with calcofluor white for cell walls (Sigma) solution (2.5 mg/ml in stock, diluted 1:50 with distilled water) and Hoechst stain for nuclei (Molecular Probes Inc.) for 15 minutes in dark with shaking. The stained tissues were then washed for 10 minutes in distilled water prior to mounting.

The results indicate that when the samples were probed with both AgroAS (red fluorescence at 543 nm) and control Zm AS antibody (green fluorescence at 488 nm) with the channels merged, the appearance of yellow color suggested co-localization of the proteins in plastids (data not shown).

To extract the amino acid fraction, 30 mg of ground kernels were placed in a centrifuge vial. One milliliter of 5% trichloroacetic acid was added to each sample. The samples were mixed by vortexing, and placed at 4° C. overnight. The samples were then mixed again and spun in a microcentrifuge for 15 minutes at 14,000 rpm. Some of the supernatant was then removed, placed in an HPLC vial and sealed. Samples were kept at 4° C. prior to analysis.

The amino acid analysis was performed as described in the Agilent Technical Publication, "Amino Acid Analysis Using Zorbax Eclipse-AAA Columns and the Agilent 1100 HPLC", Mar. 17, 2000. The analysis pre-derivatizes the amino acids with o-pthaldialdehyde (OPA) then separates the OPA conjugates by reverse phase chromatography. The separation was done using an Agilent 1100 series HPLC system (Agilent, Palo Alto, Calif.) with an Eclipse XDB-C18 5 µm, 4.6×150 mm column, and a flow rate of 1.2 ml/minute. Amino acid concentrations were measured using fluorescence: excitation at 340 nm, emission at 450 nm. Elution was with a gradient of HPLC Buffers A and B according to Table 7, where HPLC Buffer A was 40 mM $Na_2HPO_4$, pH 7.8 and HPLC Buffer B was 9:9:2::Methanol:Acetonitrile:Water.

TABLE 7

Amino Acid Elution

| | Time | | | | |
|---|---|---|---|---|---|
| | 0 | 20 | 21 | 26 | 27 |
| % Buffer A | 95 | 35 | 0 | 0 | 0 |
| % Buffer B | 5 | 65 | 100 | 100 | 100 |

Amino acid standards were prepared or purchased in concentrations ranging from 0 to 100 µg/ml. Proline analysis required an additional derivatization step using 9-fluorenyl-methyl-chloroformate (FMOC). Results, as shown in Table 8, were reported in ppm.

Example 7

Analysis of Free Tryptophan Levels in Maize

This example sets forth the analysis of free tryptophan levels in maize plants transformed with the expression vectors described in Example 5.

The F1 kernels were analyzed for free tryptophan as described in Example 6. The results from some of the transformed plants, shown in Table 8 below, indicate that the CTPs that demonstrated the ability to successfully target the GFP in the transient expression assays (data shown in Table 5) had higher levels of free tryptophan in transformed plants. Additionally, the CTPs that did not demonstrate the ability to localize the GFP in the plastid had lower levels of free tryptophan. These results indicate that not all CTPs can direct the localization of monomeric AS to the plastid and hence increase free tryptophan levels.

TABLE 8

Average free tryptophan levels in F3 homozygous transgenic maize plants.

| Construct | Vector Description | Event ID | Average of Tryptophan ppm | StdDev of Tryptophan ppm |
|---|---|---|---|---|
| PMON30167 | Vector only | RAG120 | 11 | 1 |
| Parent line | | Non-transgenic | 11 | 2 |
| PMON69755 | Zm-ASA2-CTP + 18:_wt AS | ZM_S100593 | 118 | 8 |
| | | ZM_S101241 | 99 | 45 |
| | | ZM_S103021 | 58 | 18 |
| | | ZM_S103022 | 63 | 6 |
| | | ZM_S98891 | 122 | 26 |
| PMON69757 | Zm-ASA2-CTP + 18:_F298W | ZM_S100715 | 352 | 42 |
| | | ZM_S101226 | 310 | 16 |
| | | ZM_S99658 | 286 | 37 |
| | | ZM_S99679 | 242 | 16 |
| | | ZM_S99787 | 319 | 22 |
| PMON69768 | Zm-ASA2-CTP + 18:_S51F | ZM_S104037 | 227 | 18 |
| | | ZM_S104038 | 129 | 11 |
| | | ZM_S104052 | 174 | 18 |
| | | ZM_S105091 | 258 | 30 |
| | | ZM_S105105 | 254 | 53 |
| PMON69770 | Zm-ASA2-CTP + 18:_S51C | ZM_S102618 | 677 | 174 |
| | | ZM_S102637 | 649 | 84 |
| | | ZM_S103233 | 585 | 190 |
| | | ZM_S103234 | 612 | 197 |
| | | ZM_S103245 | 632 | 160 |
| | | ZM_S103257 | 667 | 106 |
| | | ZM_S103261 | 430 | 106 |
| | | ZM_S103277 | 684 | 251 |
| PMON69779 | ZM-DHDPS-CTP + 20:_F298W | ZM_S115297 | 150 | 16 |
| | | ZM_S115309 | 129 | 32 |
| | | ZM_S115313 | 123 | 30 |
| | | ZM_S115314 | 148 | 15 |
| | | ZM_S116346 | 145 | 12 |
| PMON67146 | Zm-DHDPS-CTP + 3:_F298W | ZM_S67192 | 49 | 47 |
| | | ZM_S67201 | 41 | 49 |
| | | ZM_S67209 | 51 | 48 |
| PMON78152 | Rg long-CTP:_F298W | ZM_S111632 | 68 | 12 |
| | | ZM_S112752 | 53 | 13 |
| | | ZM_S112777 | 69 | 22 |
| | | ZM_S113086 | 89 | 36 |
| | | ZM_S113096 | 280 | 43 |
| PMON78153 | Rg short-CTP:_F298W | ZM_S113911 | 326 | 14 |
| | | ZM_S113927 | 258 | 99 |
| | | ZM_S113946 | 280 | 54 |
| | | ZM_S113953 | 241 | 47 |
| | | ZM_S114105 | 271 | 79 |
| PMON82560 | At-CTP2(E/K) + 1:_F298W | ZM_S115009 | 353 | 93 |
| | | ZM_S115027 | 340 | 24 |
| | | ZM_S115029 | 393 | 25 |
| | | ZM_S115066 | 358 | 113 |
| | | ZM_S115070 | 361 | 91 |
| PMON82561 | At-CTP2(E/K) + 10:_F298W | ZM_S113026 | 156 | 37 |
| | | ZM_S113029 | 192 | 27 |
| | | ZM_S113033 | 147 | 50 |
| | | ZM_S113194 | 145 | 40 |
| | | ZM_S113833 | 169 | 24 |
| PMON66559 | CTP1:_F298W | ZM_S44537 | 10 | 2 |
| | | ZM_S44538 | 8 | 1 |
| | | ZM_S44540 | 11 | 3 |
| | | ZM_S44542 | 8 | 0 |
| | | ZM_S46820 | 9 | 2 |
| | | ZM_S46828 | 9 | 2 |

TABLE 8-continued

Average free tryptophan levels in F3 homozygous transgenic maize plants.

| Construct | Vector Description | Event ID | Average of Tryptophan ppm | StdDev of Tryptophan ppm |
|---|---|---|---|---|
| | | ZM_S46833 | 10 | 2 |
| | | ZM_S46841 | 9 | 1 |
| | | ZM_S46842 | 10 | 2 |
| | | ZM_S46848 | 11 | 3 |
| | | ZM_S46855 | 10 | 2 |
| | | ZM_S46859 | 10 | 2 |
| | | ZM_S46861 | 9 | 1 |
| | | ZM_S46865 | 9 | 1 |
| | | ZM_S46873 | 8 | 1 |
| | | ZM_S46877 | 9 | 3 |
| | | ZM_S46878 | 10 | 1 |
| PMON68065 | Zm-ASA2-CTP + 18:_S51C | ZM_S138234 | 435 | 42 |
| | | ZM_S142738 | 512 | 95 |
| | | ZM_S137274 | 514 | 78 |
| | | ZM_S139817 | 529 | 108 |
| | | ZM_S134462 | 587 | 71 |
| | | ZM_S142742 | 594 | 135 |
| | | ZM_S142745 | 594 | 90 |
| | | ZM_S142725 | 613 | 87 |
| | | ZM_S142747 | 651 | 93 |
| | | ZM_S142728 | 814 | 395 |
| PMON68066 | Zm-ASA2-CTP + 18:_S51C_nno | ZM_S134079 | 436 | 132 |
| | | ZM_S133073 | 656 | 127 |
| | | ZM_S133076 | 774 | 57 |
| | | ZM_S134078 | 904 | 119 |
| | | ZM_S134080 | 917 | 268 |
| | | ZM_S133092 | 928 | 255 |
| | | ZM_S133080 | 943 | 154 |
| | | ZM_S133098 | 960 | 321 |
| | | ZM_S133099 | 1002 | 556 |
| | | ZM_S133082 | 1023 | 129 |
| | | ZM_S133433 | 1100 | 138 |
| | | ZM_S133093 | 1110 | 136 |
| | | ZM_S133089 | 1289 | 139 |
| | | ZM_S133434 | 1352 | 101 |
| PMON78850 | At-CTP2(E/K) + 1:*Rhizobium*_wt | ZM_S127477 | 45 | 4 |
| | | ZM_S129898 | 32 | 6 |
| | | ZM_S129905 | 35 | 3 |
| | | ZM_S129913 | 45 | 5 |
| | | ZM_S129917 | 40 | 7 |
| PMON78851 | At-CTP2(E/K) + 1:*Rhizobium*_S51C | ZM_S128450 | 595 | 103 |
| | | ZM_S128451 | 547 | 96 |
| | | ZM_S128458 | 983 | 31 |
| | | ZM_S128461 | 477 | 85 |
| | | ZM_S128463 | 548 | 72 |
| | | ZM_S128464 | 547 | 100 |
| | | ZM_S128466 | 503 | 39 |
| | | ZM_S128467 | 603 | 126 |
| | | ZM_S128469 | 532 | 69 |

Example 8

Production of Meal and Feed Products

This example sets forth methods for production of meal and feed products containing the expression vectors which have been described in Example 5.

Any of the plants or parts thereof of the present invention may be processed to produce a feed, meal, protein, or oil preparation, including feed, meal, protein and oil preparations high in total tryptophan content. A particularly preferred plant part for this purpose is a seed. In a preferred embodiment the feed, meal, protein or oil preparation is designed for livestock animals or humans, or both. Methods to produce feed, meal, protein and oil preparations are known in the art. See, for example, U.S. Pat. Nos. 4,957,748; 5,100,679; 5,219,596; 5,936,069; 6,005,076; 6,146,669; and 6,156,227. In a preferred embodiment, the feed, meal, protein or oil preparation is a high tryptophan preparation. Such a high tryptophan preparation preferably has a tryptophan content of greater than about 200 to 400 ppm, more preferably 400 to 600 ppm, and even more preferably 600 to 800 ppm.

Example 9

Methods for Detecting a CTP::AS Transgene

This sets forth methods that may be used to detect the presence in transgenic plant cells, or feed or meal products derived from such transgenic plant cells, of unique sequences belonging to a construct containing any of the CTP::AS sequence combinations described herein.
PCR Amplification of CTP::AS DNA Genomic DNA from transgenic plant cells, or from feed or meal products derived from such transgenic plant cells, can be extracted using the QIAGEN DNeasy™ Plant mini kit (Cat #69104; QIAGEN Inc.) according to manufacturer's protocol. The PCR reaction mixture generally may include about 100 mg of the extracted genomic DNA, 1×PCR reaction buffer (Expand High Fidelity PCR System, Cat #1732641; Roche Inc., Nutley, N.J.), 0.2 mM dNTP, 5 picomoles of each primer, 3.5 units of High Fidelity Taq polymerase enzyme, and water to a final volume of 50 µl. For example, the primer pairs of SEQ ID NO: 228 and SEQ ID NO: 229; or SEQ ID NO: 230 and SEQ ID NO: 231 can be used to amplify the extracted DNA to produce an amplicon that is diagnostic for DNA from the Zm-ASA2+18-CTP::AgroAS construct of a plant cell that has been transformed with pMON68066. The reaction mixture is subjected to various temperature cycles that may include: denaturing at 95° C., annealing at 60° C., and extension at 72° C., for 35 cycles. After 35 cycles of PCR, about 10 µl of the reaction mixture is separated on a 1.0% agarose gel. The presence of a 2649 base pair fragment (with primer pair SEQ ID NO: 228 and SEQ ID NO: 229) or a 2735 base pair fragment (with primer pair SEQ ID NO: 230 and SEQ ID NO: 231) indicates that the plant cell, feed or meal product comprises the Zm-ASA2+18-CTP fused to the AS allele. It is well within the means of one of ordinary skill in the art to recognize and design additional PCR primer pairs that would be useful in the detection of unique sequences belonging to a construct containing any of the other CTP::AS sequence combinations described herein.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations may be applied to the materials and methods described herein without departing from the concept, spirit and scope of the invention. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. patents, applications and application publications: U.S. application Ser. No. 09/757,089; U.S. application Ser. No. 10/138,927; U.S. application Ser. No. 10/430,011; U.S. application Ser. No. 10/732,721; U.S. application Ser. No. 11/503,532; U.S. Pat. No. 4,957,748; U.S. Pat. No. 4,957,748; U.S. Pat. No. 5,100,679; U.S. Pat. No. 5,100,679; U.S. Pat. No. 5,188,642; U.S. Pat. No. 5,219,596; U.S. Pat. No. 5,219,596; U.S. Pat. No. 5,290,924; U.S. Pat. No. 5,322,783; U.S. Pat. No. 5,322,938; U.S. Pat. No. 5,322,938; U.S. Pat. No. 5,352,605; U.S. Pat. No. 5,359,142; U.S. Pat. No. 5,378,619; U.S. Pat. No. 5,378,619; U.S. Pat. No. 5,424,412; U.S. Pat. No. 5,530,196; U.S. Pat. No. 5,538,880; U.S. Pat. No. 5,550,318; U.S. Pat. No. 5,563,055; U.S. Pat. No. 5,610,042; U.S. Pat. No. 5,641,876; U.S. Pat. No. 5,728,925; U.S. Pat. No. 5,837,848; U.S. Pat. No. 5,858,741; U.S. Pat. No. 5,936,069; U.S. Pat. No. 5,936,069; U.S. Pat. No. 6,005,076; U.S. Pat. No. 6,005,076; U.S. Pat. No. 6,118,047; U.S. Pat. No. 6,140,078; U.S. Pat. No. 6,146,669; U.S. Pat. No. 6,146,669; U.S. Pat. No. 6,156,227; U.S. Pat. No. 6,156,227; U.S. Pat. No. 6,175,060; U.S. Pat. No. 6,177,611; U.S. Pat. No. 6,232,526; U.S. Pat. No. 6,252,138; U.S. Pat. No. 6,294,714; U.S. Pat. No. 6,426,446; U.S. Pat. No. 6,429,357; U.S. Pat. No. 6,429,362; U.S. Pat. No. 6,433,252; U.S. Pat. No. 6,437,217; U.S. Pat. No. 6,635,806; U.S. Pat. No. 5,641,876; U.S. Pat. No. 7,151,204; U.S. Pat. No. 7,217,865; U.S. Publn. 20030097677; U.S. Publn. 20030213010; U.S. Publn. 20050005327

Archer et al., *J. Bioenerg. Biomemb.*, 22:789-810, 1990.
Belanger and Kriz, *Genetics* 129:863-872, 1991.
Callis et al., *Genes Dev.*, 1:1183-1200, 1987.
Chu, In: *Proceedings of Symposium on Plant Tissue Culture*, Science Press, Beijing, China, 43-50, 1978.
Ditta et al., *Proc. Nat. Acad. Sci. USA*, 77:7347-7351, 1980.
EPA 0 120 515
Fraley et al., *Proc. Natl. Acad. Sci. USA*, 80:4803-4807, 1983.
Gallie et al., *The Plant Cell*, 1:301-311, 1989.
Joshi, *Nucleic Acids Res.*, 15:6643-6653, 1987.
Jouanin et al., *Mol. Gen. Genet.*, 201:370-374, 1985.
Lopes et al., *Mol Gen Genet.*, 247:603-613, 1995.
McBride and Summerfelt, *Plant Mol. Biol.*, 14:269-276, 1990.
McElroy et al., *Mol. Gen. Genet.*, 231(1):150-160, 1991.
Odell, et al. *Nature*, 313:810-812, 1985.
PCT Appln. WO 0011200A2
PCT Appln. WO 95/06128
Schnell et al., *J. Biol. Chem.*, 266(5):3335-3342, 1991.
Sheen, *EMBO J.*, 12:3497-3505, 1993.
Silva-Filho et al., *Plant Mol. Biol.*, 30:769-780, 1996.
Silva-Filho et al., *Plant Mol. Biol.*, 30:769-780, 1996.
Tingey et al., *EMBO J.*, 6:1-9, 1987.
Vasil et al., *Plant Physiol.*, 91:1575-1579, 1989.
Withers-Martinez et. al., *Protein Engineering*, 12:1113-1120, 1999.

What is claimed is:

1. An expression vector comprising a polynucleotide molecule encoding a chloroplast transit peptide fused to a monomeric anthranilate synthase, wherein the chloroplast transit peptide is heterologous to the monomeric anthranilate synthase, wherein:
   a) the chloroplast transit peptide comprises the polypeptide sequence of SEQ ID NO: 28; or
   b) the polynucleotide molecule encoding the chloroplast transit peptide comprises SEQ ID NO: 9;

wherein said chloroplast transit peptide provides enhanced targeting of said monomeric anthranilate synthase to a chloroplast of a plant cell when compared to the targeting of said anthranilate synthase by chloroplast transit peptide 1 (CTP1) of SEQ ID NO:19;

wherein said polynucleotide molecule provides enhanced levels of at least tryptophan in a transgenic plant cell comprising said polynucleotide molecule when compared to a plant cell of the same genotype but lacking said polynucleotide molecule; and wherein said monomeric anthranilate synthase is feedback insensitive to tryptophan.

2. The expression vector of claim 1, wherein said monomeric anthranilate synthase comprises a polypeptide sequence comprising SEQ ID NO: 206.

3. The expression vector of claim 1, defined as comprising the nucleic acid sequence of SEQ ID NO: 213.

4. The expression vector of claim 1, further comprising a promoter functional in plants operably linked to said polynucleotide encoding the chloroplast transit peptide fused to the monomeric anthranilate synthase.

5. The expression vector of claim 4, wherein said promoter is a constitutive, inducible, seed-specific, or tissue-preferred promoter.

6. The expression vector of claim 4 wherein the polynucleotide encoding the chloroplast transit peptide comprises SEQ ID NO: 9, and the polynucleotide encoding the monomeric anthranilate synthase comprises SEQ ID NO: 207.

7. A transgenic cell transformed with the expression vector of claim 1.

8. The transgenic cell of claim 7, defined as a plant cell.

9. The transgenic plant cell of claim 8, defined as a monocot cell.

10. The transgenic plant cell of claim 8, defined as a dicot cell.

11. The transgenic plant cell of claim 8, wherein said monomeric anthranilate synthase comprises a polypeptide sequence comprising SEQ ID NO: 206.

12. The transgenic plant cell of claim 8, further comprising a promoter operably linked to said polynucleotide molecule encoding said chloroplast transit peptide fused to said monomeric anthranilate synthase.

13. The transgenic plant cell of claim 12, wherein said promoter is selected from the group consisting of constitutive, inducible, seed-specific, and tissue-preferred promoters.

14. The transgenic plant cell of claim 8, wherein said transgenic plant cell is a maize cell.

15. The transgenic plant cell of claim 8, wherein the polynucleotide encoding the chloroplast transit peptide comprises SEQ ID NO: 9 and the polynucleotide encoding the monomeric anthranilate synthase comprises SEQ ID NO: 207.

16. A method of increasing the levels of free tryptophan in a cell of a monocotyledonous plant comprising expressing in the cell the expression vector of claim 1, wherein said chloroplast transit peptide compartmentalizes said monomeric anthranilate synthase to a plastid in said cell.

17. A transgenic plant transformed with the expression vector of claim 1.

18. A seed of the plant of claim 17, wherein the seed comprises said expression vector.

19. A method of producing a tryptophan-enhanced corn feed product comprising processing the seed of claim 18 into said corn feed product.

* * * * *

UNITED STATES PATENT AND TRADEMARK OFFICE
CERTIFICATE OF CORRECTION

PATENT NO. : 8,138,393 B2
APPLICATION NO. : 11/836690
DATED : March 20, 2012
INVENTOR(S) : Manjunath et al.

Page 1 of 1

It is certified that error appears in the above-identified patent and that said Letters Patent is hereby corrected as shown below:

In column 9, line 59, delete "S5C" and insert --S51C--.

In column 9, line 63, delete "S5C" and insert --S51C--.

Signed and Sealed this
Twelfth Day of June, 2012

David J. Kappos
*Director of the United States Patent and Trademark Office*